(12) United States Patent
Pecker et al.

(10) Patent No.: US 7,666,651 B2
(45) Date of Patent: *Feb. 23, 2010

(54) POLYPEPTIDE HAVING HEPARANASE ACTIVITY

(75) Inventors: Iris Pecker, Rishon LeZion (IL); Israel Vlodavsky, Mevaseret Zion (IL); Elena Feinstein, Rehovot (IL)

(73) Assignees: InSight Biopharmaceuticals Ltd., Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,874

(22) Filed: Feb. 6, 2001

(65) Prior Publication Data
US 2002/0102560 A1 Aug. 1, 2002

Related U.S. Application Data

(63) Continuation of application No. 09/258,892, filed on Mar. 1, 1999, now abandoned, which is a continuation-in-part of application No. PCT/US98/17954, filed on Aug. 31, 1998.

(51) Int. Cl.
*C12N 9/00* (2006.01)
*C12N 9/14* (2006.01)
*C12N 9/24* (2006.01)

(52) U.S. Cl. ............... 435/209; 435/183; 435/195; 435/200; 435/201; 424/94.6

(58) Field of Classification Search .......... 435/209, 435/200, 195; 424/94.61
See application file for complete search history.

(56) References Cited

U.S. PATENT DOCUMENTS

| | | | |
|---|---|---|---|
| 2,295,323 A | 9/1942 | Armstrong | |
| 4,117,841 A | 10/1978 | Perrotta et al. | |
| 4,455,296 A | 6/1984 | Hansen et al. | |
| 4,683,195 A | 7/1987 | Mullis et al. | |
| 4,859,581 A | 8/1989 | Nicholson et al. | |
| 4,882,318 A | 11/1989 | Vlodavsky et al. | |
| 4,937,747 A | 6/1990 | Koller | |
| 4,946,778 A | 8/1990 | Ladner et al. | |
| 5,129,877 A | 7/1992 | Gallo et al. | |
| 5,145,679 A | 9/1992 | Hinson | |
| 5,194,596 A | 3/1993 | Tischer et al. | |
| 5,206,223 A | 4/1993 | Vlodavsky et al. | |
| 5,332,812 A | 7/1994 | Nicolson et al. | |
| 5,350,836 A | 9/1994 | Kopchick et al. | |
| 5,360,735 A | 11/1994 | Weinshank et al. | |
| 5,362,641 A * | 11/1994 | Fufs et al. ............ | 435/209 |
| 5,399,351 A | 3/1995 | Leshchiner et al. | |
| 5,474,983 A | 12/1995 | Kuna et al. | |
| 5,550,116 A | 8/1996 | Lormeau et al. | |
| 5,571,506 A | 11/1996 | Regan et al. | |
| 5,580,862 A | 12/1996 | Rosen et al. | |
| 5,589,604 A | 12/1996 | Drohan et al. | |
| 5,600,366 A | 2/1997 | Schulman | |
| 5,602,095 A | 2/1997 | Pastan et al. | |
| 5,618,709 A | 4/1997 | Gewirtz et al. | |
| 5,656,595 A | 8/1997 | Schweighoffer et al. | |
| 5,667,501 A | 9/1997 | Fowler et al. | |
| 5,688,679 A | 11/1997 | Powell | |
| 5,700,671 A | 12/1997 | Prieto et al. | |
| 5,714,345 A | 2/1998 | Clark | |
| 5,716,817 A | 2/1998 | Tornell | |
| 5,736,137 A | 4/1998 | Anderson et al. | |
| 5,739,115 A | 4/1998 | Fugedi et al. | |
| 5,799,276 A | 8/1998 | Komissarchik et al. | |
| 5,799,311 A | 8/1998 | Agrawal et al. | |
| 5,830,759 A | 11/1998 | Chang et al. | |
| 5,859,660 A | 1/1999 | Perkins et al. | |
| 5,859,929 A | 1/1999 | Zhou et al. | |
| 5,917,830 A | 6/1999 | Chen et al. | |
| 5,962,321 A | 10/1999 | Gough et al. | |
| 5,968,822 A | 10/1999 | Pecker et al. | |
| 5,997,863 A | 12/1999 | Zimmermann et al. | |
| 6,020,931 A | 2/2000 | Bilbrey et al. | |
| 6,140,552 A | 10/2000 | Deboer et al. | |
| 6,153,187 A | 11/2000 | Yacoby-Zeevi | |
| 6,177,545 B1 | 1/2001 | Pecker et al. | |
| 6,190,875 B1 | 2/2001 | Ben-Artzi et al. | |
| 6,226,792 B1 | 5/2001 | Goiffon et al. | |
| 6,230,151 B1 | 5/2001 | Agrawal et al. | |
| 6,242,238 B1 | 6/2001 | Freeman et al. | |
| 6,307,965 B1 | 10/2001 | Aggarwal et al. | |

(Continued)

FOREIGN PATENT DOCUMENTS

AU 735116 6/2001

(Continued)

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

(Continued)

*Primary Examiner*—Richard G Hutson

(57) ABSTRACT

A polynucleotide (hpa) encoding a polypeptide having heparanase activity, vectors including same, genetically modified cells expressing heparanase, a recombinant protein having heparanase activity and antisense oligonucleotides and constructs for modulating heparanase expression.

2 Claims, 50 Drawing Sheets

U.S. PATENT DOCUMENTS

| | | |
|---|---|---|
| 6,314,420 B1 | 11/2001 | Lang et al. |
| 6,348,344 B1 | 2/2002 | Ayal-Hershkovitz et al. |
| 6,387,643 B1 | 5/2002 | Heinrikson et al. |
| 6,423,312 B1 | 7/2002 | Yacoby-Zeevi |
| 6,426,209 B1 | 7/2002 | Ayal-Hershkovitz et al. |
| 6,475,763 B1 | 11/2002 | Ayal-Hershkovitz et al. |
| 6,531,129 B2 | 3/2003 | Pecker et al. |
| 6,562,950 B2 | 5/2003 | Peretz et al. |
| 6,664,105 B1 | 12/2003 | Pecker et al. |
| 6,699,672 B1 | 3/2004 | Pecker et al. |
| 6,790,658 B2 | 9/2004 | Pecker et al. |
| 6,798,658 B2 | 9/2004 | Takedomi et al. |
| 6,800,441 B2 | 10/2004 | Pecker et al. |
| 6,946,131 B2 | 9/2005 | Peretz et al. |
| 6,960,471 B2 | 11/2005 | Pecker et al. |
| 6,986,996 B2 | 1/2006 | Pecker et al. |
| 2001/0006630 A1 | 7/2001 | Yacobi-Zeevi et al. |
| 2002/0068061 A1 | 6/2002 | Peretz et al. |
| 2002/0088019 A1 | 7/2002 | Yacobi-Zeevi et al. |
| 2002/0102560 A1 | 8/2002 | Pecker et al. |
| 2002/0114801 A1 | 8/2002 | Pecker et al. |
| 2002/0168749 A1 | 11/2002 | Pecker et al. |
| 2002/0194625 A1 | 12/2002 | Zcharia et al. |
| 2003/0031660 A1 | 2/2003 | Yacobi-Zeevi et al. |
| 2003/0068806 A1 | 4/2003 | Ayal-Hershkovitz et al. |
| 2003/0161823 A1 | 8/2003 | Ilan et al. |
| 2003/0163836 A1 | 8/2003 | Garofalo et al. |
| 2003/0170860 A1 | 9/2003 | Pecker et al. |
| 2003/0181687 A1 | 9/2003 | Peretz et al. |
| 2003/0190737 A1 | 10/2003 | Pecker et al. |
| 2003/0217375 A1 | 11/2003 | Zcharia et al. |
| 2003/0236215 A1 | 12/2003 | Pecker et al. |
| 2004/0063135 A1 | 4/2004 | Pecker et al. |
| 2004/0142427 A1 | 7/2004 | Pecker et al. |
| 2004/0146497 A1 | 7/2004 | Ilan et al. |
| 2004/0146925 A1 | 7/2004 | Pecker et al. |
| 2004/0213789 A1 | 10/2004 | Yacobi-Zeevi et al. |
| 2005/0260187 A1 | 11/2005 | Ilan et al. |
| 2006/0008892 A1 | 1/2006 | Yacobi-Zeevi et al. |
| 2006/0269552 A1 | 11/2006 | Yacobi-Zeevi et al. |

FOREIGN PATENT DOCUMENTS

| | | | |
|---|---|---|---|
| AU | 768820 | | 1/2004 |
| EP | 0254067 | | 1/1988 |
| EP | 0998569 | | 5/2000 |
| IL | 133264 | | 4/2001 |
| WO | WO 88/01280 | | 2/1988 |
| WO | WO 91/02977 | | 3/1991 |
| WO | WO 91/19197 | | 12/1991 |
| WO | WO 92/01003 | | 1/1992 |
| WO | WO 95/04158 | * | 2/1995 |
| WO | WO 95/04518 | | 2/1995 |
| WO | WO 97/11684 | | 4/1997 |
| WO | WO 97/27327 | | 7/1997 |
| WO | WO 98/03638 | | 1/1998 |
| WO | WO 98/46258 | | 10/1998 |
| WO | WO 99/11798 | | 3/1999 |
| WO | WO 99/18852 | | 4/1999 |
| WO | WO 99/21975 | | 5/1999 |
| WO | WO 99/40207 | | 8/1999 |
| WO | WO 99/48478 | | 9/1999 |
| WO | WO 99/57153 | | 11/1999 |
| WO | WO 99/57244 | | 11/1999 |
| WO | WO 00/03036 | | 1/2000 |
| WO | WO 00/25817 | | 5/2000 |
| WO | WO 00/52149 | | 9/2000 |
| WO | WO 00/52178 | | 9/2000 |
| WO | WO 01/00643 | | 1/2001 |
| WO | WO 02/19962 | | 3/2002 |
| WO | WO 02/32283 | | 4/2002 |
| WO | WO 03/006645 | | 1/2003 |
| WO | WO 2004/108065 | | 12/2004 |

OTHER PUBLICATIONS

H. Guo et al., "Protein Tolerance to Random Amino Acid Change", PNAS 101(25):9205-9210, Jun. 2004.*

Flanagan et al. "Potent and Selective Gene Inhibition Using Antisense Oligodeoxynucleotides", Molecular and Cellular Biochemistry, 172: 213-225, 1997.

Frederiksen et al. "Antibiotic Treatment of Initial Colonization with *Pseudomonas aeruginosa* Postpones Chronic Infection and Prevents Deterioraton of Pulmonary Function in Cystic Fibrosis", Pediatr. Pulmonol. 23(5): 330-335, 1997. Abstract.

Frederiksen et al. Changing Epidemiology of *Pseudomonas aeruginosa* Infection in Danish Cystic Fibrosis Patients (1974.

Freeman et al. "A Rapid Quantitative Assay for the Detection of Mammalian Heparanase Activity", Biochemical Journal, 325: 229.

Freeman et al. "Evidence That Platelet and Tumor Heparanases Are Similar Enzymes", Biochem J., 342: 361.

Freeman et al. "Human Platelet Heparanase: Purification, Characterization and Catalytic Activity", Biochem. J., 330: 1341.

Friedman et al. Regulated Expression of Homeobox Genes Msx.

Gabriel et al. "In Vitro Adherence of *Pseudomonas aeruginosa* to Four Intraocular Lenses", J. Cataract Refract Surg., 24: 124.

Gantt et al. Cell Adhesion to A Motif Shared by the Malaria Circumsporozoite Protein and Thrombospondin Is Mediated by Its Glycosminoglycan.

Garner "Epidermal Regulation of Dermal Fibroblast Activity", Plast. Reconstr. Surg., 102(1):135.

Gewirtz et al. "Facilitating Oligonucleotide Delivery: Helping Antisense Deliver on Its Promise", Proc. Natl. Acad. Sci. USA, 93: 3161.

Gewirtz et al. "Nucleic Acid Therapeutics: State of the Art and Future Prospects", Blood, 92(3): 712.

Ghani et al. "Ceftazidime, Gentamicin, and Rifampicin, in Combination, Kill Biofilms of Mucoid *Pseudomonas aeruginosa*", Can. J. Microbiol., 43(11): 999.

Haisma et al. "Construction and Characterization of A Fusion Protein of Single-Chain Anti-Carcinoma Antibody 323/A3 and Human Beta-Glucuronidase".

Hammer et al. "Spontaneous Inflammatory Disease in Transgenic Rats Expressing HLA-B27 and Human ?2m: An Animal Model of HLA-B27-Associated Human Disorders".

Harlow et al. "Antibodies—A Laboratory Manual", Cold Spring Harbor Press, p. 471-510, 1988.

Harvey et al. "Expression of Exogenous Protein in the Egg White of Transgenic Chickens".

Hatano et al. "Biologic Activities of Antibodies to the Neutral-Polysaccharide Component of the *Pseudomonas aeruginosa* Lipopolysaccharide Are Blocked by O Side Chains and Mucoid Exopolysaccharide (Alginate)".

Hatch et al. "Alginate Lyase Promotes Diffusion of Aminoglycosides Through the Extracellular Polysaccharide of Mucoid *Pseudomonas aeruginosa*".

Hayward et al. "Cellular Mechanisms of Heparinase III Protection in Rat Traumatic Shock".

Hayward et al. "Heparinase III Exerts Endothelial and Cardioprotective Effects in Feline Myocardial Ischemia-Reperfusion Injury".

Herrera et al. "Mediation of Trypanosoma Cruzi Invasion by Heparan Sulfate Receptors on Host Cells and Penetrin Counter-Receptors on the Trypanosomes".

Hida et al. "Antisense E1AF Transfection Restrains Oral Cancer Invasion by Reducing Matrix Metalloproteinase Activities".

Hill et al. "Organ-Specific Over-Sulfation of Glycosaminoglycans and Altered Extracellular Matrix in A Mouse Model of Cystic Fibrosis".

Hillier et al. "The WashU-Merck EST Project" GenBank Entry N32056.

Johansen et al. "Vaccination Promotes TH1-Like Inflammation and Survival in Chronic *Pseudomonas aeruginosa* Pneumonia: A New Prophylactic Principle".

Jorba et al. "Variations in the *P. aeruginosa* Polysaccharide Synthesis Conditioned by Aminosugars".
Jusa et al. "Effect of Heparinon on Infection of Cells by Porcine Reproductive and Respiratory Syndrome Virus".
Kang et al. "Prolactin-Inducible Enhancer Activity of the First Intron of the Bovine beta-Casein Gene".
Kato et al. "Physiological Degradation Converts the Soluble Syndecan-1 Ectodomain From An Inhibitor to A Potent Activator of FGF-2".
Kawaja et al. "Employment of Fibroblasts for Gene Transfer: Applications for Grafting Into the Central Nervous System".
Kawase et al. "Effect of Partial Incision of the Zona Pellucida by Piezo-Micromanipulator for In Vitro Fertilization Using Frozen-Thawed Mouse Spermatozoa on the Developmental Rate of Embryos Transferres at the 2-Cell Stage".
Kiberstis et al. "Bone Health in the Balance".
Kizaki et al. "Cloning and Localization of Heparanase in Bovine Placenta".
Kizaki et al. "Expression of Heparanase mRNA in Bovine Placenta During Gestation", Reproduction, 121: 573-580, 2001.
Köhler et al. "Continuous Cultures of Fused Cells Secreting Antibody of Predefined Specificity", Nature, 256: 495-497, 1975.
Konstan et al. "Current Understanding of the Inflammatory Process in Cystic Fibrosis", Pediatric Pulmonology, 24: 137-142, 1997.
Konstan et al. "Patterns of Medical Practice in Cystic Fibrosis: Part II. Use of Therapies", Pediatr. Pulmonol,. 28(4): 248-54, 1999. Abstract.
Korb et al. "Stimulation of Gene Expression by Introns: Conversion of An Inhibitory Intron to A Stimulatory Intron by Alteration of the Splice Donor Sequence", Nucleic Acids Research, 21(25): 5901-5908, 1993.
Kosir et al. "Early Human Breast Carcinoma Cells Produce Extra Cellular Heparanase", Molecular Biology/Biochemistry, Proceedings of the American Association for Cancer Research, 37: 495, 1996.
Kosir et al. "Human Prostate Carcinoma Cells Produce Extracellular Heparanase", Journal of Surgical Research, 67: 98-105, 1997.
Krivit et al. "Microglia: The Effector Cell for Reconstitution of the Central Nervous System Following Bone Marrow Transplantation for Lysosomal and Peroxisomal Storage Diseases", Cell Transplant, 4(4): 385-392, 1995. Abstract.
Li et al. "Immunochemical Localization of Heparanase on Mouse and Human Melanomas", Int. J. Cancer, 45: 1088-1095, 1990.
Li et al. "In Vivo Fragmentation of Heparan Sulfate by Heparanase Overexpression Renders Mice Resistant to Amyloid Protein A Amyloidosis", PNAS, 102(18): 6473-6477, 2005.
Li et al. "β-Endorphin Omission Analogs: Dissociation of Immunoreactivity From Other Biological Activities", PNAS, 77: 3211-3214, 1980.
Lider et al. "Inhibition of T Lymphocyte Heparanase by Heparin Prevents T Cell Migration and T Cell-Mediated Immunity", European Journal of Immunology, 20(3): 493-499, 1990. Abstract.
Linhardt et al. "Polysaccharide Lyases", Applied Biochemistry and Biotechnology, 12: 135-176, 1986.
Liu et al. "Live Offspring by In Vitro Fertilization of Oocytes From Cryopreserved Primordial Mouse Follicles After Sequential In Vivo Transplantation and In Vitro Maturation", Biology of Reproduction, 64: 171.
Loredo et al. Regulation of Glycosaminoglycan Metabolism by Bone Morphogenetic Protein.
Luft "Making Sense Out of Antisense Oligodeoxynucleotide Delivery: Getting There Is Half the Fun". J. Mol. Med, p. 75.
Macone et al. "Mucoid *Escherichia coli* in Cystic Fibrosis", The New England Journal of Medicine, 304(24): 1445.
Maillard et al. "Pre-Treatment With Elastase Improves the Efficiency of Percutaneous Adenovirus-Mediated Gene Transfer to the Arterial Media", Gene Therapy, 5: 1023-1030, 1998.
Marchetti et al. "Neurotrophin Stimulation of Human Melanoma Cell Invasion: Selected Enhancement of Heparanase Activity and Heparanase Degradation of Specific Heparan Sulfate Subpopulations", Cancer Research, 56: 2856.
Marra et al. "The WashU-HHMI Mouse EST Project", Database EMBL, Accession No. A1122034, XP 002198426, 1998. Abstract.
Marra et al. "The WashU-HHMI Mouse Est Project", Database EMBL, Accession No. AA047943, XP002198424, 1996.
Oosta et al. "Purification and Properties of Human Platalets Heparitanase", J. Biol. Chem., 257(19): 11249-11255, 1982.
Ornitz et al. "Heparin Is Required for Cell-Free Binding of Basic Fibroblast Growth Factor to A Soluble Receptor and for Mitogenesis in Whole Cells", Molecular and Cellular Biology, 12: 240-247, 1992.
Pasquier et al. "Implication of Neutral Polysaccharides Associated to Alginate in Inhibition of Murine Macrophage Response to *Pseudomonas aeruginosa*", FEMS Microbiol. Lett., 147(2): 195-202, 1997. Abstract.
Pearce et al. "Development of Glucose Intolerance in Male Transgenic Mice Overexpressing Human Glycogen Synthase Kinase-3? on A Muscle-Specific Promoter", Metabolism, 53(10): 1322-1330, 2004.
Pfaff et al. "Cryobiology of Rat Embryos I: Determination of Zygote Membrane Permeability Coefficients for Water and Cryoprotectants, Their Activation Energies, and the Development of Improved Cryopreservation Methods", Biology of Reproduction, 63: 1294-1302, 2000. Abstract.
Pier "Rationale for Development of Immunotherapies That Target Mucoid *Pseudomonas aeruginosa* Infection in Cystic Fibrosis Patients", Behring Inst. Mitt., 98: 350-360, 1997. Abstract.
Pier et al. "Cystic Fibrosis Transmembrane Conductance Regulator Is An Epithelial Cell Receptor for Clearance of *Pseudomonas aeruginosa* From the Lung", Proc. Natl. Acad. Sci. USA, 94(22): 12088-12093, 1997.
Pier et al. "How Mutant CFTR May Contribute to *Pseudomonas aeruginosa* Infection in Cystic Fibrosis", Am. J. Respir. Crit. Care Med., 154(4): S175-S182, 1996. Abstract.
Pilbeam et al. "Comparison of the Effects of Various Lengths of Synthetic Human Parathyroid Hormone-Related Peptide (hPTHrP) of Malignancy on Bone Resorption and Formation in Organ Culture", Bone, 14: 717-720,1993.
Pina et al. "The Role of Fluoroquinolones in the Promotion of Alginate Synthesis and Antibiotic Resistance in *Pseudomonas aeruginosa*", Curr. Microbiol., 35(2): 103-108, 1997. Abstract.
Pomahac et al. "Tissue Engineering of Skin", Crit. Rev. Oral Biol. Med., 9(3): 333.
Prahalada et al. "Diethylstilbestrol-Induced Cervical and Vaginal Adenosis Using the Neonatal Mouse Model", Biology of Reproduction, 38: 935-943, 1988. Abstract.
Prockop "Marrow Stromal Cells as Stem Cells for Nonhematopoietic Tissues", Science, 276: 71.
Quax et al. Metastatic Behavior of Human Melanoma Cell Lines in Nude Mice Correlates With Urokinase.
Rader et al. "A Phage Display Approach for Rapid Antibody Humanization: Designed Combinatorial V Gene Libraries", Proc. Natl. Acad. Sci. USA, 95: 8910.
Raghunath et al. "Cultured Epithelial Autografts: Driving From Surgery Into Matrix Biology", Pediatr. Surg. Int., 12(7): 478.
Rahmoune et al. "Chondroitin Sulfate in Sputum From Patients With Cystic Fibrosis and Chronic Bronchitis", Am. J. Resp. Cell & Mol. Biol., 5(4): 315-320, 1991. Abstract.
Rajur et al. "Covalent Protein-Oligonucleotide Conjugates for Efficient Delivery of Antisense Molecules", Bioconjugate Chem., 8: 935-940, 1997.
Ramos et al. "Relationship Between Glycolysis and Exopolysaccharide Biosynthesis in *Lactococcus lactis*", Appl. Environ. Microbiol., 67(1): 33-41, 2001. Abstract.
Ramsey et al. "Intermittent Administration of Inhaled Tobramycin in Patients With Cystic Fibrosis. Cystic Fibrosis Inhaled Tobramycin Study Group", New England Journal of Medicine, 340(1): 23-30, 1999. Abstract.
Reddi "Role of Morphogenetic Proteins in Skeletal Tissue Engineering and Regeneration", Nature Biotechnology, 16: 247-252, 1998.
Richards et al. "Construction and Preliminary Characterization of the Rat Casein and Alpha-Lactalbumin cDNA Clones", J. Biol. Chem., 256(1): 526-32, 1981.
Richardson et al. "Regulation of Basic Fibroblast Growth Factor Binding and Avtivity by Cell Density and Haparan Sufate", J. Biological Chemistry, 274(19): 13534-13540, 1990.
Ricoveri et al. "Heparan Sulfate Endoglycosidase and Metastatic Potential in Murine Fibrosarcoma and Melanoma", Cancer Research, 46(8): 3855-3861, 1986. Abstract.

Robert et al. "Chondroitin-4-Sulphate (Proeoglycan), A Receptor for Plasmodium Falciparum-Infected Errthrocyte Adherence on Brain Microvascular Endothelial Cells", Res. Immunol., 146(6): 383-393, 1995, Abstract.

Rubin "Emerging Therapies for Cystic Fibrosis Lung Disease", Chest, 115: 1120-1126, 1999.

Shastry "Gene Disruption in Mice: Models of Development and Disease", Molecular and Cellular Biochemistry, 181: 163-179, 1998.

Shekhar et al. "Correlation of Differences in Modulation of Ras Expression With Metastatic Competence of Mouse Mammary Tumour Subpopulations", Invasion Metastasis, 14: 27-37, May 1995.

Shimazu et al. "Syndecan-3 and the Control of Chondrocyte Proliferation During Endochondral Ossification", Exp. Cell. Res., 229(1): 126-136, 1996. Abstract.

Skolnick et al. "From Genes to Protein Structure and Function: Novel Applications of Computational Approaches in the Genomic Era", Trends in Biotechnology, 18: 34-39, 2000.

Smith et al. "Expression of Heparan Sulfate Protoglycan (Perlecan) in the Mouse Blastocyst Is Regulated During Normal and Delayed Implantation", Dev. Biol., 184(1): 38-47, 1997. Abstract.

Smith et al. "The Challenges of Genome Sequence Annotation or 'The Devil Is in the Details'", Nature Biotechnology, 15: 1222-1223, 1997.

Sordat et al. "Modulation of the Malignant Phenotype With the Urokinase-Type Plasminogen Activator and the Type I Plasminogen Activator Inhibitor", Cell Differentiation and Development, 32: 277-286, 1990.

Soule et al. "Isolation and Characterization of A Spontaneously Immortalized Human Breast Epithelial Cell Line, MCF-10[1]", Cancer Res., 50: 6075-6086, 1990. Abstract.

Speert et al. "Modulation of Macrophage Function for Defense of the Lung Against Pseudomonas aeruginosa", Behring Inst. Mitt., 98: 274-282, 1997. Abstract.

Spiegel et al. "Heparanase Facilitates Development and SDF-1 Induced Migration of Hematopoietic Stem and Progenitor Cells", Blood, 102(11): 825a-826a, 2003. Abstract# 3056.

Stracke et al. "Autotaxin, Tumor Motility-Stimulating Exophosphodiesterase", Advan. Enzyme Regul., 37: 135-144, 1997. Introduction.

Suggs et al. Use of Synthetic Oligonucleotides as Hybridization Probes: Isolation of Cloned cDNA Sequences for Human ?2.

Sutherland "Structure-Function Relationships in Microbial Exopolysaccharides", Biotech. Adv., 12: 393-448, 1994.

Szczylik et al. Selective Inhibition of Leukemia Cell Proliferation by BCR.

Tang et al. "Contribution of Specific Pseudomonas aeruginosa Virulence Factors to Pathogenesis of Pneumonia in A Neonatal Mouse Model of Infection", Infect. Immun., 64(1): 37-43, 1996. Abstract.

Tatnell et al. "Characterisation of Alginates From Mucoid Strains of Pseudomonas aeruginosa", Biochemical Society Transactions, 24: 404S, 1996.

Tatnell et al. "Chemical Analysis of Alginates From Mucoid Strains of Pseudomonas aeruginosa", Biochemical Society Transactions, 22: 310S, 1994.

Tatnell et al. "Colonisation of Cystic Fibrosis Patients by Non-Mucoid Pseudomonas aeruginosa—Characterisation of the Alginate From Mucoid Variants", Biochemical Society Transactions, 24: 406S, 1996.

Taurog et al. "HLA-B27 in Inbred and Non-Inbred Transgenic Mice", The Journal of Immunology, 141(11): 4020-4023, 1988.

Taylor et al. "A Colorimetric Method for the Quantitation of Uronic Acids and A Specific Assay for Galacturonic Acid", Analytical Biochemistry, 201: 190-196, 1992.

Thompson et al. "Identification of Chondroitin Sulfate E in Human Lung Mast Cells", J. Immunol., 140(8): 2708-2713, 1988. Abstract.

Thuong et al. "Sequence-Specific Recognition and Modification of Double-Helical DNA by Oligonucleotides", Angew.Chem. Int. Ed. Engl. 32: 666-690, 1993.

Toyoshima et al. "Human Heparanase: Purification, Characterization, Cloning, and Expression", J. Biolog. Chemistry, 274(34): 24153-24160, 1999.

Uno et al. "Antisense-Mediated Suppression of Human Heparanase Gene Expression Inhibits Pleural Dissemination of Human Cancer Cells", Cancer Research, 61(21): 7855-7860, 2001.

Van Heeckeren et al. "Excessive Inflammatory Response of Cystic Fibrosis Mice to Bronchopulmonary Infection With Pseudomonas aeruginosa", J. Clin. Invest., 100(11): 2810-2815, 1997.

Vernet et al. "Virulence Factors (Aerobactin and Mucoid Phenotype) in Klebsiella Pneumoniae and Escherichia coli Blood Culture Isolates", FEMS Microbiol. Lett., 130(1): 51-57, 1995. Abstract.

Vlodavsky et al. "Mammalian Heparanase: Gene Cloning, Expression and Function in Tumor Progression and Metastasis", Nature Medicine, 5(7): 793-802, 1999.

Vlodavsky et al. "Morphological Appearance, Growth Behaviour and Migratory Activity of Human Tumor Cells Maintained on Extracellular Matrix Versus Plastic", Cell, 19: 607-616, 1980.

Vogel et al. "Production of Proteoglycans by Human Lung Fibroblasts (IMR-90) Maintained in A Low Concentration of Serum", Biochem. J., 207(3): 369-379. Abstract.

Vukicevic et al. "Induction of Nephrrogenic Mesenchyme by Osteogenic Protein 1 (Bone Morphogenetic Protein 7)", Proc. Natl. Acad. Sci. USA, 93: 9021-9026, 1996.

Walch et al. "Correlation of Overexpression of the Low-Affinity p75 Neutrotrophin Receptor With Augmented Invasion and Heparanase Production in Human Malignant Melanoma Cells", Int. J. Cancer, 82: 112-120, 1999.

Wall "Transgenic Livestock: Progress and Prospects for the Future", Theriogenology, 45: 57-68, 1996.

Walton et al. "Prediction of Antisense Oligonucleotide Binding Affinity to A Structured RNA Target", Biotechnology and Bioengineering, 65(1): 1-9, 1999.

Wang "Basic Fibroblast Growth Factor for Stimulation of Bone Formation in Osteoinductive or Conductive Implants", Acta Orthop. Scand. Suppl., 269: 1-33, 1996. Abstract.

Wang "Basic Fibroblast Growth Factor Infused at Different Times During Bone Graft Incorporation. Titanium Chamber Study in Rats", Acta Orthop. Scand., 67(3): 229-236, 1996. Abstract.

Wang et al. "Basic Fibroblast Growth Factor Enhances Bone-Graft Incorporation: Dose and Time Dependence in Rats", J. Orthop. Res., 14(2): 316-323, 1996. Abstract. Suppl. IDS in 22716.

Wang et al. "Isolation and Characterization of Pseudomonas aeruginosa Genes Inducible by Respiratory Mucus Derived From Cystic Fibrosis Patients", Mol. Microbiol., 22(5): 1005-1012, 1996. Abstract.

Watson et al. "A Growth Factor Phenotype Map for Ovine Preimplantation Development", Biology of Reproduction, 50(4): 725-733, 1994. Abstract.

Webster et al. "FGFR Activation in Skeletal Disorders: Too Much of A Good Thing", TIG, 13(5): 178-182, 1997.

Welch et al. "Complex Saccharide Metabolism in Cyctic Fibrosis Fibroblasts", Pediatr. Research, 9(9): 698-702, 1975.

Gilat et al. "Molecular Behaviour Adapts to Context: Heparanase Functions as An Extracellular Matrix-Degrading Enzyme or as A T-Cell Adhesion Molecule, Depending in the Local PH", Journal of Experimental Medicine, 181: 1929-1934, 1995.

Hillier et al. "The WashU-Merck EST Project", Database EMBL Accession No. N45367, XP 002198420, 1996. Abstract.

InSight "Monoclonal Anti-Human Heparanase 1 (HPA1) Antibody Clone HP130", InSight Biopharmaceuticals Ltd., 2 P., 2008.

InSight "Monoclonal Anti-Human Heparanase 1 (HPA1) Antibody Clone HP3/17", InSight Biopharmaceuticals Ltd., 2 P., 2008.

Pontremoli et al. "Changes in Activity of Fructose-1,6-Bisphosphate Aldolase in Livers of Fasted Rabbits and Accumulation of Crossreacting Immune Material", Proc. Natl. Acad. Sci, USA, 76(12): 6323-6325, 1979.

Abaza et al. "Effects of Amino Acid Substititions Outside An Antigenic Site on Protein Binding to Monoclonal Antibodies of Predetermined Specificity Obtained by Peptide Immunization: Demonstration With Region 94-100 (Antigenic Site 3) of Myoglobin", Journal of Protein Chemistry, 11(5): 433-444, 1992.

Abrahamsohn et al. "Implantation and Decidualization in Rodents", J. Exp. Zool., 266(6): 603-628, 1993. Abstract.

Adams et al. "Initial Assesment of Human Gene Diversity and Expression Patterns Based Upon 83 Million Nucleotides of cDNA Sequence", Nature, 377(6547): 3-174, 1995. GenBank Entry AA304653, 1997.

Agrawal "Antisense Oligonucleotides: Towards Clinical Trials", TIBTech, Trends in Biotechnology, 14: 376-387, 1996.

Albus et al. "*Staphylococcus aureus* Capsular Types and Antibody Response to Lung Infection in Patients With Cystic Fibrosis", J. Clin. Microbiol., 26(12): 2505-2509, 1988. Abstract.

Alexander et al. "Complete Sequence of the Bovine ?-Lactoglobulin cDNA", Nucleic Acids Research, 17(16): 6739-6744, 1989.

Allen "Opportunities for the Use Aerosolized ?1—Antitrypsin for the Treatment of Cystic Fibrosis", Chest, 110: 256S-260S, 1996.

Allison et al. "Polysaccharide Production in *Pseudomonas cepacia*", J. Basic. Microbiol., 34(1): 3-10, 1994. Abstract.

Alvarez-Dominguez et al. "Host Cell Heparian Sulfate Proteoglycans Mediate Attachment and Entry of Listeria Monocytogenes, and the Listerial Surface Protein ActA Is Involved in Heparan Sulfate Receptor Recognition", Infection & Immun., 65(1): 78-88, 1997. Abstract.

Anatolii "Hyaluronic Capsule as One of the Factors of *Hemolytic streptococcus* Pathogenicity", Chem. Abstracts 86(17): 339, 1977. Abstr.118714 in Zh. Mikrobiol. Epidemiol. Immunobiol., 2: 22-27, 1977.

Aoki et al. "In Vivo Transfer Efficiency of Antisense Oligonucleotides Into the Myocardium Using HVJ-Liposome Method", Biochemical and Biophysical Research Communications, 231: 540-545, 1997.

Aplin "Adhesion Molecules in Implantation", Reviews of Reproduction, 2(2): 84-93, 1997.

Armstrong et al. "Lower Airway Inflammation in Infants and Young Children With Cystic Fibrosis", Am. J. Respir. Crit. Care Med., 156(4 Pt.1): 1197-1204, 1997. Abstract.

Asagoe et al. "Effect of Heparin on Infection of Cells by Equine Arteritis Virus", J. Vet. Med. Sci., 59(8): 727-728, 1997. Abstract.

Aspenberg et al. "Dose-Dependent Stimulation of Bone Induction by Basic Fibroblast Growth Factor in Rats", Acta Orthop. Scand., 62(5): 481-484, 1991. Abstract.

Aspenberg et al. "Fibroblast Growth Factor Stimulates Bone Formation. Bone Induction Studied in Rats", Acta Orthop. Scand., 60(4): 473-476, 1989. Abstract.

Aviezer et al. "Differential Structural Requirements of Heparin and Heparan Sulfate Proteoglycans That Promote Binding of Basic Fibroblast Growth to Its Receptor", J. Biol. Chem., 269(1): 114-121, 1994.

Azghani et al. "A Beta-Linked Mannan Inhibits Adherence of *Pseudomonas aeruginosa* to Human Lung Epithelial Cells", Glycobiology, 5(1): 39-44, 1995. Abstract.

Barghouthi et al. "Nonopsonic Phagocytosis of *Pseudomonas aeruginosa* Requires Facilitated Transport of D-Glucose by Macrophages", J. Immunol., 154(7): 3420-3428, 1995. Abstract.

Bartlett et al. "Comparative Analysis of the Ability of Leucocytes, Endothelial Cells, and Platelets to Degrade the Subendothelial Basement Membrane: Evidence for Cytokine Dependence and Detection of A Novel Sulfatase", Immunology and Cell Biol., 73: 113-124, 1995.

Basu et al. "Analysis of Glycospingolipids by Fluorophore-Assisted Carbohydrate Electrophoresis Using Ceramide Glycanase From Mercenaria Mercenaria", Analytical Biochemistry, 222: 270-274, 1994.

Bean et al. "Fertilization In Vitro Increases Non-Disjunction During Early Cleavage Divisions in A Mouse Model System", Human Reproduction, 17(9): 2362-2367, 2002. Abstract.

Benathan et al. "Living Epidermal and Dermal Substitutes for Treatment of Severely Burned Patients", Rev. Med. Suisse Romande, 118(2): 149-153, 1998. Abstract-Art. in French.

Bendayan "Possibilities of False Immunocytochemical Results Generated by the Use of Monoclonal Antibodies: The Example of the Anti-Proinsulin Antibody", J. Histochem. Cytochem. 43: 881-886, 1995.

Bendig et al. "Humanization of Rodent Monoclonal Antibodies by CDR Grafting", Methods in Enzymology, 8: 83-93, 1995.

Benezra et al. "Antiproliferative Activity to Vascular Smooth Muscle Cells and Receptor Binding of Heparain-Mimicking Polyaromatic Anionic Compounds", Arteriosclerosis and Thrombosis, 14(12): 1992-1999, 1993.

Benezra et al. "Reversal of Fibroblast Growth Factor-Mediated Autocrine Cell Transformation by Aromatic Anionic Compounds", Cancer Research, 52: 5656-5662, 1992.

Benezra et al. "Thrombin Enhances the Degradation of Heparan Sulfate in the Extracellular Matrix by Tumor Cell Heparanase", Exptl. Cell. Res., 201: 208-215, 1992.

Benjamin et al. "A Plasticity Window for Blood Vessel Remodelling Is Defined by Pericyte Coverage of the Preformed Endothelial Network and Is Regulated by PDGF-B and VEGF", Development, 125: 1591-1598, 1998.

Bennett et al. "Effect of Uridine 5'-Triphosphate Plus Amiloride on Mucociliary Clearance in Adult Cystic Fibrosis", Am. J. Respir. Crit. Care Med., 153(6 Pt.1): 1796-1801, 1996. Abstract.

Berkow "The Merck Manual", Merck Research Laboratories, p. 201, 204, 1308, 177-179, 1016-1017, 194-197, 885, 601, 1997.

Beuth et al. "Lectin-Mediated Bacterial Adhesion to Human Tissue", Eur. J. Clin. Microbiol., 6(5): 591-593, 1987. Abstract.

Bhaskar et al. "Dysregulation of Proteoglycan Production by Intraheptic Biliary Epithelial Cells Bearing Defective (Delta-f508) Cystic Fibrosis Transmembrane Conductance Regulator", Hepatology, 27(1): 7-14, 1998. Abstract.

Bischof et al. "The Regulation of Endometrial and Trophoblastic Metalloproteinases During Blastocyst Implantation", Contracept Fertil Sex, 22(1): 48-51, 1994. Abstract.

Blanquaert et al. "CMDBS, Functional Analogs of Sulfate Heparanes, Used as Osseous Cicatrizing Agents", Ann. Endocrinol., 55(2): 121-123, 1994. Abstract.

Blanquaert et al. "Heparan-Like Molecules Induce the Repair of Skull Defects", Bone, 17(6): 499-506, 1995. Abstract.

Boat et al. "Biochemistry of Airway Mucus Secretions", Fed. Proc., 39(13): 3067-3074, 1980. Abstract.

Boat et al. "Epithelial Cell Dysfunction in Cystic Fibrosis: Implications for Airways Disease", Acta Paediatr. Scand. Suppl., 363: 25-29, 1989.

Bork "Go Hunting in Sequence Databases But Watch Out for the Traps", Trends in Genetics, 12(10): 425-427, 1996.

Bork "Powers and Pitfalls in Sequence Analysis: The 70% Hurdle", Genome Research, 10 : 398-400, 2000.

Bost et al. "Antibodies Against A Peptide Sequence Within the HIV Envelope Protein Crossreacts With Human Interleukin-2", Immunol. Invest., 17: 577-586, 1988.

Boucher et al. "Mucoid *Pseudomonas aeruginosa* in Cystic Fibrosis: Characterization of Muc Mutations in Clinical Isolates and Analysis of Clearance in A Mouse Model of Respiratory Infection", Infect. Immun., 65(9): 3838-3846, 1997. Abstract.

Boucher et al. "Two Distinct Loci Affecting Conversion to Mucoidy *Pseudomonas aeruginosa* in Cystic Fibrosis Encode Homologs of the Serine Protease HtrA", J. Bacteriol., 178(2): 511-523, 1996. Abstract.

Bowie et al. "Deciphering the Message in Protein Sequences: Tolerance to Amino Acid Substitutions", Science, 247: 1306-1310, 1990.

Brenner "Errors in Genome Annotation", Trends in Genetics, 15(4): 132-133, 1999.

Brinster et al. "Restoration of Fertility by Germ Cell Transplantation Requires Effective Recipient Preparation", Biology of Reproduction 69: 412-420, 2003. Abstract.

Burch et al. "Oligodeoxynucleotides Antisense to the Interleukin 1 Receptor mRN Block the Effects of Interleukin I in Cultured Murine and Human Fibroblasts and in Mice", Journal of Clinical Investigation, 88: 1190, 1991. Abstract.

Burrows et al. "Trophoblast Migration During Human Placental Implantation", Hum. Reprod. Update, 2(4): 307-321, 1996.

Cai et al. "Comparison of Sputum Processing Techniques in Cystic Fibrosis", Pediatr. Pulmonol., 22(6): 402-407, 1996. Abstract.

Calabretta et al. "Normal and Leukemic Hematopoietic Cell Manifest Differential Sensitivity to Inhibitory Effects of C-myc Antisense Oligodeoxynucleotides: An In Vitro Study Relevent to Bone Marrow Purging", Proc. Natl. Acad. Sci. USA, 88: 2351-2355, 1991.

Campbell et al. "Comparison of the Whey Acidic Protein Genes of the Rat and Mouse", Nucleic Acids Res., 12(22): 8685-8697, 1984.

Carlone et al. "Embryonic Modulation of Basic Fibroblast Growth Factor in the Rat Uterus", Biology of Reproduction, 49(4): 653-665, 1993.

Carpentier et al. "DNA Vaccination With HuD Inhibits Growth of A Neuroblastoma in Mice", Clinical Cancer Research, 4: 2819-2824. 1998.

Carson et al. Mucin and Proteoglucan Functions in Embryo Implantation, BioEssays, 20(7): 577-583, 1998. Abstract, p. 580, col. 2, § 2, p. 582, col. 1, Fig. 1.

Chang et al. "Differential Ability of Heparan Sulfate Protecoglycans to Assemble the Fibroblast Growth Factor Receptor Complex In Situ", FASEB Journal, 14: 137-144, 2000.

Chase et al. "Respiratory Mucous Secretions in Patients With Cystic Fibrosis: Relationship Between Levels of Highly Sulfate Mucin Component and Severity of the Disease", Clinica Chimica Acta, 132: 143-155, 1983.

Cheng et al. "Increased Sulfation of Glycoconjugates NY Cultured Nasal Epithelia Cells From Patients With Cystic Fibrosis", Journal of Clinical Invetment, 84(1): 68-72, 1989. Abstract.

Chleboun et al. "The Development and Enhancement of the Collateral Circulation in An Animal Model of Lower Limb Ischaemia", Aust. NZ Surg., 64(3): 202-207, 1994. Abstract.

Chow et al. "Development of An Epithelium-Specific Expression Cassette With Human DNA Regulatory Elements for Transgene Expression in Lung Airways", Proc. Natl. Acad. Sci. USA, 94: 14695-14700, 1997.

Chubet et al. "Vectors for Expression and Secretion of FLAG Epitope-Tagged Proteins in Mammalian Cells", BioTechniques, 20: 136-141, 1996.

Clark "The Mammary Gland as A Bioreactor: Expression, Processing, and Production of Recombinant Proteins", J. Mammary Gland Biol. and Neoplasia, 3(3): 337-350, 1998.

Cohen "Oligonucleotide Therapeutics", Trends in Biotechnology 10: 87-91, 1992. Abstract.

Coligan et al. "Current Protocols in Immunology", Immunology—Laboratory Manuals, 1991.

Colman "Effects of Amino Acid Sequence Changes on Antibody-Antigen Interactions", Research in Immunology, 145(1): 33-36. 1994.

Coombe et al. "Analysis of the Inhibition of Tumor Metastasis by Sulphated Polysaccharides", Int. J. Cancer, 39: 82-88, 1987. Abstract.

Crystal "Gene Therapy Strategies for Pulmonary Disease", American Journal of Medicine, 92 (Suppl.64): 6A-44S-6A-52S, 1992.

Dasgupta et al. "Reproduction in Viscoelasticity in Cystic Fibrosis Sputum In Vitro Using Combined Treatment With Nacystelyn and RhDNase", Pediatric Pulmonology, 22: 161-166, 1996.

Davies et al. "The Involvement of Cell-to-Cell Signals in the Development of A Bacterial Biofilm", Science, 280: 295-298, 1998.

De Vouge et al. "Immunoselection of GRP94/Endoplasmin From A KNRK Cell-Specific λgt11 Library Using Antibodies Directed Against A Putative Heparanase Amino-Terminal Peptide", Int. J. Cancer, 56: 286-294, 1994.

Dempsey et al. "Heparanase Expression in Invasive Trophoblasts and Acute Vascular Damage", Glycobiology, 10(5): 467-475, 2000. Abstract, p. 470, col. 1—p. 471, col. 1, p. 472, col. 1, § 4-col. 2, § 2.

Dempsey et al. "Heparanase, A Potential Regulator of CellMatrix Interactions", TIBS, 25(8): 349-351, 2000. p. 350, col. 1, § 1, col. 3, § 1, Claims 1-24.

Dibrino "RT-PCR Method & Applications", Clonotech Laboratories, 1st Ed., 1: 11, 15, 23, 41, 26, 1991.

Doerks et al. "Protein Annotation: Detective Work for Function Prediction", Trends in Genetics, 14(6): 248-250, 1998.

Doetschman "Interpretation of Phenotype in Genetically Engineered Mice", Laboratory Animal Science, 49(2): 137-143, 1999.

Drigues et al. "Comparative Studies of Lipopolysaccharide and Exopolysaccharide From A Virulent Strain of *Pseudomonas solanacearum* and From Three Avirulent Mutants", Journal of Bacteriology, 162(2): 504-509, 1985. Abstract.

Ducy et al. "The Osteoblast: A Sophisticated Fibroblast Under Central Surveillance", Science, 289: 1501-1504, 2000.

Duff "Transgenic Mice Overexpressing Presenilin cDNAs: Phenotype and Utility in the Modeling of Alzheimer's Disease", Central Nervous System Diseases, p. 123-128, 2000. Abstract.

Duffy et al. "Maximizing Flap Survival in A Prefabrication Model Using Exogenous and Endogenous bFGF: A New Approach", Microsurgery, 17(4): 176-179, 1996. Abstract.

Durand et al. "Active-Site Motifs of Lysosomal Acid Hydrolases: Invariant Features of Clan GH-A Glycosyl Hydrolases Deduced From Hydrophobic Cluster Analysis", Glycobiology, 7(2): 277-284, 1997.

Edwards et al. "Some Properties and Applications of Monoclonal Antibodies", Biochem. Journal, 200: 1-10, 1981.

Ehle et al. "Immunoaffinity Chromatography of Enzymes", Bioseparation, 1(2): 97-110, 1990.

Ejima et al. "Induction of Apoptosis in Placentas of Pregnant Mice Exposed to Lipopolysaccharides: Possible Involvement of Fas/Fas Ligand System", Biology of Reproduction, 62: 178-185, 2000. Abstract.

Elkin et al. "Heparanase as Mediator of Angiogenesis: Mode of Action", The FASEB Journal, 15: 1661-1663, 2001.

Elkin et al. "Heparanase as Mediator of Angiogenesis: Mode of Action", The FASEB Journal, Published Online, 10 P. 2001.

Ennis et al. "Rapid Cloning of HLA-A,B cDNA by Using the Polymerase Chain Reaction: Frequency and Nature of Errors Produced in Amplification", PNAS USA, 87: 2833-2837, 1990.

Esko et al. "Tumor Formation Dependent on Proeoglycans Biosynthesis", Science, 241(4869): 1092-1096, 1988. Abstract.

Evans et al. "Human Chromosome 11 187a8 Cosmid, Complete Sequence", Database EMBL, Accession No. U73640, XP002198427, 1996. Abstract.

Faber-Elman et al. "Involvement of Wound-Associated Factors in Rat Brain Astrocyte Migratory Response to Axonal Injury: In Vitro Simulation", J. Clin. Invest., 97(1): 162-171, 1996.

Fairbanks et al. "Processing of the Human Heparanase Precursor and Evidence that the Active Enzyme Is A Heterodimer", The Journal of Biological Chemistry, 274(42): 29587-29590, 1999.

Farndale et al. "A Direct Spectrophotometric Microassay for Sulfated Glycosaminoglycans in Cartilage Cultures", Connective Tissue Research, 9: 247-248, 1982.

Ferber et al. "Pancreatic and Duodenal Homeobox Gene 1 Induces Expression of Insulin Genes in Liver and Ameliorates Streptozotocin-Induced Hyperglycemia", Nature Medicine, 6(5): 568-572, 2000.

Finkel "Potential Target Found for Anitimetastasis Drugs", Science, 285: 33-34, 1999.

Flanagan et al. "Potent and Selective Gene Inhibition Using Antisense Oligodeoxynucleotides", Molecular and Cellular Biochemistry, 172: 213-225, 1997.

Frederiksen et al. "Antibiotic Treatment of Initial Colonization with *Pseudomonas aeruginosa* Postpones Chronic Infection and Prevents Deterioraton of Pulmonary Function in Cystic Fibrosis", Pediatr. Pulmonol. 23(5): 330-335, 1997. Abstract.

Frederiksen et al. Changing Epidemiology of *Pseudomonas aeruginosa* Infection in Danish Cystic Fibrosis Patients (1974.

Freeman et al. "A Rapid Quantitative Assay for the Detection of Mammalian Heparanse Activity", Biochemical Journal, 325: 229, 1997.

Freeman et al. "Evidence That Platelet and Tumour Heparanases Are Similar Enzymes", Biochem J., 342: 361, 1999.

Freeman et al. "Human Platelet Heparanase: Purification, Characterization and Catalytic Activity", Biochem. J., 330: 1341, 1998.

Friedman et al. Regulated Expression of Homeobox Genes Msx, Dev. Biol, vol. 177, pp. 347-355, 1996.

Gabriel et al. "In Vitro Adherence of *Pseudomonas aeruginosa* to Four Intraocular Lenses", J. Cataract Refract Surg., 24: 124, 1998.

Gantt et al. Cell Adhesion to A Motif Shared by the Malaria Circumsporozoite Protein and Thrombospondin Is Mediated by Its Glycosminoglycan, Bio. Mol Biol., vol. 27,pp. 19205-19213, 1997.

Garner "Epidermal Regulation of Dermal Fibroblast Activity", Plast. Reconstr. Surg., 102(1):135, 1998.

Gewirtz et al. "Facilitating Oligonucleotide Delivery: Helping Antisense Deliver on Its Promise", Proc. Natl. Acad. Sci. USA, 93: 3161, 1996.

Gewirtz et al. "Nucleic Acid Therapeutics: State of the Art and Future Prospects", Blood, 92(3): 712, 1998.

Ghani et al. "Ceftazidime, Gentamicin, and Rifampicin, in Combination, Kill Biofilms of Mucoid *Pseudomonas aeruginosa*", Can. J. Microbiol., 43(11): 999, 1997.

Giuffre et al. "Monocyte Adhesion to Activated Aortic Endothelium: Role of L-Selectin and Heparan Sulfate Proteoglycans", J. Cell Biol., 136(4): 945-956, 1997. Abstract.

Godder et al. "Heparanase Activity in Cultured Endothelial Cells", Journal of Cellular Physiology, 148: 274-280, 1991.

Goldberg et al. "An Improved Method for Determining Proteoglycans Synthesized by Chondrocytes in Culture", Live Tissue Research, 24: 265-275, 1990.

Goldshmidt et al. "Cell Surface Expression and Secretion of Heparanase Markedly Promote Tumor Angiogenesis and Metastasis", Proc. Natl. Acad. Sci. USA, 99(15): 10031-10036, 2002.

Gordon-Cardo et al. "Expression of Basic Fibroplast Growth Factor in Normal Human Tissues", Laboratory Investigation, 63: 832-840, 1990. Abstract.

Gorodetsky et al. "Isolation and Characterization of the Bos Taurus β-Casein Gene", Gene, 66: 87-96, 1988. Abstract.

Gottschalk et al. "Somatic Gene Therapy. Present Situation and Future Perspective", Arzneimittelforschung, 48(11): 1111-1120, 1998. Abstract.

Graham et al. "Comparison of the Heparanase Enzymes From Mouse Melanoma Cells, Mouse Microphages, and Human Platelets", Biochemistry and Molecular Biology International, 39(3): 563-571, 1996. Abstract.

Green et al. "Antisense Oligonucleotides: An Evolving Technology for the Modulation of Gene Expression in Human Disease", Journal of American Cell Surgery, 191(1): 93-105, 2000.

Guriec et al. "CD44 Isoforms With Exon V6 and Mestastasis of Primary N0M0 Breast carcinomas", Breast Cancer Res. Treat., 44(3):261-268, 1997. Abstract.

Hagiwara et al. "Inhibitory Effect of Heparin on Red Blood Cell Invasion by Theileria Sergenti Merozoites", Int. J. Parasitol., 27(5): 535-539, 1997. Abstract.

Haimov-Kochman et al. "Localization of Hepranase in Normal and Pathological Human Placenta", Molecular Human Reproduction, 8(6): 566-573, 2002.

Haisma et al. "Construction and Characterization of A Fusion Protein of Single-Chain Anti-Carcinoma Antibody 323/A3 and Human Beta-Glucuronidase" Can.Immu.(45), 1997, p. 266 abs.

Hammer et al. "Spontaneous Inflammatory Disease in Transgenic Rats Expressing HLA-B27 and Human ?2m: An Animal Model of HLA-B27-Associated Human Disorders" Cell,(63) pp. 1099-1112, 1990.

Harlow et al. "Antibodies—A Laboratory Manual", Cold Spring Harbor Press, p. 471-510, 1988.

Harvey et al. "Expression of Exogenous Protein in the Egg White of Transgenic Chickens" Nat. Biotec.2002(4)p. 396 abs.

Hatano et al. "Biologic Activities of Antobodies to the Neutral-Polysaccharide Component of the *Pseudomonas aeruginosa* Lipopolysaccharide Are Blocked by O Side Chains and Mucoid Exopolysaccharide (Alginate)", 1996.

Hatch et al. "Alginate Lyase Promotes Diffusion of Aminoglycosides Through the Extracellular Polysaccharide of Muoid *Pseudomonas aeruginosa*" Anti.Micro.ag.chemo.(42)p. 974-977, 1998.

Hayward et al. "Cellular Mechanisms of Heparinase III Protection in Rat Traumatic Shock", 1996.

Hayward et al. "Heparinase III Exerts Endothelial and Cardioprotective Effects in Feline Myocardial Ischemia-Reperfusion Injury", 1996.

Herrera et al. "Mediation of Trypanosoma Cruzi Invasion by Heparan Sulfate Receptors on Host Cells and Penetrin Counter-Receptors on the Trypanosomes", 1996.

Hida et al. "Antisense E1AF Transfection Restrains Oral Cancer Invasion by Reducing Matrix Metalloproteinase Activities", 1996.

Hill et al. "Organ-Specific Over-Sulfation of Glycosaminoglycans and Altered Extracellular Matrix in A Mouse Model of Cystic Fibrosis", 1996.

Hillier et al. "The WashU-Merck EST Project" GenBank Entry N32056, 1996.

Hillier et al. "The WashU-Merck EST Project", No. N30824, Database GenBank on STN, US National Library of Medicine (Bethesda MD), 1996.

Hillier et al. "The WashU-Merck EST Project", No. N30845, Database GenBank on STN, US National Library of Medicine (Bethesda MD), 1996.

Hoogewerf et al. "CXC Chemokines Connective Tissue Activating Peptide-III and Neutrophil Activating Peptide-2 Are Heparin/Heparan Sulfate-Degrading Enzymes", Journal of Biological Chemistry, 270(7): 3268-3277, 1995.p. 3269.

Hormuzdi et al. "A Gene-Targeting Approach Identifies A Function for the First Intron in Expression of the ?1 (I) Collagen Gene.", Mol Cell Biol., 18(6): 3368-3375, 1998. Abstract.

Hsuch et al. "Invasive *Streptococci pneumoniae* Infection Associated With Rapidly Fatal Outcome in Taiwan", J. Formos Med. Assoc., 95(5): 364-371, 1996. Abstract.

Hudson "Recombinant Antibody Fragment", Curr. Opin. Biotech., 4:395-402, 1998.

Hulett et al. "Cloning of Mammalian Heparanase, An Important Enzyme in Tumor Invasion and Metastasis", Nature Medicine, 5(7): 803-809, 1999.

Imai et al. "Osteoblast Recruitment and Bone Formation Enhanced by Cell Matrix-Associated Heparin-Binding Growth-Associated Molecule (HB-GAM)", J. Cell. Biol. 143(4): 1113-1128, 1998. [Abstract].

Inui et al. "Local Application of Basic Fibroblast Growth Factor Minipellet Induces the Healing of Segmental Bony Defects in Rabbits", Calcified Tissue International, 63(6): 490-495, 1998. Abstract.

Irimura et al. "Chemically Modified Heparins as Inhibitors of Heparan Sulfate Specific Endo-?-Glucuronidase (Heparanase) of Metastatic Melanoma Cells", Biochemistry, 25: 5322-5328, 1986. Abstract.

Jackson "The Use of Polyacrylamide-Gel Electrophoresis for the High-Resolution of Separation of Reducing Saccharides Labelled With the Fluorophore 8-Aminonaphtalene-1, 3, 6-Trisulphonic Acid", Biochem J., 270: 705-713, 1990.

Jayaraman et al. "Rational Selection and Quantitative Evaluation of Antisense Oligonucleotides", Biochimica et Biophysica Acta, 1520: 105-114, 2001.

Jin et al. "Immunochemical Localization of Heparanase in Mouse and Human Melanomas", International Journal of Cancer, 45: 1088-1095, 1990.

Jin et al. "Molecular Cloning and Expression of Human Heparanase cDNA", Proceedings American Association for Cancer Research Annual Meeting, 1992, 33: 57, 1992. Abstract.

Johansen et al. "Vaccination Promotes TH1-Like Inflammation and Survival in Chronic *Pseudomonas aeruginosa* Pneumonia: A New Prophylactic Principle" Behrng. Inst. Mitt,1997,(98)p. 269.ab.

Jorba et al. "Variations in the *P. aeruginosa* Polysaccharide Synthesis Conditioned by Aminosugars" Rev.Esp.Fisiol(36)p. 155,1080,abs.

Jusa et al. "Effect of Heparinon on Infection of Cells by Porcine Reproductive and Respiratory Syndrome Virus" Am.J.Vet.Res. ,(58)p. 488, 1997,abs.

Kang et al. "Prolactin-Inducible Enhancer Activity of the First Intron of the Bovine beta-Casein Gene" Mol.Cells.(3)pp. 259, 1998,abs.

Kato et al. "Physiological Degradation Converts the Soluble Syndecan-1 Ectodomain From An Inhibitor to A Potent Activator of FGF-2" Nat.Med(4)p. 691-698, 1991.

Kawaja et al. "Employment of Fibroblasts for Gene Transfer: Applications for Grafting Into the Central Nervous System" Gen Engin. (13)p. 205, 1991,abs.

Kawase et al. "Effect of Partial Incision of the Zona Pellucida by Piezo-Micromanipulator for In Vitro Fertilization Using Frozen-Thawed Mouse Spermatozoa on the Developmental Rate of Embryos Transferred at the 2-Cell Stage" Bio.Rep.(2)p. 381,2002,abs.

Kiberstis et al. "Bone Health in the Balance" Science,(289)p. 1497,2000,abs.

Kizaki et al. "Cloning and Localization of Heparanase in Bovine Placenta" Placenta,(24)pp. 424-430,2003.

Kizaki et al. "Expression of Heparanase mRNA in Bovine Placenta During Gestation", Reproduction, 121: 573-580, 2001.

Köhler et al. "Continuous Cultures of Fused Cells Secreting Antibody of Predefined Specificity", Nature, 256: 495-497, 1975.

Konstan et al. "Current Understanding of the Inflammatory Process in Cystic Fibrosis", Pediatric Pulmonology, 24: 137-142, 1997.

Konstan et al. "Patterns of Medical Practice in Cystic Fibrosis: Part II. Use of Therapies", Pediatr. Pulmonol,. 28(4): 248-54, 1999. Abstract.

Korb et al. "Stimulation of Gene Expression by Introns: Conversion of An Inhibitory Intron to A Stimulatory Intron by Alteration of the Splice Donor Sequence", Nucleic Acids Research, 21(25): 5901-5908, 1993.

Kosir et al. "Early Human Breast Carcinoma Cells Produce Extra Cellular Heparanase", Molecular Biology/Biochemistry, Proceedings of the American Association for Cancer Research, 37: 495, 1996.

Kosir et al. "Human Prostate Carcinoma Cells Produce Extracellular Heparanase", Journal of Surgical Reserach, 67: 98-105, 1997.

Krivit et al. "Microglia: The Effector Cell for Reconstitution of the Central Nervous System Following Bone Marrow Transplantation for Lysosomal and Peroxisomal Storage Diseases", Cell Transplant, 4(4): 385-392, 1995. Abstract.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Krusat et al. "Heparin-Dependent Attachment of Respiratory Syncytial Virus (RSV) to Host Cells", Arch. Virol., 142(6): 1247-1254, 1997. Abstract.

Kurachi et al. "Role of Intron I in Expression of the Human Factor IX Gene", Journal of Biological Chemistry, 270(10): 5276-5281, 1995.

Kussie et al. "Cloning and Functional Expression of A Human Heparanase Gene", Biochemical and Biophysical Research Communication, 26(1): 183-187, 1999. Suppl. IDS in 23665; Suppl. IDS in 22716; Suppl. IDS in 25783.

Kuyvenhoven et al. "Assessment of Serum Matrix Metalloproteinases MMP-2 and MMP-9 After Human Liver Transplantation: Increased Serum MMP-9 Level in Acute Rejection", Transplantation, 77(11): 1646-1652, 2004. Abstract.

Lai et al. "DNA Vaccines", Critical Reviews in Immunology, 18: 449-484, 1998.

Lai et al. "Homologus Recombination Based Gene Therapy", Exp. Nephrol, 7(1):11-14, 1999. Abstract.

Lampard et al. "Secretion of Foreign Proteins Mediated by Chicken Lysozyme Gene Regulatory Sequences", Biochem. Cell Biol., 80(6): 777-788, 2002. Abstract.

Laskov et al. "Production of Heparanase by Normal and Neoplastic Murine—B-Lymphocytes", International Journal of Cancer, 47(1): 92-98, 1991.

Lazarus et al. "Ex Vivo Expansion and Subsequent Infusion of Human Bone Marrow-Derived Stromal Progenitor Cells (Mesenchymal Progenitor Cells): Implications for Therapeutic Use", Bone Marrow Transplantation, 16(4): 557-564, 1995. Abstract.

Le Fur et al. "Selective Increase in Specific Alternative Splice Variants of Tyrosinase in Murine Melanomas: A Projected Basis for Immunotherapy", Proc. Natl. Acad. Sci. USA, 94: 5332-5337, 1997.

Lederman et al. "A Single Amino Acid Substitution in A Common African Allele of the CD4 Molecule Ablates Binding of the Monoclonal Antibody, OKT4", Molecular Immunology, 28: 1171-1181, 1991.

Leong et al. "Different Classes of Proteoglycans Contribute to the Attachment of Borrelia Burgdorferi to Cultured Endiothelial and Brain Cells", Infect. Immun., 66(3): 994-999, 1998. Abstract.

Lessey et al. "Paracrine Signaling in the Endometrium: Integrins and the Establishement of Uterine Receptivity", J. Reprod. Immunol., 39(1-2): 105-116, 1998. Abstract.

Li et al. "Immunochemical Localization of Heparanase in Mouse and Human Melanomas", Int. J. Cancer, 45: 1088-1095, 1990.

Li et al. "In Vivo Fragmentation of Heparan Sulfate by Heparanase Overexpression Renders Mice Resistant to Amyloid Protein A Amyloidosis", PNAS, 102(18): 6473-6477, 2005.

Li et al. "β-Endorphin Omission Analogs: Dissociation of Immunoreactivity From Other Biological Activities", PNAS, 77: 3211-3214, 1980.

Lider et al. "Inhibition of T Lymphocyte Heparanase by Heparin Prevents T Cell Migration and T Cell-Mediated Immunity", European Journal of Immunology, 20(3): 493-499, 1990. Abstract.

Linhardt et al. "Polysaccharide Lyases", Applied Biochemistry and Biotechnology, 12: 135-176, 1986.

Liu et al. "Live Offspring by In Vitro Fertilization of Oocytes From Cryopreserved Primordial Mouse Follicles After Sequential In Vivo Transplantation and In Vitro Maturation", Biology of Reproduction, 64: 171, 2001.

Loredo et al. Regulation of Glycosaminoglycan Metabolism by Bone Morphogenetic Protein, Am.J.Vet.Res.(57), 1996,p. 554,abs.

Luft "Making Sense Out of Antisense Oligodeoxynucleotide Delivery: Getting There Is Half the Fun". J. Mol. Med, p. 75, 1998.

Macone et al. "Mucoid *Escherichia coli* in Cystic Fibrosis", The New England Journal of Medicine, 304(24): 1445, 1998.

Maillard et al. "Pre-Treatment With Elastase Improves the Efficiency of Percutaneous Adenovirus-Mediated Gene Transfer to the Arterial Media", Gene Therapy, 5: 1023-1030, 1998.

Marchetti et al. "Neurotrophin Stimulation of Human Melanoma Cell Invasion: Selected Enhancement of Heparanase Activity and Heparanase Degradation of Specific Heparan Sulfate Subpopulations", Cancer Research, 56: 2856, 1998.

Marra et al. "The WashU-HHMI Mouse EST Project", Database EMBL, Accession No. A1122034, XP 002198426, 1998. Abstract.

Marra et al. "The WashU-HHMI Mouse Est Project", Database EMBL, Accession No. AA047943, XP002198424, 1996.

Marty et al. "Influence of Nutrient Media on the Chemical Composition of the Expolysaccharide From Mucoid and Non-Mucoid *Pseudomonas aeruginosa*", FEMS Microbiol. Letters, 77(1-3): 35-44, 1992. Abstract.

Massague "The TGF-Beta Family of Growth and differentiation Factors", Cell, 49: 437-438, 1987.

Mateo et al. "Humanization of A Mouse Monoclonal Antibody That Blocks the Epidermal Growth Factor Receptor: Recovery Antagonistic Activity", Immunotechnology, 3: 71-81, 1997. Abstract.

Matoba et al. "Evaluation of Omental Implantation for Perforated Gastric Ulcer Therapy: Findings in A Rat Model", J. Gastroenterol., 31(6): 777-784, 1996. Abstract.

Matzner et al. "Degradation of Heparan Sulfate in the Subendothelial Extracellular Matrix by A Readily Released Heparanase From Human Neutrophils", Journal of Clinical Investigation, 76(4): 1306-1313, 1985.

McKenzie et al. "Biochemical Characterization of the Active Heterodimer Form of Human Heparanase (Hpa1) Protein Expressed in Insect Cells", Biochemical Journal, 373: 423-435, 2003.

Meluleni et al. "Mucoid Pseudomonas Aeruginosa Growing in A Biofilm In Vitro Are Killed by Opsonic Antibodies to the Mucoid Exopolysaccharide Capsule But Not by Antibodies Produced During Chtonic Lung Infection in Cystic Fibrosis Patients", J. Immun., 155(4): 2029-2038, 1995. Abstract.

Menezo et al. "Mouse and Bovine Models for Human IVF", Reproductive BioMedicine Online 2002, 4(2): 170-175, 2002. Abstract.

Mengistu et al. "Continuous Culture Studies on the Synthesis of Capsular Polysaccharide by Klebsiella Pneumoniae K1", J. Appl. Bacteriol., 76(5): 424-430, 1994. Abstract.

Miao et al. "Cloning, Expression and Purification of Mouse Heparanase", Protein Expression and Purification, 26: 425-431, 2002.

Miller et al. "Xenograft Model of Progressive Human Proliferative Breast Disease", J. Nat. Cancer Inst., 85: 1725-1732, 1993. Abstract.

Mirault et al. "Transgenic Glutathione Peroxidase Mouse Models for Neuroprotection Studies", Ann. NY Acad. Sci., 738: 104-115, 1994. Abstract.

Miao et al. "Modulation of Fibroblast Growth Factor-2 Receptor Binding Dimerization, Signaling, and Angiogenic Activity by A Synthetic Heparain-Mimicking Polyaromatic Compound", J. Clin. Invest., 99(7): 1565-1575, 1997.

Miyake et al. "Highly Specific and Sensitive Detection of Malignancy in Urine Samples From Patients With Urothelial Cancer by CD44v8-10/CD44v10 Competitive RT-PCR", Int. J. Cancer, 79(6): 560-564, 1998. Abstract.

Mohapatra et al. "Alteration of Sulfation of Glycoconjugates, But Not Sulfate Transport and Intracellular Inorganic Sulfate Content in Cystic Fibrosis Airway Epithelial Cells", Pediatr. Res., 38(1): 42-48, 1995. Abstract.

Mollinedo et al. "Major Co-Localization of the Extracellular-Matrix Degradative Enzymes Heparanase and Gelatinase in Tertiary Granules of Human Neutrophils", Biochemical Journal, 327: 917-923, 1997.

Morel et al. "Human Neutrophil Gelitanase Is A Collagenase Type IV", Biochem. & Biophys. Res. Comm., 191: 269-274, 1993.

Morrison et al. "Sequences in Antibody Molecules Important for Receptor-Mediated Transport Into the Chicken Egg Yolk", Mol. Immunol., 38(8): 619-625, 2002.

Moser et al. "Chronic *Pseudomonas aeruginosa* Lung Infection Is More Severe in Th2 Responding BALB/c Mice Compared to Th1 Responding C3H/HeN Mice", APMIS, 105(11): 838-842, 1997. Abstract.

Moses et al. "Relative Contributions of Hyaluronic Capsule and M Protein to Virulence in A Mucoid Strain of the Group A *Streptococcus*", Infect. Immun., 65(1): 64-71, 1997.

Muir et al. "Histomorphometric Analysis of the Effects of Standard Heparin on Trabecular Bone In Vivo", Blood, 88(4): 1314-1320, 1996. Abstract.

Mullins et al. "Expression of the DBA/2J Ren-2 Gene in the Adrenal Gland of Transgenic Mice", The EMBO Journal, 8(13): 4065-4072, 1989.

Mullins et al. "Fulminant Hypertension in Transgenic Rats Harbouring the Mouse Ren-2 Gene", Nature, 344: 541-544, 1990.

Murphy et al. "The Latent Collagenase and Gelatin of Human Polymorphonuclear Neutrophil Leucicytes", Biochem. J., 192: 517-525, 1980.

Murray et al. "The Extracellular Matrix", Harper's Biochemistry, McGraw-Hill Professional, 24th Ed., Chap.57, p. 667-685, 1998.

Nadav et al. "Activation, Processing and Trafficking of Extracellular Heparanase by Primary Human Fibroblasts", Journal of Cell Science, 115(10): 2179-2187, 2002.

Nadir et al. "Co- Interaction and Increased Release of Tissue Factor Pathway Inhibitor by Heparanse", Blood, 106(11/Part 2): 90B, 2005. Abstract# 4038, 1996.

Nakajima "Heparanase and Tumor Metastasis", Tanpakushitsu Kakusan Koso, 37(11): 1753-1758, 1992. Abstract.

Nakajima et al. "A Solid-Phase Substrate of Heparanase: Its Application to Assay of Human Melanoma for Heparan Sulfate Degradative Activity", Analytical Biochemistry, 157: 162-171, 1986.

Nakajima et al. "Heparan Sulfate Degradation: Relation to Tumor Invasion and Metastatic Properties of Mouse B16 Melanoma Sublines", Science, 220: 611-613, 1983.

Naparstek et al. "Activated T Lymphocytes Produce A Matrix-Degrading Heparan Sulphate Endoglycosidase", Nature, 310(5974): 241-244, 1984. Abstract.

Nasser et al. "Heparanase Neutralizes the Anticoagulation Properties of Heparin and Low-Molecular-Weight Heparin", Journal of Thrombosis and Haemostasis, 4: 560-565, 2006.

Newbold et al. "Exposure to Diethylstilbestrol During Pregnancy Permanently Alters the Ovary and Oviduct", Biology of Reproduction, 28: 735-744, 1983. Abstract.

Nilsson et al. "The Role of Staphylococcal Polysaccharide Microcapsule Expression in Septricemia and Septic Arthritis", Infect. Immun., 65(10): 4216-21, 1997. Abstract.

Niwa et al. "Efficient Selection for High-Expression Transfectants With A Novel Eukaryotic Vector", Gene, 108(2): 193-199, 1991. Abstract.

Novagen "PET System Manual", Novagen, 6th Ed., p. 11, 1995.

Ofek et al. "Bacterial Adhesion to Cells and Tissues", Chapman & Hall, NY, p. 114-118, 148-153, 418-423, 420-423, 1994.

Oldberg et al. "Characterization of A Platelet Endoglycosidase Degrading Heparin-Like Polysaccharides", Biochemistry, 19: 5755-5762, 1980.

Oosta et al. "Purification and Properties of Human Platelets Heparitanase", J. Biol. Chem., 257(19): 11249-11255, 1982.

Ornitz et al. "Heparin Is Required for Cell-Free Binding of Basic Fibroblast Growth Factor to A Soluble Receptor and for Mitogenesis in Whole Cells", Molecular and Cellular Biology, 12: 240-247, 1992.

Pasquier et al. "Implication of Neutral Polysaccharides Associated to Alginate in Inhibition of Murine Macrophage Response to *Pseudomonas aeruginosa*", FEMS Microbiol. Lett., 147(2): 195-202, 1997. Abstract.

Pearce et al. "Development of Glucose Intolerance in Male Transgenic Mice Overexpressing Human Glycogen Synthase Kinase-3? on A Muscle-Specific Promoter", Metabolism, 53(10): 1322-1330, 2004.

Pfaff et al. "Cryobiology of Rat Embryos I: Determination of Zygote Membrane Permeability Coefficients for Water and Cryoprotectants, Their Activation Energies, and the Development of Improved Cryopreservation Methods", Biology of Reproduction, 63: 1294-1302, 2000. Abstract.

Pier "Rationale for Development of Immunotherapies That Target Mucoid *Pseudomonas aeruginosa* Infection in Cystic Fibrosis Patients", Behring Inst. Mitt., 98: 350-360, 1997. Abstract.

Pier et al. "Cystic Fibrosis Transmembrane Conductance Regulator Is An Epithelial Cell Receptor for Clearance of *Pseudomonas aeruginosa* From the Lung", Proc. Natl. Acad. Sci. USA, 94(22): 12088-12093, 1997.

Pier et al. "How Mutant CFTR May Contribute to *Pseudomonas aeruginosa* Infection in Cystic Fibrosis", Am. J. Respir. Crit. Care Med., 154(4): S175-S182, 1996. Abstract.

Pilbeam et al. "Comparison of the Effects of Various Lengths of Synthetic Human Parathyroid Hormone-Related Peptide (hPTHrP) of Malignancy on Bone Resorption and Formation in Organ Culture", Bone, 14: 717-720, 1993.

Pina et al. "The Role of Fluoroquinolones in the Promotion of Alginate Synthesis and Antibiotic Resistance in *Pseudomonas aeruginosa*", Curr. Microbiol., 35(2): 103-108, 1997. Abstract.

Pomahac et al. "Tissue Engineering of Skin", Crit. Rev. Oral Biol. Med., 9(3): 333, 1996.

Prahalada et al. "Diethylstilbestrol-Induced Cervical and Vaginal Adenosis Using the Neonatal Mouse Model", Biology of Reproduction, 38: 935-943, 1988. Abstract.

Prockop "Marrow Stromal Cells as Stem Cells for Nonhematopoitic Tissues", Science, 276: 71, 1996.

Quax et al. Metastatic Behavior of Human Melanoma Cell Lines in Nude Mice Correlates With Urokinase, JCB,p. 191-199,(115)1991.

Rader et al. "A Phage Display Approach for Rapid Antibody Humanization: Designed Combinatorial V Gene Libraries", Proc. Natl. Acad. Sci. USA, 95: 8910, 1996.

Raghunath et al. "Cultured Epithelial Autografts: Diving From Surgery Into Matrix Biology", Pediatr. Surg. Int., 12(7): 478, 1996.

Rahmoune et al. "Chrondroitin Sulfate in Sputum From Patients With Cystic Fibrosis and Chronic Bronchitis", Am. J. Resp. Cell & Mol. Biol., 5(4): 315-320, 1991. Abstract.

Rajur et al. "Covalent Protein-Oligonucleotide Conjugates for Efficient Delivery of Antisense Molecules", Bioconjugate Chem., 8: 935-940, 1997.

Ramos et al. "Relationship Between Glycolysis and Exopolysaccharide Biosynthesis in *Lactococcus latice*", Appl. Environ. Microbiol., 67(1): 33-41, 2001. Abstract.

Ramsey et al. "Intermittent Administration of Inhaled Tobramycin in Patients With Cystic Fibrosis. Cystic Fibrosis Inhaled Tobramycin Study Group", New England Journal of Medicine, 340(1): 23-30, 1999. Abstract.

Reddi "Role of Morphogenetic Proteins in Skeletal Tissue Engineering and Regeneration", Nature Biotechnology, 16: 247-252, 1998.

Richards et al. "Construction and Preliminary Characterization of the Rat Casein and Alpha-Lactalbumin cDNA Clones", J. Biol. Chem., 256(1): 526-32, 1981.

Richardson et al. "Regulation of Basic Fibroblast Growth Factor Binding and Avtivity by Cell Density and Heparan Sufate", J. Biological Chemistry, 274(19): 13534-13540, 1990.

Ricoveri et al. "Heparan Sulfate Endoglycosidase and Metastatic Potential in Murine Fibrosarcoma and Melanoma", Cancer Research, 46(8): 3855-3861, 1986. Abstract.

Robert et al. "Chondroitin-4-Sulphate (Proeoglycan), A Receptor for Plasmodium Falciparum-Infected Erthrocyte Adherence on Brain Microvascular Endothelial Cells", Res. Immunol., 146(6): 383-393, 1995. Abstract.

Rubin "Emerging Therapies for Cystic Fibrosis Lung Disease", Chest, 115: 1120-1126, 1999.

Ruppert et al. "Human Bone Morphogenic Protein 2 Contains A Heparin-Binding Site Which Modifies Its Biological Activity", Eur. J. Biochem., 237(1): 295-302, 1996. Abstract.

Sasisekharan et al. "Cloning and Expression of Heparinase I Gene From Flavobacterium Heparinum", Proc. Natl. Acad. Sci. USA, 90: 3660-3664, 1993.

Sasisekharan et al. "Heparinase Inhibits Neovascularization", Proc. Natl. Acad.Sci. USA, 91: 1524-1528, 1994.

Savion et al. "Murine Macrophage Heparanase: Inhibition and Comparison With Metastatic Tumor Cells", Journal of Cellular Physiology, 130: 77-84, 1987.

Schoepe et al. "Neutralization of Hemolytic and Mouse Lethal Activities of C. Perfringens Alpha-Toxin Need Simultaneous Blockage of Two Epitopes by Monoclonal Antibodies", Microb. Pathogenesis, 23(1): 1-10, 1997. Abstract.

Schultz et al. "Growth Factors in Preimplantation Mammalian Embryos", Oxford Review of Reproduction in Biology, 15: 43-81, 1993. Abstract.

Schwatz et al. "CpG Motifs in Bacterial DNA Cause Inflammation in the Lower Respiratory Tract", J. Clin. Invest., 100(1): 68-73, 1997. Abstract.

Scott et al. "Visualization of An Extracellular Mucoid Layer of Treponema Denticola ATCC 35405 and Surface Sugar Lectin Analysis of Some Treponema Species", Oral Microbiol. Immunol., 12(2): 121-125, 1997. Abstract.

Selvan et al. "Heparan Sulfate in Immune Response", Ann. NY Acad. Sci., 797: 127-139, 1996.

Service "Tissue Engineers Build New Bone", Science, 289: 1498-1500, 2000.

Sewell et al. "Human Mononuclear Cells Contain An Endoglycosidase Specific for Heparan Sulfate Glycosaminoglycan Demonstrable With the Use of A Specific Solid-Phase Metabolically Radiolabelled Substrate", Biochem J., 264: 777-783, 1989.

Shakibaei et al. "Dual Interaction of the Malaria Circumsporozoite Protein With the Low Density Lipoprotein Receptor-Related Protein (LRP) and Heparan Sulfate Proteoglycans", J. Exp. Med., 184(5): 1699-1711, 1996. Abstract.

Shastry "Gene Disruption in Mice: Models of Development and Disease", Molecular and Cellular Biochemistry, 181: 163-179, 1998.

Shekhar et al. "Correlation of Differences in Modulation of Ras Expression With Metastatic Competence of Mouse Mammary Tumour Subpopulations", Invasion Metastasis, 14: 27-37, 1994/5.

Shimazu et al. "Syndecan-3 and the Control of Chondrocyte Proliferation During Endochondral Ossification", Exp. Cell. Res., 229(1): 126-136, 1996. Abstract.

Skolnick et al. "From Genes to Protein Structure and Function: Novel Applications of Computational Approaches in the Genomic Era", Trends in Biotechnology, 18: 34-39, 2000.

Smith et al. "Expression of Heparan Sulfate Protoglycan (Perlecan) in the Mouse Blastocyst Is Regulated During Normal and Delayed Implantation", Dev. Biol., 184(1): 38-47, 1997. Abstract.

Smith et al. "The Challenges of Genome Sequence Annotation or 'The Devil Is in the Details'", Nature Biotechnology, 15: 1222-1223, 1997.

Sordat et al. "Modulation of the Malignant Phenotype With the Urokinase-Type Plasminogen Activator and the Type I Plasminogen Activator Inhibitor", Cell Differentiation and Development, 32: 277-286, 1990.

Soule et al. "Isolation and Characterization of A Spontaneously Immortalized Human Breast Epithelial Cell Line, MCF-10[1]", Cancer Res., 50: 6075-6086, 1990. Abstract.

Speert et al. "Modulation of Macrophage Function for Defense of the Lung Against *Pseudomonas aeruginosa*", Behring Inst. Mitt., 98: 274-282, 1997. Abstract.

Spiegel et al. "Heparanase Facilities Development and SDF-1 Induced Migration of Hematopoietic Stem and Progenitor Cells", Blood, 102(11): 825a-826a, 2003. Astract# 3056.

Stracke et al. "Autotaxin, Tumor Motility-Stimulating Exophosphodiesterase", Advan. Enzyme Regul., 37: 135-144, 1997. Introduction.

Suggs et al. Use of Synthetic Oligonucleotides as Hybridization Probes: Isolation of Cloned cDNA Sequenced for Human ?2, 1996.

Sutherland "Structure-Function Relationships in Microbial Exopolysaccharides", Biotech. Adv., 12: 393-448, 1994.

Szczylik et al. Selective Inhibition of Leukemia Cell Proliferation by BCR, Am.J.Vet.Res.(57), 1996,p. 554,abs.

Tang et al. "Contribution of Specific *Pseudomonas aeruginosa* Virulence Factors to Pathogenesis of Pneumonia in A Neonatal Mouse Model of Infection", Infect. Immun., 64(1): 37-43, 1996. Abstract.

Tatnell et al. "Characterisation of Alginates From Mucoid Strains of *Pseudomonas aeruginosa*", Biochemical Society Transactions, 24: 404S, 1996.

Tatnell et al. "Chemical Analysis of Alginates From Mucoid Strains of *Pseudomonas aeruginosa*", Biochemical Society Transactions, 22: 310S, 1994.

Tatnell et al. "Colonisation of Cystic Fibrosis Patients by Non-Mucoid *Pseudomonas aeruginosa*—Characterisation of the Alginate From Mucoid Variants", Biochemistry Society Transactions, 24: 406S, 1996.

Taurog et al. "HLA-B27 in Inbred and Non-Inbred Transgenic Mice", The Journal of Immunology, 141(11): 4020-4023, 1988.

Taylor et al. "A Colorimetric Method for the Quantitation of Uronic Acids and A Specific Assay for Galacturonic Acid", Analytical Biochemistry, 201: 190-196, 1992.

Thompson et al. "Identification of Chondroitin Sulfate E in Human Lung Mast Cells", J. Immunol., 140(8): 2708-2713, 1988. Abstract.

Thuong et al. "Sequence-Specific Recognition and Modification of Double-Helical DNA by Oligonucleotides", Angew.Chem. Int. Ed. Engl. 32: 666-690, 1993.

Toyoshima et al. "Human Heparanase: Purification, Characterization, Cloning, and Expression", J. Biolog. Chemistry, 274(34): 24153-24160, 1999.

Uno et al. "Antisense-Mediated Suppression of Human Heparanase Gene Expression Inhibits Pleural Dissemination of Human Cancer Cells", Cancer Research, 61(21): 7855-7860, 2001.

Van Heeckeren et al. "Excessive Inflammatory Response of Cystic Fibrosis Mice to Bronchopulmonary Infection With *Pseudomonas aeruginosa*", J. Clin. Invest., 100(11): 2810-2815, 1997.

Vernet et al. "Virulence Factors (Aerobactin and Mucoid Phenotype) in *Klebsiella pneumoniae* and *Escherichia coli* Blood Cultures Isolates", FEMS Microbiol. Lett., 130(1): 51-57, 1995. Abstract.

Vlodavsky et al. "Mammalian Heparanase: Gene Cloning, Expression and Function in Tumor Progression and Metastasis", Nature Medicine, 5(7): 793-802, 1999.

Vlodavsky et al. "Morphological Appearance, Growth Behavior and Migratory Activity of Human Tumor Cells Maintained on Extracellular Matrix Versus Plastic", Cell, 19: 607-616, 1980.

Vogel et al. "Production of Proteoglycans by Human Lung Fibroblasts (IMR-90) Maintained in A Low Concentration of Serum", Biochem. J., 207(3): 369-379. Abstract, 1996.

Vukicevic et al. "Induction of Nephrrogenic Mesenchyme by Osteogenic Protein I (Bone Morphogenetic Protein 7)", Proc. Natl. Acad. Sci. USA, 93: 9021-9026, 1996.

Walch et al. "Correlation of Overexpression of the Low-Affinity p75 Neutrotrophin Receptor With Augmented Invasion and Heparanase Production in Human Malignant Melanoma Cells", Int. J. Cancer, 82: 112-120, 1999.

Wall "Transgenic Livestock: Progress and Prospects for the Future", Theriogenology, 45: 57-68, 1996.

Walton et al. "Prediction of Antisense Oligonucleotide Binding Affinity to A Structured RNA Target", Biotechnology and Bioengineering, 65(1): 1-9, 1999.

Wang "Basic Fibroblast Growth Factor for Stimulation of Bone Formation in Osteoinductive or Conductive Implants", Acta Orthop. Scand. Suppl., 269: 1-33, 1996. Abstract.

Wang "Basic Fibroblast Growth Factor Infused at Different Times During Bone Graft Incorporation. Titanium Chamber Study in Rats", Acta Orthop. Scand., 67(3): 229-236, 1996. Abstract.

Wang et al. "Basic Fibroblast Growth Enhances Bone-Graft Incorporation: Dose and Time Dependence in Rats", J. Orthop. Res., 14(2): 316-323, 1996. Abstract. Suppl. IDS in 22716.

Wang et al. "Isolation and Characterization of *Pseudomonas aeruginosa* Genes Inducible by Respiratory Mucus Derived From Cystic Fibrosis Patients", Mol. Microbiol., 22(5): 1005-1012, 1996, Abstract.

Watson et al. "A Growth Factor Phenotype Map for Ovine Preimplantation Development", Biology of Reproduction, 50(4): 725-733, 1994. Abstract.

Webster et al. "FGFR Activation in Skeletal Disorders: Too Much of A Good Thing", TIG, 13(5): 178-182, 1997.

Welch et al. "Complex Saccharide Metabolism in Cystic Fibrosis Fibroblasts", Pediatr. Research, 9(9): 698-702, 1975.

Welch et al. "Expression of Ribozymes in Gene Transfer Systems to Modulate Target RNA Levels", Curr. Opin. Biotechnol., 9(5): 486-496, 1998. Abstract.

Weller "Implications of Early Inflammation and Infection in Cystic Fibrosis: A Review of New and Potential Interventions", Pediatric Pulmonology, 24: 143-146, 1997.

Wessels et al. "Effects on Virulence of Mutations in A Locus Essential for Hyaluronic Acid Capsule Expression in Group A Streptococci", Infect. Immun., 62(2): 433-441, 1994. Abstract.

Whitelock et al. "The Degradation of Human Endothelial Cell-Derived Perlecan and Release of Bound Basic Fibroblast Growth Factor by Stromelysin, Collagenase, Plasmin, and Heparanases", Journal of Biological Chemistry, 271(17): 10079-10086, 1996.

Wordinger et al. "The Immunolocalzation of Basic Fibrobast Growth Factor in the Mouse Uterus During the Initial Stages of Embryo Implantation", Growth Factors, 11(3): 175-186, 1994. Abstract.

Yagel et al. "Normal Nonmetastatic Human Trophoblast Cells Share In Vitro Invasive Properties of Malignant Cells", J. Cellular Physiology, 136: 455-462, 1988.

Yazaki et al. "The Structure and Expression of the FGF Receptor-1 mRNA Isoforms in Rat Tissues", Biochimica et Biophysica Acta, 1172: 37-42, 1993.

Ye et al. "Targeted Gene Correction: A New Strategy for Molecular Medicine", Molecular Medicine Today, p. 431-437, 1998.

Yesildaglar et al. "The Mouse as A Model to Study Adhesion Formation Following Endoscopic Surgery: A Preliminary Report", Human Reproduction, 14(1): 55-59, 1999. Abstract.

Yoshida "Effects of Basic Fibroblast Growth Factor on the Development of Mouse Preimplantation Embryos", Nippon Sanka Fujinka Gakkai Zasshi, 48(3): 170-176, 1996. Abstract.

Yu et al. "Microbial Pathogens in Cystic Fibrosis: Pulmonary Clearance of Mucoid *Pseudomonas aeruginosa* and Inflammation in A Mouse Model of Repeated Respiratory Challenge", Infection and Immunity, 66(1): 280-288, 1998.

Zahm et al. "Early Alterations in Airway Mucociliary Clearance and Inflamation of the Lamina Propria in CF Mice", Am. J. Physiol., 272(3 Pt 1): C853-C859, 1997. Abstract.

Zcharia et al. "Heparanase Acclerates Wound Angiogenesis and Wound Healing in Mouse and Rat Models", The FASEB Journal, 19: 211-221, 2005.

Zcharia et al. "Heparanase Regulates Murine Hair Growth", American Journal of Pathology, 166(4): 999-1008, 2005.

Zcharia et al. "Molecular Properties and Involvement of Heparanase in Cancer Progression and Mammary Gland Morphogenesis", Journal of Mammary Gland Biology and Neoplasia, 6(3): 311-322, 2001.

Zcharia et al. "Transgenic Expression of Mammalian Heparanase Uncovers Physiological Functions of Heparan Sulfate in Tissue Morphogenesis, Vascularization, and Feeding Behavior", The FASEB Journal, 18: 252-263, 2004.

Zheng et al. "Increment of hFIX Expression With Endogenous Intron 1 In Vitro", Cell Res., 7(1):21-29, 1997 Abstract.

Zhou et al. "A 182 Bp Fragment of the Mouse Pro?1(11) Collagen Gene Is Sufficient to Direct Chondrocyte Expression in Transgenic Mice", J. Cell Science, 108: 3677-3684, 1995.

Zhou et al. "HFE Gene Knockout Produces Mouse Model of Hereditary Hemochromatosis", PNAS, 95(5): 2492-2497, 1998.

Zhu et al. "Development of Heritable Melanoma in Transgenic Mice", The Journal of Investigative Dermatology, 110: 247-252, 1998.

Goshen et al. "Purification and Characterization of Placental Heparanase and Its Expression by Cultured Cytotrophoblasts", Molecular Human Reproduction, 2(9): 679-684, 1996.

Bar-Ner et al. "Inhibition of Heparanase-Mediated Degradation of Extracellular Matrix Heparan Sulphate by Non-Anticoagulant Heparin Species", Blood, 70(2): 551-557, 1987.

Bashkin et al. "Basic Fibroblast Growth Factor Binds to Subendothlial ExtraCellular Matrix and Is Released by Heparitanase and Heparin-Like Molecules", Biochemistry, 28: 1737-1743, 1989.

Burgess et al. "The Heparin-Binding (Fibroblast) Growth Factor of Proteins", Annu. Rev. Biochem., 58:.575-606, 1989.

Chen et al. "Dengue Virus Infectivity Depends on Envelope Protein Bin to Target Cell Heparan Sulfate", Nature Medicine, 3(8): 866-871, 1997.

Cordon-Cardo et al. "Expression of Basic Fibroblast Growth Factor in Normal Human Tissue", Laboratory Investigation, 63(6): 832-840, 1990. Abstract.

Eisenberg et al. "Lipoprotein Lipase Enhances Binding of Lipoproteins to Heparan Sulfate on Cell Surface and Extracellular Matrix", Journal of Clinical Investigation, 90: 2013-2021, 1992.

Gitay-Goren et al. "The Binding of Vascular Endothelial Growth Factor to Its Receptors Is Dependent on Cell Surface-Associated Heparin-Like Molecules", Journal of Biological Chemistry, 267(9): 6093-6098, 1992.

Narindrasorasak et al. "High Affinity Interactions Between the Altzheimer's ?-Amyloid Precursor Proteins and the Basement Membrane Form of Heparan Sulfate Proteoglycan", J. Biol. Chem., 266(20): 12878-12883, 1991.

Shieh et al. "Cell Surface Receptors for Herpes Simplex Virus Are Heparan Sulfate Proteoglycan Proteoglycans"J. Cell. Biol., 116(5): 1273-1281, 1992.

Rapraeger et al. "Requirement of Heparan Sulfate for bFGF-Mediated Fibroblast Growth and Myoblast Differentiation", Science, 252: 1705-1709, 1991.

Lider et al. "A Disaccharide That Inhibits Tumor Necrosis Factor ? Is Formed From the Extracellular Matrix by the Enzyme Heparanase", Proc. Natl. Acad. Sci. USA, 92: 5037-5041, 1995.

Lider et al. "Suppression of Experimental Autoimmune Disease and Prolongation of Allograft Survival by Treatment of Animals With Low Doses of Heparin", The Journal of Clinical Investigation, 83: 752-756, 1989.

Ornitz et al. "FGF Binding and FGF Receptor Activation by Synthetic Heparin-Derived Di- and Trisaccharides", Science, 268: 432-436, 1995.

Spivak-Kroizman et al. "Heparin-Induced Oligomerization of FGF Molecules Is Responsible For FGF Receptor Dimerization, Activation, and Cell Proliferation", Cell, 79: 1015-1024, 1994.

Yayon et al. "Cell Surface, Heparin-Like Molecules Are Required for Binding of Basic Fibroblast Growth Factor to Its High Affinity Receptor", Cell, 64: 841-848, 1991.

Voldavsky et al. "Extracellular Sequestration and Release of Fibroblast Growth Factor: A Regulatory Mechanism?", Trends Biochem. Sci., 16: 268-271, 1991.

Voldavsky et al. Extracellular Matrix-Bound Growth Factors, Enzmes, and Plasn Proteins, Basic Membranes: Cellular and Molecular aspects (eds. Rohrbach & Timppl) p. 327-343, 1993.

Voldavsky et al. "Endothelial Cell-Derived Basic Fibroblast Growth Factor: Synthesis and Deposition Into Subendothelial Extra-Cellular Matrix", Proc. Natl. Acad. Sci. USA, 84: 2292-2296, 1987.

Voldavsky et al. "Involvement of the ExtraCellular Matrix, Heparin Sulfate Proteoglycans, and Heparin Sulfate Degrading Enzymes in Angiogenesis and Metastis", Tumor Angeogenesis, p. 125-140, 1997.

Voldavsky et al. "Morphological Appearance, Growth Behaviour and Migratory Activity of Human Tumor Cells Maintained on Extracellular Matrix Versus Plastic", Cell, 19: 607-616, 1980.

Voldavsky et al. "Involvement of Heparanase in Tumor Metastasis and Angiogenesis", Isr. J. Med. Sci., 24(9-10): 464-470, 1988.

Voldavsky et al. "Lymphoma Cell-Mediated Degradation of Sulfated Proteoglycans in the Subendothelial ExtraCellular Matrix: Relationship to Tumor Cell Metastasis", Cancer Research, 43: 2704-2711, 1983.

Ishai-Michaeli et al, "Importance of Size and Sulfation of Heparin in Release of Basic Fibroblast Growth Factor From the Vascular Endothelium and ExtraCellular Matrix", Biochemistry, 31(7): 2080-2088, 1992.

Ishai-Michaeli et al, "Heparanase Activity Expressed by Platelets, Neutrophilis, and Lymphoma Cells releases Active Fibroblast Growth Factor from ExtraCellular Matrix", Cell Regulation, 1: 833-842, 1990.

Folkman et al. Angiogenic Factors, Science, 235: p. 442-447, 1987.

Folkman et al. "A Heparin-Binding Angiogenic Protein—Basic Fibroblast Growth Factor—Is Stored Within Basement Membrane", Am. J. Pathology, 130(2): 393-400, 1988.

Parish et al. "Evidence That Sulphated Polysaccharides Inhibit Tumor Metastasis by Blocking Tumor-Cell-Derived Heparanases", Int. J. Cancer, 40: 511-517, 1987.

Gospodarowicz et al. "Permissive Effect of the ExtraCellular Matrix on Cell Proliferation In Vitro", Proc. Natl. Acad. Sci. USA., 77(7): 4049-4098, 1980.

Liotta et al. "Tumor Invasion and the ExtraCellular Matrix", Laboratory Investigation, 49(6): 636-647, 1983.

Niclson, G.I., "Organ Specificity of Tumor Metastis: Role of Preferential Adhesion, Invasion and Growth of Malignant Cells at Specific Secondary Sites", Cancer Met. Rev., 7: 143-188, 1988.

Nakajima et al. "Heparanases and Tumor Metastasis", Journal of Cellular Biochemistry, 36(2): 157-167, 1988.

Voldavsky et al. "Inhibition of Tumor Metastasis by Heparanase Inhibiting Species of Heparin", Invasion & Metastasis, 14(1-6): 290-302, 1994/95.

Voldavsky et al. "Expression of Heparanase by Platelets and Circulating Cells of the Immune Systems: Possible Involvement in Diapedesis and Extra Vasation", Invasion & Matastasis, 12(2): 112-127, 1992.

Ruoslahti et al. "Proteoglycans as Modulators of Growth Factor Activities", Cell, 64: 867-869, 1991.

Kjellen et al. "Proteoglycans: Structures and Interactions", Annual Reviews in Biochemistry, 60: 443-475, 1991.

Wight et al. "Cell Biology of Arterial Proteoglycans", Arteriosclerosis, 9(1): 1-20, 1989.

Jackson et al. "Glycosaminoglycans: Molecular Properties, Protein Interactions, and Role in Physiological Processes", Physiological Reviews, 71(2): 481-539, 1991.

Wight et al. "The Role of Proteoglycans in Cell Adhesion, Migration and Proliferation", Current Opinion in Cell Biology, 4: 793-801, 1992.

* cited by examiner

```
   1 CTAGAGCTTTCGACTCTCCGCTGCGCGGCAGCTGGCGGGGGGAGCAGCCAGGTGAGCCCA

61 AGATGCTGCTGCGCTCGAAGCCTGCGCTGCCGCCGCCGCTGATGCTGCTGCTCCTGGGGC
       M  L  L  R  S  K  P  A  L  P  P  P  L  M  L  L  L  G  P

121 CGCTGGGTCCCCTCTCCCCTGGCGCCCTGCCCCGACCTGCGCAAGCACAGGACGTCGTGG
       L  G  P  L  S  P  G  A  L  P  R  P  A  Q  A  Q  D  V  V  D

181 ACCTGGACTTCTTCACCCAGGAGCCGCTGCACCTGGTGAGCCCCTCGTTCCTGTCCGTCA
       L  D  F  F  T  Q  E  P  L  H  L  V  S  P  S  F  L  S  V  T

241 CCATTGACGCCAACCTGGCCACGGACCCGCGGTTCCTCATCCTCCTGGGTTCTCCAAAGC
       I  D  A  N  L  A  T  D  P  R  F  L  I  L  L  G  S  P  K  L

301 TTCGTACCTTGGCCAGAGGCTTGTCTCCTGCGTACCTGAGGTTTGGTGGCACCAAGACAG
       R  T  L  A  R  G  L  S  P  A  Y  L  R  F  G  G  T  K  T  D

361 ACTTCCTAATTTTCGATCCCAAGAAGGAATCAACCTTTGAAGAGAGAAGTTACTGGCAAT
       F  L  I  F  D  P  K  K  E  S  T  F  E  E  R  S  Y  W  Q  S

421 CTCAAGTCAACCAGGATATTTGCAAATATGGATCCATCCCTCCTGATGTGGAGGAGAAGT
       Q  V  N  Q  D  I  C  K  Y  G  S  I  P  P  D  V  E  E  K  L

481 TACGGTTGGAATGGCCCTACCAGGAGCAATTGCTACTCCGAGAACACTACCAGAAAAAGT
       R  L  E  W  P  Y  Q  E  Q  L  L  L  R  E  H  Y  Q  K  K  F

541 TCAAGAACAGCACCTACTCAAGAAGCTCTGTAGATGTGCTATACACTTTTGCAAACTGCT
       K  N  S  T  Y  S  R  S  S  V  D  V  L  Y  T  F  A  N  C  S

601 CAGGACTGGACTTGATCTTTGGCCTAAATGCGTTATTAAGAACAGCAGATTTGCAGTGGA
       G  L  D  L  I  F  G  L  N  A  L  L  R  T  A  D  L  Q  W  N

661 ACAGTTCTAATGCTCAGTTGCTCCTGGACTACTGCTCTTCCAAGGGGTATAACATTTCTT
       S  S  N  A  Q  L  L  L  D  Y  C  S  S  K  G  Y  N  I  S  W

721 GGGAACTAGGCAATGAACCTAACAGTTTCCTTAAGAAGGCTGATATTTTCATCAATGGGT
       E  L  G  N  E  P  N  S  F  L  K  K  A  D  I  F  I  N  G  S
                        (T)
 781 CGCAGTTAGGAGAAGATTATATTCAATTGCATAAACTTCTAAGAAAGTCCACCTTCAAAA
       Q  L  G  E  D  Y  I  Q  L  H  K  L  L  R  K  S  T  F  K  N
                        (F)
 841 ATGCAAAACTCTATGGTCCTGATGTTGGTCAGCCTCGAAGAAAGACGGCTAAGATGCTGA
       A  K  L  Y  G  P  D  V  G  Q  P  R  R  K  T  A  K  M  L  K

901 AGAGCTTCCTGAAGGCTGGTGGAGAAGTGATTGATTCAGTTACATGGCATCACTACTATT
       S  F  L  K  A  G  G  E  V  I  D  S  V  T  W  H  H  Y  Y  L

961 TGAATGGACGGACTGCTACCAGGGAAGATTTTCTAAACCCTGATGTATTGGACATTTTTA
       N  G  R  T  A  T  R  E  D  F  L  N  P  D  V  L  D  I  F  I

1021 TTTCATCTGTGCAAAAAGTTTTCCAGGTGGTTGAGAGCACCAGGCCTGGCAAGAAGGTCT
       S  S  V  Q  K  V  F  Q  V  V  E  S  T  R  P  G  K  K  V  W

1081 GGTTAGGAGAAACAAGCTCTGCATATGGAGGCGGAGCGCCCTTGCTATCCGACACCTTTG
       L  G  E  T  S  S  A  Y  G  G  G  A  P  L  L  S  D  T  F  A

1141 CAGCTGGCTTTATGTGGCTGGATAAATTGGGCCTGTCAGCCCGAATGGGAATAGAAGTGG
       A  G  F  M  W  L  D  K  L  G  L  S  A  R  M  G  I  E  V  V

1201 TGATGAGGCAAGTATTCTTTGGAGCAGGAAACTACCATTTAGTGGATGAAAACTTCGATC
       M  R  Q  V  F  F  G  A  G  N  Y  H  L  V  D  E  N  F  D  P

1261 CTTTACCTGATTATTGGCTATCTCTTCTGTTCAAGAAATTGGTGGGCACCAAGGTGTTAA
       L  P  D  Y  W  L  S  L  L  F  K  K  L  V  G  T  K  V  L  M

1321 TGGCAAGCGTGCAAGGTTCAAAGAGAAGGAAGCTTCGAGTATACCTTCATTGCACAAACA
       A  S  V  Q  G  S  K  R  R  K  L  R  V  Y  L  H  C  T  N  T

1381 CTGACAATCCAAGGTATAAAGAAGGAGATTTAACTCTGTATGCCATAAACCTCCATAACG
       D  N  P  R  Y  K  E  G  D  L  T  L  Y  A  I  N  L  H  N  V

1441 TCACCAAGTACTTGCGGTTACCCTATCCTTTTTCTAACAAGCAAGTGGATAAATACCTTC
       T  K  Y  L  R  L  P  Y  P  F  S  N  K  Q  V  D  K  Y  L  L

1501 TAAGACCTTTGGGACCTCATGGATTACTTTCCAAATCTGTCCAACTCAATGGTCTAACTC
       R  P  L  G  P  H  G  L  L  S  K  S  V  Q  L  N  G  L  T  L

1561 TAAAGATGGTGGATGATCAAACCTTGCCACCTTTAATGGAAAAACCTCTCCGGCCAGGAA
       K  M  V  D  D  Q  T  L  P  P  L  M  E  K  P  L  R  P  G  S

1621 GTTCACTGGGCTTGCCAGCTTTCTCATATAGTTTTTTTGTGATAAGAAATGCCAAAGTTG
       S  L  G  L  P  A  F  S  Y  S  F  F  V  I  R  N  A  K  V  A

1681 CTGCTTGCATCTGAAAATAAAATATACTAGTCCTGACACTG
       A  C  I
```

Fig. 1

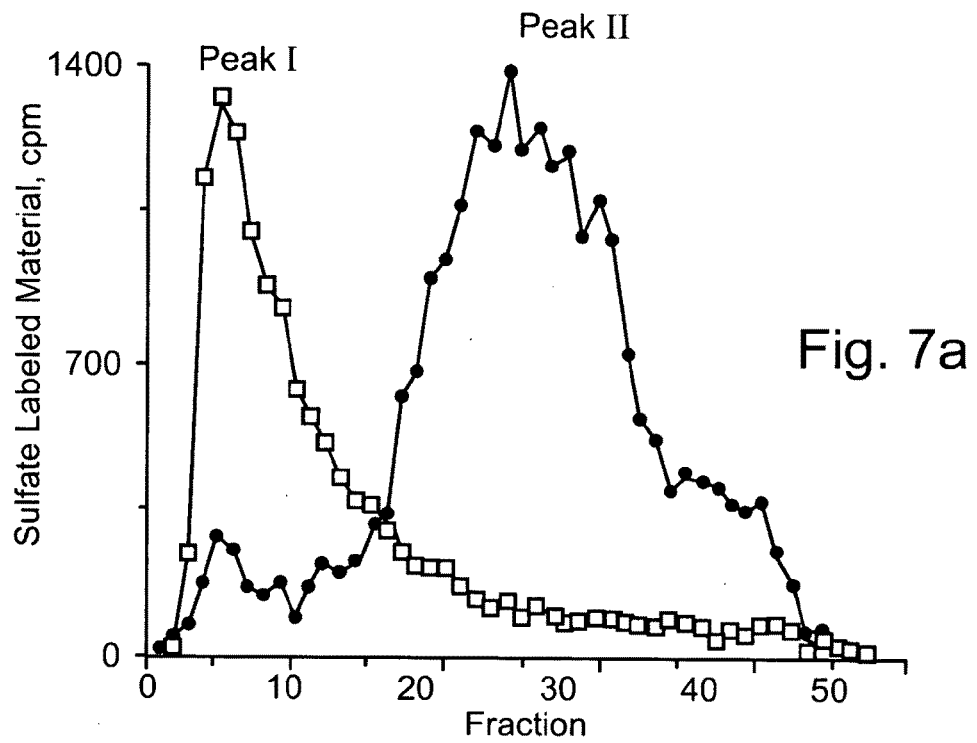
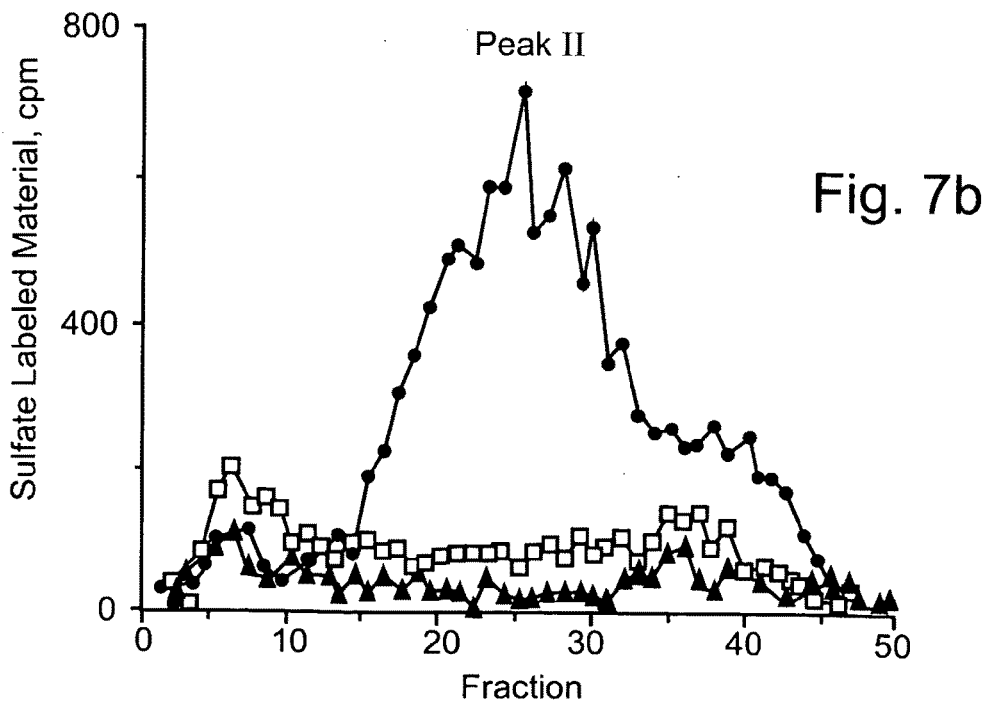

```
mouse   CTGGCAAGAAGGTCTCGGTTGGGAGAGACGAGCTCAGCTTACGGGTGGCGGT     50
        |||||||||||||||||| ||||  |||| ||||| |||| || ||  ||||
human   CTGGCAAGAAGGTCTCGGTTAGGAGAGAAACAAGCTCTGCATATGGAGGCGGA   1115 mouse   GCACCCTTGCTGTGTCCAACACCTTTGCAGCTGGCTTTATGTGGCTGGATAA    100
        |  ||||||||||||| |||||||||||||||||||||||| |||||||||
human   GCGCCCTTGCTGTGTCTGACACCTTTGCAGCTGGCTTTATGTGGCTGGATAA   1165 mouse   ATTGGGCCTGTCAGCCCAGATGGGCATAGAAGTCGTGATGAGGCAGGTGT    150
        |||||||||||||||||| ||||||| |||| ||||||||||||| |||
human   ATTGGGCCTGTCAGCCCGAATGGGAATAGAAGTGGTGATGAGGCAAGTAT   1215 mouse   TCTTCGGAGCAGGCAACTACCACTTAGTGGATGAAAACTTTGAGCCTTTA    200
        ||||  ||||||||||||||||| |||||||||||||||||| ||||||
human   TCTTTGGAGCAGGCAAACTACCATTTAGTGGATGAAAACTTTCGATCCTTTA 1265 mouse   CCTGATTACTGGCTCTCTCTCTGTTCAAGAAAACTGGTAGGTCCAGGGT    250
        ||||||| |||||  ||| ||| ||||| ||| ||||| |||||||||
human   CCTGATTATTGGCTATCTCTTCTGTTCAAGAAATTGGTGGGCACCAAGGT   1315 mouse   GTTACTGTCAAGAGTGAAAGGCCCAGACAGGAGCAAACTCCGAGTGTATC    300
        |||| |||  ||| ||| || ||| |||||||||||||| |||||| ||
human   GTTAATGGCAAGCGTGCAAGGTTCAAAGAGAAGGAAGCTTCGAGTATACC   1365 mouse   TCCACTGCACTAACGTCTATCACCCACGATATCAGGAAGGAGATCTAACT    350
        |  ||||||||| ||||| || ||| |  ||||||| ||||||| ||||
human   TTCATTGCACAAACACTGACAATCCAAGGTATAAAGAAGGAGATTTAACT   1415
```

Fig. 13

```
mouse  CTGTATGTCCTGAACCTCCATAATGTCACCAAGCACTTGAAGGTACCGCC  400
       ||||||| | ||||||||||||||||||| |||||||||||||||| |||
human  CTGTATGCCATAAACCTCCATAACGTCACCAAGTACTTGCGGTTACCCTA  1465 mouse  TCCGTTGTTCAGGAAACCAGTGGATACGTACCTTCTGAAGCCTTCGGGGC  450
       ||| || ||   || |  ||||||||| |||||| ||||| ||| || |
human  TCCTTTTTCTAACAGCAAGTGGATAAATACCTTCTAAGACCTTTGGGAC   1515 mouse  CGGATGGATTACTTTCCAAATCTGTCCAACTGAACGGTCAAATTCTGAAG  500
       | ||| ||||||||||||||||||||||| ||| ||||||||| |||||
human  CTCATGGATTACTTTCCAAATCTGTCCAACTCTCCAATGGTCTAACTCTAAAG 1565 mouse  ATGGTGGATGAGCAGACCCTGCCAGCTTTGACAGAAAAACCTCTCCCGCC  550
       ||||||||||| |||| ||||||||  ||||  | |||||||||||| |
human  ATGGTGGATGATCAAACCCTTGCCACCTTTAATGAAAAAACCTCTCCGGCC  1615 mouse  AGGAAGTGCACTAAGCCTGCCTGCCTTTTCCTATGGTTTTTTGTCATAA   600
       |||| ||||| | ||||| ||  || | |  ||| |||||||||||||
human  AGGAAGTTCACTGGGCTTGCCAGCTTTTCTCAGCTTTCTCATAGTTTTTTGTGATAA 1665 mouse  GAAATGCCAAAATCGCTGCTTGTATATGAAAATAAAA  637
       ||||||||||| ||| ||||||||| || ||||||||
human  GAAATGCCAAAGTTGCTGCTTGCATCTGAAAATAAAA  1702
```

Fig. 13 (Continued)

| Fig. 16a | Fig. 16b |
|---|---|
| Fig. 16c | Fig. 16d |
| Fig. 16e | Fig. 16f |
| Fig. 16g | Fig. 16h |
| Fig. 16i | Fig. 16j |
| Fig. 16k | Fig. 16l |
| Fig. 16m | Fig. 16n |
| Fig. 16o | Fig. 16p |
| Fig. 16q | Fig. 16r |
| Fig. 16s | Fig. 16t |
| Fig. 16u | Fig. 16v |
| Fig. 16w | Fig. 16x |
| Fig. 16y | Fig. 16z |
| Fig. 16aa | Fig. 16bb |
| Fig. 16cc | Fig. 16dd |
| Fig. 16ee | |

Fig. 16

```
ggatcttggctcactgctctctgctcccatgcaattcttatgcatca       50
gcctcctgagtagcttggattataggtctgcgccaccactcctgctaca    100
ccatgttgccagctggtcttgaacttcttggctcttagtgatcaccccg    150
ccttgcctcccaaagtgctggattacaggtgtgagccatcacaccgg      200
cccccgtttccatattagtaactcacatgtagaccacaaggatgcacta    250
tttagaaaacttgcaatgtccacttttcaaatcacccaaacatgttaaa    300
gaaattggtatgactggcatggcacagtgctcatgctgcaatcctag      350
cattttgtgaggctgagacgggcagatcacgagtcaggagattgagacc    400
atcctgacagacatggtgaaatcccatctctactaaaaatacaaaacaat   450
tagccgggggtgatggcaggcccctgtagtccagctactcgggaggctg    500
aggcaggagaatggcgtgaatccaggaggcagagcttgcagtgagccgag   550
atggtgccactgcactccagcctgggcgacagagcgagactccgtctcaa   600
aaaaaaaaaagaaagaaaattggtatgactgttgactcacaacaggag     650
tcagggcatgggggtgggtgtaagattaatgtcatgacaaatgtgaaa     700
agaaacttctgttttttccaactccacgtctgctactacatattattacactc 750
ttctggtagtgtgttttatgtgtgaatttttttcatatgtatacagt      800
aattgtaggatatgaacctgattctagttgcaaaactcactatgagctta   850
gcttttaagttgcttaagaataggtagatctcactttgtcaccaggctgagtgc 900
ttattattttaagagagggtcactgcaacctccacctcccagctcaaataa  950
agtggtgattaaggtgcactgaacctgaacagcacgggccacc         1000
acctcccacctcagcctcccagtagctgaaccacaggcacgggccacc    1050
acgcctgctaattttttgtatttttgtagagatggggtttcatcatgt    1100
tgcccaggctgtcttgaacctcctcggctcaagcaatctcccacctgg     1150
cctcccaaaatgctggcatcacagcatgatggcatcactggcatcacat    1200
accatgcctggcctgatttatgcaaattagatatgcatttcaaaataatc   1250
tattttatttgttgccttattgtggtacaatctcaagtgaaaaatct      1300
aagggttttggttgttatttgcttactcaaccaatatttattagactctta  1350
ctaagcaccaacatgatcacatgcctgagctatgctagcatagctgtg     1400
agacaaacttaatctctgttttgtggagcatataatctagtagatgaag    1450
```

Fig. 16a

```
ccaatgttgagcaacatcacaatactaacaaattgaggatgctacgagag     1500
tgtctaacaaattgaggatgctacgagagtgctctaacaaattgaggatgc    1550
tatgagagtgtgtcatgagagctgcctgagattgagagaaagcttcct       1600
tgagggaagttacatttcagctgaaacacactgccatctgctcgaggttt     1650
tgtaactgcattcacatccgattctgacacttcacatcccgattctgac      1700
acttcacccagttactgtctcagacttgggtccgcatgttgtaaaacaag     1750
gacagtatgcacttggcaggttgtgagaaggaagagaacacaagtaaa       1800
gcacctgtatcaggcatacagtaggcactaagcgtgcgatgcttgctatg     1850
attatacatcagtgtaagcatcaaggaaaagctgaagaaaagtctgacca     1900
acagcgaaagataaatgcgcagagagaaatttgcaaaggctccaaatt       1950
caggggcagtcgtactctacactttgtatgggcttcaggtcctgagt        2000
tccagacattggagcaactaacccttaagattgctaaatattgtcttaa      2050
tgagaagtcgtgataaagaattttgggtggttgatctcttttccagctgcagt  2100
ttagcgtatgctgaggccagattgctcaagcaaaagtaaaatacctgag      2150
aaactgcctggccagaggacaatcagattttgctggctcaagtgacaag      2200
caagtgtttataagctagatgggagaggaaggatgaatactccattgga      2250
ggttttactcgagggtcagagggtcgccatcagaatggatct            2300
gggagtcgaaacgctgggttcccacgagagcgcgcagaacacgtgcgtc      2350
aggaagcctggtccgggatgcccagcgctgctcccccggcgctcctccc      2400
gggcgctcctccaagtgggtgtggtgttcgtaagtgaacgtgaccgccacg    2450
accccttcaagtgggtgtggtgattcgtaagtgaacgtgaccgccacg       2500
aggggaaagcgagcagtagcaaggaagtaggagagagcggcaggcggg       2550
ttggattggagcagtgggaggatgcagaagaggagtgggaggtgga         2600
gggcgcagtgggaggggtgaggagggctaacgGCGGAGGAAAGGAGAA       2650
AAGGGCGCTCGGGCAGCTGGCGGGGGGAGCAGCCAGGTGAGCCCAAGATGCTGCTGCTGGGGC  2700
CTGCGCGGCAGCTGGCGGGGGGAGCAGCCAGGTGAGCCCAAGATGCTGCT     2750
                                        M  L
GCGCTCGAAGCCTGCCGCCTGCCGCCGCGCTGATGCTGCTCCTGGGGC       2800
R  S  K  P  A  L  P  P  P  L  M  L  L  L  G
CGCTGGGGTCCCCTCTCCCCTGGCGCCCTGCCCTGCCCGACCTGCAAGCACAG  2850
```

Fig. 16b

```
         P   L   G   P   L   S   P   G   A   L   P   R   P   A   Q   A   Q
        GACGTCGTGGACCTGGACTTCTTCACCCAGGAGCCGCTGCACCTGGTGAG              2900
         D   V   D   L   D   F   F   T   Q   E   P   L   H   L   V   S
        CCCCTCGTTCCTGTCCGTCACCATTGACAACTGGCCAACTGGCCACGGACCCGC          2950
         P   F   L   S   V   T   I   D   A   N   L   A   T   D   P
        GGTTCCTCATCCTCCTGGGgtaagcgccagcctcctggtcctgtcccctt              3000
         R   F   L   I   L   G
        tcctgtcctcctgacacctatgtctgccccgccagcggctctctcctt                3050
        tgcgcggaaacaacttcacacccgaacctcccccgcctgtctctctcccacc            3100
        ccacttcccgcctctcattctccctctccctcccttactctcagaccccca             3150
        aaccgcttttgggggtatcatttaaaaaatagatttaggggttacaag                3200
        tgcagttctgttccatggtatatggtcattgtgtggtgcatctggctctt              3250
        agtgtaactgtcaccccgaatgttgtacattgtatctaataggtaatttct             3300
        catccctcatccctctcccacccctccaccctttggagtctccagtgtct              3350
        actattccactaagtccatgtgtacacattgttttagcgccactctaaat              3400
        gagccttttgtttcattcattctgtaagtgttgaatagtgcaccacctaa              3450
        ggtcaggtataagtggaaatttgaaaagaaactgccccacttgccccagt              3500
        acttccctagccaagaggagggaaaccaggcaggtgcacctgaaggcctg              3550
        tgagtgcttgatttgctgtgcagtgtgtaggacaagtaagattgtgcatagc            3600
        cttctgtatttaagactgtgttaggaagatttctcttcttttctcttttct             3650
        ttttctttttcttttcttttttttttaggcagatgaaaagggcgtca                 3700
        cagaacaggaataaaatctaaatattcaataaaagatgagacctaggagact            3750
        actgcagtgacttacaagtcctaatgtgtctctccaaaatggg                     3800
        gctgcaaaatgtggtgctgcctttatcagctctcaagttttttccttacctg            3850
        agaaggaagaacctgatgcagagttcagggctccctgcccatgaatgcag              3900
        gctgactccaagatgggagctacaggagacaatcccaggtcttctaggcc              3950
        tcttattaggccctgggagcctccagagatggccacatcttgaccagcc               4000
        cagatagaggaaagatcaccattatctcacctctgtgtcaaatacctag               4050
        atgctgtcctccctgagcccactagttgccagcgctaatttaatgg                  4100
        gtagtgtactggttaagagatggacagagaccatcctgtgcttgactctcagc           4150
```

Fig. 16c

```
tctggcaaagatgagtgacttggttttccatatctcttggccacaccaa    4200
ccttgattcttcagctgtagaatgaatttctcaagcttgcctcaagga    4250
ttattgcccgagatttgatgatatggtaagagcttctcagtgtttgacc   4300
catagtaagtgtttgacgtttcaaacgaattgttttcttctctaggacatgg 4350
tgagcattggtagccattcacggtttctgttcttttgatcatagtt      4400
aacctctccttttcctttctgccactacaattttctgtgtgggaagaatcc 4450
ttactttctgcccttccccttaaggataggaagctgatactaggcagcaa  4500
ctagttggggataggaagattgttccagagaaatgctgaaccataggc    4550
tccagatcacaggacccagtcttagcttgctggggtgtgggtgggggg    4600
gggcggttactgaacatggtatgaagtagatgtccatttactgaaatgt   4650
gaggacctgagcctctctattgctgtagccagcatatcccaacctc      4700
tcccaagaaagacagatggggttccccctgagtaacaggtccaaa       4750
agaaaaaacatacagtgggacttccaggatctgggcctgatcaccagca   4800
gtcaagctcccccgcaattgactgactaacaccccctaacacgtagaaattcca 4850
atctgcaattagtgaggatgatactttttcctctttattctctaaatacatctct 4900
tcatttcccagagcaccctttttcccctcctctgcaccttttgttaaa    4950
gactggagtataatgaaataccaagagagcataacatgtgatacataaaa  5000
ctttttttctgttacaaaacagttcattcttgtccatacgtgcttctc    5050
tccaaggctggctgctctgtctgtgagggtcgcttcgcttgttgagaggccat 5100
ctgccataccctgctctcccagacgcatcgacaagcacacaccagagtgttat 5150
ctgctaagacctaaagaccagaagaggagaaccccctctcctcatctaagaccta 5200
gcttctaaattagagtgtgagggtccatctcccaggagggcacagggc    5250
ccaaacagccagccatctcagaagccaaacactaagctttgtaggggtcc  5300
acagtagaggagagtaagtaagacgcctgttgtttattacagttcctca   5350
aagtgaagatgtgtgggcgggatggcaagagctgagcagacgaaagctg   5400
aaggaataaggaaaagagaggaggacacaaacagctgacacttcctcagtt 5450
cttgtcatttgcctgcctgtctaagcaccttctaggtattaatccat    5500
ttagtcttggctacaacactgtgagtaactagttttgtcaccccatttt   5550
aaaaatgaagaaaagtgaggctcaggaggttaagtaacttggccacagtt  5600
tgaaactagactctgatcacatgagataatagtgcccataaaaaggaaa   5650
gcagattatattttttaaaggaaagagagtaggataggtagaaaaagat   5700
```

Fig. 16d

```
tgtttggaaaggaattgagagattgatataatgaaaagaagcattcacat      5750
gagagtaacagtatcaggcccaaacccttcatctaaggtacttcaaagag      5800
gcctaagcaaacttagtcactggcgtggttctagtctccatgatgcaaa       5850
tacattgtgtacagcccaactccacacaaaacttaaatacccatgataga      5900
gcaatctaaaatttgaaagaaaaatctttcaattgtcgtcttcccaga        5950
gggacttaatcaagaaaaccaatcaaatactcctaagcctaactgtgtg       6000
cagaactccaaagagagcccagcctaaatcaacactgtcccatggaaat       6050
ataatataatgtgggcctcatatgcaaggtcatatgttttaaatttt         6100
ctagtagccatattaaaaagtaaaagaaacaagtgaattaatttttaa        6150
taattttatttagttcaatagatccaaaatgttttctcagcatgtaatca      6200
atataaaaatattaatgagtattattattttacagcacttctcagactatt     6250
tattctataatctggcgtgtatatttgctctcttgtcacccaagct          6300
ctttcttctttttttttccgagacaatttgctctcttgtcacccaagct       6350
agagtacaatggcgttacctcggctcactgcaacctccgcctcccggtt       6400
caagtgattctcctgcctcagtcctctcccaagtagctggactagaggcatg    6450
caccaccacgcctgctaattgtgtatttttagtagagacagggtttcac       6500
catgttggccaggctaatctcaaactcctgagctcaggtgatatgcccac      6550
ctcggcctccaaagtgttggattacaggcgtgagccacatgcaccggc        6600
ctcagattaactatatttcaagcgttcagtagcacatcaattaagacac       6650
gtatacaag                                               6650
atggtagtggacagtacagatctgcatttcaattaagacacgtatacaag      6700
catagttcactaatgcacgtaaaaaagtatagtgctgagtcggtggt         6750
agaaatcctaaatactgcttgcttttcattgcaatctaatcagcaatctcagt   6800
gataatgcaaccatgtccattttgccaattcaataaatattactgataaaaac   6850
gcaaagttcatccattttgccatcttcatagacagagttgcttttcacatt     6900
tttcaatattagattccttgcatcttcatagacagagttgcttttcacatt     6950
tagaaattacttatcaatgttaaacacacgtttgataaccagtgttgg        7000
aaagaggtgcagactccccatgtgccattgatggcagaaatattcacag       7050
ccaaaggaaacaaaggctgggacaatcacacacctcatgtctcctaa         7100
ctcctgggaagtgctgtccctctgattgagctcttattattgccttccc       7150
actaaccctgtccactgtgccctggagcccctttgcaggttacctgctct      7200
gtcctcctcacagaatatctcctctacctccttgtccttgtccaagctacaacttg 7250
```

Fig. 16e

```
gctattctctgatgacactgtcttccctgtagcccttttgagtaatggct     7300
gcatattctcccatagtccagttcttttcctgttctccagtctggcttct     7350
ggatgacagcccactagtttgaactccatactgctatagttcaagtccct     7400
tttgacttgttacctggcaaaatgccatttgcttcagtggttcccttgt      7450
ttgtaaaatgacgataatagcgggtagcttccctacacgctcagtgagaa     7500
ttgagtgaaagaaggcgggtagcttccctacacgctcagtgtagactagc     7550
ctgatgtgcattacgggtgatgctcagtgcctgcttcctgttctttccatctc  7600
cacatctggctctcatccagtgctcctgcttacggcactctgtcccctc      7650
ttacttactccccctattaactgaagactggcactgatctcacagtttc      7700
ctctccacttcctagtctccactcatcatctgatgacttcaagtcaccta     7750
gataaactgtctcagtttcttcactcacatttttatacagataatgt        7800
tacactcaagttgtaacagaaccagcttatccagctcatgaaatgtatgc     7850
atttcatctcaactctgtattcagtgacatcctgtgggtatctgaaatc      7900
agccatggtgagaatatttacaggtgcaaatactaaaaagcag            7950
agcacccttttttctgagagccagaagctctttctactccatagcac        8000
ccatcataacaattttttaaataacctccactgaacagctccttcctctc     8050
tacttcttccatatctgatttgagcttcttaatttatcatgtgaaccact     8100
cttgtaataataacccaaatcccctgttccattgttcttcctgctaaaat    8150
actaaacctggtttagtccaaccaatgaaatgaaaaatattacttattactttttaatgt  8200
gtggcccaaaaactggaaatgaaaatgcttcattttccagtctcagtggccaccct    8250
atattaataagccattttaatgcttccagtgtccagtggccaccct        8300
gtatagctgggctattgttacccttgagctcttgcgggaggaggtggacagtctcc    8350
cagccacacagactgatgttgcaccaaacattttttagcttccagacttc    8400
cctgccccttagtgttaccttaactctctgactctccaccttatcattcttagc   8450
ctctacttttttaaaaatctctgcttcccaaagaaaatgagcaatacttcctttt  8500
acatgaccatacttctgtcatcaaatctgcagacatgtcatgcctaagtccagc   8550
ccttttcctccttcctctgtcagtctgcttcttccattcctgccctgaat    8600
tttccctcctttcttctgatctcagtctgcttcttccattcctgccctgaat  8650
ccgtccccctcccaacccccaaggactctgctcatcagtcacctcttc      8700
cctctcctgtatctttcaactcctcctcccatttactgctcttcctcaagc   8750
```

Fig. 16f

```
ctttccccaagcctttccatctcaattacctcctcgcacatgcctctgc      8800
agaaccaccccgtttcttccctccctccctgtgtcactaaatcaatctctccgac 8850
tgccctcatgatggcaccatcattgtgtgggaaacctaataaacactttatctta 8900
atcatcaatggccttccttgttggttgaatgaggttacccgaaatccatattaga 8950
tttggtctttgttatgggttgaatgaggttacccgaaatccatattaga      9000
agtcctaaccccagtacctcagaatgtgactttagttgactttggaataggtc  9050
attgcagacgttattagttaggatgaggtcatactgaatgtgatggct       9100
gcttatctaatatgactgatgtccttataacaaggagaaatttggagaca     9150
gacacgcacataggagaatacatgtgatgacaggagttatggagttgg       9200
agtcaaaaagctatgggaacttaggagagaagacctgaacaaatcctttc     9250
ctgcgcctagagagaggagtatggccctgccactacattctgttgttcaacgtt 9300
tcggcttttcaaaactgtaagacaatacatttctgttgttcaaaccaatt     9350
agtttgcagtactctgcgactgcagccctaacaaactaatacagtctctt     9400
ggaggcatttgcaagttgacaatggaagcacttttcttaccccctttagg     9450
tctgtcgccttctgttggggggtgttttctaacaattcctctccatct       9500
ctctctctagtttgtcttaaacattgtgttcttcagacttctgacct        9550
agccttcttttcacttcactcccctggtgtctgctgctgtctccaccttcc    9600
agaaattacttaaattactgctcatgctcagtactgctgctgaaactgttta   9650
acaactggctctctgggaagaggggagactggttgatggttttttgctgat    9700
ttctgtgtgtaaatactccctccatgccaattccaaactgccaacagt       9750
ttaacaactggctcacaaattttctccaactccagcacacctctgcttttcaca 9800
ggccaacaacgtgtacagccactccagcacacctctgcttttgtgtca       9850
gagagaagtaacttatttttgtacaaaaggtaaaataaaaacacctgcag     9900
gcccccttttttttcctttatttaactgctctagaaatagaatagctgaagc   9950
ttctttatgcattcatctgttatttccatgtcactgtggtggtgggatt      10000
attttcctttattttctttgtatatggttgaaatactgtaccttttgatc     10050
agtttagttttatggcatgtttttgcaccccatatttaaatctagttttgt    10100
cagaggcgtcaatattattttctcaaaacaagaaaatatttcattgcaa      10150
aggagacaaacaaaaggtccttaatacaccaaaactttgaaatgtgatttc    10200
ttgtacttggcagtgtccaagtggtgtaaaccccaaacagtattggggttttca 10250
ttttgttcaggaaagtctttgtctggcagcgacttgtccccttaccctacatcaggc 10300
```

Fig. 16g

```
gggccttgctcattcattcacttaagtattattaaacaccagcggtgtg    10350
ccaagtacttattatctctagtatcggtagattctgataagtcagtcaggtcc  10400
ctgctctcagggagcttgcagcagagatgggggctgcaatagagagtaag    10450
ccaaggaaatgaaaaaggaagttgatttcagagagtgatgaatgctatga    10500
agaaaatgaaggcagcgagctgcagtgtgtgagactgtgacccaaggtgtacag 10550
tttgtacctctaaggaccagcagcaacttttccaggtgctcgttcctcccacttcc 10600
tcatgtgatgccacagcagccgcgactgcttacaaatacagctagaggaatcta 10650
cagtctcttgcccagccgcgactgcttacaaatacagctagaggaatcta   10700
aatgaggttcctctatcatcaaaccaatcaaaatgccaaggaacagaat    10750
cagtgcctgctgaaggcagtgagacaggccagcctggagtggttctct     10800
ctgaggaagttcctcatcttggtttaggccatacctttgtgacctgtga    10850
gctaggggttgccagtccctgacatttctactgaggactcgcctgtctat   10900
attcccggcctgtatgtgtctcctgagttccagacacacaggcgaagcg    10950
cctgatggatggaagtatgttttttggtgttccattggtatctcaaattc   11000
tacaaaacttagtgcccctctctctccgttcctcccatcttcagtct      11050
atcacctgttcctcatccagcaaatgatatattaccatcttccaaggagctt 11100
cccaggagtaatccttgactcctccagtcctcaacatccaattaataatcaaatc 11150
taggccaggtacaatagctcacgcctataatcccagcacttttgggaggct  11200
gaggcaggtggatcatttgaggccaggagttcaagaccagcctggccaac   11250
aaggtgaaacctgtctgtctcatttaaaaaaaagttatttataatccatctctctccatct 11300
attatttctacctctgtgtcttgaatttatcacgttttgtctacgttaacatg 11350
ctgagctgttacctgttcttagtctggtgagtcactccagctgcttcagatc 11400
accagagtcttgttcttagtctggtgagtcactccagctgcttcagatc   11450
cttccatgctcaccgttgccctgccatataaagttggcactcctggacatg  11500
tggcttacgggccctcctccgtgatgtggccatctctaggcaccaaccacccttct 11550
tctctccccagcctctctgcgcccccatctctctttctatctctcggtctttgacagact 11600
gctcgtcaatggtgccagcttcttccatctctctaccccactctctttaat  11650
tttccctcacctggtttattcttttgaatgtctagcagtgaaaccattcccc 11700
ctagataaggtttattcttttgaatgtctagcagtgaaaccattcccc    11750
tgaaaacctttctctaaccaaccccctcagccccctcagcccaagtctagatt 11800
```

Fig. 16h

```
aggagtccctctgaatgtttccatagcattttaaagaattgcctatta      11850
cttgttcgtatctatcactaaactacaaattgtatgagaacagccactat    11900
ctctgcctggttcaccattcatctccagcaactagcataatgcctggcag    11950
agtcagcctgcaacaaatcttgtttttcacctattaaaacagacgcacagcc  12000
tccttaagtaaatcttgctttttcacctattaaaacagacgcacaggcc     12050
agtgtggtggcccatgcctgggtcaggaggttcaagaccactttggcaggtg  12100
ggcggatcacctgaggtcaggagttcaagaccagcctggccaacatggtg    12150
aaacccatctctaataaaaatacaaaaattagctgggcatggtggtggg     12200
tgcgtatagtcccagctactagggaggctgaggcaagagaatcgcttgaa    12250
cccaggaggcagagttgcagtgagccgagatcatgccactgtactccag     12300
cctgatgacacacacacacacctgtctcaaaacacacacacacacacaca    12350
cacacacacacacacacacacacacaagttgtataattttaaaata        12400
taacgtgctgttgttgaacacttgtaaaatacaggaaagtaatgaaaaa     12450
gtctaccatctagctcaccaccacataatgaccattgctatcatcctggcata 12500
attctctcctgtatatatatatttcttttattgttaaaattacacta       12550
tgagtactattttattttactgtgcaaaatgcgcaaaacataaat         12600
cttgccattttaaggtatgcagtttggtgcattcaccacactcacattgt    12650
tgtgcaaatatcaccactatctatccagaacttcttctgtcttcccaaac    12700
tgaaactctgtaccattaaacaatagtgcatcctctgttttcccctccc     12750
tacaatttattttttatttggtttgttgtaccaaactgaaaatagctgcttct 12800
tccttacttagttcagattagcattccatttattagccgtggtttga       12850
ggatgccatgacagatgccatccttcctccagagctctttgggctgtcagg   12900
tatttcagtcaggtgaattcgggttgataacatttaaaatctcactttt     12950
attctgagttcctagtgtcagagcccaccgtattttaggactcccaa       13000
gttacaaacaaaaatatggtgaggaggaatcactgaagttttaacacaag    13050
agacttacattttgttcaatttcttctatctttttagtttattctaagcata  13100
aagaaatactttgaaaatttacatagcattatacatattaattaagca      13150
tgagcacatcttaaaacttaaattttagatcagatcttaattcctagg      13200
atattaagaggtactggcaatttggccaggtgtggttggttcacgcctata   13250
atcccaacactttggagggtgaagtgggcgaattgctagagcccaggag     13300
gtgaggctgcaatggcctgagatcacgccatccatcgtactccagcctggatg 13350
atgagaatgaaatcctgtctcaaaaaaaaaaaaaaaaaaagaagaa        13400
```

Fig. 16 i

```
gaagaagtattggcaatcagtgctccaggaataattcctgacttgaaat      13450
aaacctacacatgtagacaaactagttttcagagcattccaggaagttgctagcat   13500
tggtttaatatgttttcagagcattccaggaagcagtgtggccagcattg         13550
catgtttgatacttcagaaatgtatgacagagtgtttctcttaccagtgtc        13600
ttctgtttttcttagttttgctcatgtaaatatttatgaacatcctcatct        13650
ttttgaggaaggattatagatcattctaattccattttctagcatttg           13700
gtaccattctaagcacatgataggcacccatttgagcatttttggcttg          13750
acagaatatgcattagaattgttcaaattagaggtgtcagtgatgggaa          13800
ttagaatactatataattctaagtcatttgacttaaatacaaaagaatga         13850
tttcttggtgggaatggtgaaggaggcaggagttaagagaagaggaga           13900
agagatcctaagtcattttataaacttctctgaaagacaggtgtgtgaag         13950
acttttaaaaagtcattcaccaaattgtgtgtgtgtgtgtgtgtgtgtt          14000
ttaaatagactttatttttagagcagtttaggttcacagcaaaattga           14050
atgcaaggacagagattccataaaccccctgcccacacacacatgcatag         14100
cctccctcattatcaacatcccaccagagagtgtttgttctagttcacggcag      14150
gaacctacactgacacatcattatcaccaaagtccatagttcacggcag          14200
ggttcactgtcgtgtacattagtaacatacagagtatttcagtgccctgcaaat     14250
tgtatccaccattatagtaacatacagagtatttcagtgccctgcaaat          14300
cccctgttctccacctattcatcctcctgtccacttccaccccag              14350
ccctggtaaccgctgatctttttactgtcttccctagttctctattcat          14400
tttttcagacagacacagagctgtctcttccctagttctctattcat            14450
tcttttctcccatccatcataaaaggctatgagttttttttaagtgttg          14500
aacaccatcctacttgtcaagttaaaacataagctcctggctgggtacag         14550
tggctcatgcctgtaatctcagcattttgggaggctgtggcagaagcatc         14600
acttgaggccagaagtttgagaccagcctggcaacatagcaagacccca          14650
tccctccacacacacaaaaacaagctcttgccagaattagagctacaaattg       14700
cacacacacacaaaaacaagctcttgccagaattagagctacaaattg           14750
ccctcagttcctagaagatcagtccttcaattagattcagattgagatg          14800
cttcctcttttaaacaatgattccctttctctatccatgcccaataagaaaac      14850
```

Fig. 16j

```
aaataaaaattaaacaatactgcctgtaatctcagctacccaggaggcag      14900
agcagaactgcttcaacccggcaagcagacagagagcaagatttgcagtgaagtgagatc   14950
gcgccactgcactccagctggaaacagagcaagattctgtctcaaaaa              15000
caaacaatgtgattcctccctctaagtcctgcacaggaaatgttaaga              15050
aatagtccaccagaaagaagaagtaagaatgtttgactagattgtct               15100
tggaaaaaatagttatactttcttgcttgtcttcctaacagTTCTCCAAA            15150
                                          S  P  K
GCTTCGTACCTTGGCCAGAGGCTTGTCTCCTGCGTACCTGAGGTTTGGTG            15200
 L  R  T  L  A  R  G  L  S  P  A  Y  L  R  F  G
GCACCAAGACAGACTTCCTAATTTCGATCCCAAGAAGGAATCAACCTTT             15250
 G  T  K  T  D  F  L  I  F  D  P  K  K  E  S  T  F
GAAGAGAGAAGTTACTGGCAATCTCAAGTCAACCAGGgtgaaaattttta            15300
 E  E  R  S  Y  W  Q  S  Q  V  N  Q
aagattcactctatattttaattaacgtcagtcgtcatgagaatgcttt             15350
gagaaaactgttatttctcacacctaacaattaatgagattaacttcctc            15400
tcccctcatctgacctgtggaggaatctgaacaagagagaggcagtgg              15450
gcaggttcctatcatgatgttttgtcatgttcagtgtgaggcctcacaa             15500
aaaaaaaaaaaatattaataaaacagtgattgtgtagctaagagctcattg           15550
tacagtaaatattaataaaacagtagttgtagctaaactaaagagaactgct          15600
tggagggagcaagtgggtagaatcgcgtcaaactaaagagcattctagc             15650
caaagacacaatgatagattgaaggatatttattctaaatatagaatatg            15700
ggtgaacgagatctgtgacttctgggctccaacgttagattctgatttt             15750
agcaagcttgtgccctaggggattctgatattgaaaagcgtggcttcacctg          15800
agaaacctgcctgccctaggggccatgaaaatttgtcctgtcttttcagaagtg        15850
ctatcagacatcaaatggaagttaaatcgtatcttaacaattactaggat            15900
gggcgcagtgactcacacctgtaatcccaacactttgggaggctgaggca            15950
ggaggatcacttgagcccaggagtctcggaccagcctgggcaacatagag            16000
agacgttgtctctatttttaataattaaagagaaaaaaatactgaaaa              16050
tattgtatacaccactgaattatataataatgtgtatataatgtatatattc          16100
attatgaggaatatttgattatttcatatattatatctctttcctctgtt            16150
tatttatccagttatgaagtattagaacaattcatcagtaattgggggc             16200
```

Fig. 16k

```
taaattgacagaataqtaatcagagaaataqaaaaaqacaqatqqtta      16250
tctttgaataccaggttggagttgtttgtttatgggttgtttttgttttggg  16300
ggcgtttttttagacagagtcccactcctgttgccactctgttgccaggctgagtgcagt  16350
ggcacaagcatgcctcctgagtagctggaccacagtgcatgtcaccaca     16400
tccaccttagcctctgagtagctggaccacagtgtcttctatgttatcca    16450
cccagctaatttttttatttttgtagagacagtctttctatgttatcca     16500
ggctgatctcaaactcctgcactcaagtgatcccctgcctggcgtccc      16550
aaagtattgggattataggcatagccaccacgcccaacctagtttctatt    16600
tagacttgcgccctttccccaccagtcatttgtgtccaaaagatctcataaa  16650
tgtagacaggaaactgtcctttgctcatcagtttttctttcatcctgtgtct  16700
aggggatggtcgtgggggaaactgggttatgcaagttcctctgaaac       16750
atcctctgtgagccagggatggatgaggcaccagccgcagtcag          16800
tgtgcagctttccagaaagaagtcatcagcagtcagccggcccctggca     16850
gccagcaccggcaaccctgctgtctgtctgtgataaagaaatggtctgcctg  16900
acaggatggtgtgctctgtcgcccaggctggagtgcaatggcgggatcttgagacagg    16950
gtctggctctgtcgcccaggctggagtgcaatggcgggatcttggctcac    17000
tgcagcctctgcctcccaggctcaaggcatcctccaccgcccaactaagttttctgta    17050
agtagctgggaccacaggcacacacacaccacctagtttctgta          17100
tttttagtagaggcagggtttttactatgttgttgtccaggctagtctcaaact       17150
cctgagctcaagctatccatctgcctgcctccaaagagctgaatta        17200
caagcgtgagccactgtgcctgaccaggtggatttttcaagtgcacat      17250
gttggtgtcccagaagctctgatggtaccaaattccaagcgaaaaaagt     17300
caatggttcccaccccatcctccatgatgcaagaggaaatcacca         17350
cactgcagatacagtgcactatgcctataaacaaattgctatgaaagtg     17400
aacttaagagaactgcactatgtttcttcattagagttctctggtaat      17450
ttccagctctttttttttttttttagacagtgtctcgctttgtcgcc       17500
agtgtcaccaggctggagtgcagtgacgtgatctcgctcactgcaacc      17550
tccgcctcgtgggttgaagtgattctctgcctcagcctcctgagtagct     17600
gtatttttagtagagacgaggtttcaccatttggccaggctgtctcgaac    17650
tcctgacctcaagtgattcgcccatctcagcctcccaaagtgctgggatt    17700
```

Fig. 161

```
acaggtgtgagccactgcaccccggccagtaatttcaagcttctgaggagc     17750
cctttgaattgttaaataacttgtagctatgtccaacatatccatgttca      17800
gtgtatgttcgatatttcttaggaaacctgccctggttgttttctttgt       17850
ggtaattcatgagccggcaaatttgacatgtgttacagaatataccttttt     17900
ctctgctctcctacctcataacaacagaacttaattatcctgctttagtcac    17950
ataaatagctaactaaataaataatatgagatttcagtctgtcactgtga      18000
aaatagaccttctaaatgatctcttccacttgcagATATTTGCAAATATG      18050
                                     D  I  C  K  Y
GATCCATCCCTCCTGATGTGGAGGAAGTTACGGTTGGAATGGCCCTAC        18100
 G  S  I  P  P  D  V  E  E  K  L  R  L  E  W  P  Y
CAGGAGCAATTGCTACTCCGAGAACACTACCAGAAAAAGTTCAAGAACAG      18150
 Q  E  Q  L  L  R  E  H  Y  Q  K  K  F  K  N  S
CACCTACTCAAgtaagaaatgaaaggcacccctagagatgttccagcccca     18200
 T  Y  S
aagatatttgaataggttggactcgggcaccaatctagcaagtcctacgg      18250
aagttgtataaagctgaaaatactgaagcattcccaaatgggaaatcct       18300
aaactcaaaacttgcttttggttttttgttttgttttgttttctcttcat      18350
ctgacattgcttagtagtcacagaatgaaagataaatcaatcattcatga     18400
tctaacaatgaccttcagtgtctaaaaaaatacgagtcaaggaaaaca        18450
tgaatatattccttcatgtaaaattaaaatacagacatataaagggcaaaa     18500
catgaacatcattcataccttgagtccgtccccctcccagaaataaccc       18550
ccagtatgccttggtttagagcattaagcaggaggccctgagtcactcc       18600
agacagtcttgaccaccaggctagctcagctcagtcttctctgtgtggct      18650
tttgcaaaacagggctcttccagtcttcaaattaggatgatgcattgtcagtcac  18700
taaaacagtcttccagtcttcaaattaggatgacattgtcacatgggct       18750
ttaaagcaagtgaaacaaggaaacaaggaaccccctttttttttttgagatga   18800
atctcactcttgtcgcccagctggagtgcaatgcaatcttggctca         18850
ctgcaacctccacctcccaggttcaagagattctctgcctagcctcct        18900
attcattatgaggaatatatttgattattcagttcctgtagggtaaagatat    18950
taccccgatcatattattgattgatctgagtagctgagatacaggtgcct      19000
gccaccacgaccggctccaggctccaggtctcgtctcgaactcctgacctcaggt  19050
accatgttggccaggctccaggctccaggtctcgtctcgaactcctgacctcaggtga 19100
```

Fig. 16m

```
tccacccacctcagcctcccaaagttctgggattacaggcgtgagccacc      19150
actcctgccacaatccttttttaactatgaaatatattttatctgaag        19200
tttgatgttatacccaactgagggatgatgttcccatatctcagttaaa       19250
gaaataacctgctcagatacttcaagctcttgttttgggttagttaacattatttaa   (19300)
aatgatcttgaagttactatactttgtttgggttagttaacattatttaa      19350
agtatattatttttaattaattatcttttgtaagatttttactgtatactacc   19400
tggagttcaatgtatcagatgattcaaatttatgtacattttatgt          19450
atatggtacagaaaaaatgtgatccataagaaatcagaaaatagcgcat       19500
atgctaatagctaatgttgtgtcctctaaaaaactatttttgcattttaa      19550
gagggatatactctgacactttaatagtgtaattaattattgactgg         19600
aatttggcatgaggcaggccatttcagatcccattaaaggaatgacaca       19650
taccagagaaccacagaagtaaggccacatttgtaataatcattatagc       19700
tctgctaggagaagaccagttgtattagtaattaatgatttgctctt         19750
aaaacacatgtcccggaagatacttcattcactttactactttacag         19800
cattataccaatgtatcttacatttctaagaaagtttactactttacag       19850
gatcttttctgttaccacaggggaaatgccttccttgctaactatgcaacca    19900
catagttcctacaccaggggaaatgccttccttgctaactatgcaacca       19950
ggttagttgtaagtccagcacgtcatttgtaaacatttgattctgctcga      20000
acaaacacagaattttattgcattgcacgtcatgtgacaaatattcagaagccaatagg  20050
aattttcagtttttcatggcacgtcatgtgacaaatattcagaagccaatagg   20100
agtttgggcacctactcattgttctgaacctgtagtgctgagactggtaatggctgag   20150
ggattccacaaattgttctgaacctgtagtgctgagactggtaatggctgag    20200
tgacatggggacataccaccatgcttagctagtggcctgcacccttaaaacacatgt    20250
aaggacatgttcattgcttagctagtggctcacgcctgtaatccagcactttgggagg  20300
cccaggctgggcggtgttacctgaggtcagagttcgagaccaacctggcca     20350
ctgaggcgggtggattacctgaggtcagagttcgagaccaacctggcca       20400
acatagtgaaacctcattctactaaaaatacaaaaattagccaggcatg       20450
gtggcgggcgcctgtagtcccagctactcaggaggcaggagattgcgccaccgca  20500
cttgaatctgggaggcagaggttgtgtgagccgagattgcgccaccgca       20550
```

```
cgctagcctggggcgacaaagtgagactctgtctcaaaaaacaaaacaa      20600
aaaacaaacaaaaacaaacaacaacaacaaaaaaacgggtatcccagaa      20650
gatacaggtaagttttctaacacagtcctctgtatggtgcgttccact       20700
taagtagagatgacaaaaacatttgtcatgagaatatagactcacattt      20750
taaacctgtttgagcaggaaaaggaagcaatgttacagatgtaattctgg     20800
gtgtgactgcagaaaggatgactccctattaaagtagtcatcctgagtg      20850
agctaactctttgtacttcctcctctcctgttccctcatcaccca          20900
ttcttccgttgcctacacccaggcccacattggatgctgacatagactta     20950
catggtacagtccaagggaaagatctgccatttttttcaatgtgtcatct     21000
tggttatcttcattccaagatctctccactctttatacagtaagagatg      21050
agagtctgaaagtgggaataagataatgaattgtaagttttaaatt         21100
gttcttcgtatttgggaaggagtaggctaggtggtccagacgtggtggctcacgcc 21150
ttttgttttttttttaaagtagatgtggccagacgtggtggctcacgcc     21200
tgtaatcccagcactttgagaggctgaggcaggcaggtgatcacttgatgtca  21250
ggagttcaagaccagcgcctgccaacacagtgaaacccgtctttactaaa     21300
aatacaaaaaactagccggcttggtgcgtccacctgtagtccagctac       21350
tgcagaggtggaggcaggagaatcacttgaacccggagctggaggttgc      21400
agtgagccaagatcatgccattgtactccagcctgggcgacagaacaata     21450
ctctgtctcaaaaaagaacctctattccaggagatgttacagttgattatgt  21500
actcagtcgtcaatagcctctataatttcgagctatgtaaattccaagtgcatt 21550
tataggggtgtataataagaaatggaggaaggtaaagtatgagtgcaagcattcc 21600
tggaagaatgaagaaatgctataatctttgttcagggctagtacaaagtgct   21650
agttttttgaaaatctctataatctgaggttcctgtccaggctagtacaaagtgct 21700
atttagctgtaagggttttttgtgattacagacagttttcacatgtgtc      21750
atttcaaccttggtttatgggaagcatgtgatggtgcttgtcccagg        21800
actttagatccatatctgaggttcctgtcgggcaaagatattaccccctga    21850
tcatattatagtctataagtggggacttcctacaacatgattttgcaagtctta 21900
tgattctgatccaggcacttcctacaacatgatttgcaatataaaag        21950
cctataatgtgactaaagcaggtcactcacccccttgtaacagactcta      22000
gtaatggtactgccaccaaacggctgcgtgatattgggcaaagactttacc    22050
ttatttgaatctcagttcctcctagaaaaatgagggtgaggttaagca       22100
```

Fig. 16o

```
taggctgtgatcctaaagcctccatactgcccctaaactgtgctctaag      22150
atccagtagaatgctgggtcacaggactctaggagctcttcaaacccaa      22200
atgtctgtcattccttgatggtaggcagcagtttatgaagtgggcgaca      22250
cagcaaatatcaaaatacctaaagcagcttgcaagagttgtttctgccta      22300
gtggtctttatagttaatattaaatagttaattttttttttttgagac      22350
agagtgtttgctctgttacccaggctgcagtgcagtggcacaatctcggct    22400
cactgcaacctccacctcccggtttgagcatttctgtctcagcctccca      22450
agtagctgggactacaggtgcatgcaccctgcaccagctaattttttgtat    22500
ttttagtagagacggggtttcaccatattgggcaggctggtctcgaactc     22550
ttgacctcaggtgatccacctgcctcagcctcccaaagtgctgggattac     22600
agcatgagccactgcacccagcttaaatagctaatatttaatattattc      22650
tatagttattcaagtaattcaggccaaagactttagaaaacaaaacaaaaaag  22700
ccactttttaaggagaaagggtgtaagtttgccagatagatagatctttt     22750
cttttttaactacaagagttcaggaatgaattactctttaacaaacgact     22800
atagatatacatgaaagatctattatgcatatgataatcaat             22850
ttaaagacaacacttaaaattatatttgttgccactctcaaaaagtggtaa    22900
tagaacagctaatgttaaaaagcagagtacagaagttcccaaacttat       22950
ggcaccttaatatcgcagaaaaacttttaaaattgtaaggtctacacaacctaataagt 23000
aatacctgtattttgattattaaattgtaaggtctacacaacctaatagt    23050
gcaaacttaaaagatcctacagtgctctgtaaatagcactgcctgttta     23100
gagttgaatttcagatataatttttttttcatgttaattattttcttt      23150
ctttacttttttttttttgtttttttgttttttttttgagaca           23200
gggtctcattctgtcgttgccaggctgctgtgtgcaatggcatggctc       23250
actgcagccttgacctcctgggctacagtgcttacaagtgatcatggctc    23300
ccaagtagctagctgggactacaggtgcttaccatcatgcccgctaatt      23350
tttgtttttttgtagagatgtggtttgccatgttgccagctggtct        23400
tgaactcctggcctcaagtgatccgccgcctcggcctcccaaagtgcta     23450
ggatgacaggcatgagccactgcacctgcgccctggggcgaagtatttctt   23500
aatggttacataggacatacactaaacattattgtctatatgaagt        23550
```

Fig. 16p

```
tcaagtttaactagtgtgccctgcacttttagttgctaaatcctgtagctg      23650
tacccatgcattcactggtgctcccagcttgcccttgcacagagtttgga        23700
aaccatagtcctataataataacagaatttttttaaaaatttgattc           23750
attttaaattaaaaattatcaaaatatttttaaacttgtgttttaaa           23800
tataattaaaattatcaaaatatttttaactgctaactaatgacagtctggcta    23850
atttagattatgaagagtggggtttatgctaactaatgacagtctggcta        23900
tgcatgtggagcactgagctagctataaattgtggcttcccaattctcctgat     23950
gtcacttgaacaaaacctaagtgtcagacagcaaatgaagtcagattgattttttt  24000
tgggatttcattcaacagctgtgagcaaatgaagtcagattgatttttttt       24050
aatttgtccaattttgtgtctccaaaaacaacataattataatcattattag      24100
aactagaatttcttcagtttaacaacagaaatagttattcattatgaaaa        24150
gcgaatctggaggcctcattgtggtgccaatctaaccattaaattgtga         24200
cgttttctttttagGAAGCTCTGTAGATGTGCTATACACTTTTGCAAACT        24250
               R  S  S  V  D  V  L  Y  T  F  A  N
GCTCAGGACTGGACTTGATCTTTGGCCTAAATGCGTTATTAAGAACAGCA        24300
 C  S  G  L  D  L  I  F  G  L  N  A  L  L  R  T  A
GATTTGCAGTGGAACAGTTCTAAATGCTCAGTTGCTCCTGGACTACTGCTC       24350
 D  L  Q  W  N  S  S  N  A  Q  L  L  D  Y  C  S
TTCCAAGGGGTATAACATTTCTTGGGAACTAGGCAATGgtgagtacccca        24400
 S  K  G  Y  N  I  S  W  E  L  G  N
gggaacaattcattaataaggagattcccactagcattattcttttttct        24450
ttctttttctttttctttttttttttttttgagacagagtctcgcactgc        24500
tgcccaggctggagtgcagtggcgcaatctcggctcacttgaagctctgc        24550
ctcccaaaacgccattctcctgcctcagcctccgagtagtgggactac          24600
aggcaccgccacgcgcccggctaattttttttttttttttttttttttt         24650
ttttttgcatttttagtagagacggggtttcaccgtgttagccaggatg         24700
gtcttgatctcctgacctcgtgatctgcccttccggcctcccaaagtgc         24750
tgggattacaggcgtgagccaccaggcccggctagcattattcttatga         24800
cacttttttttttttgagacggagtctcgctctgtcgcccaggctgg           24850
agtgcagtggcgccatctcggctcactgcaagctccacctccccaggttca       24900
cgccattcctcctgcctcctgcctccagcctcccgagtagctagctgggactacacgcacccg  24950
```

Fig. 16q

```
ccaccacgcccggctaatttttttgtattttagtagagacggggtttca    25000
ccgtgttagccaggatggtctctatatcctgacctgatctgcccgcc      25050
tcggcctcccaaagtgtgggattacaggcgtgagccactgcgcccggcc    25100
aacactctttttattattagcaaatatactctgcctggcacattcttg     25150
caagtgctcaacaatgcaactttggaagtgcatgtggcagaaactcctg    25200
ctgtatttattccagaacctattattgctaatcccagtttatgttacatt   25250
tgaagtgagaaccagttggagccagcaacgttcccagctccaaagttccc   25300
ttgagatttccagaatcacttaaccctattatgcttggcaacctggactc   25350
agcaaaactgggaagtcagcagttgttttattcatccctccttctca      25400
gtttctcaaatgtgtcagttaatctcagtaaccccattgcaaccttcatt   25450
acctgcccaagcggtctagaacttgccagtatagaatcctacgtgggtca   25500
agctcctgactgtctcctttcttcactcttttttgcaaagaacttgtaaa   25550
ttttaactataagtattcatgattcgccacattcattcaaaaacatagagt  25600
gcttttttccacatatcagcaatgacaagtcttcttcctgctcaaacttttttt 25650
atgtagtaataggataacaagatcttctctctgttaccaggctggagtgcagt 25700
tttttttttcagacaacaagatcttctctctgttaccaggctggagtgcagt  25700
ggcgtgttcatagtcaatgtcaacctccaactcctggctcatgcaatct    25750
ctcacacctcagccctgattagctaggactacactatgcctagccaat     25800
tttttttctttttgtctggttgtgtgtgcccggccttctgatctcctggc   25850
ctcaagtaatcctcctgcccggtctccttgcctgcctcaaaccttttttccaaagtaagtaatgaagtt 25900
tgagccactgtgcccggtatatagtctagttccagatatccattgttt    26000
attagatatgaattaactttcaaattgtttttctggagtatcttatttataa 26050
attaccctcattattaacttcaaattgttttctggagtatcttatttataa  26100
ttatacagtttaaattttgtttctttgatttttttgagacagacgcttg   26150
ctatgagtttttacttacttatttatttttgagacagacgcttg        26200
ctctgtcactcaggctgagtgcgtgcgtgatcatgctcactaggc        26250
ctcgaccttctgggctcaagtgatcctccctcagcctcccaagctgag    26300
actacaggcatgcaccaccatgttaccacgagtggtctcaaactcctgccctcag 26350
aacaaggcttactatgttaccacgagtggtctcaaactcctgccctcag    26400
gggatcctcctgtctcagctcagcctaccaaaatgctggattacaggcatgagc 26450
```

Fig. 16r

```
cataqcqccaqacctqtqtttctacttttcttqacttttqaattacaaqtttt       26500
tgtaatttggaaaatgttttgtctttaaatactgctgtatgttttgct            26550
tttaaatacaacatttctcgatatatatttgagaatttgctgtctttcag          26600
AACCTAACAGTTTCCTTAAGAGGCTGATATTTTCATCAATGGGTCGCAG           26650
 E  P  N  S  F  L  K  K  A  D  I  F  I  N  G  S  Q
TTAGGAGAAGATTTTATTCAATTGCATAAACTTCTAAGAAAGTCCACCTT          26700
 L  G  E  D  F  I  Q  L  H  K  L  L  R  K  S  T  F
CAAAAATGCAAAACTCTATGGTCCTGATGTTGGTCAGCCTCGAAGAAAGA          26750
 K  N  A  K  L  Y  G  P  D  V  G  Q  P  R  R  K
CGGCTAAGATGCTGAAGAGgtaggaactagagatgcagaatcactttac           26800
 T  A  K  M  L  K  S
ttttctcttttcctttgagacagagtctcactctgtcagccagactg             26850
gagtgcagtggtgcaatcatgctcactgcgacctccaggctc                  26900
aagcaatcctccatcgctactttaaaaatagctggactacaggtgcac            26950
atcaccacacctgtgccaggctggtctcttgaattcctgtgctcaagccatcct      27000
ccctgttgccacctcagcctcccagagtgccagagttacaggcatgagccaccacac   27050
tccacctcagcctcccagagtgccagagattacaggcatgagccaccacac         27100
ccagccaccactttttcttaaaaaaaaaaagattctctctgtagacaa            27150
tcctcaatagtccacatgttattaaacaatctgctgcctgaatacatgat          27200
ttaccaaaaaaggaaatttgacgggttcagaatatcaagggatctgag            27250
gcaaatgtcacctatgatgataatgcagtaacagtcctatcaaaatttaggaagtttgtgt 27300
ttacctgatcctaaagcagtacatatatgtctaggaatactgact               27350
catgcgtatatttgtcatataatgactgatgatgatgataatgaa               27400
atttttttttctagCTTCCTGAAGCTGGTGGAGAAGTGATTGATTCAGTT          27450
 F  L  K  A  G  G  E  V  I  D  S  V
                                                            27500
ACATGGCATCAgtaagtatgtctcctattcttaatactaggaaagtaagg          27550
 T  W  H  H
ctagcttttattattacctagtattcaaaaagttagttcatttaactgcc          27600
aattgactgcagttcagttcaaataagaacaaatagtgtctcaagtagcactgt      27650
actccaattttaatattaataataaaaaatttaagttatttaaataatg           27700
tagtggtttctataaagatcacttatacagaagaacagtgccaattaac           27700
```

Fig. 16s

```
ccatgaacatataagtagctaaaccaattgcttgccaagaaccagta            27750
accagagtacatgtccttgccactgtgttttcaagacagagtaact              27800
gatttctagttacttgcatagaatggactcctcctcataactcccttcca          27850
tcttgtctttccctagtagaacttctctacctttttagtaacaggtgag           27900
tgggaggtaaggaagaggagaataaggtcagcaattaacctaaaagcagaa         27950
agtaaaattgttgttattttttctgaatatttttctgtgtaatttagCTAC         28000
                                                   Y
TATTTGAATGGACGACTGCTACCAGGGAAGATTTCTAAACCCTGATGT            28050
 Y  L  N  G  R  T  A  T  R  E  D  F  I  N  P  D  V
ATTGGACATTTTATTTCATCTGTGCAAAAAGTTTTCCAGtaatagtct            28100
 L  D  F  I  S  S  V  Q  K  V  F  Q
ttttaaacttttttaatgtaaaaccagaatcctatttatagtctagcta           28150
gttctaaattctatagtatgtattacatgttttctaatttagag                28200
aacaagcactatgacttatccactgttagtttcccttagcattgggtc            28250
ttacccatgtacgtgattagaatatgagttgaaatatttccaatagcctttag       28300
tagaattaactcacatagatgataagaatggttggttcacttcatgttc           28350
cttccacacgcctactatttcaataactatataggaggggtttcccaagacctaaatg   28400
actatgaacatatttttataactcttcaacaccacagttgaaaccacaggtca       28450
aagtttgaatgctgttaatcttctgttaatcttctatacttttctgttctataGTGGTTGAGA  28500
gcttttttgcaattaccatgatacttttctgttctataGTGGTTGAGA            28550
                                          V  E
GCACCAGGCCTGGCAAGAAGGTCTGGTTAGGAGAAACAAGCTCTGCATAT          28600
 S  T  R  P  G  K  K  V  W  L  G  E  T  S  S  A  Y
GGAGGCGGAGCCGCCCTTGCTATCCGACACCTTTGCAGCTGGCTTTATgtg         28650
 G  G  A  P  L  L  S  D  T  F  A  A  G  F  M
agtgaagcagcgctggcctaggggtcagagtgcagctcttctccatcct            28700
tctattctgctgaaatagctccccagctccaaaaagcagatcaaagaccgtt         28750
tcagtggctgagctgaggacatcttaacaagtgttccaaattaatcactata        28800
actaaagcttgagggacatcttaacaagtgttccaaattaatcactata           28850
aggatgaattgtttcagaaattttggcctttaattatgccataaatat            28900
```

Fig. 16t

| | |
|---|---|
| gtcaagtagtcctactctaaagaagtacactgtaaaagaatgcatatag | 28950 |
| ccggatatggtagttccctgtaatcccaatactttgggaggccaaggtgg | 29000 |
| gaggattgcttgagcccagagtttgagcctgcagtgagttatgatggtg | 29050 |
| ccactgcactctagactggcaacagagtgagactgtctcttttttccc | 29100 |
| ctctgtcaccagactggagggcagtggcacgatctcacctcactgcaac | 29150 |
| ctctgcctcccggattgaagcgattctcctgcctcagcgtcctgagtagc | 29200 |
| tgggactacaggagtatcaccgcactgggctaattttttgtattttagta | 29250 |
| gagacggggttttgacatgttgcccagcgtggtctgaaaccatgagctc | 29300 |
| aagtgatctgcctacctcagccttccaaaatgctggattacggacatga | 29350 |
| gctaccacgcccggccacacccctgtctctctcaggaggatactagtgtatgtag | 29400 |
| ttagagcatattacagctttgtcttcaagaagtttagagcctaaagtatgaggtccc | 29450 |
| ctataattcatagattcccaagaagtttagagccttaagtatgaggtccc | 29500 |
| accagagggctatcattaaatttaaagatttgttaaatcatctcattgt | 29550 |
| ccaacaccacaaacttgattgcttttaaatctgtttagttacatttag | 29600 |
| taactctattagtgctttctcttccatctcttctctatatctgtctatatcctcacattgagat | 29650 |
| tttttttctttctcttcatcttattttacattttacccgctgactgca | 29700 |
| ttataagcctagaataacatcacaaatcctttatgccataactaagatgtccatat | 29750 |
| gaataaagaatggagatgtttgttttgccattaactaaagatctggggtg | 29800 |
| tcggggagaaggggatagagaaggagaagtggaagagagtgtccataat | 29850 |
| agcttagtgcaattctgcttattttcacattttaccccgctgactgcca | 29900 |
| ctttttcttcagccctcacacattgtttgtgcaggaccctcatagagacca | 29950 |
| ggaattgtctatagaggtgggaattttgtctccacctgaaagggatacctc | 30000 |
| tagcatgtaatagtcttctagagattgttatcatatgaaagatgtaaa | 30050 |
| gggaggattctgctgctgctgctgcatgcagttgccatttcat | 30100 |
| ttaaatgacttattttataattgatgacactttctgcttcctgttaatt | 30150 |
| cctccctcaaagatcaataaaccagaaccagagttcacctgccatgcacttg | 30200 |
| tggtcctgtaaccaccccaacaggttccacctgcctgctgtctagatagag | 30250 |
| ccaattatcaagacagggaattgcaaaggagaaagagtaatttatgcag | 30300 |
| agccagctgtgcaggagaccagagctttaattactcaaatcagtctcc | 30350 |
| ccgaacattcgaggatcagagctttaaggataatttggccggtaggggc | 30400 |
| ttaggaagtggagagtgctgttggtcaggttggagatggaatggaatcacaggg | 30450 |

Fig. 16u

```
agtggaagtgaggttttcttgctgtcttcctgtcctgatgggatggcag            30500
aactggttgggccagattaccgtctggtggtctcaaatgatccaccca             30550
gttcagggtctgcaagatatctcaagcactgatcttaggttttacaacag           30600
tgatgttatcccaggaacaatttgggaggttcagactcctggagccag             30650
aggctgcattatccctaaaccgtaatctctaatgttgtagctaattttgtt          30700
agtcctgcaaagtagacttgtccccagcaagaaggggtcttttcaga              30750
aaaggctattatcatttttgtttcagagtcaaaccatgaactgaatttc            30800
ttcccaaagttagttcagcctacacccaggaatgaagaaggacagcttaa           30850
aggttagaagcaagatggagtcaatgaggtctgatctctcttcactgtcat          30900
aatttcctcagttataattttttgcaaaggcggtttcagtcccagctactt          30950
gggaggctgagacaggaggattaatgagcccaggagtttgaggttgcag             31000
agagctatgatcacgccactgcactccagcctggtgacagagtgagacc             31050
ctgtctctaaataataaataagtaataataaatacataaataaaatc              31100
aagatggtgcaattagaattgagcgattttgtttccaaacctcaagaa             31150
agcttggtcttgctctgtcccagGTGGCTGGATAAATTGGGCCTGTCAGC            31200
                        W  L  D  K  L  G  L  S  A
CCGAATGGAATAGAAGTGGTGATGAGGCAAGTATTCTTTGGAGCAGGAA             31250
 R  M  G  I  E  V  V  M  R  Q  V  F  F  G  A  G
ACTACCATTTAGTGGATGAAAACTTCGATCCTTTACCTgtaagtgaccat           31300
 N  Y  H  L  V  D  E  N  F  D  P  L  P
tattttcctaattctagtggagtagattaaagtcaactcaggacctctgg           31350
tgttaacctcctatgaacagtcagtcctctcagtaactagccaaatcatg           31400
agatgattagaatgaaggagcccttagatagcatccaatctaacattttt           31450
tgtgtgtttgaaagagaagaaatcaagagctagaataacttttaaaggt            31500
aagccatttgcagtatagtgtggattgtgttaaaataagttggattttcaaatgttt    31550
atttatgactcattatacaagacaaaataagttggattttcaaatgttt            51600
tacaaagtaaatcaagttatattgcctacagtacgcaaagcttcaaaa             31650
cattttttatgttatgaattgtaatttatttaacctaaaatgagcag              31700
taccatgtgtttgcttaaaaatctcatgctaagaatttactatgttgtta           31750
ataatcttcaagatatttatgaataaagtcttatttctaatccttcctcc           31800
```

Fig. 16v

```
aactgtatctggtgctaaatcaggaaatgttcttcccaaaagcctcgt    31850
ggaagatctgtatgtctaaatatatgtcaggatatgtcaggatgtagccc  31900
tgcgaagcatgacctttgattttatagtctaaaatgtcatttgcagatat  31950
ctattttctaagaataattcctaaaagaattatttgaatgttgtaggaaa  32000
gctaagaaatttgcaaagagcgtacgtgaaaatataagctaggcttttg   32050
tggtttgtgatagacttcccaacaaaattgcttttttatctatagtgatc  32100
caagcttgtgaacatattagtcatctcttttgaaaattcttagaaaa     32150
gtgatcttgcaaaaatgaattatcttcccaagtatattctgtcatg      32200
tatagagttaaactaagcatagtaattcaccagacaaacattcaaaatc   32250
tactcctgaccttttatctcatccaaatttcccaggcccagacataa     32300
acctttgccttacgaactctctttgtatatgcactaaatatgcttctcttc 32350
aaggttctcagtcagctagataaaatgtgcaagagtaaatgtaccctct   32400
cacttgtagatccaagagaattagacttaaactcactctacatgtctgtg  32450
actttatttattttgcatgacagtcctgtgaggtggcaaggcaggtatct  32500
tggatccattttttagataaggaagttcaaattgagaagaggttgcatga  32550
tttacaggaagccatactgtagtcctagtctaaaatcccattc         32600
aaatcctgcttctgaggcctgcatacttctacccacccagtcattgacc   32650
catgcttatgtctcctttgaaaacattgattccactcttgtctgttgtgtt 32700
aaaagtggaatttaagcagagagaaacaaagccattgtggggtatgtg    32750
actttcccctactttcaagagaaagtggggtatgtgttttgaatggtg    32800
atttatttattattttattttaaaaattgatacaaggtcttactgta     32850
tgtgcaggctggtctccaaactcctggctcaagtgatcatcccaccctca  32900
gcctcccagtgttgggattacagcatgaaccattgtgccaccaccgatc   32950
cgcagttttaagaaaaactttactatagaaattttaatcatataca      33000
aaatacagagaagtatatgaaccaccttttaggagactagaatatgcca   33050
cccaaaatatgccactttggcataaaaagttctgtcctttctccattgc   33100
tgggaagaaacacatagaagaaagttctccccctccttttctacccagga  33150
aagcaggacatgaatcttaaaagtcgaagataacttcagaccctta      33200
aaaacaagagttaatcactgaagatattacatactcattcatttccttccac 33250
gatggcactagaagaactctatattcagacccttatcagtgtaga       33300
aacttgccaccccagagactaagctggagtctcatgtctcttg         33350
tccaaaaatttqctctataagctggagttctaagcctgagtcttaqaqaat 33400
```

Fig. 16 w

```
tacttgttccctggtatttctgttaacatacatgtattaatatacatgt   33450
taacaagcttctgttgttttgttttctctgttttctgttcctgttacagaggt   33500
ccatcccaactaagaactaaagagtaggaggaaaatataatttcctcctg   33550
catactttgatcctgttaatccgtaaccctcccacttttcacctccta    33600
cctattagattacttgaagcaaatttcagatatattacttatctataa    33650
atattcagtatgtgctaggtgtggtggctcacacctgtaatcccaacac   33700
tttgggaagctgaggcaggaggatcacttgagcccaggagttcaagacca  33750
gctacggcaacaaaaatcaaaaacttatctgggcatgtggcacatgcc    33800
tgtggtcccagctacatgagaggctgaggcaggagatcgcttagccca    33850
ggaggttgaggctgcagtaagctgcattcacaccactgccactccagcctg 33900
ggtgacagagtaagaccatgtctcaaaaaaaatacatattttagtatgtat 33950
cctttttgtaaaaacacacaaatattttatcatactttaaataataacaata 34000
attccttagtatcaccaaatattttgtcagtgtctcacattttccttatt  34050
gtctaaaatattgttgatagtattcaaatcagaatccaaaacaaggtcca  34100
tatattacattggttgacaagtctcttaagttgttcatctttaagttc    34150
ttcctccctctcttttcatctctcttgtaattttattaatgtgaaaaacaggt 34200
aatttgttctatagtattcctacattatagagtttgctacattttattcc  34250
ctatgatatcattagcatgttcctctgtccctgtgtttcctgtaaact    34300
ggtagttataccatagaagcttgagtttattcaggtttttaattgtattt  34350
tttgcaagaattcttttattatctgcttctggaagcacagaatgtctggt  34400
tgtgtctggttttgatcttgacagctactgatgacattgcctaatccat   34450
tacttttattgggtgtggggaataaggttttaaaataaattttttttaaa  34500
gattttttaactgttatttgagacagtgtctcattcgttctgttcccaggc  34550
tggagtgcagtggcacaatcacggctcactgccttgacctcctggga    34600
tcaggtgatcttctcacctcagcctcccgggtacctgaactacaggtgc   34650
acaccaccacacctggctaattttttgtattttttgtgtacagaaggggttt  34700
catcatgttcccagactggtcttgaactcctggttcaagtgatctacc    34750
cacttcagctcccaaaatcctggattacactttggccaccgtgcctgg   34800
cctaaatgaaattattgtctctaaacagacagaagtttacttttaaaaa   34850
```

Fig. 16x

```
tttgtctttgtgtgtacatgtgtttgtgtatgtgtgtctaaaagtt         34900
tggctttgagctttgtgcttgaattcttgatgaacaataaccaagaatac     34950
ttaaactctgatcattctgacagatatccctacaggctatggccttt        35000
gaattgtcctccagtgatgataaaaagcagcaagcacgatactgctctcag    35050
attcatggtggtcacatgtgaggtgaacagtgatactcttgtagataactattg 35100
tttaaatgccccaggataacagtgatactcttgtagataactatttg        35150
cttgccactggtttcattaataaggacataagtaaagatctattttgt       35200
ctcttctcccccaaccaccaccaactagGATTATTGGCTATCTCTTCTGTT    35250
                              D  Y  W  L  S  L  F
CAAGAAATTGGTGGCCACCAAGGTGTTAATGGCAAGCGTGCAAGGTTCAA     35300
 K  K  L  V  G  T  K  V  L  M  A  S  V  Q  G  S
AGAGAAGGAAGCTTCGAGTATACCTTCATTGCCACAAACACTGACAAgtaa    35350
 K  R  R  K  L  R  V  Y  L  H  C  T  N  T  D  N
gtatgaaacacaccctttaccaatcatcaagttttagtgggtaagcctgt     35400
aacttactcaaacaccctgttgcatgtctatacattgcataagtata        35450
ggcagttgcaattagtaaagtctactttgttgttgttgttgcataagttttat  35500
ttttagaagaaaaaatgctacttgtgtgttgttgtttttgagacgggc      35550
ctcgctcgtcaccaggctgagtgctgcagtgtgcaatctcagctcactgc     35600
aacctccgcctcccgggttcaagtgattcttgaagagagaacaataata      35650
acaacaatattattttgtagcctccatactcttgcttcttaggtagtagcaaaaat 35700
gacatcgagatttttgtagcctccatactcttgcttcttaggtagtagcaaaaat 35750
gttcctaaatctcaggaatatctctagacactctagatagtttcaatctatcattcc 35800
tgataagatgatgctgaaatctagcaaataacctcgatagtgaggaccccagtag 35850
atttccgattgttggggaatgtttgaatggataaattcataaaaatgtcag    35900
gaagtagcgagggaatgttgaatggataaattcataaaaatgtcag         35950
tagatttaattcttctactttcagtcttttataaggctaggaaaaag        36000
cccctgttttatggttttatagtttaattgaatcacatgaaccacaaattt    36050
gccttttaccttcctatgtctgaaatgatagtctggtgtctctagcccagaca  36100
caaccagctgcaagctgtgaacattttaattgtgttttcaaatagagca      36150
ttggtagcatgaacggcaacattttaattgtgttttcaaatagagca        36200
cactagcggtctaaaacgatcataaagaaggatactaagagggcccact      36250
```

Fig. 16y

```
gtcattatggatcctaatacttaggatgcattatggattgtcattatgga         36300
tactaatacttaggatcacatttgtaattgagttttaattgcttaaatt          36350
agatacatattctattaagttaaccctctctttgctcttttagTCCAAGGTATA     36400
                                          P  R  Y
AAGAAGGAGATTAACTCTGTATGCCATAAACCTCCATAATGTCACCAAG          36450
 K  E  G  D  L  T  L  Y  A  I  N  L  L  H  N  V  T  K
TACTTGCGGTTACCCTATCCTTTTTCTAACAAGCAAGTGGATAAATACCT         36500
 Y  L  R  L  P  Y  P  F  S  N  K  Q  V  D  K  Y  L
TCTAAGACCTTTGGGACCTCATGGATTACTTTCCAAgtaagtaattttcc         36550
 L  R  P  L  G  P  H  G  L  L  S  K
ttgttcattccaaactttcaataaatttattggtgtttatcagaatagag         36600
agtttggacaggggagcaaaagacaaagtcaactatatcaagttctaataa        36650
ttcttaatattcaggaaatttatgtatgaatactactaatatgagtata         36700
actcatcctaagagtctaagcaaaggatgtgaacacaaactagcagtt           36750
atcttagagaataagtttgcatttcaaataacttgacatatcaagatcc          36800
actcaacgcatttaaattattactctaaaaagacataattcttggtaac          36850
acattcactaaagcaaaatatcatacctttatataattgctatcaaaggtatg      36900
tgggttggtataaatttattggttagagtaagaaatagctagagtatat          36950
agcattaatttttattgtttctcatacacttgttcaaaaaccaattattgact      37000
ttcttaagtagattctcatacacctgtattcaatgagtgcaaaaatgactatgag    37050
acatcttataaaagcctgttaggcatataatatttttaaggttttctgttcaatgtatg 37100
tcttaaagagttaggcatataatatttttaaggttttctgttcaatgtatg        37150
ttggaaggagttccttcctttctcatgactattctcatattggagcataaaaag     37200
agtttacaggcttggcgcagtgcgcagtgcctgtaatcccaatacttttgg        37250
gaagctgaagcaggcaggcagaactctctctcacttcagcaggagtttgagaccagcctg 37300
ggcaatatggcaaactctgtagtccagctacttgggaagctgagtgggagg        37350
tggtggtgcatgcctgtagtcccagctacttgggaagctgagtgggagg          37400
attgcttgagcccagcctgggtgcagtggctgctgagctgtgatggtgcct        37450
ctgtcacccagcctgggtgacagagtgacagaccctgtctcaaaaaataaa        37500
taaataaaattaagagtttacaaatttctcaccatctcctcccatcttt          37550
```

Fig. 16z

```
gcaaatgccacataagtgatgtgttccaggactattagcctcggaacctg      37600
aggcagtacagtaagcacgcttctccaaagtcctgtccccacacagacaa      37650
acattattacactgggtactgctctcttttattttcccctctatgcttt       37700
attttactactataactataatcatataacatgtaataggaaaaaggcaggt    37750
cggggagagatccagaagtcttcccagagccttccaacatagcctct         37800
gtagacatttttctttcttcttttttttttttttctgagaca              37850
gagtctcactctgttgtccaggctagagtgcagtggcgtgatctaggctc      37900
actgcaacctccgcctcctggttcaagcaattctcccacctcagcctcc       37950
ctagtagctgggattagaggcatgcatcaccacgcctggctaatttttgt      38000
attttagtagagatgagtttcaccatgtgggccagctggtcttgaac         38050
tcctgacctcaagtgatccacctgcctagcctcccaaagtgctaggatt       38100
acacgagtgagccaccgtgcccctgcccctattacattctgatcacacatt     38150
tcatgttttataattggaaaactggtgaaattatagacaatgttttgttc      38200
ccctaaattctctttgatgagtatattactttactacactctctgtcttta    38250
aaatttgcaaaatagtatcctagatatagtttatgagtgcacagtctgta     38300
cgcttactcatattaatgacctcggagagtaaacaacagtcacacttaa       38350
aaattattactatcattatcattatttttgaggcggggtctcattctgt     38400
ctcccaggctggagtagtggtgcggtcacagtcactgcagccacgc          38450
tacctgggctcaagtgatcctcctcagccttctgagtagctgagac          38500
cacaggcttatgcgtacaccacacctggctaatttttttaacttttttgtagaga 38550
cgatgtctcattatgttgccaggctgtctccaaactcctaagctcaagt       38600
gatcttcctcagcctccaaaattattaggtcctgcatagctgaaaaactgc     38650
accagccctaaaaattctgtttttttaaaaaaaaatagagacaaggtctc      38700
atttaaatgaacatctctgttcttcatctgaactcctggactcacgcaatcctgct 38750
actatattgcccaagctgctggttctcgaactcctggactccacgcaatcctgct 38800
gccttagccgcccaagtgctgggattacaggcatgacccacctcatctg       38850
ggctgagtgaacatattttaacataaaggccgtatttttatattatctc      38900
atacattttgcccagcatcccccattttccgccgaatctgttgttgctaat    38950
tccttccagcttcattcatctgaaatttgacaaacatcttctattttctt    39000
tgtcgtcatgttattgacttcagaatataaaatataaaacactataccaa    39050
ttaaaccccacccctcattgccagcctgatgtgtgaaaataatcagcataca    39100
```

Fig. 16aa

```
ttaagcttacccttgatatatgtgtagcatcttttagataaatatacagc    39150
tgattaagcaatatagcctgatggtataatatcttgcccatgtacctcat    39200
cttatctccagcaggattaattcacagtgatcagatttacctttaaactt    39250
tgtagcaaaatatcctctccaaaagcatatctaaaactttgtgtgtact    39300
cttgcaagtttcttaatttcatgcagaacaggctcttaccactgttagct    39350
ggagatattttcaagacctattttgttgtggttcctgatgatggtca      39400
tggcatttcccccttcactcctccatctaaaaattgaggtgatacaggctttt 39450
aaacaaaccaactcatatagactgagtacaactgtcaatgcaggcatgct    39500
aacctctgctacaatcatgggcgtgctattgatatgtcttaagttacaga    39550
acacaggctgagcgtcttaattagtcaaaatgtaaaccagttttttctgc    39600
tcactgatgcttaatgaggacaggtgtgagagatattcttttaaggaaaac   39650
aaatatataataatactaatatctcaacattagaagaattaag           39700
taaataaactaatatactcacaccatggttgtgagaaaaatacagtattaaaat 39750
tatgtagtggatggatgtttaatggtgtgagaaaaatacagttaggatgtgctg 39800
gggtgggggaagaatcaagttttaagaaatacagtatacccatactta      39850
agtaaaaaaaaaaaggtatgtacagtcagtcatgtgttgctcctgttgatgg  39900
ggatacattccgagaagtgaacttacacacaaacctagatggtcgatggtgtgaac 39950
atcatagagtgaacttacacacaaacctagatggtctagctactatgtatc   40000
taggctatatgactagcctgttgctctcctaggctacacaacctgtaaagcat  40050
gttactgtagcgaatatacaaatacttaacacacttaacacatgcaagctatcattg 40100
tgttaagtagttgtgtatctaaatgacatagacatcataaaacataaaactataagt 40150
gttgtgctacaatgttacaatgttacatgacatgctaggcaatagaatt    40200
ataatttatccttttatggaaccacacttatatatgcggtccatggtgg     40250
accaaacatcctatgtggcatatgactgtatacatgtacacaaaaaat     40300
agatgaaagaatgaatatacatcaaatatttaaaatgttataatgact      40350
taggtacttttattattcttagtaataataatgatgatagatatactt     40400
ttatagtgtttactatataaaagacactgttataactgttctacatactt    40450
tacatgtattacctaaatgatataaatataactctgacagtaactaatct   40500
tatacgttctctttttctttttttttttctttttttagacagaatctt    40550
gctctaccaggctgagctggagtgcaggtgcaatctcgctcactgcaacctcc 40600
```

Fig. 16bb

```
gcctccaggttcaaacgattctcatgtctcagcctcctgagtagctggg       40650
actacaggcacacaccatgcccgctggccatgccctaattttgtattttgggtag  40700
agatggagtttgccatgttgccaggctgatcttgaactcctgcctca          40750
agtgatctgcctgcctcagcctcccaaagtgctggattacaggtgtgaa        40800
ccactgtgctcggcctaatcttacaagtttcaatatttaaagagtgcta        40850
actttgttgacaatataaaacatatttgagaaaaagagatataagcatct       40900
tatttagaattatgaaatatcaatagacctacagccgactaaagctttt        40950
cttcataagctcttgcctatattgattcgctcctgtgaatatgcattaat       41000
ttgatttaaataataagtatgttttaattgtataagaaataacacttttccttaatttt 41050
taagaacgttcaacagtttttaatttgaattccaatagtgaaatacatag       41100
aaaatataaaatttctgtagtttagcacagtaagaaaattgttttgtttcaccaca 41150
gcattctaccaaaatttcttaataacagtaagaaatgaatgcatacctc        41200
ctgcaggagggggagttaggcagtttatggcatagttacaagtgaga          41250
aatttcattgctaccatttcgctaaattcataaaaactgcattcaatt         41300
ctatatctatttctttacatataaaaggtttcaattattggccatta          41350
aataaatagccaccattccagaagttgtgtcatgttctgttttctata         41400
ccaccatcatattgcctattatatagattgtgtgttgttccatttctgta       41450
atgggccagacagtaagtatttctgcttggcttccatatggtctctat         41500
cataactactcatctctgccattgtagcttaaagattatctaggtcaaat       41550
gcctaagtgatatagtgttgaaatacaagttatataatataggctgccac       41600
aaaaaaaatttattggtctaaaaagatttcatgactttgtagcagc          41650
atgggtggcatgcaccacttgttaactcggtgtatcttctccttg            41700
cagATCTGTCCAACTGTCTAACTCTAAAGATGGTGATGATCAAA             41750
   S V Q L S N G L T L K M V D D Q CCTTGCCACCTTTAATGGAAAACCCTCTCCGGCCAGGAAGTTCACTGGGC       41800
 T L P P L M E K P L R P G S S L G TTGCCAGCTTTCTCATATAGTTTTTTGTGATAAGAAATGCCAAAGTTGC        41850
 L P A F S Y S F F V I R N A K V A TGCTTGCATCTGAAAATAAAATATACTAGTCCTGACACTGaattttcaa        41900
```

Fig. 16cc

```
          A  C  I  *
gtatactaagtaaagcaactcaagttatagagaaggaagcagatacct    41950
tgcaaagcaactagtgggtgcttgagagacactgggacactgtcagtgct   42000
agatttagcacagtattttgatctcgctaggtagaacactgctaataata   42050
atagctaataataccttgttccaaatactgcttagcatttgcatgtttt    42100
actttatctaaagtttttgttttgtcttgtcacccaggctgagtgccatggtgcgat  42150
ttgagacagaatctctctgtcacccaggctgagtgccatggtgcgat     42200
cttggctcactgcaacttaagcaattctcctgcctcagctcctgagta    42250
gctgggattataggcgtgtgccaccgcccagctactttctatattttt    42300
tgtagagatggagtttcgtcctcaagtgccaagctgtctcgaactcctgt   42350
cctcgaactcctgtcctcaagtgatccaccgcctcagcctctcaaagtg   42400
ctgggattacaggtgtgagccaccacaccccagcagtgttttatttttgag   42450
acagggtcattctgttgcccaggcttgagtgcagtgtgcaatcatag     42500
atcactgcagcctttaactcctggctcaagtcatcctcctgcttagcc    42550
tcccaagtagctaggaccacagacacatgccatcacacttggctatttt   42600
aaaaaatttttgtagagatgggtctctgctatgttaccaaactggtcc    42650
tgaactcctggactcaattgatcctccacttggccttccagttgctgg    42700
gatttcttgggagtacagcatggtacagcaggagatcatttgatgttac   42750
ctctgtgcagtgttgctagtcagcgaaagactatataaccgtgtggggaca   42800
gcgattagccaccacaaccagtcttcatttattaaagttattaaaatggctg 42850
ggcgcagtggctcacacctgtaatcctagcactttgggaggccgaggcag  42900
atggatcacctgacgtgaggaatttgagaccagcctgccaacatggtga   42950
aacccatctctactaaaaatacaaaaaattagctgggtgtggtcctgta   43000
gtcccagctacttgggaggctggggcaggagaattacttgaacccaggag  43050
gcagaggttgcagtgagccgagattgtgccactgcactccagcctgggtg  43100
acagagagattccatctcaaaaaaacaagttattaaaaatgtatatga    43150
atgctcctaatatgtcaggaagcaaggaagcgaaggatatattatgagt   43200
tttaagaaggtgcttagctgtatatttatcttcaaaatgtattagaaga   43250
tttagaattctttccttcctcatgtgccatctctacaggcaccatcagaa  43300
aagcatactgccgttaccgtgaaactggtttgtaaaagagaaatatctat   43350
ttgcaccttaaaagacagctagattttgctgatttttctttctttcggtttt  43400
```

Fig. 16dd

```
ctttgtcagcaataatatgtgagaggacagatt gttagatatgatagtat    43450
aaaaaatggttaatgacaattcagaggcgaggagattctgtaaacttaaa      43500
attactataaatgaaattgattgtcaagagagataaatttagaaaacac       43550
ccaataccttataactgtctgtcttggctta gcttgcttttctctacctt ctt 43600
cctgtttcagttggaagctttggctgcaagtaacagaaactcctaat         43650
tcaaatggcttaagcaataagga aatgtatattccacataactagacgt      43700
tcaaacaggccaggctccagctcgctctgccatcttta gcgctggcttcattctcagac  43750
cttcccagctctctgctctgccatcttagcgctggccccttcaaacctcat      43800
tctggtagcatgatggctgtagctgtttca tggctgtctcctt catagact    43850
agcaaccagaggaagaaaatgagccattttt tgagtctccttcatagact     43900
tgaataactcttttcagagcttctcacagcaaacctctcctcatgtctc        43950
ctcatgtcttatt gtttcagaaatgggtaatgtggccatttcaccagtcac     44000
tgccaacaacaacgaggttcctataattgtctctgagtaacccttt ggaa     44050
tggagagggtgtgtcagtctacaaactgaacactgcagttctgcgctt         44100
tttaccagtgaaaaaaatgtaattatttt ccccctcttaaggattaatattc    44150
ttcaaatgtatgcctgttatggatagtatcttt aaaatttttatttt         44200
aatagctttagggg tacacactttt gcttacagggg tgaattgtgtagt    44250
ggtgaagactcggcttttaatgtacttgtcacctgagtgatgtacattgt      44300
acccaataggtaatt tt catccctta taccactgtgta tgtt ct ccctt   44350
ctgagtctccaacatccccttataagtgagaaca tgagata tttg ttt ttccatt 44400
agctaagcttccacttccccttaggatataacagccccagttccgtccaagttgct 44450
cctgagttactt ccccttaggatataacagccccagttccgtccaagttgct   44500
gcaaatacattatt cttcttt tatgctgagtaatagtccatgg tacata     44550
tataccacattttcctttat ccactta tcagttgatggacacttaggt taa    44600
ttccatt caattt catt caatt tttcaatactctta aatttt ataaccttgatatt   44650
aaaaatta aattttaga tctt ccaa tactctt aaatttt atatgtaagtgg        44700
ttt tatatttt cacattt gaaa taa gtaa ag cctacact ctt gatatt         44750
gtatgactatt ctttt tagtaa tgtaa ag ccta cagact ccta cattt ga       44800
accactagtgtgttgttt caccccttg ttata ctatcaggatcctcga            44898
```

Fig. 16ee

```
human   MLLRSKPALP PPLMLLLIGP LGPLSPGALP RPAQAQDVVD LDFFTQEPLH      50
mouse   ~~~~~~~~ML RLLLWLWGP LGALAQGAPA GTAPTDDVVD LEFYTKRPLR
rat     ~~~~~~~~~~ ~LLLLWLWGR LRALTQGTPA GTAPTKDVVD LEFYTKRLFQ human   LVSPSFLSVT IDANLATDPR FLILLGSPKL RTLARGLSPA YLRFGGTKTD     100
mouse   SVSPSFLSIT IDASLATDPR FLTFLGSPRL RALARGLSPA YLRFGGTKTD
rat     SVSPSFLSIT IDASLATDPR FLTFLSSPRL RALSRGLSPA YLRFGGTKTD human   FLIFDPKKES TFEERSYWQS QVNQDICKYG SIPPDVEEKL RLEWPYQEQL     150
mouse   FLIFDPDKEP TSEERSYWKS QVNHDICRSE PVSAAVLRKL QVEWPFQELL
rat     FLIFDPNNEP TSEERSYWQS QDNNDICGSD RVSADVL~~~ ~~~~~~~~~~ human   LLREHYQKKF KNSTYSRSSV DVLYTFANCS GLDLIFGLNA LLRTADLQWN     200
mouse   LLREYQKEF  KNSTYSRSSV DMLYSFAKCS GLDLIFGLNA LLRTPDLRWN
rat     ~~~~~~~~~~ ~~~~~~~~~~ ~~~~~~~~~~ ~~~~~~~~~~ ~~~~~~~~~~ human   SSNAQLLLDY CSSKGYNISW ELGNEPNSFL KKADIFINGS QLGEDYIQLH     250
mouse   SSNAQLLLDY CSSKGYNISW ELGNEPNSEW KKAHILIDGL QLGEDFVELH
rat     ~~~~~~~~~~ ~~~~~~~~~~ ~~~~~~~~~~ ~~~~~~~~~~ ~~~~~~~~~~ human   KLLRKSTFKN AKLYGPDVGQ PRRKTAKMLK SFLKAGGEVI DSVTWHHYYL     300
mouse   KLLQRSAFQN AKLYGPDIGQ PRGKTVKLLR SFLKAGGEVI DSLTWHHYYL
rat     ~~~~~~~~~~ ~~~~~~~~~~ ~~~~~~~~~~ ~~~~~~~~~~ ~~~~~~~~~~
```

Fig. 17

```
rat       ----------  ----------  ----------  ----------  ----------
                                                                     350
human     NGRTATREDF  LNPDVLDIFI  SSVQKVFQVV  ESTRPGKKVW  LGETSSAYGG
mouse     NGRIATKEDF  LSSDALDTFI  LSVQKILKVT  KEITPGKKVW  LGETSSAYGG
rat       ----------  ----------  ----------  ----------  ----------
                                                                     400
human     GAPLLSDTFA  AGFMWLDKLG  LSARMGIEVV  MRQVFFGAGN  YHLVDENFDP
mouse     GAPLLSNTFA  AGFMWLDKLG  LSAQMGIEVV  MRQVFFGAGN  YHLVDENFEP
rat       ----------  ----------  ----------  ----------  ---------- human     LPDYWLSLLF  KKLVGTKVLM  ASVQGSKRRK  LRVYLHCTNI  DNPRYKEGDL
mouse     LPDYWLSLLF  KKLVGPRVLL  SRVKGPDRSK  LRVYLHCTNV  YHPRYQEGDL
rat       ----------  ----------  ----------  ----------  ----------
                                                                     500
human     TLYAINLHNV  TKYLRLPYPF  SNKQVDKYLL  RPLGPHGLLS  KSVQLNGLTL
mouse     TLYVLNLHNV  TKHLKVPPPL  FRKPVDTYLL  KPSGPDGLLS  KSVQLNGQIL
rat       ----------  ----------  ----------  ----------  -------- L
                      543
human     KMVDDQTLPP  LMEKPLRPGS  SLGLPAFSYS  FFVIRNAKVA  ACI-
mouse     KMVDEQTLPA  LTEKPLPAGS  ALSLPAFSYG  FFVIRNAKIA  ACI-
rat       KMVDEQTXPA  LTEKPLPAGS  SLSVPAFSYG  FFVIRNAKIA  ACI-
```

Fig. 17 (continued)

```
    |MLLRSKPALPPPLMLLLLGPLGPLSPGALPRPAQAQDVVDLDFFTQEPLHLVSPSFLSVT|  60
PHD |      EEEEE                     HHH         EEEE    EEE|

|IDANLATDPRFLILLGSPKLRTLARGLSPAYLRFGGTKTDFLIFDPKKESTFEERSYWQS| 120
PHD |EEE      EEEEE  HHHHHH  HHIHE     EEEEE             HHHHHH|

|QVNQDICKYGSIPPDVEEKLRLEWPYQEQLLLREHYQKKFKNSTYSRSSVDVLYTFANCS| 180
PHD |HHHHHHHH    HHHHHHH HHHHHHHHHHHHHHHH      EEEEEEEEEEEE    |

|GLDLIFGLNALLRTADLQWNSSNAQLLLDYCSSKGYNISWELGNEPNSFLKKADIFINGS| 240
PHD |  HHHHHHHHHHHHHHHHHHHHHHHHHHHHHHH    EEEEE   HHHHHHH EEEE  |

|QLGEDYIQLHKLLRKSTFKNAKLYGPDVGQPRRKTAKMLKSFLKAGGEVIDSVTWHHYYL| 300
PHD |   HHHHHHHHHHHHHHHH             HHHHHHHHHHHH    EEEEEEEEEE |

|NGRTATREDFLNPVLDIFISSVQKVFQVVESTRPGKKVWLGETSSAYGGGAPLLSDTFA | 360
PHD |            HHHHHHHHHHEEEEEEE    EEEEEE          HHHHHHHH |

|AGFMWLDKLGLSARMGIEVVMRQVFFGAGNYHLVDENFDPLPDYWLSLLFKKLVGTKVLM| 420
PHD |HHHHHHHH   HHHH HHHHHHHHHHH    EEEEE     HHHHHHHHHHH  EEEEE|

|ASVQGSKRRKLRVYLHCTNTDNPRYKEGDLTLYAINLHNVTKYLRLPYPFSNKQVDKYLL| 480
PHD |EEE   E  EEEEEEEE       EEEEEE     EEEEE        HHHHHHHH|

|RPLGPHGLLSKSVQLNGLTLKMVDDQTLPPLMEKPLRPGSSLGLPAFSYSFFVIRNAKVA| 540
PHD |HH    EEEEEEE  EEEEE                        EEEEEEEE EE  |

|ACT|                                                         543
PHD |   |
```

Fig. 19 und POLYPEPTIDE HAVING HEPARANASE ACTIVITY

This is a continuation of U.S. patent application Ser. No. 09/258,892, filed Mar. 1, 1999, now abandoned which is a continuation-in-part of PCT/US98/17954, filed Aug. 31, 1998, which claims priority from U.S. patent application Ser. No. 09/109,386, filed Jul. 2, 1998, now abandoned, which is a continuation-in-part of U.S. patent application Ser. No. 08/922,170, filed Sep. 2, 1997, now, U.S. Pat. No. 5,968,822.

FIELD AND BACKGROUND OF THE INVENTION

The present invention relates to a polynucleotide, referred to hereinbelow as hpa, encoding a polypeptide having heparanase activity, vectors (nucleic acid constructs) including same and genetically modified cells expressing heparanase. The invention further relates to a recombinant protein having heparanase activity and to antisense oligonucleotides, constructs and ribozymes for down regulating heparanase activity. In addition, the invention relates to heparanase promoter sequences and their uses.

Heparan sulfate proteoglycans: Heparan sulfate proteoglycans (HSPG) are ubiquitous macromolecules associated with the cell surface and extra cellular matrix (ECM) of a wide range of cells of vertebrate and invertebrate tissues (1-4). The basic HSPG structure includes a protein core to which several linear heparan sulfate chains are covalently attached. These polysaccharide chains are typically composed of repeating hexuronic and D-glucosamine disaccharide units that are substituted to a varying extent with N- and O-linked sulfate moieties and N-linked acetyl groups (1 -4). Studies on the involvement of ECM molecules in cell attachment, growth and differentiation revealed a central role of HSPG in embryonic morphogenesis, angiogenesis, neurite outgrowth and tissue repair (1-5). HSPG are prominent components of blood vessels (3). In large blood vessels they are concentrated mostly in the intima and inner media, whereas in capillaries they are found mainly in the subendothelial basement membrane where they support proliferating and migrating endothelial cells and stabilize the structure of the capillary wall. The ability of HSPG to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of the heparan sulfate (HS) chains may therefore result in degradation of the subendothelial ECM and hence may play a decisive role in extravasation of blood-borne cells. HS catabolism is observed in inflammation, wound repair, diabetes, and cancer metastasis, suggesting that enzymes which degrade HS play important roles in pathologic processes. Heparanase activity has been described in activated immune system cells and highly metastatic cancer cells (6-8), but research has been handicapped by the lack of biologic tools to explore potential causative roles of heparanase in disease conditions.

Involvement of Heparanase in Tumor Cell Invasion and Metastasis: Circulating tumor cells arrested in the capillary beds of different organs must invade the endothelial cell lining and degrade its underlying basement membrane (BM) in order to invade into the extravascular tissue(s) where they establish metastasis (9, 10). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (9). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (10). Among these enzymes is an endo-β-D-glucuronidase (heparanase) that cleaves HS at specific intrachain sites (6, 8, 11). Expression of a HS degrading heparanase was found to correlate with the metastatic potential of mouse lymphoma (11), fibrosarcoma and melanoma (8) cells. Moreover, elevated levels of heparanase were detected in sera from metastatic tumor bearing animals and melanoma patients (8) and in tumor biopsies of cancer patients (12).

The control of cell proliferation and tumor progression by the local microenvironment, focusing on the interaction of cells with the extracellular matrix (ECM) produced by cultured corneal and vascular endothelial cells, was investigated previously by the present inventors. This cultured ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13, 14). The ability of cells to degrade HS in the cultured ECM was studied by allowing cells to interact with a metabolically sulfate labeled ECM, followed by gel filtration (Sepharose 6B) analysis of degradation products released into the culture medium (11). While intact HSPG are eluted next to the void volume of the column (Kav<0.2, Mr~$0.5 \times 10^6$), labeled degradation fragments of HS side chains are eluted more toward the $V_t$ of the column (0.5<kav<0.8, Mr=$5-7 \times 10^3$) (11).

The heparanase inhibitory effect of various non-anticoagulant species of heparin that might be of potential use in preventing extravasation of blood-borne cells was also investigated by the present inventors. Inhibition of heparanase was best achieved by heparin species containing 16 sugar units or more and having sulfate groups at both the N and O positions. While O-desulfation abolished the heparanase inhibiting effect of heparin, O-sulfated, N-acetylated heparin retained a high inhibitory activity, provided that the N-substituted molecules had a molecular size of about 4,000 daltons or more (7). Treatment of experimental animals with heparanase inhibitors (e.g., non-anticoagulant species of heparin) markedly reduced (>90%) the incidence of lung metastases induced by B 16 melanoma, Lewis lung carcinoma and mammary adenocarcinoma cells (7, 8, 16). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide (7).

Heparanase activity in the urine of cancer patients: In an attempt to further elucidate the involvement of heparanase in tumor progression and its relevance to human cancer, urine samples for heparanase activity were screened (16a). Heparanase activity was detected in the urine of some, but not all, cancer patients. High levels of heparanase activity were determined in the urine of patients with an aggressive metastatic disease and there was no detectable activity in the urine of healthy donors.

Heparanase activity was also found in the urine of 20% of normal and microalbuminuric insulin dependent diabetes mellitus (IDDM) patients, most likely due to diabetic nephropathy, the most important single disorder leading to renal failure in adults.

Possible involvement of heparanase in tumor angiogenesis: Fibroblast growth factors are a family of structurally related polypeptides characterized by high affinity to heparin (17). They are highly mitogenic for vascular endothelial cells and are among the most potent inducers of neovascularization (17, 18). Basic fibroblast growth factor (bFGF) has been extracted from the subendothelial ECM produced in vitro (19) and from basement membranes of the cornea (20), suggesting that ECM may serve as a reservoir for bFGF. Immunohistochemical staining revealed the localization of bFGF in basement membranes of diverse tissues and blood vessels (21). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (15, 20, 22). It was demonstrated that heparanase activity expressed by platelets, mast cells, neutrophils, and lymphoma cells is involved in release of active bFGF from ECM and basement membranes (23), suggesting that heparanase activity may not only function in cell migration and invasion, but may also elicit an indirect neovascular response. These results suggest that the ECM HSPG provides a natural storage depot for bFGF and possibly other heparin-binding growth promoting factors (24, 25). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (26, 27). Moreover, the size of HS required for optimal effect was similar to that of HS fragments released by heparanase (28). Similar results were obtained with vascular endothelial cells growth factor (VEGF) (29), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (24, 25).

Expression of heparanase by cells of the immune system: Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of HS by a specific heparanase activity (6). The enzyme is released from intracellular compartments (e.g., lysosomes, specific granules, etc.) in response to various activation signals (e.g., thrombin, calcium ionophore, immune complexes, antigens, mitogens, etc.), suggesting its regulated involvement in inflammation and cellular immunity.

Some of the observations regarding the heparanase enzyme were reviewed in reference No. 6 and are listed hereinbelow:

First, a proteolytic activity (plasminogen activator) and heparanase participate synergistically in sequential degradation of the ECM HSPG by inflammatory leukocytes and malignant cells.

Second, a large proportion of the platelet heparanase exists in a latent form, probably as a complex with chondroitin sulfate. The latent enzyme is activated by tumor cell-derived factor(s) and may then facilitate cell invasion through the vascular endothelium in the process of tumor metastasis.

Third, release of the platelet heparanase from $\alpha$-granules is induced by a strong stimulant (i.e., thrombin), but not in response to platelet activation on ECM.

Fourth, the neutrophil heparanase is preferentially and readily released in response to a threshold activation and upon incubation of the cells on ECM.

Fifth, contact of neutrophils with ECM inhibited release of noxious enzymes (proteases, lysozyme) and oxygen radicals, but not of enzymes (heparanase, gelatinase) which may enable diapedesis. This protective role of the subendothelial ECM was observed when the cells were stimulated with soluble factors but not with phagocytosable stimulants.

Sixth, intracellular heparanase is secreted within minutes after exposure of T cell lines to specific antigens.

Seventh, mitogens (Con A, LPS) induce synthesis and secretion of heparanase by normal T and B lymphocytes maintained in vitro. T lymphocyte heparanase is also induced by immunization with antigen in vivo.

Eighth, heparanase activity is expressed by pre-B lymphomas and B-lymphomas, but not by plasmacytomas and resting normal B lymphocytes.

Ninth, heparanase activity is expressed by activated macrophages during incubation with ECM, but there was little or no release of the enzyme into the incubation medium. Similar results were obtained with human myeloid leukemia cells induced to differentiate to mature macrophages.

Tenth, T-cell mediated delayed type hypersensitivity and experimental autoimmunity are suppressed by low doses of heparanase inhibiting non-anticoagulant species of heparin (30).

Eleventh, heparanase activity expressed by platelets, neutrophils and metastatic tumor cells releases active bFGF from ECM and basement membranes. Release of bFGF from storage in ECM may elicit a localized neovascular response in processes such as wound healing, inflammation and tumor development.

Twelfth, among the breakdown products of the ECM generated by heparanase is a tri-sulfated disaccharide that can inhibit T-cell mediated inflammation in vivo (31). This inhibition was associated with an inhibitory effect of the disaccharide on the production of biologically active TNF$\alpha$ by activated T cells in vitro (31).

Other potential therapeutic applications: Apart from its involvement in tumor cell metastasis, inflammation and autoimmunity, mammalian heparanase may be applied to modulate: bioavailability of heparin-binding growth factors (15); cellular responses to heparin-binding growth factors (e.g., bFGF, VEGF) and cytokines (IL-8) (31a, 29); cell interaction with plasma lipoproteins (32); cellular susceptibility to certain viral and some bacterial and protozoa infections (33, 33a, 33b); and disintegration of amyloid plaques (34). Heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids. Common use in basic research is expected.

The identification of the hpa gene encoding for heparanase enzyme will enable the production of a recombinant enzyme in heterologous expression systems. Availability of the recombinant protein will pave the way for solving the protein structure function relationship and will provide a tool for developing new inhibitors.

Viral Infection: The presence of heparan sulfate on cell surfaces have been shown to be the principal requirement for the binding of Herpes Simplex (33) and Dengue (33a) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (33). There are some indications that the cell surface heparan sulfate is also involved in HIV infection (33b).

Neurodegenerative diseases: Heparan sulfate proteoglycans were identified in the prion protein amyloid plaques of Genstmann-Straussler Syndrome, Creutzfeldt-Jakob disease and Scrape (34). Heparanase may disintegrate these amyloid plaques which are also thought to play a role in the pathogenesis of Alzheimer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (35). Apart from its involvement in SMC proliferation (i.e., low affinity receptors for heparin-binding growth factors), HS is also involved in lipoprotein binding, retention and uptake (36). It was demonstrated that HSPG and lipoprotein lipase participate in a novel catabolic pathway that may allow substantial cellular and interstitial accumulation of cholesterol rich lipoproteins (32). The latter pathway is expected to be highly atherogenic by promoting accumulation of apoB and apoE rich lipoproteins (i.e. LDL, VLDL, chylomicrons), independent of feed back inhibition by the cellular sterol content. Removal of SMC HS by heparanase is therefore expected to inhibit both SMC proliferation and lipid accumulation and thus may halt the progression of restenosis and atherosclerosis.

Gene Therapy:

The ultimate goal in the management of inherited as well as acquired diseases is a rational therapy with the aim to eliminate the underlying biochemical defects associated with the disease rather then symptomatic treatment. Gene therapy is a promising candidate to meet these objectives. Initially it was developed for treatment of genetic disorders, however, the consensus view today is that it offers the prospect of providing therapy for a variety of acquired diseases, including cancer, viral infections, vascular diseases and neurodegenerative disorders.

The gene-based therapeutic can act either intracellularly, affecting only the cells to which it is delivered, or extracellularly, using the recipient cells as local endogenous factories for the therapeutic product(s). The application of gene therapy may follow any of the following strategies: (i) prophylactic gene therapy, such as using gene transfer to protect cells against viral infection; (ii) cytotoxic gene therapy, such as cancer therapy, where genes encode cytotoxic products to render the target cells vulnerable to attack by the normal immune response; (iii) biochemical correction, primarily for the treatment of single gene defects, where a normal copy of the gene is added to the affected or other cells.

To allow efficient transfer of the therapeutic genes, a variety of gene delivery techniques have been developed based on viral and non-viral vector systems. The most widely used and most efficient systems for delivering genetic material into target cells are viral vectors. So far, 329 clinical studies (phase I, I/II and II) with over 2,500 patients have been initiated Worldwide since 1989 (50).

The approach of gene addition pose serious barriers. The expression of many genes is tightly regulated and context dependent, so achieving the correct balance and function of expression is challenging. The gene itself is often quite large, containing many exons and introns. The delivery vector is usually a virus, which can infect with a high efficiency but may, on the other hand, induce immunological response and consequently decreases effectiveness, especially upon secondary administration. Most of the current expression vector-based gene therapy protocols fail to achieve clinically significant transgene expression required for treating genetic diseases. Apparently, it is difficult to deliver enough virus to the right cell type to elicit an effective and therapeutic effect (51).

Homologous recombination, which was initially considered to be of limited use for gene therapy because of its low frequency in mammalian cells, has recently emerged as a potential strategy for developing gene therapy. Different approaches have been used to study homologous recombination in mammalian cells; some involve DNA repair mechanisms. These studies aimed at either gene disruption or gene correction and include RNA/DNA chimeric oligonucleotides, small or large homologous DNA fragments, or adeno-associated viral vectors. Most of these studies show a reasonable frequency of homologous recombination, which warrants further in vivo testing (52). Homologous recombination-based gene therapy has the potential to develop into a powerful therapeutic modality for genetic diseases. It can offer permanent expression and normal regulation of corrected genes in appropriate cells or organs and probably can be used for treating dominantly inherited diseases such as polycystic kidney disease.

Genomic Sequences Function in Regulation of Gene Expression:

The efficient expression of therapeutic genes in target cells or tissues is an important component of efficient and safe gene therapy. The expression of genes is driven by the promoter region upstream of the coding sequence, although regulation of expression may be supplemented by farther upstream or downstream DNA sequences or DNA in the introns of the gene. Since this important information is embedded in the DNA, the description of gene structure is crucial to the analysis of gene regulation. Characterization of cell specific or tissue specific promoters, as well as other tissue specific regulatory elements enables the use of such sequences to direct efficient cell specific, or developmental stage specific gene expression. This information provides the basis for targeting individual genes and for control of their expression by exogenous agents, such as drugs. Identification of transcription factors and other regulatory proteins required for proper gene expression will point at new potential targets for modulating gene expression, when so desired or required.

Efficient expression of many mammalian genes depends on the presence of at least one intron. The expression of mouse thymidylate synthase (TS) gene, for example, is greatly influenced by intron sequences. The addition of almost any of the introns from the mouse TS gene to an intronless TS minigene leads to a large increase in expression (42). The involvement of intron 1 in the regulation of expression was demonstrated for many other genes. In human factor IX (hFIX), intron 1 is able to increase the expression level about 3 fold mare as compared to that of the hFIX cDNA (43). The expression enhancing activity of intron 1 is due to efficient functional splicing sequences, present in the precursor mRNA. By being efficiently assembled into spliceosome complexes, transcripts with splicing sequences may be better protected in the nucleus from random degradations, than those without such sequences (44).

A forward-inserted intronl-carrying HFIX expression cassette suggested to be useful for directed gene transfer, while for retroviral-mediated gene transfer system, reversely-inserted intron 1-carrying HFIX expression cassette was considered (43).

A highly conserved cis-acting sequence element was identified in the first intron of the mouse and rat c-Ha-ras, and in the first exon of Ha- and Ki-ras genes of human, mouse and rat. This cis-acting regulatory sequence confers strong transcription enhancer activity that is differentially modulated by steroid hormones in metastatic and nonmetastatic subpopulations. Perturbations in the regulatory activities of such cis-acting sequences may play an important role in governing oncogenic potency of Ha-ras through transcriptional control mechanisms (45).

Intron sequences affect tissue specific, as well as inducible gene expression. A 182 bp intron 1 DNA segment of the mouse Co12a1 gene contains the necessary information to confer high-level, temporally correct, chondrocyte expression on a reporter gene in intact mouse embryos, while Co12a1 promoter sequences are dispensable for chondrocyte expression (46). In Co11A1 gene the intron plays little or no role in constitutive expression of collagen in the skin, and in cultured cells derived from the skin, however, in the lungs of young mice, intron deletion results in decrease of expression to less than 50% (47).

A classical enhancer activity was shown in the 2 kb intron fragment in bovine beta-casein gene. The enhancer activity was largely dependent on the lactogenic hormones, especially prolactin. It was suggested that several elements in the intron-1 of the bovine beta-casein gene cooperatively interact not only with each other but also with its promoter for hormonal induction (48).

Identification and characterization of regulatory elements in genomic non-coding sequences, such as introns, provides a tool for designing and constructing novel vectors for tissue specific, hormone regulated or any other defined expression pattern, for gene therapy. Such an expression cassette was developed, utilizing regulatory elements from the human cytokeratin 18 (K18) gene, including 5' genomic sequences and one of its introns. This cassette efficiently expresses reporter genes, as well as the human cystic fibrosis transmembrane conductance regulator (CFTR) gene, in cultured lung epithelial cells (49).

Alternative Splicing:

Alternative splicing of pre mRNA is a powerful and versatile regulatory mechanism that can effect quantitative control of gene expression and functional diversification of proteins. It contributes to major developmental decisions and also to a fine-tuning of gene function. Genetic and biochemical approaches have identified cis-acting regulatory elements and trans-acting factors that control alternative splicing of specific mRNAs. This mechanism results in the generation of variant isoforms of various proteins from a single gene. These include cell surface molecules such as CD44, receptors, cytokines such as VEGF and enzymes. Products of alternatively spliced transcripts differ in their expression pattern, substrate specificity and other biological parameters.

The FGF receptor RNA undergoes alternative splicing which results in the production of several isoforms, which exhibit different ligand binding specificities. The alternative splicing is regulated in a cell specific manner (53).

Alternative spliced mRNAs are often correlated with malignancy. An increase in specific splice variant of tyrosinase was identified in murine melanomas (54). Multiple splicing variants of estrogen receptor are present in individual human breast tumors. CD44 has various isoform, some are characteristic of malignant tissues.

Identification of tumor specific alternative splice variants provide new tool for cancer diagnostics. CD44 variants have been used for detection of malignancy in urine samples from patients with urothelial cancer by competitive RT-PCR (55). CD44 exon 6 was suggested as prognostic indicator of metastasis in breast cancer (56).

Different enzymes or polypeptides generated by alternative splicing may have different function or catalytic specificity. The identification and characterization of the enzyme forms, which are involved in pathological processes, is crucial for the design of appropriate and efficient drugs.

Modulation of Gene Expression—Antisense Technology:

An antisense oligonucleotide (e.g., antisense oligodeoxyribonucleotide) may bind its target nucleic acid either by Watson-Crick base pairing or Hoogsteen and anti-Hoogsteen base pairing (64). According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triple helix structure.

According to both the Watson-Crick and the Hoogsteen base pairing models, antisense oligonucleotides have the potential to regulate gene expression and to disrupt the essential functions of the nucleic acids in cells. Therefore, antisense oligonucleotides have possible uses in modulating a wide range of diseases in which gene expression is altered.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, the regulation of transcription or translation levels.

Gene expression involves few distinct and well regulated steps. The first major step of gene expression involves transcription of a messenger RNA (mRNA) which is an RNA sequence complementary to the antisense (i.e., −) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the MRNA interacts with ribosomal RNA complexes (ribosomes) and amino acid activated transfer RNAs (tRNAs) to direct the synthesis of the protein coded for by the MRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more transcription factors to the promoter sequence. Additional proteins which bind at or close to the promoter sequence may trans upregulate transcription via cis elements known as enhancer sequences. Other proteins which bind to or close to the promoter, but whose binding prohibits the action of RNA polymerase, are known as repressors.

There are also evidence that in some cases gene expression is downregulated by endogenous antisense RNA repressors that bind a complementary mRNA transcript and thereby prevent its translation into a functional protein.

Thus, gene expression is typically upregulated by transcription factors and enhancers and downregulated by repressors.

However, in many disease situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites, bacteria or viruses, the disease progression depends on expression of the pathogen genes, this phenomenon may also be considered as far as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$-$10^{-1}$ millimoles per kilogram of body weight or $10^{-3}$-10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription (64).

At the transcript level, antisense oligonucleotides or analogs that bind target mRNA molecules lead to the enzymatic cleavage of the hybrid by intracellular RNase H (65). In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing (66). As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs (67).

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool (68).

For example, several antisense oligonucleotides have been shown to arrest hematopoietic cell proliferation (69), growth (70), entry into the S phase of the cell cycle (71), reduced survival (72) and prevent receptor mediated responses (73). For use of antisense oligonucleotides as antiviral agents the reader is referred to reference 74.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters (75).

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho intemucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives. For further details the reader is referred to reference 76.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—$SO_2$—). However, the application provides no data supporting the specific binding of an oligonucleotide analog to a target oligonucleotide.

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other (77). PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense oligonucleotides are typically synthesized in lengths of 13-30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials (57). A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dosens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target a MRNA that encodes an abundant and long-lived protein (57).

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Another approach is the use of specific nucleic acid sequences to act as decoys for transcription factors. Since transcription factors bind specific DNA sequences it is possible to synthesize oligonucleotides that will effectively compete with the native DNA sequences for available transcription factors in vivo. This approach requires the identification of gene specific transcription factor (57).

Indirect inhibition of gene expression was demonstrated for matrix metalloproteinase genes (MMP-1,-3, and -9), which are associated with invasive potential of human cancer cells. E1AF is a transcription activator of MMP genes. Expression of E1AF antisense RNA in HSC3AS cells showed decrease in mRNA and protein levels of MMP-1,-3, and -9. Moreover, HSC3AS showed lower invasive potential in vitro and in vivo. These results imply that transfection of antisense inhibits tumor invasion by down-regulating MMP genes (58).

Ribozymes:

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials (62). More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Gene Disruption in Animal Models:

The emergence of gene inactivation by homologous recombination methodology in embryonic stem cells has revolutionized the field of mouse genetics. The availability of a rapidly growing number of mouse null mutants has represented an invaluable source of knowledge on mammalian development, cellular biology and physiology, and has provided many models for human inherited diseases. Animal models are required for an effective drug delivery development program and evaluation of gene therapy approach. The improvement of the original knockout strategy, as well as exploitation of exogenous enzymatic systems that are active in the recombination process, has been considerably extended the range of genetic manipulations that can be produced. Additional methods have been developed to provide versatile research tools: Double replacement method, sequential gene targeting, conditional cell type specific gene targeting, single copy integration method, inducible gene targeting, gene disruption by viral delivery, replacing one gene with another, the so called knock-in method and the induction of specific balanced chromosomal translocation. It is now possible to introduce a point mutation as a unique change in the entire genome, therefore allowing very fine dissection of gene function in vivo. Furthermore, the advent of methods allowing conditional gene targeting opens the way for analysis of consequence of a particular mutation in a defined organ and at a specific time during the life of the experimental animal (59).

DNA Vaccination:

Observations in the early 1990s that plasmid DNA could directly transfect animal cells in vivo sparked exploration of the use of DNA plasmids to induce immune response by direct injection into animal of DNA encoding antigenic protein. When a DNA vaccine plasmid enters the eukaryotic cell, the protein it encodes is transcribed and translated within the cell. In the case of pathogens, these proteins are presented to the immune system in their native form, mimicking the presentation of antigens during a natural infection. DNA vaccination is particularly useful for the induction of T cell activation. It was applied for viral and bacterial infectious diseases, as well as for allergy and for cancer. The central hypothesis behind active specific immunotherapy for cancer is that tumor cells express unique antigens that should stimulate the immune system. The first DNA vaccine against tumor was carcino-embrionic antigen (CEA). DNA vaccinated animals expressed immunoprotection and immunotherapy of human CEA-expressing syngeneic mouse colon and breast carcinoma (61). In a mouse model of neuroblastoma, DNA immunization with HuD resulted in tumor growth inhibition with no neurological disease (60). Immunity to the brown locus protein, $gp^{75}$ tyrosinase-related protein-1, associated with melanoma, was investigated in a syngeneic mouse model. Priming with human gp75 DNA broke tolerance to mouse gp75. Immunity against mouse gp75 provided significant tumor protection (60).

Glycosyl Hydrolases:

Glycosyl hydrolases are a widespread group of enzymes that hydrolyze the o-glycosidic bond between two or more carbohydrates or between a carbohydrate and a noncarbohydrate moiety. The enzymatic hydrolysis of glycosidic bond occurs by using major one or two mechanisms leading to overall retention or inversion of the anomeric configuration. In both mechanisms catalysis involves two residues: a proton donor and a nucleophile. Glycosyl hydrolyses have been classified into 58 families based on amino acid similarities. The glycosyl hydrolyses from families 1, 2, 5, 10, 17, 30, 35, 39 and 42 act on a large variety of substrates, however, they all hydrolyze the glycosidic bond in a general acid catalysis mechanism, with retention of the anomeric configuration. The mechanism involves two glutamic acid residues, which are the proton donors and the nucleophile, with an aspargine always preceding the proton donor. Analyses of a set of known 3D structures from this group revealed that their catalytic domains, despite the low level of sequence identity, adopt a similar ($\alpha/\beta$) 8 fold with the proton donor and the nucleophile located at the C-terminal ends of strands $\beta 4$ and $\beta 7$, respectively. Mutations in the functional conserved amino acids of lysosomal glycosyl hydrolases were identified in lysosomal storage diseases.

Lysosomal glycosyl hydrolases including $\beta$-glucuronidase, $\beta$-manosidase, $\beta$-glucocerebrosidase, $\beta$-galactosidase and $\alpha$-L iduronidase, are all exo-glycosyl hydrolases, belong to the GH-A clan and share a similar catalytic site. However, many endo-glucanases from various organisms, such as bacterial and fungal xylenases and cellulases share this catalytic domain.

Genomic Sequence of hpa Gene and its Implications:

It is well established that heparanase activity is correlated with cancer metastasis. This correlation was demonstrated at the level of enzymatic activity as well as the levels of protein and hpa cDNA expression in highly metastatic cancer cells as compared with non-metastatic cells. As such, inhibition of heparanase activity is desirable, and has been attempted by several means. The genomic region, encoding the hpa gene and the surrounding, provides a new powerful tool for regulation of heparanase activity at the level of gene expression. Regulatory sequences may reside in noncoding regions both upstream and downstream the transcribed region as well as in intron sequences. A DNA sequence upstream of the transcription start site contains the promoter region and potential regulatory elements. Regulatory factors, which interact with the promoter region may be identified and be used as potential drugs for inhibition of cancer, metastasis and inflammation. The promoter region can be used to screen for inhibitors of heparanase gene expression. Furthermore, the hpa promoter can be used to direct cell specific, particularly cancer cell specific, expression of foreign genes, such as cytotoxic or apoptotic genes, in order to specifically destroy cancer cells.

Cancer and yet unknown related genetic disorders may involve rearrangements and mutations in the heparanase gene, either in coding or non-coding regions. Such mutations may affect expression level or enzymatic activity. The genomic sequence of hpa enables the amplification of specific genomic DNA fragments, identification and diagnosis of mutations.

There is thus a widely recognized need for, and it would be highly advantageous to have genomic, cDNA and composite polynucleotides encoding a polypeptide having heparanase activity, vectors including same, genetically modified cells expressing heparanase and a recombinant protein having heparanase activity, as well as antisense oligonucleotides, constructs and ribozymes which can be used for down regulation heparanase activity.

SUMMARY OF THE INVENTION

Cloning of the human hpa gene which encodes heparanase, and expression of recombinant heparanase by transfected host cells is reported herein, as well as downregulation of heparanase activity by antisense technology.

A purified preparation of heparanase isolated from human hepatoma cells was subjected to tryptic digestion and microsequencing. The YGPDVGQPR (SEQ ID NO:8) sequence revealed was used to screen EST databases for homology to the corresponding back translated DNA sequence. Two closely related EST sequences were identified and were thereafter found to be identical. Both clones contained an insert of 1020 bp which included an open reading frame of 973 bp followed by a 27 bp of 3' untranslated region and a Poly A tail. Translation start site was not identified.

Cloning of the missing 5' end of hpa was performed by PCR amplification of DNA from placenta Marathon RACE cDNA composite using primers selected according to the EST clones sequence and the linkers of the composite. A 900 bp PCR fragment, partially overlapping with the identified 3' encoding EST clones was obtained. The joined cDNA fragment (hpa), 1721 bp long (SEQ ID NO:9), contained an open reading frame which encodes a polypeptide of 543 amino acids (SEQ ID NO:10) with a calculated molecular weight of 61,192 daltons.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs:13 and 15, which encodes, as shown in SEQ ID NOs:14 and 15, a polypeptide of 592 amino acids with a calculated molecular weight of 66,407 daltons.

The ability of the hpa gene product to catalyze degradation of heparan sulfate in an in vitro assay was examined by expressing the entire open reading frame of hpa in insect cells, using the Baculovirus expression system. Extracts and conditioned media of cells infected with virus containing the hpa gene, demonstrated a high level of heparan sulfate degradation activity both towards soluble ECM-derived HSPG and intact ECM. This degradation activity was inhibited by heparin, which is another substrate of heparanase. Cells infected with a similar construct containing no hpa gene had no such activity, nor did non-infected cells. The ability of heparanase expressed from the extended 5' clone towards heparin was demonstrated in a mammalian expression system.

The expression pattern of hpa RNA in various tissues and cell lines was investigated using RT-PCR. It was found to be expressed only in tissues and cells previously known to have heparanase activity.

A panel of monochromosomal human/CHO and human/mouse somatic cell hybrids was used to localize the human heparanase gene to human chromosome 4. The newly isolated heparanase sequence can be used to identify a chromosome region harboring a human heparanase gene in a chromosome spread.

A human genomic library was screened and the human locus harboring the heparanase gene isolated, sequenced and characterized. Alternatively spliced heparanase mRNAs were identified and characterized. The human heparanase promoter has been isolated, identified and positively tested for activity. The mouse heparanase promoter has been isolated and identified as well. Antisense heparanase constructs were prepared and their influence on cells in vitro tested. A predicted heparanase active site was identified. And finally, the presence of sequences hybridizing with human heparanase sequences was demonstrated for a variety of mammalians and for an avian.

According to one aspect of the present invention there is provided an isolated nucleic acid comprising a genomic, complementary or composite polynucleotide sequence encoding a polypeptide having heparanase catalytic activity.

According to further features in preferred embodiments of the invention described below, the polynucleotide or a portion thereof is hybridizable with SEQ ID NOs: 9, 13, 42, 43 or a portion thereof at 68° C. in 6× SSC, 1% SDS, 5× Denharts, 10% dextran sulfate, 100 µg/ml salmon sperm DNA, and $^{32}$p labeled probe and wash at 68° C. with 3× SSC and 0.1% SDS.

According to still further features in the described preferred embodiments the polynucleotide or a portion thereof is at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to still further features in the described preferred embodiments the polypeptide is as set forth in SEQ ID NOs:10, 14, 44 or portions thereof.

According to still further features in the described preferred embodiments the polypeptide is at least 60% homologous to SEQ ID NOs:10, 14, 44 or portions thereof as determined with the Smith-Waterman algorithm, using the Bioaccelerator platform developed by Compugene (gapop: 10.0, gapext: 0.5, matrix: blosum62).

According to additional aspects of the present invention there are provided a nucleic acid construct (vector) comprising the isolated nucleic acid described herein and a host cell comprising the construct.

According to a further aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide having heparanase catalytic activity.

According to an additional aspect of the present invention there is provided a method of in vivo downregulating heparanase activity comprising the step of in vivo administering the antisense oligonucleotide herein described.

According to yet an additional aspect of the present invention there is provided a pharmaceutical composition comprising the antisense oligonucleotide herein described and a pharmaceutically acceptable carrier.

According to still an additional aspect of the present invention there is provided a ribozyme comprising the antisense oligonucleotide described herein and a ribozyme sequence.

According to a further aspect of the present invention there is provided an antisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity.

According to further features in preferred embodiments of the invention described below, the polynucleotide strand encoding the polypeptide having heparanase catalytic activity is as set forth in SEQ ID NOs: 9, 13, 42 or 43.

According to still further features in the described preferred embodiments the polypeptide having heparanase catalytic activity is as set forth in SEQ ID NOs: 10, 14 or 44.

According to still a further aspect of the present invention there is provided a method of in vivo downregulating heparanase activity comprising the step of in vivo administering the antisense nucleic acid construct herein described.

According to yet a further aspect of the present invention there is provided a pharmaceutical composition comprising the antisense nucleic acid construct herein described and a pharmaceutically acceptable carrier.

According to a further aspect of the present invention there is provided a nucleic acid construct comprising a polynucleotide sequence functioning as a promoter, the polynucleotide sequence is derived from SEQ ID NO:42 and includes at least nucleotides 2535-2635 thereof or from SEQ ID NO:43 and includes at least nucleotides 320-420.

According to a further aspect of the present invention there is provided a method of expressing a polynucleotide sequence comprising the step of ligating the polynucleotide sequence into the nucleic acid construct described above, downstream of the polynucleotide sequence derived from SEQ ID NOs:42 or 43.

According to a further aspect of the present invention there is provided a recombinant protein comprising a polypeptide having heparanase catalytic activity.

According to further features in preferred embodiments of the invention described below, the polypeptide includes at least a portion of SEQ ID NOs:10, 14 or 44.

According to still further features in the described preferred embodiments the protein is encoded by a polynucleotide hybridizable with SEQ ID NOs: 9, 13, 42, 43 or a portion thereof at 68° C. in 6× SSC, 1% SDS, 5× Denharts, 10% dextran sulfate, 100 μg/ml salmon sperm DNA, and $^{32}$p labeled probe and wash at 68° C. with 3× SSC and 0.1% SDS.

According to still further features in the described preferred embodiments the protein is encoded by a polynucleotide at least 60% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4).

According to a further aspect of the present invention there is provided a pharmaceutical composition comprising, as an active ingredient, the recombinant protein herein described.

According to a further aspect of the present invention there is provided a method of identifying a chromosome region harboring a heparanase gene in a chromosome spread comprising the steps of (a) hybridizing the chromosome spread with a tagged polynucleotide probe encoding heparanase; (b) washing the chromosome spread, thereby removing excess of non-hybridized probe; and (c) searching for signals associated with the hybridized tagged polynucleotide probe, wherein detected signals being indicative of a chromosome region harboring a heparanase gene.

According to a further aspect of the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo.

The present invention can be used to develop new drugs to inhibit tumor cell metastasis, inflammation and autoimmunity. The identification of the hpa gene encoding for heparanase enzyme enables the production of a recombinant enzyme in heterologous expression systems. Additional features, advantages, uses and applications of the present invention in biological science and in diagnostic and therapeutic medicine are described hereinafter.

BRIEF DESCRIPTION OF THE DRAWINGS

The invention herein described, by way of example only, with reference to the accompanying drawings, wherein:

FIG. 1 presents nucleotide sequence (SEQ ID NO:9) and deduced amino acid sequence (SEQ ID NO:10) of hpa cDNA. A single nucleotide difference at position 799 (A to T) between the EST (Expressed Sequence Tag) and the PCR amplified cDNA (reverse transcribed RNA) and the resulting amino acid substitution (Tyr to Phe) are indicated above and below the substituted unit, respectively. Cysteine residues and the poly adenylation consensus sequence are underlined. The asterisk denotes the stop codon TGA.

FIGS. 7a-b demonstrate degradation of sulfate labeled intact ECM by virus infected cells. High Five (7a) and Sf21 (7b) cells were plated on sulfate labeled ECM and infected (48 h, 28° C.) with pFhpa4 (●) or control pF1 (□) viruses. Control non-infected Sf21 cells (R) were plate on labeled ECM as well. The pH of the cultured medium was adjusted to 6.0-6.2, followed by 48 h incubation at 28° C. Sulfate labeled degradation fragments released into the incubation medium was analyzed by gel filtration on Sepharose 6B. HS degradation fragments were produced only by cells infected with the hpa containing virus.

FIG. 13 presents a comparison between nucleotide sequences of the human hpa and a mouse EST cDNA fragment (SEQ ID NO:12) which is 80% homologous to the 3' end (starting at nucleotide 1066 of SEQ ID NO:9) of the human hpa. The aligned termination codons are underlined.

FIG. 16 presents the nucleotide sequence of the genomic region of the hpa gene with regard to SEQ ID NO: 42. Exon sequences appear in upper case and intron sequences in lower case. The deduced amino acid sequence of the twelve exons is printed below the nucleotide sequence. These twelve deduced amino acids sequences are: positions 1 to 76 of SEQ ID NO:10(exon 1); positions 77 to 124 of SEQ ID NO:10(exon 2); positions 125 to 166 of SEQ ID NO:10 (exon 3); positions 167 to 224 of SEQ ID NO:10 (exon 4); positions 225 to 281 of SEQ ID NO:10 (exon 5); positions 282 to 297 of SEQ ID NO:10(exon 6); positions 298 to 328 of SEQ ID NO:10 (exon 7); positions 329 to 364 of SEQ ID NO:10 (exon 8); positions 365 to 402 of SEQ ID NO:10 (exon 9); positions 403 to 442 of SEQ ID NO:10 (exon 10); positions 443 to 491 of SEQ ID NO:10 (exon 11); and positions 492 to 543 of SEQ ID NO:10 (exon 12). Two predicted transcription start sites are shown in bold.

FIG. 17 presents an alignment of the amino acid sequences of human heparanase, mouse and partial sequences of rat homologues with regard to SEQ ID NOs: 10, 44and 45. The human and the mouse sequences were determined by sequence analysis of the isolated cDNAs. The rat sequence is derived from two different EST clones, which represent two different regions (5' and 3') of the rat hpa cDNA. The human sequence and the amino acids in the mouse and rat homologues, which are identical to the human sequence, appear in bold.

Figure 2:
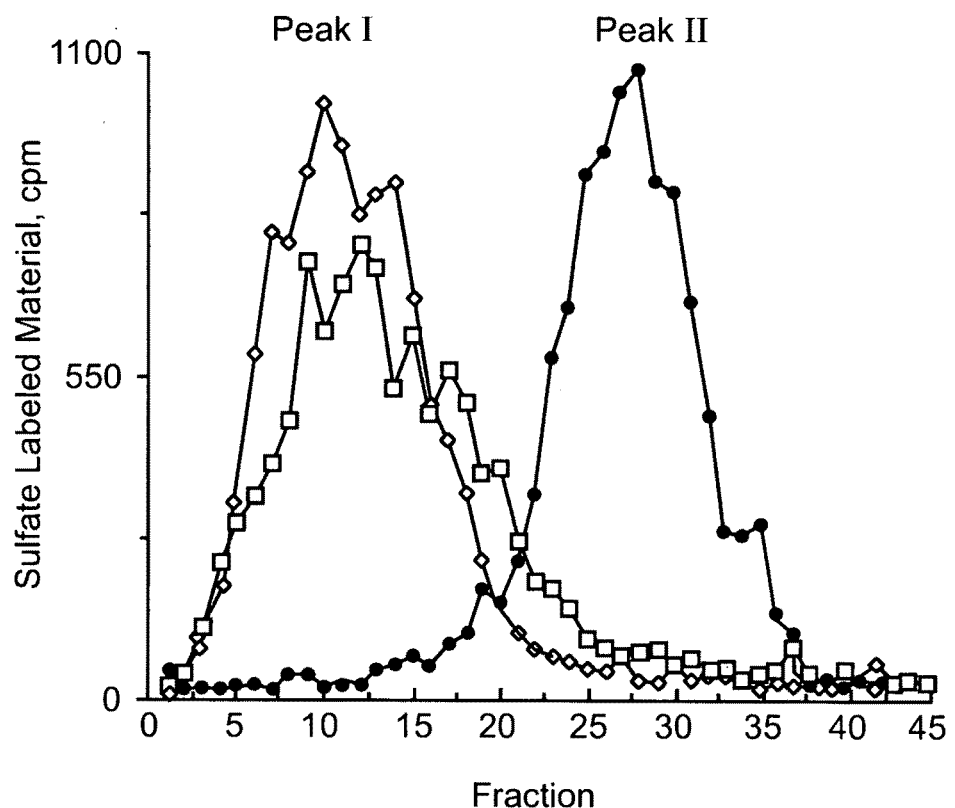
FIG. 2 demonstrates degradation of soluble sulfate labeled HSPG substrate by lysates of High Five cells infected with pFhpa2 virus. Lysates of High Five cells that were infected with pFhpa2 virus (●) or control pF2 virus (□) were incubated (18 h, 37° C.) with sulfate labeled ECM-derived soluble HSPG (peak I). The incubation medium was then subjected to gel filtration on Sepharose 6B. Low molecular weight HS degradation fragments (peak II) were produced only during incubation with the pFhpa2 infected cells, but there was no degradation of the HSPG substrate (◊) by lysates of pF2 infected cells.

Hr—Horse; S—Sheep; Rb—Rabbit; D—Dog; Ch—Chicken; F—Fish. Size markers (Lambda BsteII) are shown on the left FIG. 19 demonstrates the secondary structure prediction for heparanase (SEQ ID NO:10)performed using the PHD server—Profile network Prediction Heidelberg. H—helix, E—extended (beta strand), The glutamic acid predicted as the proton donor is marked by asterisk and the possible nucleophiles are underlined.

DESCRIPTION OF THE PREFERRED EMBODIMENTS

The present invention is of a polynucleotide or nucleic acid, referred to hereinbelow interchangeably as hpa, hpa cDNA or hpa gene or identified by its SEQ ID NOs, encoding a polypeptide having heparanase activity, vectors or nucleic acid constructs including same and which are used for overexpression or antisense inhibition of heparanase, genetically modified cells expressing same, recombinant protein having heparanase activity, antisense oligonucleotides and ribozymes for heparanase modulation, and heparanase promoter sequences which can be used to direct the expression of desired genes.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cloning of the human and mouse hpa genes, cDNAs and genomic sequence (for human), encoding heparanase and expressing recombinant heparanase by transfected cells is reported herein. These are the first mammalian heparanase genes to be cloned.

A purified preparation of heparanase isolated from human hepatoma cells was subjected to tryptic digestion and microsequencing.

The YGPDVGQPR (SEQ ID NO:8) sequence revealed was used to screen EST databases for homology to the corresponding back translated DNA sequences. Two closely related EST sequences were identified and were thereafter found to be identical.

Both clones contained an insert of 1020 bp which includes an open reading frame of 973 bp followed by a 3' untranslated region of 27 bp and a Poly A tail, whereas a translation start site was not identified.

Cloning of the missing 5' end was performed by PCR amplification of DNA from placenta Marathon RACE cDNA composite using primers selected according to the EST clones sequence and the linkers of the composite.

A 900 bp PCR fragment, partially overlapping with the identified 3' encoding EST clones was obtained. The joined cDNA fragment (hpa), 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons.

A single nucleotide difference at position 799 (A to T) between the EST clones and the PCR amplified cDNA was observed. This difference results in a single amino acid substitution (Tyr to Phe) (FIG. 1). Furthermore, the published EST sequences contained an unidentified nucleotide, which following DNA sequencing of both the EST clones was resolved into two nucleotides (G and C at positions 1630 and 1631 in SEQ ID NO:9, respectively).

The ability of the hpa gene product to catalyze degradation of heparan sulfate in an in vitro assay was examined by expressing the entire open reading frame in insect cells, using the Baculovirus expression system.

Extracts and conditioned media of cells infected with virus containing the hpa gene, demonstrated a high level of heparan sulfate degradation activity both towards soluble ECM-derived HSPG and intact ECM, which was inhibited by heparin, while cells infected with a similar construct containing no hpa gene had no such activity, nor did non-infected cells.

The expression pattern of hpa RNA in various tissues and cell lines was investigated using RT-PCR. It was found to be expressed only in tissues and cells previously known to have heparanase activity.

Cloning an extended 5' sequence was enabled from the human SK-hep1 cell line by PCR amplification using the Marathon RACE. The 5' extended sequence of the SK-hep1 hpa cDNA was assembled with the sequence of the hpa cDNA isolated from human placenta (SEQ ID NO:9). The assembled sequence contained an open reading frame, SEQ ID NOs: 13 and 15, which encodes, as shown in SEQ ID NOs:14 and 15, a polypeptide of 592 amino acids, with a calculated molecular weight of 66,407 daltons. This open reading frame was shown to direct the expression of catalytically active heparanase in a mammalian cell expression system. The expressed heparanase was detectable by anti heparanase antibodies in Western blot analysis.

A panel of monochromosomal human/CHO and human/mouse somatic cell hybrids was used to localize the human heparanase gene to human chromosome 4. The newly isolated heparanase sequence can therefore be used to identify a chromosome region harboring a human heparanase gene in a chromosome spread.

The hpa cDNA was then used as a probe to screen a a human genomic library. Several phages were positive. These phages were analyzed and were found to cover most of the hpa locus, except for a small portion which was recovered by bridging PCR. The hpa locus covers about 50,000 bp. The hpa gene includes 12 exons separated by 11 introns.

RT-PCR performed on a variety of cells revealed alternatively spliced hpa transcripts.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, AI122034, all sharing an identical sequence and correspond to amino acids 336-543 of the human heparanase sequence. The entire mouse heparanase cDNA was cloned, based on the nucleotide sequence of the mouse EST's using Marathon cDNA libraries. The mouse and the human hpa genes share an average homology of 78% between the nucleotide sequences and 81% similarity between the deduced amino acid sequences. hpa homologous sequences from rat were also uncovered (EST's AI060284 and AI237828).

Homology search of heparanase amino acid sequence against the DNA and the protein databases and prediction of its protein secondary structure enabled to identify candidate amino acids that participate in the heparanase active site.

Expression of hpa antisense in mammalian cell lines resulted in about five fold decrease in the number of recoverable cells as compared to controls.

Human Hpa cDNA was shown to hybridize with genomic DNAs of a variety of mammalian species and with an avian.

The human and mouse hpa promoters were identified and the human promoter was tested positive in directing the expression of a reporter gene.

Thus, according to the present invention there is provided an isolated nucleic acid comprising a genomic, complementary or composite polynucleotide sequence encoding a polypeptide having heparanase catalytic activity.

The phrase "composite polynucleotide sequence" refers to a sequence which includes exonal sequences required to encode the polypeptide having heparanase activity, as well as any number of intronal sequences. The intronal sequences can be of any source and typically will include conserved splicing signal sequences. Such intronal sequences may further include cis acting expression regulatory elements.

The term "heparanase catalytic activity" or its equivalent term "heparanase activity" both refer to a mammalian endoglycosidase hydrolyzing activity which is specific for heparan or heparan sulfate proteoglycan substrates, as opposed to the activity of bacterial enzymes (heparinase I, II and III) which degrade heparin or heparan sulfate by means of β-elimination (37).

According to a preferred embodiment of the present invention the polynucleotide or a portion thereof is hybridizable with SEQ ID NOs: 9, 13, 42, 43 or a portion thereof at 68° C. in 6× SSC, 1% SDS, 5× Denharts, 10 % dextran sulfate, 100 µg/ml salmon sperm DNA, and 32p labeled probe and wash at 68° C. with 3, 2, 1, 0.5 or 0.1× SSC and 0.1% SDS.

According to another preferred embodiment of the present invention the polynucleotide or a portion thereof is at least 60%, preferably at least 65% more preferably at least 70%, more preferably at least 75%, more preferably at least 80%, more preferably at least 85%, more preferably at least 90%, most preferably, 95-100% identical with SEQ ID NOs: 9, 13, 42, 43 or portions thereof as determined using the Bestfit procedure of the DNA sequence analysis software package developed by the Genetic Computer Group (GCG) at the university of Wisconsin (gap creation penalty—12, gap extension penalty—4—which are the default parameters).

According to another preferred embodiment of the present invention the polypeptide encoded by the polynucleotide sequence is as set forth in SEQ ID NOs:10, 14, 44 or portions thereof having heparanase catalytic activity. Such portions are expected to include amino acids Asp-Glu 224-225 (SEQ ID NO:10), which can serve as proton donors and glutamic acid 343 or 396 which can serve as a nucleophile.

According to another preferred embodiment of the present invention the polypeptide encoded by the polynucleotide sequence is at least 60%, preferably at least 65%, more preferably at least 70%, more preferably at least 75%, more preferably at least 80%, more preferably at least 85%, more preferably at least 90%, most preferably, 95-100% homologous (both similar and identical acids) to SEQ ID NOs:10, 14, 44 or portions thereof as determined with the Smith-Waterman algorithm, using the Bioaccelerator platform developed by Compugene (gapop: 10.0, gapext: 0.5, matrix: blosum62, see also the description to FIG. 17).

Further according to the present invention there is provided a nucleic acid construct comprising the isolated nucleic acid described herein. The construct may and preferably further include an origin of replication and trans regulatory elements, such as promoter and enhancer sequences.

The construct or vector can be of any type. It may be a phage which infects bacteria or a virus which infects eukaryotic cells. It may also be a plasmid, phagemid, cosmid, bacmid or an artificial chromosome.

Further according to the present invention there is provided a host cell comprising the nucleic acid construct described herein. The host cell can be of any type. It may be a prokaryotic cell, an eukaryotic cell, a cell line, or a cell as a portion of an organism. The polynucleotide encoding heparanase can be permanently or transiently present in the cell. In other words, genetically modified cells obtained following stable or transient transfection, transformation or transduction are all within the scope of the present invention. The polynucleotide can be present in the cell in low copy (say 1-5 copies) or high copy number (say 5-50 copies or more). It may be integrated in one or more chromosomes at any location or be present as an extrachromosomal material.

The present invention is further directed at providing a heparanase over-expression system which includes a cell overexpressing heparanase catalytic activity. The cell may be a genetically modified host cell transiently or stably transfected or transformed with any suitable vector which includes a polynucleotide sequence encoding a polypeptide having heparanase activity and a suitable promoter and enhancer sequences to direct over-expression of heparanase. However, the overexpressing cell may also be a product of an insertion (e.g., via homologous recombination) of a promoter and/or enhancer sequence downstream to the endogenous heparanase gene of the expressing cell, which will direct over-expression from the endogenous gene.

The term "over-expression" as used herein in the specification and claims below refers to a level of expression which is higher than a basal level of expression typically characterizing a given cell under otherwise identical conditions.

According to another aspect the present invention provides an antisense oligonucleotide comprising a polynucleotide or a polynucleotide analog of at least 10, preferably 11-15, more preferably 16-17, more preferably 18, more preferably 19-25, more preferably 26-35, most preferably 35-100 bases being hybridizable in vivo, under physiological conditions, with a portion of a polynucleotide strand encoding a polypeptide having heparanase catalytic activity. The antisense oligonucleotide can be used for downregulating heparanase activity by in vivo administration thereof to a patient. As such, the antisense oligonucleotide according to the present invention can be used to treat types of cancers which are characterized by impaired (over) expression of heparanase, and are dependent on the expression of heparanase for proliferating or forming metastases.

The antisense oligonucleotide can be DNA or RNA or even include nucleotide analogs, examples of which are provided in the Background section hereinabove. The antisense oligonucleotide according to the present invention can be synthetic and is preferably prepared by solid phase synthesis. In addition, it can be of any desired length which still provides specific base pairing (e.g., 8 or 10, preferably more, nucleotides long) and it can include mismatches that do not hamper base pairing under physiological conditions.

Further according to the present invention there is provided a pharmaceutical composition comprising the antisense oligonucleotide herein described and a pharmaceutically acceptable carrier. The carrier can be, for example, a liposome loadable with the antisense oligonucleotide.

According to a preferred embodiment of the present invention the antisense oligonucleotide further includes a ribozyme sequence. The ribozyme sequence serves to cleave a heparanase RNA molecule to which the antisense oligonucleotide binds, to thereby downregulate heparanase expression.

Further according to the present invention there is provided an antisense nucleic acid construct comprising a promoter sequence and a polynucleotide sequence directing the synthesis of an antisense RNA sequence of at least 10 bases being hybridizable in vivo, under physiological conditions, with a portion of a polynucleotide strand encoding a polypeptide having heparanase catalytic activity. Like the antisense oligonucleotide, the antisense construct can be used for down-regulating heparanase activity by in vivo administration thereof to a patient. As such, the antisense construct, like the antisense oligonucleotide, according to the present invention can be used to treat types of cancers which are characterized by impaired (over) expression of heparanase, and are dependent on the expression of heparanase for proliferating or forming metastases.

Thus, further according to the present invention there is provided a pharmaceutical composition comprising the antisense construct herein described and a pharmaceutically acceptable carrier. The carrier can be, for example, a liposome loadable with the antisense construct.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Coated condoms, stents, active pads, and other medical devices may also be useful. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile aqueous solutions which may also contain buffers, diluents and other suitable additives.

Dosing is dependent on severity and responsiveness of the condition to be treated, but will normally be one or more doses per day, week or month with course of treatment lasting from several days to several months or until a cure is effected or a diminution of disease state is achieved. Persons ordinarily skilled in the art can easily determine optimum dosages, dosing methodologies and repetition rates.

Further according to the present invention there is provided a nucleic acid construct comprising a polynucleotide sequence functioning as a promoter, the polynucleotide sequence is derived from SEQ ID NO:42 and includes at least nucleotides 2135-2635, preferably 2235-2635, more preferably 2335-2635, more preferably 2435-2635, most preferably 2535-2635 thereof, or SEQ ID NO:43 and includes at least nucleotides 1-420, preferably 120-420, more preferably 220-420, most preferably 320-420, thereof. These nucleotides are shown in the example section that follows to direct the synthesis of a reporter gene in transformed cells. Thus, further according to the present invention there is provided a method of expressing a polynucleotide sequence comprising the step of ligating the polynucleotide sequence downstream to either of the promoter sequences described herein. Heparanase promoters can be isolated from a variety of mammalian an other species by cloning genomic regions present 5' to the coding sequence thereof. This can be readily achievable by one ordinarily skilled in the art using the heparanase polynucleotides described herein, which are shown in the Examples section that follows to participate in efficient cross species hybridization.

Further according to the present invention there is provided a recombinant protein comprising a polypeptide having heparanase catalytic activity. The protein according to the present invention include modifications known as post translational modifications, including, but not limited to, proteolysis (e.g., removal of a signal peptide and of a pro- or preprotein sequence), methionine modification, glycosylation, alkylation (e.g., methylation), acetylation, etc. According to preferred embodiments the polypeptide includes at least a portion of SEQ ID NOs:10, 14 or 44, the portion has heparanase catalytic activity. According to preferred embodiments of the present invention the protein is encoded by any of the above described isolated nucleic acids. Further according to the present invention there is provided a pharmaceutical composition comprising, as an active ingredient, the recombinant protein described herein.

The recombinant protein may be purified by any conventional protein purification procedure close to homogeneity and/or be mixed with additives. The recombinant protein may be manufactured using any of the genetically modified cells described above, which include any of the expression nucleic acid constructs described herein. The recombinant protein may be in any form. It may be in a crystallized form, a dehydrated powder form or in solution. The recombinant protein may be useful in obtaining pure heparanase, which in turn may be useful in eliciting anti-heparanase antibodies, either poly or monoclonal antibodies, and as a screening active ingredient in an anti-heparanase inhibitors or drugs screening assay or system.

Further according to the present invention there is provided a method of identifying a chromosome region harboring a human heparanase gene in a chromosome spread. the method is executed implementing the following method steps, in which in a first step the chromosome spread (either interphase or metaphase spread) is hybridized with a tagged polynucleotide probe encoding heparanase. The tag is preferably a fluorescent tag. In a second step according to the method the chromosome spread is washed, thereby excess of non-hybridized probe is removed. Finally, signals associated with the hybridized tagged polynucleotide probe are searched for, wherein detected signals being indicative of a chromosome region harboring the human heparanase gene. One ordinarily skilled in the art would know how to use the sequences disclosed herein in suitable labeling reactions and how to use the tagged probes to detect, using in situ hybridization, a chromosome region harboring a human heparanase gene.

Further according to the present invention there is provided a method of in vivo eliciting anti-heparanase antibodies comprising the steps of administering a nucleic acid construct including a polynucleotide segment corresponding to at least a portion of SEQ ID NOs:9, 13 or 43 and a promoter for directing the expression of said polynucleotide segment in vivo. Accordingly, there is provided also a DNA vaccine for in vivo eliciting anti-heparanase antibodies comprising a nucleic acid construct including a polynucleotide segment corresponding to at least a portion of SEQ ID NOs:9, 13 or 43 and a promoter for directing the expression of said polynucleotide segment in vivo. The vaccine optionally further includes a pharmaceutically acceptable carrier, such as a virus, liposome or an antigen presenting cell. Alternatively, the vaccine is employed as a naked DNA vaccine The present invention can be used to develop treatments for various diseases, to develop diagnostic assays for these diseases and to provide new tools for basic research especially in the fields of medicine and biology.

Specifically, the present invention can be used to develop new drugs to inhibit tumor cell metastasis, inflammation and autoimmunity. The identification of the hpa gene encoding for the heparanase enzyme enables the production of a recombinant enzyme in heterologous expression systems.

Furthermore, the present invention can be used to modulate bioavailability of heparin-binding growth factors, cellular responses to heparin-binding growth factors (e.g., bFGF, VEGF) and cytokines (e.g., IL-8), cell interaction with plasma lipoproteins, cellular susceptibility to viral, protozoa and some bacterial infections, and disintegration of neurodegenerative plaques. Recombinant heparanase offers a potential treatment for wound healing, angiogenesis, restenosis, atherosclerosis, inflammation, neurodegenerative diseases (such as, for example, Genstmann-Straussler Syndrome, Creutzfeldt-Jakob disease, Scrape and Alzheimer's disease) and certain viral and some bacterial and protozoa infections. Recombinant heparanase can be used to neutralize plasma heparin, as a potential replacement of protamine.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoon life cycle, or which reduces or prevents infection by the virus, bacterium or protozoon in a subject, such as a human or lower animal.

As used herein, the term "wound" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne, etc.

Anti-heparanase antibodies, raised against the recombinant enzyme, would be useful for immunodetection and diagnosis of micrometastases, autoimmune lesions and renal failure in biopsy specimens, plasma samples, and body fluids. Such antibodies may also serve as neutralizing agents for heparanase activity.

The genomic heparanase sequences described herein can be used to construct knock-in and knock-out constructs. Such constructs include a fragment of 10-20 Kb of a heparanase locus and a negative and a positive selection markers and can be used to provide heparanase knock-in and knock-out animal models by methods known to the skilled artisan. Such animal models can be used for studying the function of heparanase in developmental processes, and in normal as well as pathological processes. They can also serve as an experimental model for testing drugs and gene therapy protocols. The complementary heparanase sequence (cDNA) can be used to derive transgenic animals, overexpressing heparanase for same. Alternatively, if cloned in the antisense orientation, the complementary heparanase sequence (cDNA) can be used to derive transgenic animals under-expressing heparanase for same.

The heparanase promoter sequences described herein and other cis regulatory elements linked to the heparanase locus can be used to regulated the expression of genes. For example, these promoters can be used to direct the expression of a cytotoxic protein, such as TNF, in tumor cells. It will be appreciated that heparanase itself is abnormally expressed under the control of its own promoter and other cis acting elements in a variety of tumors, and its expression is correlated with metastasis. It is also abnormally highly expressed in inflammatory cells. The introns of the heparanase gene can be used for the same purpose, as it is known that introns, especially upstream introns include cis acting element which affect expression. A heparanase promoter fused to a reporter protein can be used to study/monitor its activity.

The polynucleotide sequences described herein can also be used to provide DNA vaccines which will elicit in vivo anti heparanase antibodies. Such vaccines can therefore be used to combat inflammatory and cancer.

Antisense oligonucleotides derived according to the heparanase sequences described herein, especially such oligonucleotides supplemented with ribozyme activity, can be used to modulate heparanase expression. Such oligonucleotides can be from the coding region, from the introns or promoter specific. Antisense heparanase nucleic acid constructs can similarly function, as well known in the art.

The heparanase sequences described herein can be used to study the catalytic mechanism of heparanase. Carefully selected site directed mutagenesis can be employed to provide modified heparanase proteins having modified characteristics in terms of, for example, substrate specificity, sensitivity to inhibitors, etc.

While studying heparanase expression in a variety of cell types alternatively spliced transcripts were identified. Such transcripts if found characteristic of certain pathological conditions can be used as markers for such conditions. Such transcripts are expected to direct the synthesis of heparanases with altered functions.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989), which is incorporated herein by reference. Other general references are provided throughout this document. The procedures therein are believed to be well known in the art and are provided for the convenience of the reader. All the information contained therein is incorporated herein by reference.

The following protocols and experimental details are referenced in the Examples that follow:

Purification and characterization of heparanase from a human hepatoma cell line and human placenta: A human hepatoma cell line (Sk-hep-1) was chosen as a source for purification of a human tumor-derived heparanase. Purification was essentially as described in U.S. Pat. No. 5,362,641 to Fuks, which is incorporated by reference as if fully set forth herein. Briefly, 500 liter, $5 \times 10^{11}$ cells were grown in suspension and the heparanase enzyme was purified about 240,000 fold by applying the following steps: (i) cation exchange (CM-Sephadex) chromatography performed at pH 6.0, 0.3-1.4 M NaCl gradient; (ii) cation exchange (CM-Sephadex) chromatography performed at pH 7.4 in the presence of 0.1%

CHAPS, 0.3-1.1 M NaCl gradient; (iii) heparin-Sepharose chromatography performed at pH 7.4 in the presence of 0.1% CHAPS, 0.35-1.1 M NaCl gradient; (iv) ConA-Sepharose chromatography performed at pH 6.0 in buffer containing 0.1% CHAPS and 1 M NaCl, elution with 0.25 M α-methyl mannoside; and (v) HPLC cation exchange (Mono-S) chromatography performed at pH 7.4 in the presence of 0.1% CHAPS, 0.25-1 M NaCl gradient.

Active fractions were pooled, precipitated with TCA and the precipitate subjected to SDS polyacrylamide gel electrophoresis and/or tryptic digestion and reverse phase HPLC. Tryptic peptides of the purified protein were separated by reverse phase HPLC (C8 column) and homogeneous peaks were subjected to amino acid sequence analysis.

The purified enzyme was applied to reverse phase HPLC and subjected to N-terminal amino acid sequencing using the amino acid sequencer (Applied Biosystems).

Cells: Cultures of bovine corneal endothelial cells (BCECs) were established from steer eyes as previously described (19, 38). Stock cultures were maintained in DMEM (1 g glucose/liter) supplemented with 10% newborn calf serum and 5% FCS. bFGF (1 ng/ml) was added every other day during the phase of active cell growth (13, 14).

Preparation of dishes coated with ECM: BCECs (second to fifth passage) were plated into 4-well plates at an initial density of $2\times10^5$ cells/ml, and cultured in sulfate-free Fisher medium plus 5% dextran T-40 for 12 days. $Na_2^{35}SO_4$ (25 µCi/ml) was added on day 1 and 5 after seeding and the cultures were incubated with the label without medium change. The subendothelial ECM was exposed by dissolving (5 min., room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (19, 22).

To prepare soluble sulfate labeled proteoglycans (peak I material), the ECM was digested with trypsin (25 µg/ml, 6 h, 37° C.), the digest was concentrated by reverse dialysis and the concentrated material was applied onto a Sepharose 6B gel filtration column. The resulting high molecular weight material (Kav<0.2, peak I) was collected. More than 80% of the labeled material was shown to be composed of heparan sulfate proteoglycans (11, 39).

Heparanase activity: Cells ($1\times10^6$/35-mm dish), cell lysates or conditioned media were incubated on top of $^{35}$S-labeled ECM (18 h, 37° C.) in the presence of 20 mM phosphate buffer (pH 6.2). Cell lysates and conditioned media were also incubated with sulfate labeled peak I material (10-20 µl). The incubation medium was collected, centrifuged (18,000× g, 4° C., 3 min.), and sulfate labeled material analyzed by gel filtration on a Sepharose CL-6B column (0.9×30 cm). Fractions (0.2 ml) were eluted with PBS at a flow rate of 5 ml/h and counted for radioactivity using Bio-fluor scintillation fluid. The excluded volume ($V_O$) was marked by blue dextran and the total included volume ($V_t$) by phenol red. The latter was shown to comigrate with free sulfate (7, 11, 23). Degradation fragments of HS side chains were eluted from Sepharose 6B at 0.5<Kav <0.8 (peak II) (7, 11, 23). A nearly intact HSPG released from ECM by trypsin—and, to a lower extent, during incubation with PBS alone—was eluted next to $V_O$ (Kav<0.2, peak I). Recoveries of labeled material applied on the columns ranged from 85 to 95% in different experiments (11). Each experiment was performed at least three times and the variation of elution positions (Kav values) did not exceed +/-15%.

Cloning of hpa cDNA: cDNA clones 257548 and 260138 were obtained from the I.M.A.G.E Consortium (2130 Memorial Parkway SW, Hunstville, Ala. 35801). The cDNAs were originally cloned in EcoRI and NotI cloning sites in the plasmid vector pT3T7D-Pac. Although these clones are reported to be somewhat different, DNA sequencing demonstrated that these clones are identical to one another. Marathon RACE (rapid amplification of cDNA ends) human placenta (poly-A) cDNA composite was a gift of Prof. Yossi Shiloh of Tel Aviv University. This composite is vector free, as it includes reverse transcribed cDNA fragments to which double, partially single stranded adapters are attached on both sides. The construction of the specific composite employed is described in reference 39a.

Amplification of hp3 PCR fragment was performed according to the protocol provided by Clontech laboratories. The template used for amplification was a sample taken from the above composite. The primers used for amplification were:

First step: 5'-primer: API: 5'-CCATCCTAATACGACT-CACT ATAGGGC-3', SEQ ID NO:1; 3'-primer: HPL229: 5'-GTAGTGATGCCA TGTAACTGAATC-3', SEQ ID NO: 2.

Second step: nested 5'-primer: AP2: 5'-ACTCACTAT-AGGGCTCG AGCGGC-3', SEQ ID NO:3; nested 3'-primer: HPL171: 5'-GCATCTTAGCCGTCTTTCTTCG-3', SEQ ID NO: 4. The HPL229 and HPL171 were selected according to the sequence of the EST clones. They include nucleotides 933-956 and 876-897 of SEQ ID NO:9, respectively.

PCR program was 94° C.—4 min., followed by 30 cycles of 94° C.—40 sec., 62° C.—1 min., 72° C.—2.5 min. Amplification was performed with Expand High Fidelity (Boehringer Mannheim). The resulting ca. 900 bp hp3 PCR product was digested with BfrI and PvuII. Clone 257548 (phpa1) was digested with EcoRI, followed by end filling and was then further digested with BfrI. Thereafter the PvuII-BfrI fragment of the hp3 PCR product was cloned into the blunt end-BfrI end of clone phpa1 which resulted in having the entire cDNA cloned in pT3T7-pac vector, designated phpa2.

RT-PCR: RNA was prepared using TRI-Reagent (Molecular research center Inc.) according to the manufacturer instructions. 1.25 µg were taken for reverse transcription reaction using MuMLV Reverse transcriptase (Gibco BRL) and Oligo $(dT)_{15}$ primer, SEQ ID NO:5, (Promega). Amplification of the resultant first strand cDNA was performed with Taq polymerase (Promega). The following primers were used:

```
                                            SEQ ID NO:6,
HPU-355: 5'-TTCGATCCCAAGAAGGAATCAAC-3',
nucleotides 372-394 in SEQ ID NOs:9 or 11.

SEQ ID NO:7,
HPL-229: 5'-GTAGTGATGCCATGTAACTGAATC-3',
nucleotides 933-956 in SEQ ID NOs:9 or 11.
```

PCR program: 94° C.—4 min., followed by 30 cycles of 94° C.—40 sec., 62° C.—1 min., 72° C.—1 min.

Alternatively, total RNA was prepared from cell cultures using Tri-reagent (Molecular Research Center, Inc.) according to the manufacturer recommendation. Poly A+RNA was isolated from total RNA using mRNA separator (Clontech). Reverse transcription was performed with total RNA using Superscript II (GibcoBRL). PCR was performed with Expand high fidelity (Boehringer Mannheim). Primers used for amplification were as follows:

| | | |
|---|---|---|
| Hpu-685, | 5'-GAGCAGCCAGGTGAGCCCAAGAT-3', | SEQ ID NO:24 |
| Hpu-355, | 5'-TTCGATCCCAAGAAGGAATCAAC-3', | SEQ ID NO:25 |
| Hpu 565, | 5'-AGCTCTGTAGATGTGCTATACAC-3', | SEQ ID NO:26 |
| Hpl 967, | 5'-TCAGATGCAAGCAGCAACTTTGGC-3', | SEQ ID NO:27 |
| Hpl 171, | 5'-GCATCTTAGCCGTCTTTCTTCG-3', | SEQ ID NO:28 |
| Hpl 229, | 5'-GTAGTGATGCCATGTAACTGAATC-3', | SEQ ID NO:29 |

PCR reaction was performed as follows: 94° C. 3 minutes, followed by 32 cycles of 94° C. 40 seconds, 64° C. 1 minute, 72° C. 3 minutes, and one cycle 72° C., 7 minutes.

Expression of recombinant heparanase in insect cells: Cells, High Five and Sf21 insect cell lines were maintained as monolayer cultures in SF900II-SFM medium (GibcoBRL).

Recombinant Baculovirus: Recombinant virus containing the hpa gene was constructed using the Bac to Bac system (GibcoBRL). The transfer vector pFastBac was digested with SalI and NotI and ligated with a 1.7 kb fragment of phpa2 digested with XhoI and NotI. The resulting plasmid was designated pFasthpa2. An identical plasmid designated pFasthpa4 was prepared as a duplicate and both independently served for further experimentations. Recombinant bacmid was generated according to the instructions of the manufacturer with pFasthpa2, pFasthpa4 and with pFastBac. The latter served as a negative control. Recombinant bacmid DNAs were transfected into Sf21 insect cells. Five days after transfection recombinant viruses were harvested and used to infect High Five insect cells, 3×10⁶ cells in T-25 flasks. Cells were harvested 2-3 days after infection. 4×10⁶ cells were centrifuged and resuspended in a reaction buffer containing 20 mM phosphate citrate buffer, 50 mM NaCl. Cells underwent three cycles of freeze and thaw and lysates were stored at –80 ° C. Conditioned medium was stored at 4° C.

Figure 10A:
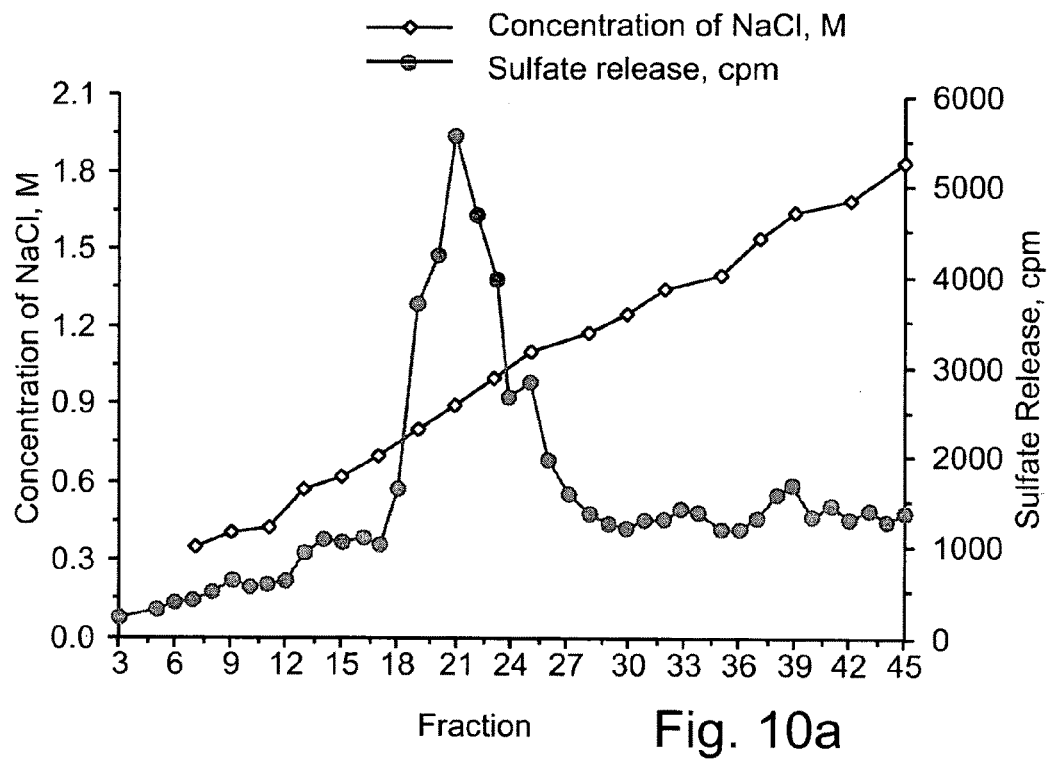
FIGS. 10a-b demonstrate purification of recombinant heparanase on heparin-Sepharose. Culture medium of Sf21 cells infected with pFhpa4 virus was subjected to heparin-Sepharose chromatography. Elution of fractions was performed with 0.35-2 M NaCl gradient (◇). Heparanase activity in the eluted fractions is demonstrated in FIG. 10a (●). Fractions 15-28 were subjected to 15% SDS-polyacrylamide gel electrophoresis followed by silver nitrate staining. A correlation is demonstrated between a major protein band (MW~63,000) in fractions 19-24 and heparanase activity.

Partial purification of recombinant heparanase: Partial purification of recombinant heparanase was performed by heparin-Sepharose column chromatography followed by Superdex 75 column gel filtration. Culture medium (150 ml) of Sf21 cells infected with pFhpa4 virus was subjected to heparin-Sepharose chromatography. Elution of 1 ml fractions was performed with 0.35-2 M NaCl gradient in presence of 0.1% CHAPS and 1 mM DTT in 10 mM sodium acetate buffer, pH 5.0. A 25 µl sample of each fraction was tested for heparanase activity. Heparanase activity was eluted at the range of 0.65-1.1 M NaCl (fractions 18-26, FIG. 10a). 5 µl of each fraction was subjected to 15% SDS-polyacrylamide gel electrophoresis followed by silver nitrate staining. Active fractions eluted from heparin-Sepharose (FIG. 10a) were pooled and concentrated (×6) on YM3 cut-off membrane. 0.5 ml of the concentrated material was applied onto 30 ml Superdex 75 FPLC column equilibrated with 10 mM sodium acetate buffer, pH 5.0, containing 0.8 M NaCl, 1 mM DTT and 0.1% CHAPS. Fractions (0.56 ml) were collected at a flow rate of 0.75 ml/min. Aliquots of each fraction were tested for heparanase activity and were subjected to SDS-polyacrylamide gel electrophoresis followed by silver nitrate staining (FIG. 11b).

PCR amplification of genomic DNA: 94° C. 3 minutes, followed by 32 cycles of 94° C. 45 seconds, 64° C. 1 minute, 68° C. 5 minutes, and one cycle at 72° C., 7 minutes. Primers used for amplification of genomic DNA included:

| | | |
|---|---|---|
| GHpu-L3 | 5'-AGGCACCCTAGAGATGTTCCAG-3', | SEQ ID NO:30 |
| GHpl-L6 | 5'-GAAGATTTCTGTTTCCATGACGTG-3', | SEQ ID NO:31 |

Screening of genomic libraries: A human genomic library in Lambda phage EMBLE3 SP6/T7 (Clontech, Paulo Alto, Calif.) was screened. 5×10⁵ plaques were plated at 5×10⁴ pfu/plate on NZCYM agar/top agarose plates. Phages were absorbed on nylon membranes in duplicates (Qiagen). Hybridization was performed at 65° C. in 5× SSC, 5 x Denhart's, 10% dextran sulfate, 100 µg/ml Salmon sperm, ³²p labeled probe (10⁶ cpm/ml). A 1.6 kb fragment, containing the entire hpa cDNA was labeled by random priming (Boehringer Mannheim). Following hybridization membranes were washed once with 2× SSC, 0.1% SDS at 65° C. for 20 minutes, and twice with 0.2× SSC, 0.1% SDS at 65° C. for 15 minutes. Hybridizing plaques were picked, and plated at 100 pfu/plate. Hybridization was performed as above and single isolated positive plaques were picked.

Phage DNA was extracted using a Lambda DNA extraction kit (Qiagen). DNA was digested with XhoI and EcoRI, separated on 0.7% agarose gel and transferred to nylon membrane Hybond N+ (Amersham). Hybridization and washes were performed as above.

cDNA Sequence analysis: Sequence determinations were performed with vector specific and gene specific primers, using an automated DNA sequencer (Applied Biosystems, model 373A). Each nucleotide was read from at least two independent primers.

Genomic sequence analysis: Large-scale sequencing was performed by Commonwealth Biotechnology Incorporation.

Isolation of mouse hpa: Mouse hpa cDNA was amplified from either Marathon ready cDNA library of mouse embryo or from mRNA isolated from mouse melanoma cell line BL6, using the Marathon RACE kit from Clontech. Both procedures were performed according to the manufacturer's recommendation.

Primers used for PCR amplification of mouse hpa:

| | | |
|---|---|---|
| Mhp1773 | 5'-CCACACTGAATGTAATACTGAAGTG-3', | SEQ ID NO:32 |
| MHp1736 | 5'-CGAAGCTCTGGAACTCGGCAAG-3', | SEQ ID NO:33 |
| MHp183 | 5'-GCCAGCTGCAAAGGTGTTGGAC-3', | SEQ ID NO:34 |
| Mhp1152 | 5'-AACACCTGCCTCATCACGACTTC-3', | SEQ ID NO:35 |
| Mhp1114 | 5'-GCCAGGCTGGCGTCGATGGTGA-3', | SEQ ID NO:36 |

-continued

| | | |
|---|---|---|
| MHp1103 | 5'-GTCGATGGTGATGGACAGGAAC-3', | SEQ ID NO:37 |
| Ap1 (Genome walker) | 5'-GTAATACGACTCACTATAGGGC-3', | SEQ ID NO:38 - |
| Ap2 (Genome walker) | 5'-ACTATAGGGCACGCGTGGT-3', | SEQ ID NO:39 - |
| Ap1 (Marathon RACE) | 5'-CCATCCTAATACGACTCACTATAGGGC-3', | SEQ ID NO:40 - |
| Ap2 (Marathon RACE) | 5'-ACTCACTATAGGGCTCGAGCGGC-3', | SEQ ID NO:41 - |

Southern analysis of genomic DNA: Genomic DNA was extracted from animal or from human blood using Blood and cell culture DNA maxi kit (Qiagene). DNA was digested with EcoRI, separated by gel electrophoresis and transferred to a nylon membrane Hybond N+ (Amersham). Hybridization was performed at 68° C. in 6× SSC, 1% SDS, 5× Denharts, 10% dextran sulfate, 100 μg/ml salmon sperm DNA, and $^{32}$p labeled probe. A 1.6 kb fragment, containing the entire hpa cDNA was used as a probe. Following hybridization, the membrane was washed with 3× SSC, 0.1% SDS, at 68° C. and exposed to X-ray film for 3 days. Membranes were then washed with 1× SSC, 0.1% SDS, at 68° C. and were reexposed for 5 days.

Construction of hpa promoter-GFP expression vector: Lambda DNA of phage L3, was digested with SacI and BglII, resulting in a 1712 bp fragment which contained the hpa promoter (877-2688 of SEQ ID NO:42). The pEGFP-1 plasmid (Clontech) was digested with BglII and SacI and ligated with the 1712 bp fragment of the hpa promoter sequence. The resulting plasmid was designated phpEGL. A second hpa promoter-GFP plasmid was constructed containing a shorter fragment of the hpa promoter region: phpEGL was digested with HindIII, and the resulting 1095 bp fragment (nucleotides 1593-2688 of SEQ ID NO: 42) was ligated with HindIII digested pEGFP-1. The resulting plasmid was designated phpEGS.

Computer analysis of sequences: Homology searches were performed using several computer servers, and various databases. Blast 2.0 service, at the NCBI server was used to screen the protein database swplus and DNA databases such as GenBank, EMBL, and the EST databases. Blast 2.0 search was performed using the basic search option of the NCBI server. Sequence analysis and alignments were done using the DNA sequence analysis software package developed by the Genetic Computer Group (GCG) at the university of Wisconsin. Alignments of two sequences were performed using Bestfit (gap creation penalty—12, gap extension penalty—4). Protein homology search was performed with the Smith-Waterman algorithm, using the Bioaccelerator platform developed by Compugene. The protein database swplus was searched using the following parameters: gapop: 10.0, gapext: 0.5, matrix: blosum62. Blocks homology was performed using the Blocks WWW server developed at Fred Hutchinson Cancer Research Center in Seattle, Wash., USA. Secondary structure prediction was performed using the PHD server—Profile network Prediction Heidelberg. Fold recognition (threading) was performed using the UCLA-DOE structure prediction server. The method used for prediction was gonnet+predss. Alignment of three sequences was performed using the pileup application (gap creation penalty—5, gap extension penalty—1). Promoter analysis was performed using TSSW and TSSG programs (BCM Search Launcher Human Genome Center, Baylor College of Medicine, Houston Tex.).

Example 1

Cloning of Human hpa cDNA

Purified fraction of heparanase isolated from human hepatoma cells (SK-hep-1) was subjected to tryptic digestion and microsequencing. EST (Expressed Sequence Tag) databases were screened for homology to the back translated DNA sequences corresponding to the obtained peptides. Two EST sequences (accession Nos. N41349 and N45367) contained a DNA sequence encoding the peptide YGPDVGQPR (SEQ ID NO:8). These two sequences were derived from clones 257548 and 260138 (I.M.A.G.E Consortium) prepared from 8 to 9 weeks placenta cDNA library (Soares). Both clones which were found to be identical contained an insert of 1020 bp which included an open reading frame (ORF) of 973 bp followed by a 3' untranslated region of 27 bp and a Poly A tail. No translation start site (AUG) was identified at the 5' end of these clones.

Cloning of the missing 5' end was performed by PCR amplification of DNA from a placenta Marathon RACE cDNA composite. A 900 bp fragment (designated hp3), partially overlapping with the identified 3' encoding EST clones was obtained.

The joined cDNA fragment, 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons. The 3' end of the partial cDNA inserts contained in clones 257548 and 260138 started at nucleotide $G^{721}$ of SEQ ID NO: 9 and FIG. 1.

As further shown in FIG. 1, there was a single sequence discrepancy between the EST clones and the PCR amplified sequence, which led to an amino acid substitution from $Tyr^{246}$ in the EST to $Phe^{246}$ in the amplified cDNA. The nucleotide sequence of the PCR amplified cDNA fragment was verified from two independent amplification products. The new gene was designated hpa.

As stated above, the 3' end of the partial cDNA inserts contained in EST clones 257548 and 260138 started at nucleotide 721 of hpa (SEQ ID NO:9). The ability of the hpa cDNA to form stable secondary structures, such as stem and loop structures involving nucleotide stretches in the vicinity of position 721 was investigated using computer modeling. It was found that stable stem and loop structures are likely to be formed involving nucleotides 698-724 (SEQ ID NO:9). In addition, a high GC content, up to 70%, characterizes the 5' end region of the hpa gene, as compared to about only 40% in the 3' region. These findings may explain the immature termination and therefore lack of 5' ends in the EST clones.

To examine the ability of the hpa gene product to catalyze degradation of heparan sulfate in an in vitro assay the entire open reading frame was expressed in insect cells, using the Baculovirus expression system. Extracts of cells, infected with virus containing the hpa gene, demonstrated a high level of heparan sulfate degradation activity, while cells infected with a similar construct containing no hpa gene had no such activity, nor did non-infected cells. These results are further demonstrated in the following Examples.

Example 2

Degradation of Soluble ECM-derived HSPG

Monolayer cultures of High Five cells were infected (72 h, 28° C.) with recombinant Bacoluvirus containing the pFasthpa plasmid or with control virus containing an insert free plasmid. The cells were harvested and lysed in heparanase reaction buffer by three cycles of freezing and thawing. The cell lysates were then incubated (18 h, 37° C.) with sulfate labeled, ECM-derived HSPG (peak I), followed by gel filtration analysis (Sepharose 6B) of the reaction mixture.

As shown in FIG. 2, the substrate alone included almost entirely high molecular weight (Mr) material eluted next to $V_O$ (peak I, fractions 5-20, Kav<0.35). A similar elution pattern was obtained when the HSPG substrate was incubated with lysates of cells that were infected with control virus. In contrast, incubation of the HSPG substrate with lysates of cells infected with the hpa containing virus resulted in a complete conversion of the high Mr substrate into low Mr labeled degradation fragments (peak II, fractions 22-35, 0.5<Kav<0.75).

Fragments eluted in peak II were shown to be degradation products of heparan sulfate, as they were (i) 5- to 6-fold smaller than intact heparan sulfate side chains (Kav approx. 0.33) released from ECM by treatment with either alkaline borohydride or papain; and (ii) resistant to further digestion with papain or chondroitinase ABC, and susceptible to deamination by nitrous acid (6, 11). Similar results (not shown) were obtained with Sf21 cells. Again, heparanase activity was detected in cells infected with the hpa containing virus (pFhpa), but not with control virus (pF). This result was obtained with two independently generated recombinant viruses. Lysates of control not infected High Five cells failed to degrade the HSPG substrate.

In subsequent experiments, the labeled HSPG substrate was incubated with medium conditioned by infected High Five or Sf21 cells.

Figure 3A:
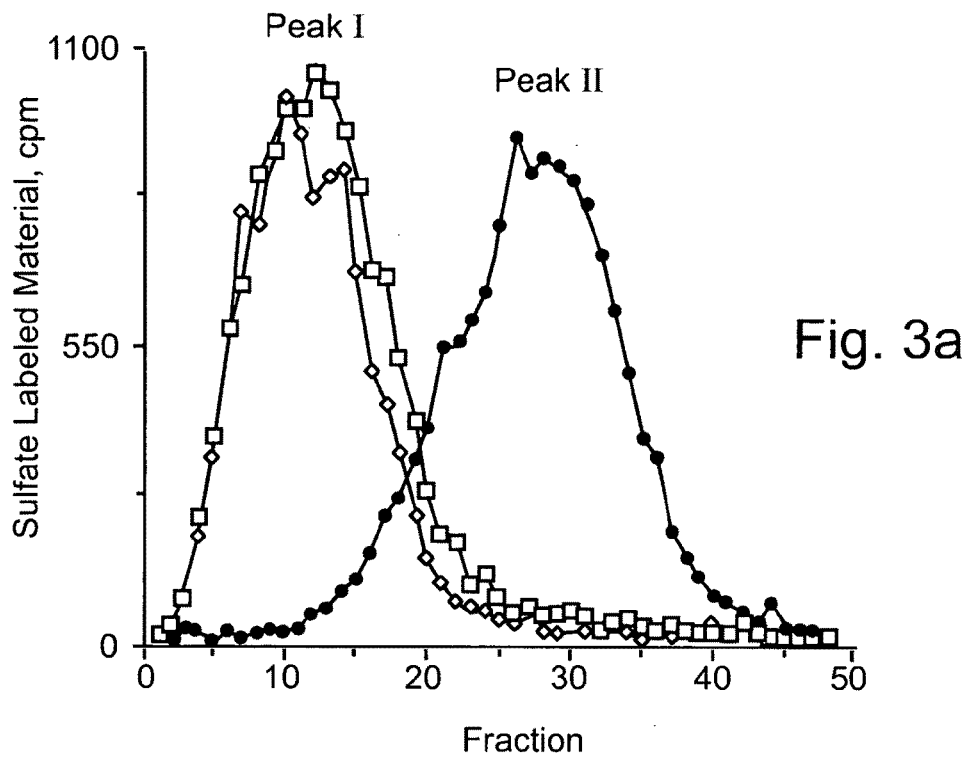
FIGS. 3a-b demonstrate degradation of soluble sulfate labeled HSPG substrate by the culture medium of pFhpa2 and pFhpa4 infected cells. 1 o Culture media of High Five cells infected with pFhpa2 (3a) or pFhpa4 (3b) viruses (●), or with control viruses (□) were incubated (18 h, 37° C.) with sulfate labeled ECM-derived soluble HSPG (peak I, ◊). The incubation media were then subjected to gel filtration on Sepharose 6B. Low molecular weight HS degradation fragments (peak II) were produced only during incubation with the hpa gene containing viruses. There was no degradation of the HSPG substrate by the culture medium of cells infected with control viruses.
Figure 3B:
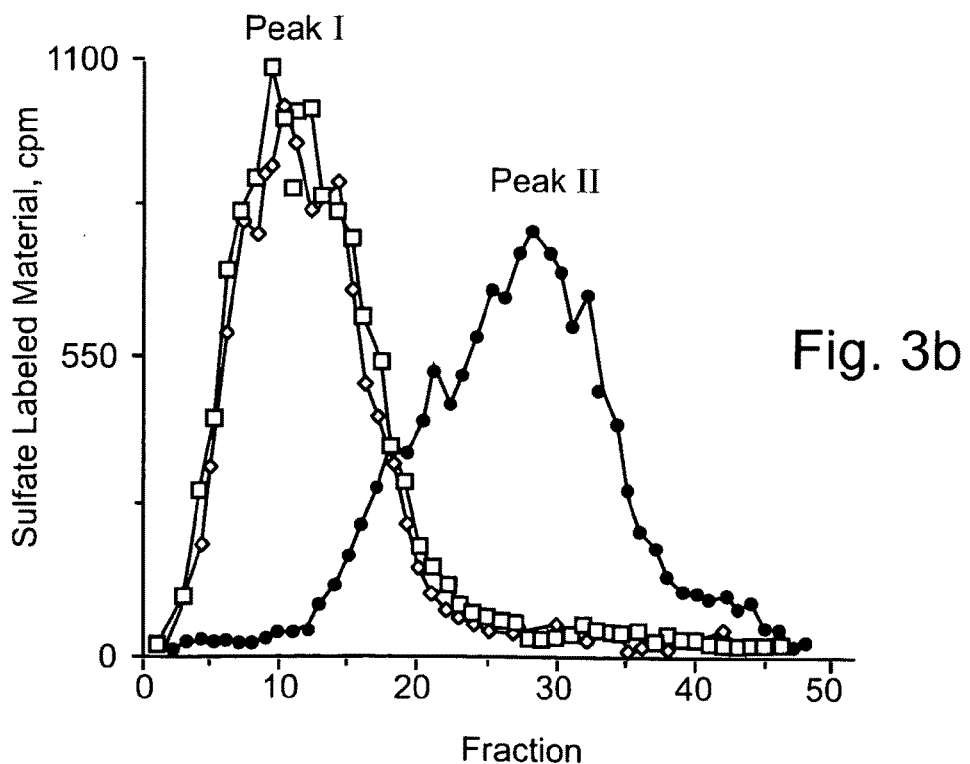

As shown in FIGS. 3a-b, heparanase activity, reflected by the conversion of the high Mr peak I substrate into the low Mr peak II which represents HS degradation fragments, was found in the culture medium of cells infected with the pFhpa2 or pFhpa4 viruses, but not with the control pF1 or pF2 viruses. No heparanase activity was detected in the culture medium of control non-infected High Five or Sf21 cells.

Figure 4:
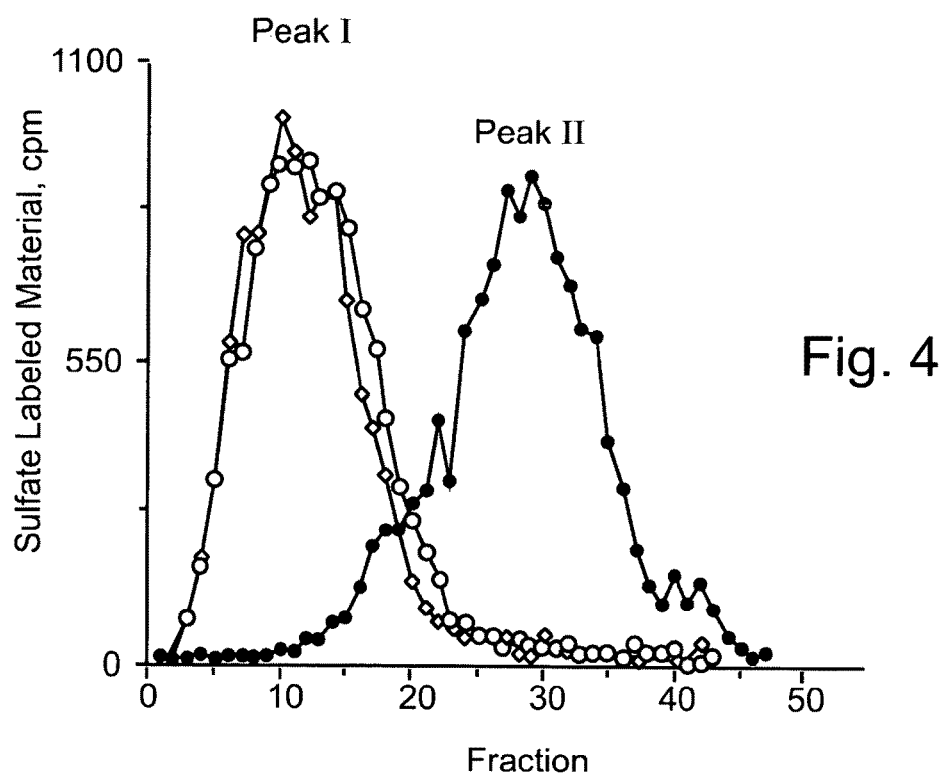
FIG. 4 presents size fractionation of heparanase activity expressed by pFhpa2 infected cells. Culture medium of pFhpa2 infected High Five cells was applied onto a 50 kDa cut-off membrane. Heparanase activity (conversion of the peak I substrate, (◊) into peak II HS degradation fragments) was found in the high (>50 kDa) (●), but not low (<50 kDa) (○) molecular weight compartment.

The medium of cells infected with the pFhpa4 virus was passed through a 50 kDa cut off membrane to obtain a crude estimation of the molecular weight of the recombinant heparanase enzyme. As demonstrated in FIG. 4, all the enzymatic activity was retained in the upper compartment and there was no activity in the flow through (<50 kDa) material. This result is consistent with the expected molecular weight of the hpa gene product.

In order to further characterize the hpa product the inhibitory effect of heparin, a potent inhibitor of heparanase mediated HS degradation (40) was examined.

Figure 5A:
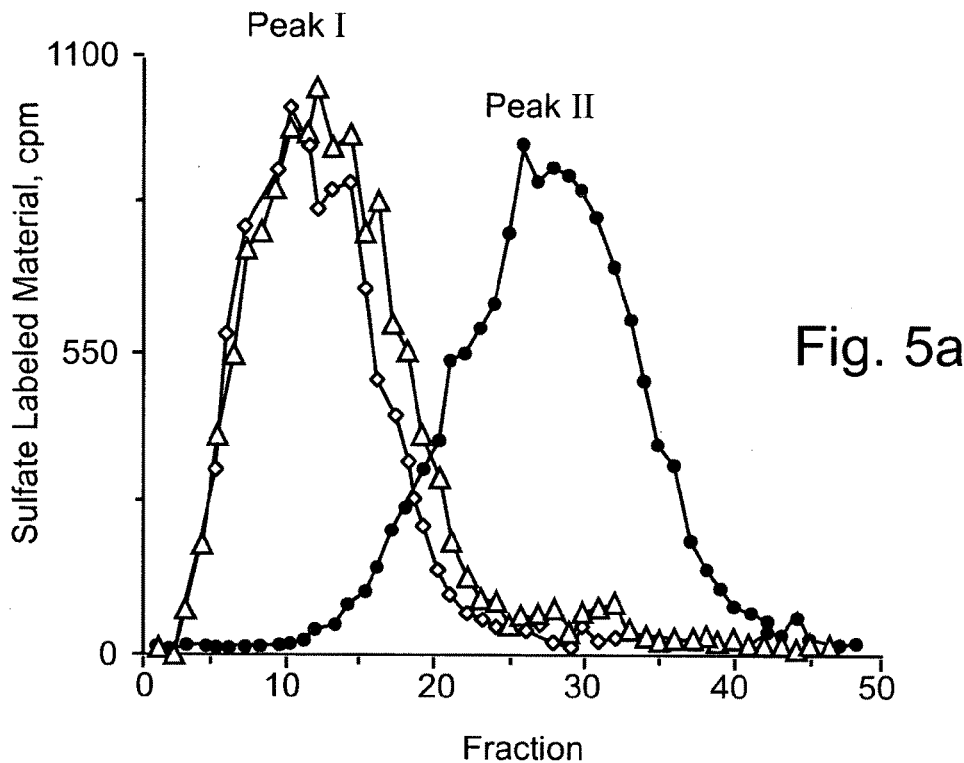
FIGS. 5a-b demonstrate the effect of heparin on heparanase activity expressed by pFhpa2 and pFhpa4 infected High Five cells. Culture media of pFhpa2 (5a) and pFhpa4 (5b) infected High Five cells were incubated (18 h, 37° C.) with sulfate labeled ECM-derived soluble HSPG (peak I, ◊) in the absence (●) or presence (Δ) of 10 μg/ml heparin. Production of low molecular weight HS degradation fragments was completely abolished in the presence of heparin, a potent inhibitor of heparanase activity (6, 7).
Figure 5B:
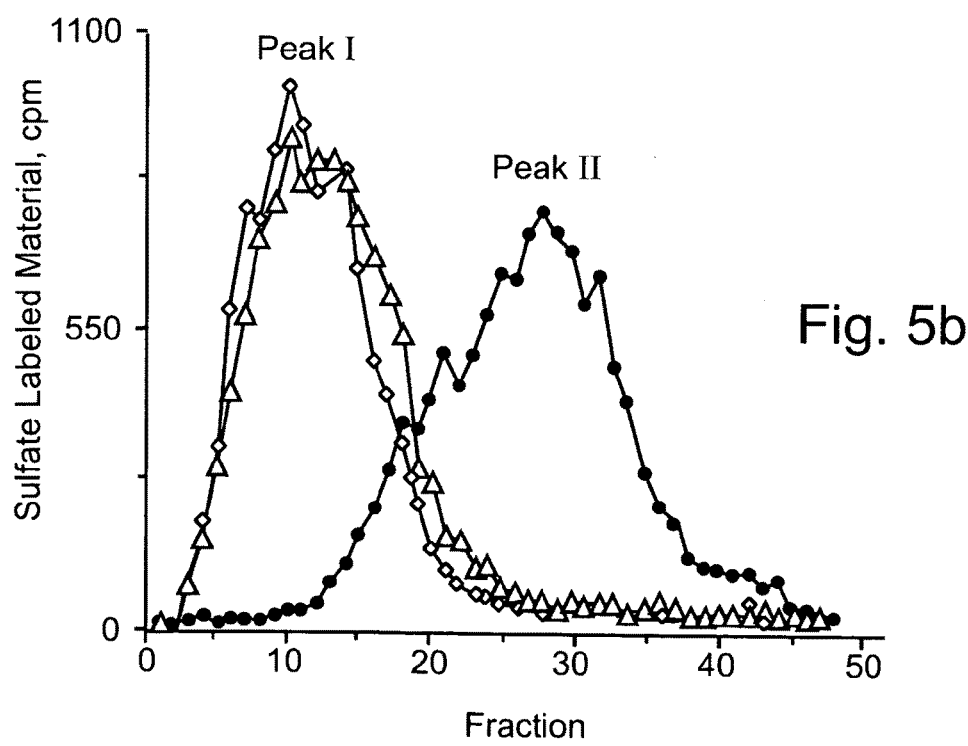
Figure 6A:
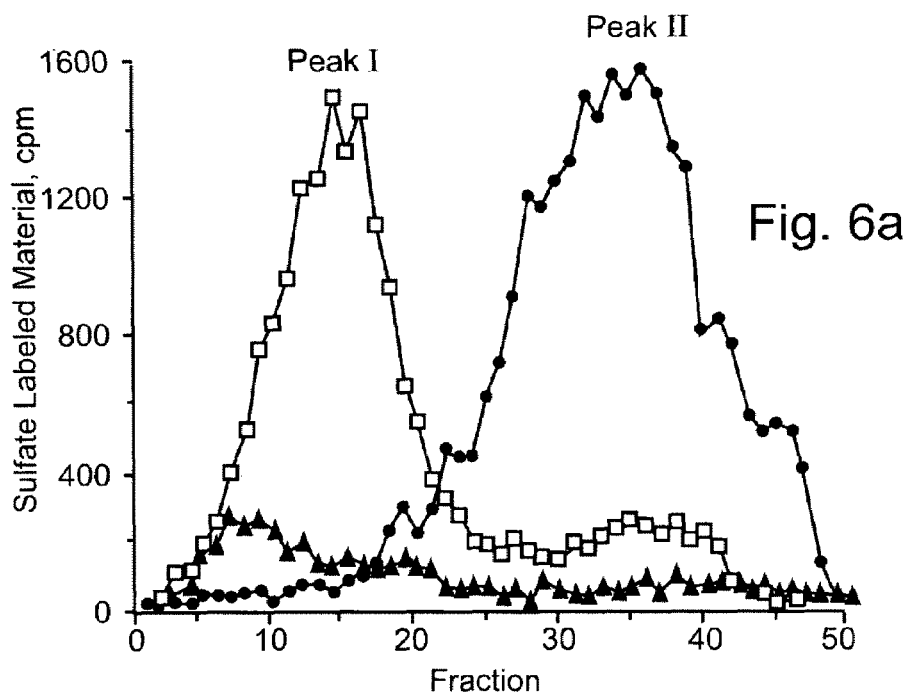
FIGS. 6a-b demonstrate degradation of sulfate labeled intact ECM by virus infected High Five and Sf21 cells. High Five (6a) and Sf21 (6b) cells were plated on sulfate labeled ECM and infected (48 h, 28° C.) with pFhpa4 (●) or control pF1 (□) viruses. Control non-infected Sf21 cells (R) were plated on the labeled ECM as well. The pH of the cultured medium was adjusted to 6.0-6.2 followed by 24 h incubation at 37° C. Sulfate labeled material released into the incubation medium was analyzed by gel filtration on Sepharose 6B. HS degradation fragments were produced only by cells infected with the hpa containing virus.
Figure 6B:
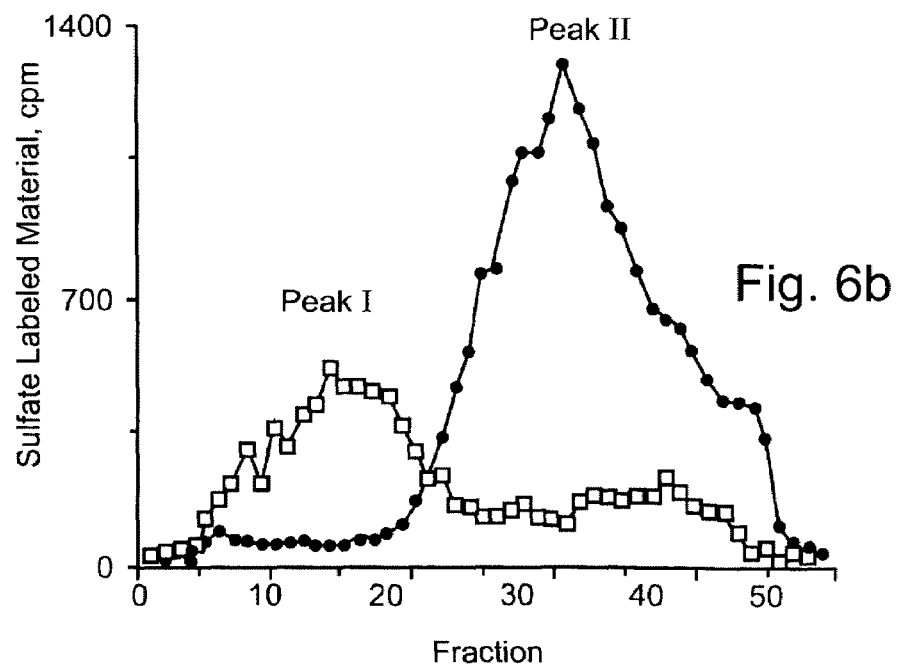

As demonstrated in FIGS. 5a-b, conversion of the peak I substrate into peak II HS degradation fragments was completely abolished in the presence of heparin.

Altogether, these results indicate that the heparanase enzyme is expressed in an active form by insect cells infected with Baculovirus containing the newly identified human hpa gene.

Example 3

Degradation of HSPG in intact ECM

Next, the ability of intact infected insect cells to degrade HS in intact, naturally produced ECM was investigated. For this purpose, High Five or Sf21 cells were seeded on metabolically sulfate labeled ECM followed by infection (48 h, 28° C.) with either the pFhpa4 or control pF2 viruses. The pH of the medium was then adjusted to pH 6.2-6.4 and the cells further incubated with the labeled ECM for another 48 h at 28° C. or 24 h at 37° C. Sulfate labeled material released into the incubation medium was analyzed by gel filtration on Sepharose 6B.

As shown in FIGS. 6a-b and 7a-b, incubation of the ECM with cells infected with the control pF2 virus resulted in a constant release of labeled material that consisted almost entirely (>90%) of high Mr fragments (peak I) eluted with or next to $V_O$. It was previously shown that a proteolytic activity residing in the ECM itself and/or expressed by cells is responsible for release of the high Mr material (6). This nearly intact HSPG provides a soluble substrate for subsequent degradation by heparanase, as also indicated by the relatively large amount of peak I material accumulating when the heparanase enzyme is inhibited by heparin (6, 7, 12, FIG. 9). On the other hand, incubation of the labeled ECM with cells infected with the pFhpa4 virus resulted in release of 60-70% of the ECM-associated radioactivity in the form of low Mr sulfate-labeled fragments (peak II, 0.5<Kav<0.75), regardless of whether the infected cells were incubated with the ECM at 28° C. or 37° C. Control intact non-infected Sf21 or High Five cells failed to degrade the ECM HS side chains.

Figure 8A:
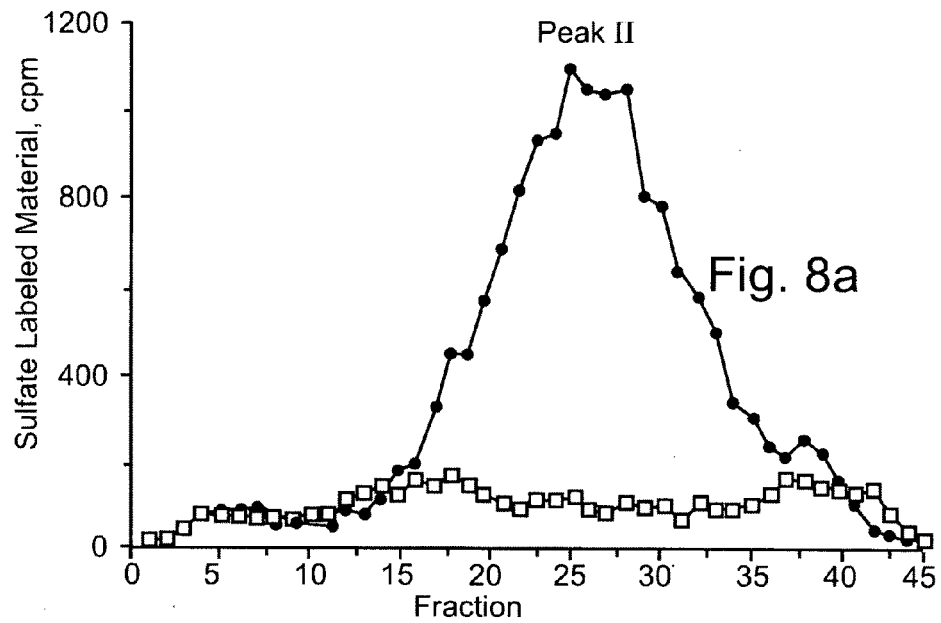
FIGS. 8a-b demonstrate degradation of sulfate labeled intact ECM by the culture medium of pFhpa4 infected cells. Culture media of High Five (8a) and Sf21 (8b) cells that were infected with pFhpa4 (●) or control pF1 (□) viruses were incubated (48 h, 37° C., pH 6.0) with intact sulfate labeled ECM. The ECM was also incubated with the culture medium of control non-infected Sf21 cells (R). Sulfate labeled material released into the reaction mixture was subjected to gel filtration analysis. Heparanase activity was detected only in the culture medium of pFhpa4 infected cells.
Figure 8B:
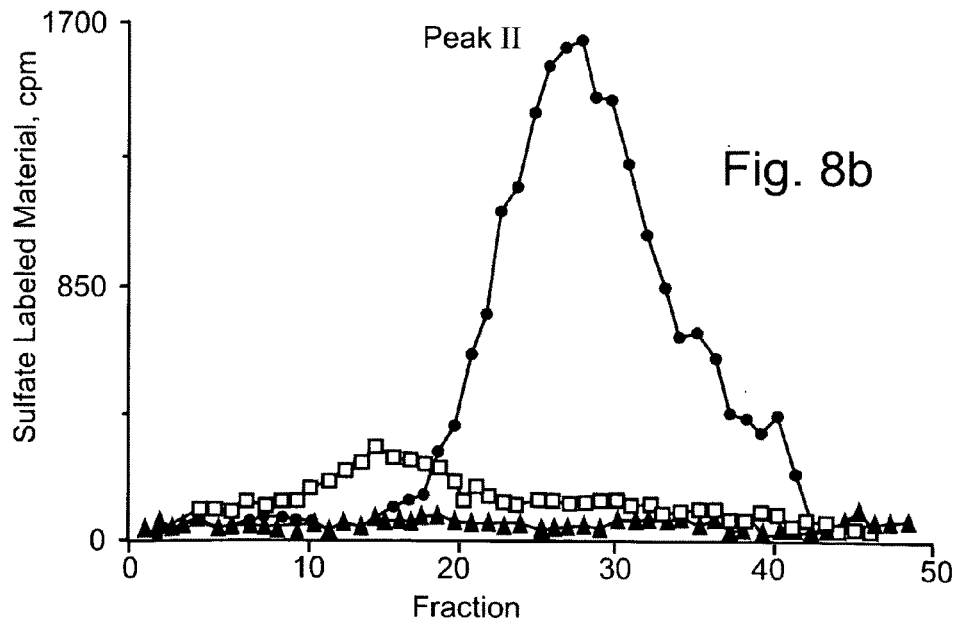
Figure 9A:
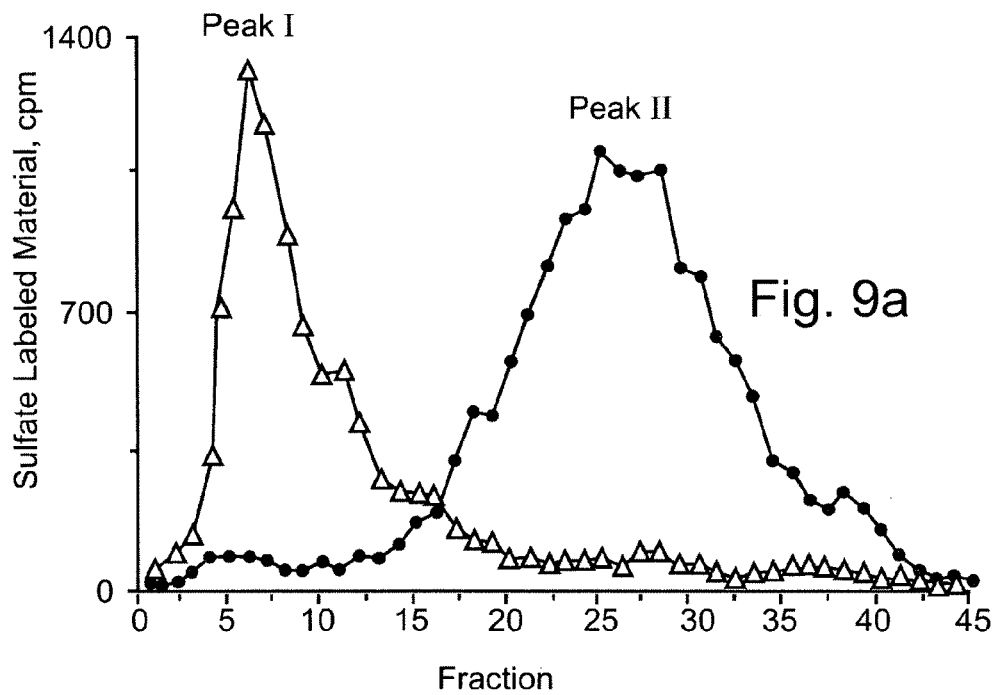
FIGS. 9a-b demonstrate the effect of heparin on heparanase activity in the culture medium of pFhpa4 infected cells. Sulfate labeled ECM was incubated (24 h, 37° C., pH 6.0) with culture medium of pFhpa4 infected High Five (9a) and Sf21 (9b) cells in the absence (●) or presence (V) of 10 µg/ml heparin. Sulfate labeled material released into the incubation medium was subjected to gel filtration on Sepharose 6B. Heparanase activity (production of peak II HS degradation fragments) was completely inhibited in the presence of heparin.
Figure 9B:
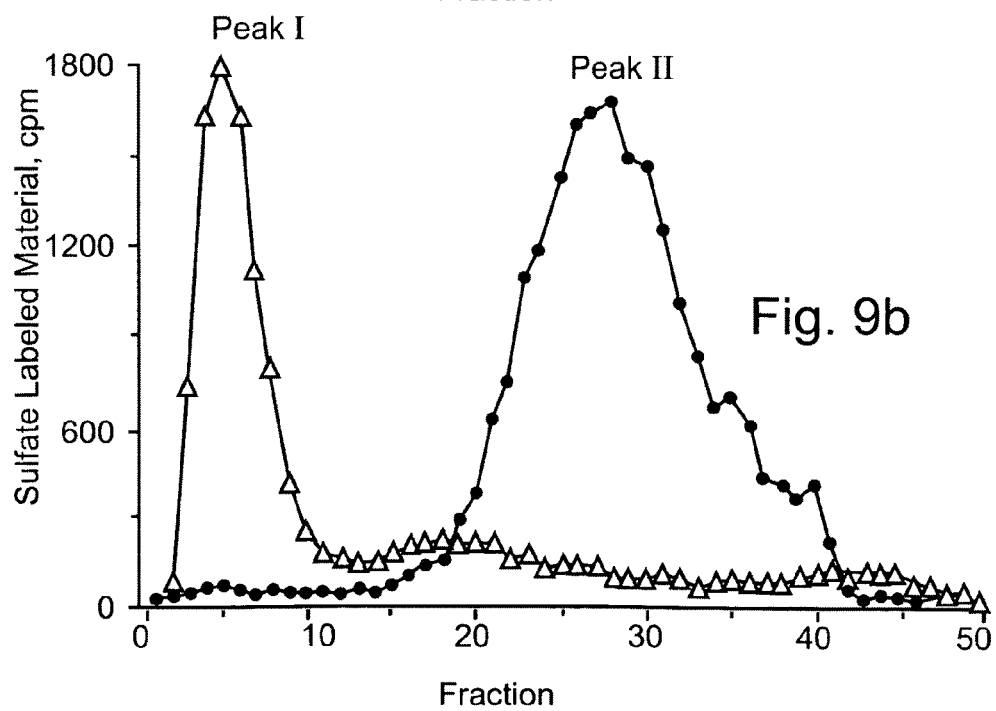

In subsequent experiments, as demonstrated in FIGS. 8a-b, High Five and Sf21 cells were infected (96 h, 28° C.) with pFhpa4 or control pF 1 viruses and the culture medium incubated with sulfate-labeled ECM. Low Mr HS degradation fragments were released from the ECM only upon incubation with medium conditioned by pFhpa4 infected cells. As shown in FIG. 9, production of these fragments was abolished in the presence of heparin. No heparanase activity was detected in the culture medium of control, non-infected cells. These results indicate that the heparanase enzyme expressed by cells infected with the pFhpa4 virus is capable of degrading HS when complexed to other macromolecular constituents (i.e. fibronectin, laminin, collagen) of a naturally produced intact ECM, in a manner similar to that reported for highly metastatic tumor cells or activated cells of the immune system (6, 7).

Example 4

Purification of Recombinant Human Heparanase

Figure 10B:
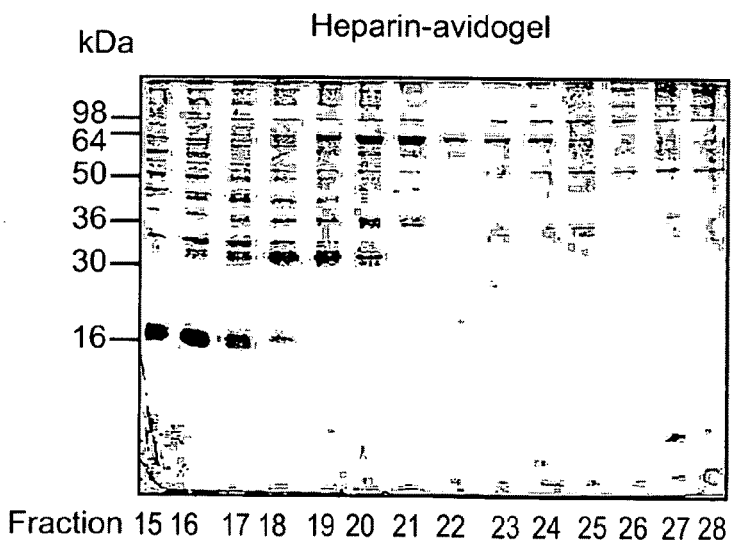
Figure 11A:
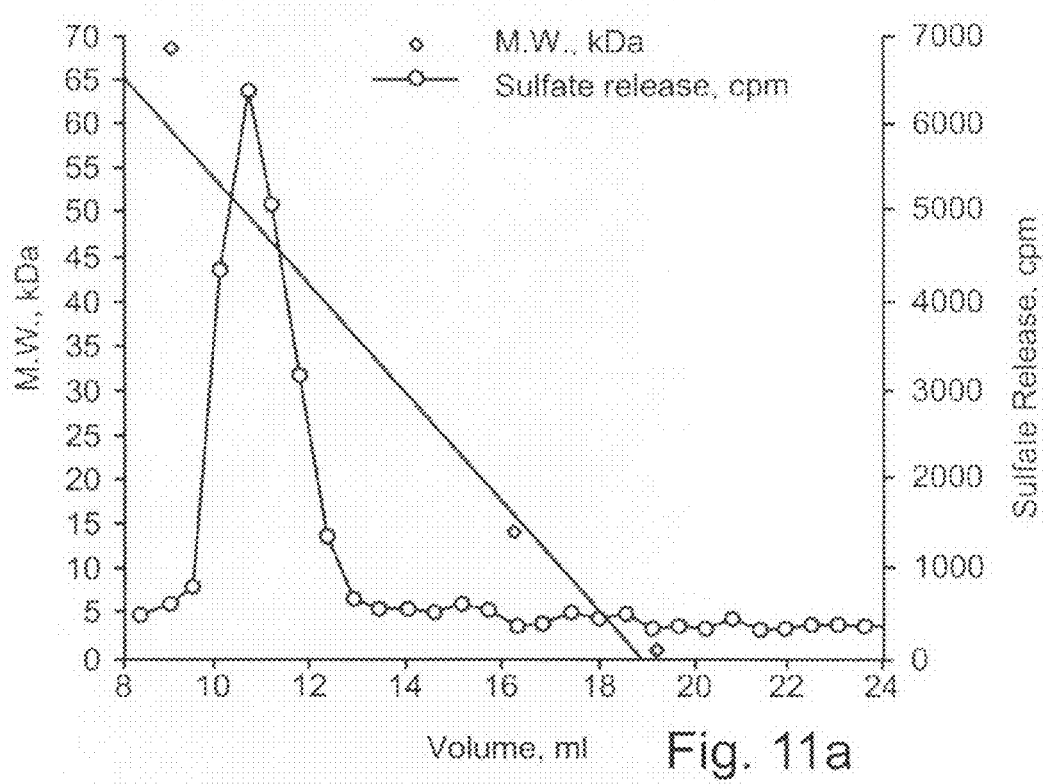
FIGS. 11a-b demonstrate purification of recombinant heparanase on a Superdex 75 gel filtration column. Active fractions eluted from heparin-Sepharose (FIG. 10a) were pooled, concentrated and applied onto Superdex 75 FPLC column. Fractions were collected and aliquots of each fraction were tested for heparanase activity (c, FIG. 11a) and analyzed by SDS-polyacrylamide gel electrophoresis followed by silver nitrate staining (FIG. 11b). A correlation is seen between the appearance of a major protein band (MW~63,000) in fractions 4-7 and heparanase activity.
Figure 11B:
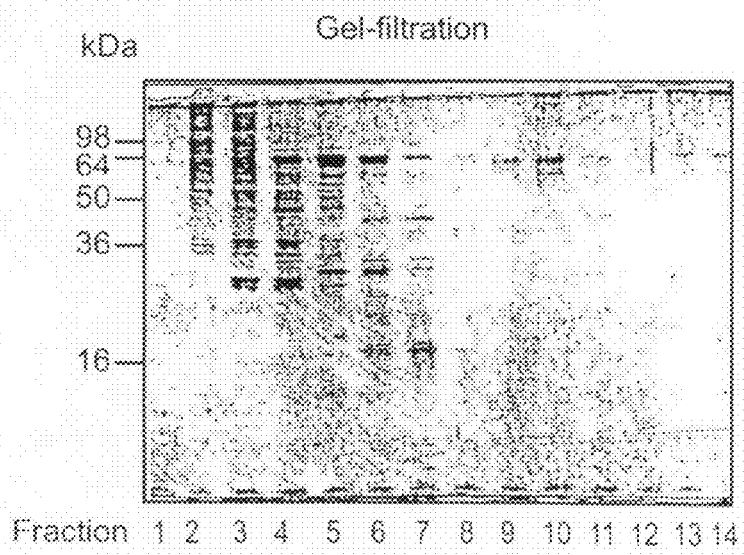

The recombinant heparanase was partially purified from medium of pFhpa4 infected Sf21 cells by Heparin-Sepharose chromatography (FIG. 10a) followed by gel filtration of the pooled active fractions over an FPLC Superdex 75 column (FIG. 11a). A ~63 kDa protein was observed, whose quantity, as was detected by silver stained SDS-polyacrylamide gel electrophoresis, correlated with heparanase activity in the relevant column fractions (FIGS. 10b and 11b, respectively). This protein was not detected in the culture medium of cells infected with the control pF1 virus and was subjected to a similar fractionation on heparin-Sepharose (not shown).

Example 5

Expression of the Human hpa cDNA in Various Cell Types, Organs and Tissues

Figure 12A:
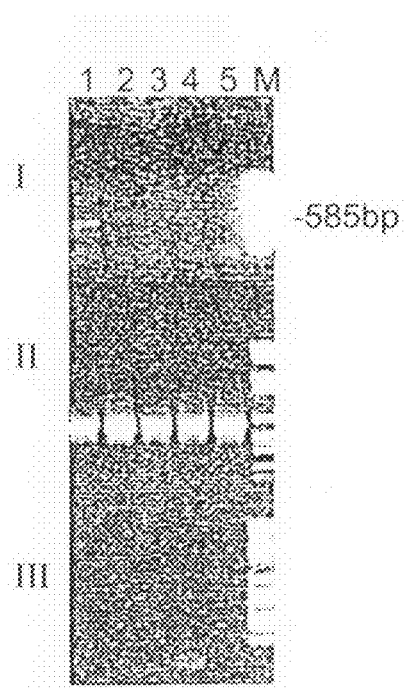
FIGS. 12a-e demonstrate expression of the hpa gene by RT-PCR with total RNA from human embryonal tissues (12a), human extra-embryonal tissues (12b) and cell lines from different origins (12c-e). RT-PCR products using hpa specific primers (I), primers for GAPDH housekeeping gene (II), and control reactions without reverse transcriptase demonstrating absence of genomic DNA or other contamination in RNA samples (III). M-DNA molecular weight marker VI (Boehringer Mannheim). For 12a: lane 1—neutrophil cells (adult), lane 2—muscle, lane 3—thymus, lane 4—heart, lane 5—adrenal. For 12b: lane 1—kidney, lane 2—placenta (8 weeks), lane 3—placenta (11 weeks), lanes 4-7—mole (complete hydatidiform mole), lane 8—cytotrophoblast cells (freshly isolated), lane 9—cytotrophoblast cells (1.5 h in vitro), lane 10—cytotrophoblast cells (6 h in vitro), lane 11—cytotrophoblast cells (18 h in vitro), lane 12—cytotrophoblast cells (48 h in vitro). For 12c: lane 1—JAR bladder cell line, lane 2—NCITT testicular tumor cell line, lane 3—SW-480 human hepatoma cell line, lane 4—HTR (cytotrophoblasts transformed by SV40), lane 5—HPTLP-I hepatocellular carcinoma cell line, lane 6—EJ-28 bladder carcinoma cell line. For 12d: lane 1—SK-hep-1 human hepatoma cell line, lane 2—DAMI human megakaryocytic cell line, lane 3—DAMI cell line+PMA, lane 4—CHRF cell line+PMA, lane 5—CHRF cell line. For 12e: lane 1—ABAE bovine aortic endothelial cells, lane 2-1063 human ovarian cell line, lane 3—human breast carcinoma MDA435 cell line, lane 4—human breast carcinoma MDA231 cell line.
Figure 12B:
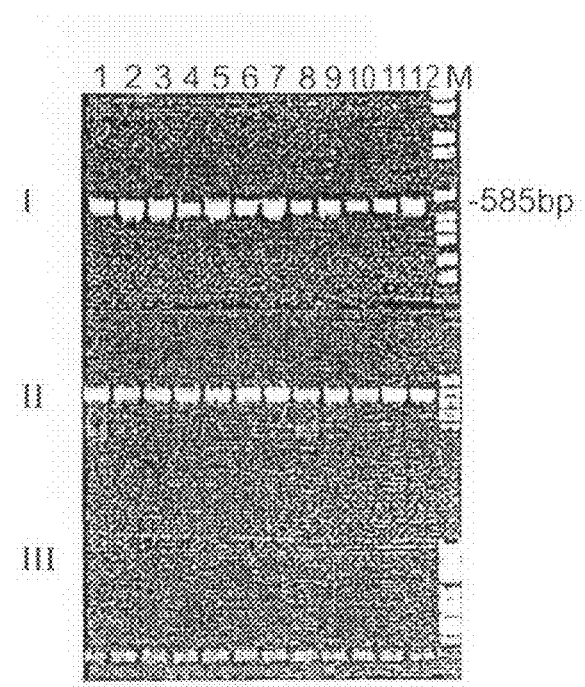
Figure 12C:
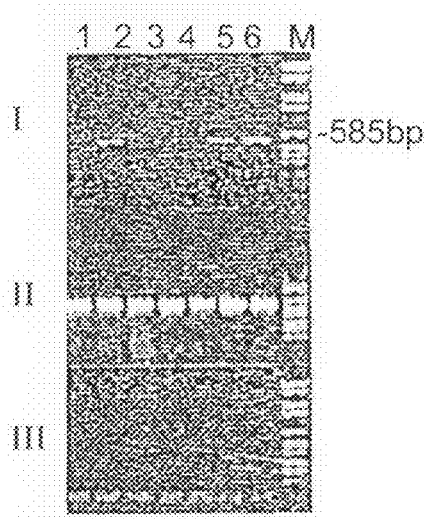
Figure 12D:
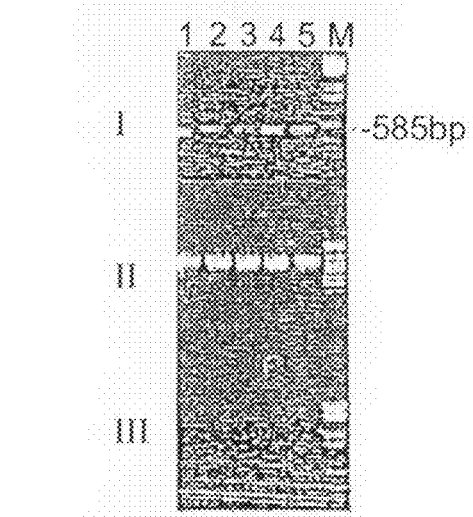
Figure 12E:
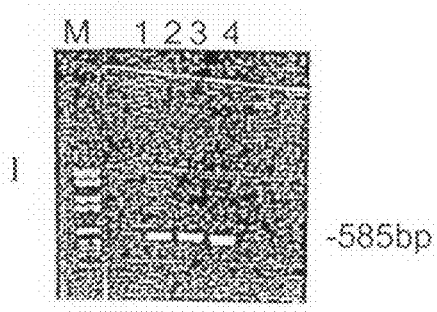

Referring now to FIGS. 12a-e, RT-PCR was applied to evaluate the expression of the hpa gene by various cell types and tissues. For this purpose, total RNA was reverse transcribed and amplified. The expected 585 bp long cDNA was clearly demonstrated in human kidney, placenta (8 and 11 weeks) and mole tissues, as well as in freshly isolated and short termed (1.5-48 h) cultured human placental cytotrophoblastic cells (FIG. 12a), all known to express a high heparanase activity (41). The hpa transcript was also expressed by normal human neutrophils (FIG. 12b). In contrast, there was no detectable expression of the hpa mRNA in embryonic human muscle tissue, thymus, heart and adrenal (FIG. 12b). The hpa gene was expressed by several, but not all, human bladder carcinoma cell lines (FIG. 12c), SK hepatoma (SK-hep-1), ovarian carcinoma (OV 1063), breast carcinoma (435, 231), melanoma and megakaryocytic (DAMI, CHRF) human cell lines (FIGS. 12d-e).

The above described expression pattern of the hpa transcript was determined to be in a very good correlation with heparanase activity levels determined in various tissues and cell types (not shown).

Example 6

Isolation of an Extended 5' end of hpa cDNA from Human SK-hep1 Cell Line

The 5' end of hpa cDNA was isolated from human SK-hep1 cell line by PCR amplification using the Marathon RACE (rapid amplification of cDNA ends) kit (Clontech). Total RNA was prepared from SK-hep1 cells using the TRI-Reagent (Molecular research center Inc.) according to the manufacturer instructions. Poly A+ RNA was isolated using the mRNA separator kit (Clonetech).

The Marahton RACE SK-hep1 cDNA composite was constructed according to the manufacturer recommendations. First round of amplification was performed using an adaptor specific primer API: 5'-CCATCCTAATACG ACTCACTAT-AGGGC-3', SEQ ID NO:1, and a hpa specific antisense primer hpl-629: 5'-CCCCAGGAGCAGCAGCATCAG -3', SEQ ID NO: 17, corresponding to nucleotides 119-99 of SEQ ID NO:9. The resulting PCR product was subjected to a second round of amplification using an adaptor specific nested primer AP2: 5'-ACTCACTATAGGGCTC-GAGCGGC-3', SEQ ID NO: 3, and a hpa specific antisense nested primer hpl-666 5'-AGGCTTCGAGCGCAGCAG-CAT-3', SEQ ID NO: 18, corresponding to nucleotides 83-63 of SEQ ID NO: 9. The PCR program was as follows: a hot start of 94° C. for 1 minute, followed by 30 cycles of 90° C.—30 seconds, 68° C.—4 minutes. The resulting 300 bp DNA fragment was extracted from an agarose gel and cloned into the vector pGEM-T Easy (Promega). The resulting recombinant plasmid was designated pHPSK1.

The nucleotide sequence of the pHPSK1 insert was determined and it was found to contain 62 nucleotides of the 5' end of the placenta hpa cDNA (SEQ ID NO:9) and additional 178 nucleotides upstream, the first 178 nucleotides of SEQ ID NOs:13 and 15.

A single nucleotide discrepancy was identified between the SK-hep1 cDNA and the placenta cDNA. The "T" derivative at position 9 of the placenta cDNA (SEQ ID NO:9), is replaced by a "C" derivative at the corresponding position 187 of the SK-hepI cDNA (SEQ ID NO:13).

The discrepancy is likely to be due to a mutation at the 5' end of the placenta cDNA clone as confirmed by sequence analysis of several additional cDNA clones isolated from placenta, which like the SK-hep1 cDNA contained C at position 9 of SEQ ID NO:9.

The 5' extended sequence of the SK-hep1 hpa cDNA was assembled with the sequence of the hpa cDNA isolated from human placenta (SEQ ID NO:9). The assembled sequence contained an open reading frame which encodes, as shown in SEQ ID NOs:14 and 15, a polypeptide of 592 amino acids with a calculated molecular weight of 66,407 daltons. The open reading frame is flanked by 93 bp 5' untranslated region (UTR).

Example 7

Isolation of the Upstream Genomic Region of the hpa Gene

The upstream region of the hpa gene was isolated using the Genome Walker kit (Clontech) according to the manufacturer recommendations. The kit includes five human genomic DNA samples each digested with a different restriction endonuclease creating blunt ends: EcoRV, ScaI, DraI, PvuII and SspI.

The blunt ended DNA fragments are ligated to partially single stranded adaptors. The Genomic DNA samples were subjected to PCR amplification using the adaptor specific primer and a gene specific primer. Amplification was performed with Expand High Fidelity (Boehringer Mannheim).

A first round of amplification was performed using the ap1 primer: 5'-G TAATACGACTCACTATAGGGC-3', SEQ ID NO:19, and the hpa specific antisense primer hpl-666: 5'-AG-GCTTCGAGCGCAGCAGCAT -3', SEQ ID NO:18, corresponding to nucleotides 83-63 of SEQ ID NO:9. The PCR program was as follows: a hot start of 94° C.—3 minutes, followed by 36 cycles of 94° C. -40 seconds, 67° C. -4 minutes.

The PCR products of the first amplification were diluted 1:50. One μl of the diluted sample was used as a template for a second amplification using a nested adaptor specific primer ap2: 5'-ACTATAGGGCACGCGTGGT-3', SEQ ID NO:20, and a hpa specific antisense primer hpl-690, 5'-CTTGGGCT-CACC TGGCTGCTC-3', SEQ ID NO:21, corresponding to nucleotides 62-42 of SEQ ID NO:9. The resulting amplification products were analyzed using agarose gel electrophoresis. Five different PCR products were obtained from the five amplification reactions. A DNA fragment of approximately 750 bp which was obtained from the SspI digested DNA sample was gel extracted. The purified fragment was ligated into the plasmid vector pGEM-T Easy (Promega). The resulting recombinant plasmid was designated pGHP6905 and the nucleotide sequence of the hpa insert was determined.

A partial sequence of 594 nucleotides is shown in SEQ ID NO:16. The last nucleotide in SEQ ID NO:13 corresponds to nucleotide 93 in SEQ ID:13. The DNA sequence in SEQ ID NO:16 contains the 5' region of the hpa cDNA and 501 nucleotides of the genomic upstream region which are predicted to contain the promoter region of the hpa gene.

Example 8

Expression of the 592 Amino Acids HPA Polypeptide in a Human 293 Cell Line

The 592 amino acids open reading frame (SEQ ID NOs:13 and 15) was constructed by ligation of the 110 bp corresponding to the 5' end of the SK-hep 1 hpa cDNA with the placenta cDNA. More specifically the Marathon RACE-PCR amplification product of the placenta hpa DNA was digested with SacI and an approximately 1 kb fragment was ligated into a SacI-digested pGHP6905 plasmid. The resulting plasmid was digested with EarI and AatII. The EarI sticky ends were blunted and an approximately 280 bp EarI/blunt-AatII fragment was isolated. This fragment was ligated with pFasthpa digested with EcoRI which was blunt ended using Klenow fragment and further digested with AatII. The resulting plasmid contained a 1827 bp insert which includes an open reading frame of 1776 bp, 31 bp of 3' UTR and 21 bp of 5' UTR. This plasmid was designated pFastLhpa.

A mammalian expression vector was constructed to drive the expression of the 592 amino acids heparanase polypeptide in human cells. The hpa cDNA was excised prom pFastLhpa with BssHII and NotI. The resulting 1850 bp BssHII-NotI fragment was ligated to a mammalian expression vector pSI (Promega) digested with MluI and NotI. The resulting recombinant plasmid, pSIhpaMet2 was transfected into a human 293 embryonic kidney cell line.

Transient expression of the 592 amino-acids heparanase was examined by western blot analysis and the enzymatic activity was tested using the gel shift assay. Both these procedures are described in length in U.S. patent application Ser. No. 09/071,739, filed May 1, 1998, which is incorporated by reference as if fully set forth herein. Cells were harvested 3 days following transfection. Harvested cells were re-suspended in lysis buffer containing 150 mM NaCl, 50 mM Tris pH 7.5, 1% Triton X-100, 1 mM PMSF and protease inhibitor cocktail (Boehringer Mannheim). 40 µg protein extract samples were used for separation on a SDS-PAGE. Proteins were transferred onto a PVDF Hybond-P membrane (Amersham). The membrane was incubated with an affinity purified polyclonal anti heparanase antibody, as described in U.S. patent application Ser. No. 09/071,739. A major band of approximately 50 kDa was observed in the transfected cells as well as a minor band of approximately 65 kDa. A similar pattern was observed in extracts of cells transfected with the pShpa as demonstrated in U.S. patent application Ser. No. 09/071,739. These two bands probably represent two forms of the recombinant heparanase protein produced by the transfected cells. The 65 kDa protein probably represents a heparanase precursor, while the 50 kDa protein is suggested herein to be the processed or mature form.

The catalytic activity of the recombinant protein expressed in the pShpaMet2 transfected cells was tested by gel shift assay. Cell extracts of transfected and of mock transfected cells were incubated overnight with heparin (6 µg in each reaction) at 37° C., in the presence of 20 mM phosphate citrate buffer pH 5.4, 1 mM $CaCl_2$, 1 mM DTT and 50 mM NaCl. Reaction mixtures were then separated on a 10% polyacrylamide gel. The catalytic activity of the recombinant heparanase was clearly demonstrated by a faster migration of the heparin molecules incubated with the transfected cell extract as compared to the control. Faster migration indicates the disappearance of high molecular weight heparin molecules and the generation of low molecular weight degradation products.

Example 9

Chromosomal Localization of the hpa Gene

Chromosomal mapping of the hpa gene was performed utilizing a panel of monochromosomal human/CHO and human/mouse somatic cell hybrids, obtained from the UK HGMP Resource Center (Cambridge, England).

40 ng of each of the somatic cell hybrid DNA samples were subjected to PCR amplification using the hpa primers: hpu565 5'-AGCTCTGTAGATGTGC TATACAC-3', SEQ ID NO: 22, corresponding to nucleotides 564-586 of SEQ ID NO: 9 and an antisense primer hp1171 5'-GCATCTTAGC-CGTCTTTCTTCG-3', SEQ ID NO: 23, corresponding to nucleotides 897-876 of SEQ ID NO:9.

The PCR program was as follows: a hot start of 94° C.—3 minutes, followed by 7 cycles of 94° C.—45 seconds, 66° C.—1 minute, 68° C.—5 minutes, followed by 30 cycles of 94° C.—45 seconds, 62° C.—1 minute, 68° C.—5 minutes, and a 10 minutes final extension at 72° C.

Figure 14:
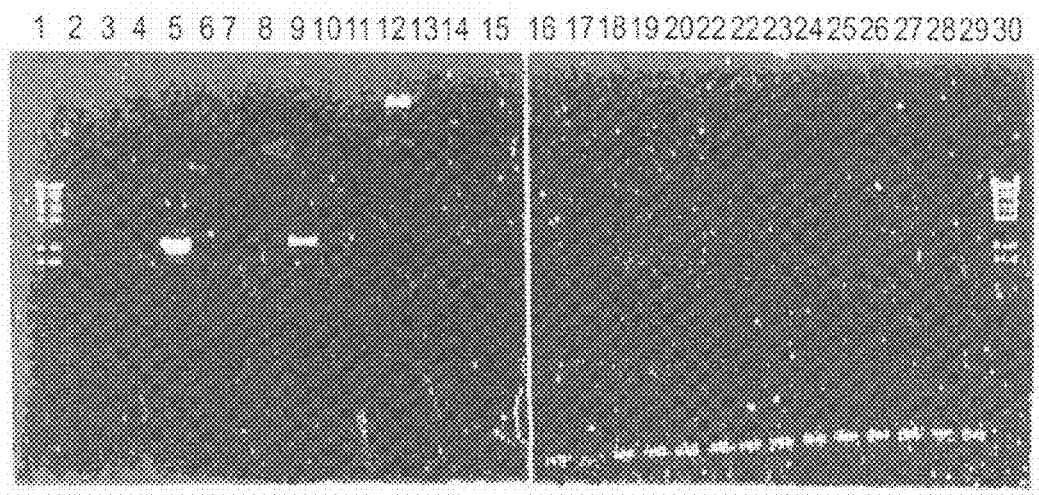
FIG. 14 demonstrates the chromosomal localization of the hpa gene. PCR products of DNA derived from somatic cell hybrids and of genomic DNA of hamster, mouse and human of were separated on 0.7% agarose gel following amplification with hpa specific primers. Lane 1—Lambda DNA digested with BstEII, lane 2—no DNA control, lanes 3-29, PCR amplification products. Lanes 3-5—human, mouse and hamster genomic DNA, respectively. Lanes 6-29, human monochromosomal somatic cell hybrids representing chromosomes 1-22 and X and Y, respectively. Lane 30—Lambda DNA digested with BstEII. An amplification product of approximately 2.8 Kb is observed only in lanes 5 and 9, representing human genomic DNA and DNA derived from cell hybrid carrying human chromosome 4, respectively. These results demonstrate that the hpa gene is localized in human chromosome 4.

The reactions were performed with Expand long PCR (Boehringer Mannheim). The resulting amplification products were analyzed using agarose gel electrophoresis. As demonstrated in FIG. 14, a single band of approximately 2.8 Kb was obtained from chromosome 4, as well as from the control human genomic DNA. A 2.8 kb amplification product is expected based on amplification of the genomic hpa clone (data not shown). No amplification products were obtained neither in the control DNA samples of hamster and mouse nor in somatic hybrids of other human chromosome.

Example 10

Human Genomic Clone Encoding Heparanase

Five plaques were isolated following screening of a human genomic library and were designated L3-1, L5-1, L8-1, L10-1 and L6-1. The phage DNAs were analyzed by Southern hybridization and by PCR with hpa specific and vector specific primers. Southern analysis was performed with three fragments of hpa cDNA: a PvuII-BamHI fragment (nucleotides 32-450, SEQ ID NO: 9), a BamHI-NdeI fragment (nucleotides 451-1102, SEQ ID NO:9) and an NdeI-XhoI fragment (nucleotides 1103-1721, SEQ ID NO:9).

Figure 15:
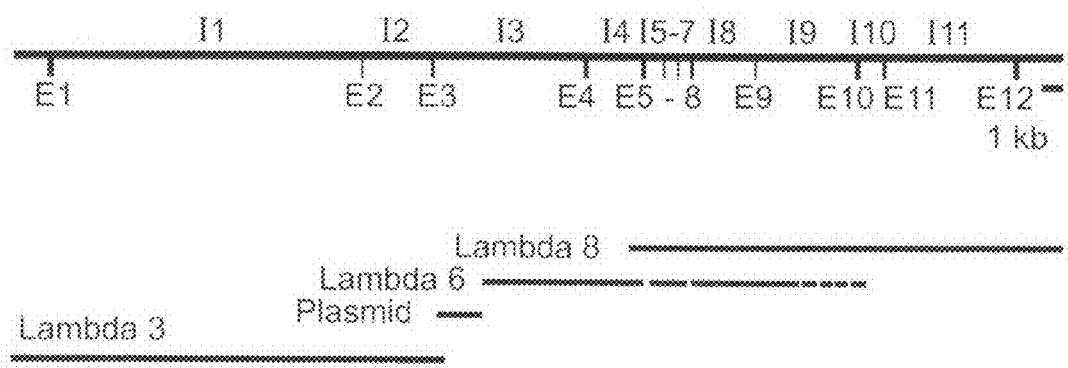
FIG. 15 demonstrates the genomic exon-intron structure of the human hpa locus (top) and the relative positions of the lambda clones used as sequencing templates to sequence the locus (below). The vertical rectangles represent exons (E) and the horizontal lines therebetween represent introns (I), upstream (U) and downstream (D) regions. Continuous lines represent DNA fragments, which were used for sequence analysis. The discontinuous line in lambda 6 represent a region, which overlaps with lambda 8 and hence was not analyzed. The plasmid contains a PCR product, which bridges the gap between L3 and L6.

Following Southern analysis, phages L3, L6, L8 were selected for further analysis. A scheme of the genomic region and the relative position of the three phage clones is depicted in FIG. 15. A 2 kb DNA fragment containing the gap between phages L6 and L3 was PCR amplified from human genomic DNA with two gene specific primers GHpuL3 and GHplL6. The PCR product was cloned into the plasmid vector pGEM-T-easy (Promega).

Large scale DNA sequencing of the three Lambda clones and the amplified fragment was performed with Lambda purified DNA by primer walking. A nucleotide sequence of 44,898 bp was analyzed (FIG. 16, SEQ ID NO:42). Comparison of the genomic sequence with that of hpa cDNA revealed 12 exons separated by 11 introns (FIGS. 15 an 16). The genomic organization of the hpa gene is depicted in FIG. 15 (top). The sequence include the coding region from the first ATG to the stop codon which spans 39,113 nucleotides, 2742 nucleotides upstream of the first ATG and 3043 nucleotides downstream of the stop codon. Splice site consensus sequences were identified at exon/intron junctions.

Example 11

Alternative Splicing

Several minor RT-PCR products were obtained from various cell types, following amplification with hpa specific primers. Each one found to contain a deletion of one or two exons. Some of these PCR products contain ORFs, which encode potential shorter proteins.

Table 1 below summarizes the alternative spliced products isolated from various cell lines.

Fragments of similar sizes were obtained following amplification with two cell lines, placenta and platelets.

| Cell type | Nucleotides deleted | Exons deleted | ORF |
|---|---|---|---|
| Platelets | 1047-1267 | 8, 9 | + |
| Platelets | 1154-1267 | 9 | − |
| Platelets | 289-435, 562-735 | 2, 4 | − |
| Sk-hep1, platelets, Zr75 | 562-735 | 4 | + |
| Sk-hep1 (hepatoma) | 561-904 | 4, 5 | − |
| Zr75 (breast carcinoma) | 96-203 | 1 (partial) | + |

Example 12

Mouse and Rat hpa

EST databases were screened for sequences homologous to the hpa gene. Three mouse EST's were identified (accession No. Aa177901, from mouse spleen, AaO67997 from mouse skin, Aa47943 from mouse embryo), assembled into a 824 bp cDNA fragment which contains a partial open reading frame (lacking a 5' end) of 629 bp and a 3' untranslated region of 195 bp (SEQ ID NO:12). As shown in FIG. 13, the coding region is 80% similar to the 3' end of the hpa cDNA sequence. These EST's are probably cDNA fragments of the mouse hpa homolog that encodes for the mouse heparanase.

Searching for consensus protein domains revealed an amino terminal homology between the heparanase and several precursor proteins such as Procollagen Alpha 1 precursor, Tyrosine-protein kinase-RYK, Fibulin-1, Insulin-like growth factor binding protein and several others. The amino terminus is highly hydrophobic and contains a potential transmembrane domain. The homology to known signal peptide sequences suggests that it could function as a signal peptide for protein localization.

The amino acid sequence of human heparanase was used to search for homologous sequences in the DNA and protein databases. Several human EST's were identified, as well as mouse sequences highly homologous to human heparanase. The following mouse EST's were identified AA177901, AA674378, AA67997, AA047943, AA690179, AI122034, all sharing an identical sequence and correspond to amino acids 336-543 of the human heparanase sequence. The entire mouse heparanase cDNA was cloned, based on the nucleotide sequence of the mouse EST's. PCR primers were designed and a Marathon RACE was performed using a Marathon cDNA library from 15 days mouse embryo (Clontech) and from BL6 mouse melanoma cell line. The mouse hpa homologous cDNA was isolated following several amplification steps. A 1.1 kb fragment was amplified from mouse embryo Marathon cDNA library. The first cycle of amplification was performed with primers mhp1773 and Ap1 and the second cycle with primers mhp1736 and AP2. A 1.1 kb fragment was then amplified from BL6 Marathon cDNA library. The first cycle of amplification was performed with the primers mhp1152 and Ap1, and the second with mhp183 and AP2. The combined sequence was homologous to nucleotides 157-1702 of the human hpa cDNA, which encode amino acids 33-543. The 5' end of the mouse hpa gene was isolated from a mouse genomic DNA library using the Genome Walker kit (Clontech). An 0.9 kb fragment was amplified from a DraI digested Genome walker DNA library. The first cycle of amplification was performed with primers mhpll 14 and Ap1 and the second with primers mhp1103 and AP2. The assembled sequence (SEQ ID NOs:43, 45) is 2396 nucleotides long. It contains an open reading frame of 1605 nucleotides, which encode a polypeptide of 535 amino acids (SEQ ID NOs:44, 45), 196 nucleotides of 3' untranslated region (UTR), and anupstream sequence which includes the promoter region and the 5'-UTR of the mouse hpa cDNA. According to two promoter predicting programs TSSW and TSSG, the transcription start site is localized to nucleotide 431 of SEQ ID NOs:43, 45, 163 nucleotides upstream of the first ATG codon. The 431 upstream genomic sequence contains the promoter region. A TATA box is predicted at position 394 of SEQ ID NOs:43, 45. The mouse and the human hpa genes share an average homology of 78% between the nucleotide sequences and 81% similarity between the deduced amino acid sequences.

Search for hpa homologous sequences, using the Blast 2.0 server revealed two EST's from rat: AI060284 (385 nucleotides, SEQ ID NO:46) which is homologous to the amino terminus (68% similarity to amino acids 12-136) of human heparanase and A1237828 (541 nucleotides, SEQ ID NO:47) which is homologous to the carboxyl terminus (81% similarity to amino acids 500-543) of human heparanase, and contains a 3'-UTR. A comparison between the human heparanase and the mouse and rat homologous sequences is demonstrated in FIG. 17.

Example 13

Prediction of Heparanase Active Site

Homology search of heparanase amino acid sequence against the DNA and the protein databases revealed no significant homologies. The protein secondary structure as predicted by the PHD program consists of alternating alpha helices and beta sheets. The fold recognition server of UCLA predicted alpha/beta barrel structure, with under-threshold confidence.

Five of 15 proteins, which were predicted to have most similar folds, were glycosyl hydrolases from various organisms: 1xyza-xylanase from Clostridium Thermocellum, 1pbga-6-phospho-beta-δ-galactosidase from Lactococcus Lactis, 1amy-alpha-amylase from Barley, lecea-endocellulase from Acidothermus Cellulolyticus and lqbc-hexosaminidase alpha chain, glycosyl hydrolase.

Protein homology search using the bioaccelerator pulled out several proteins, including glycosyl hydrolyses such as beta-fructofuranosidase from Vicia faba (broad bean) and from potato, lactase phlorizin hydrolase from human, xylanases from *Clostridium thermocellum* and from *Streptomyces halstedii* and cellulase from *Clostridium thermocellum*. Blocks 9.3 database pulled out the active site of glycosyl hydrolases family five, which includes cellulases from various bacteria and fungi. Similar active site motif is shared by several lysosomal acid hydrolases (63) and other glycosyl hydrolases. The common mechanism shared by these enzymes involves two glutamic acid residues, a proton donor and a nucleophile.

Despite the lack of an overall homology between the heparanase and other glycosyl hydolases, the amino acid couple Asp-Glu (NE), which is characteristic of the proton donor of glycosyl hydrolyses of the GH-A clan, was found at positions 224-225 of the human heparanase protein sequence. As in other clan members, this NE couple is located at the end of a β sheet.

Considering the relative location of the proton donor and the predicted secondary structure, the glutamic acid that functions as nucleophile is most likely located at position 343, or at positon 396. Identification of the active site and the amino acids directly involved in hydrolysis opens the way for expression of the defined catalytic domain. In addition, it will provide the tools for rational design of enzyme activity either by modification of the microenviroment or catalytic site itself.

Example 14

Expression of hpa Antisense in Mammalian Cell Lines

A mammalian expression vector Hpa2Kepcdna3 was constructed in order to express hpa antisense in mammalian cells. hpa cDNA (1.7 kb EcoRI fragment) was cloned into the plasmid pCDNA3 in 3'>5' (antisense) orientation. The construct was used to transfect MBT2-T50 and T24P cell lines. $2 \times 10^5$ cells in 35 mm plates were transfected using the Fugene protocol (Boehringer Mannheim). 48 hours after transfection cells were trypsinized and seeded in six well plates. 24 hours later G418 was added to initiate selection. The number of colonies per 35 mm plate following 3 weeks:

|  | Antisense | No insert |
|---|---|---|
| T24P | 15 | 60 |
| MBT-T50 | 1 | 6 |

The lower number of colonies obtained after transfection with hpa antisense, as compared with the control plasmid suggests that the introduction of hpa antisense interfere with cell growth. This experiment demonstrates the use of complementary antisense hpa DNA sequence to control heparanase expression in cells. This approach may be used to inhibit expression of heparanase in vivo, in, for example, cancer cells and in other pathological processes in which heparanase is involved.

Example 15

Zoo Blot

Figure 18:
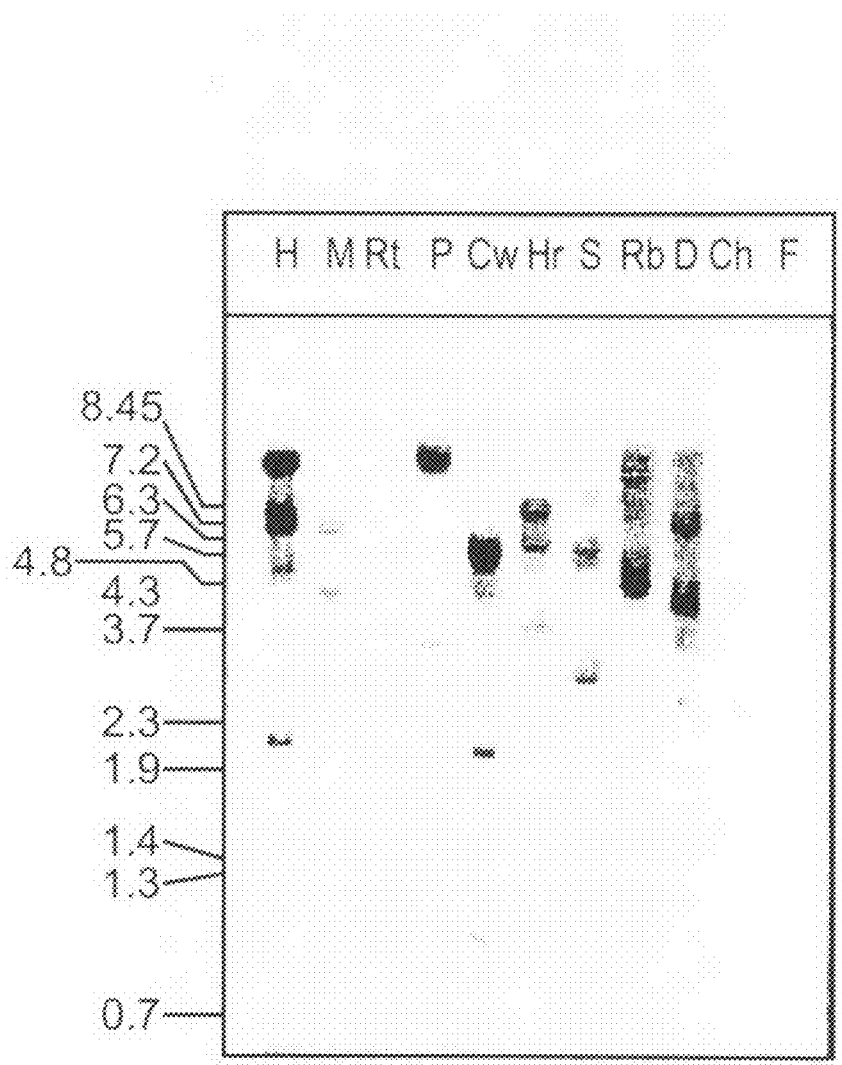
FIG. 18 presents a heparanase Zoo blot. Ten micrograms of genomic DNA from various sources were digested with EcoRI and separated on 0.7% agarose—TBE gel. Following electrophoresis, the was gel treated with HCl and than with NaOH and the DNA fragments were downward transferred to a nylon membrane (Hybond N+, Amersham) with 0.4 N NaOH. The membrane was hybridized with a 1.6 Kb DNA probe that contained the entire hpa cDNA. Lane order: H—Human; M—Mouse; Rt—Rat; P—Pig; Cw—Cow.

Hpa cDNA was used as a probe to detect homologous sequences in human DNA and in DNA of various animals. The autoradiogram of the Southern analysis is presented in FIG. 18. Several bands were detected in human DNA, which correlated with the accepted pattern according to the genomic hpa sequence. Several intense bands were detected in all mammals, while faint bands were detected in chicken. This correlates with the phylogenetic relation between human and the tested animals. The intense bands indicate that hpa is conserved among mammals as well as in more genetically distant organisms. The multiple bands patterns suggest that in all animals, like in human, the hpa locus occupy large genomic region. Alternatively, the various bands could represent homologous sequences and suggest the existence of a gene family, which can be isolated based on their homology to the human hpa reported herein. This conservation was actually found, between the isolated human hpa cDNA and the mouse homologue.

Example 16

Characterization of the hpa Promoter

The DNA sequence upstream of the hpa first ATG was subjected to computational analysis in order to localize the predicted transcription start site and to identify potential transcription factors binding sites. Recognition of human PolII promoter region and start of transcription were predicted using the TSSW and TSSG programs. Both programs identified a promoter region upstream of the coding region. TSSW pointed at nucleotide 2644 and TSSG at 2635 of SEQ ID NO:42. These two predicted transcription start sites are located 4 and 13 nucleotides upstream of the longest hpa cDNA isolated by RACE.

A hpa promoter-GFP reporter vector was constructed in order to investigate the regulation of hpa transcription. Two constructs were made, containing 1.8 kb and 1.1 kb of the hpa promoter region. The reporter vector was transfected into T50-mouse bladder carcinoma cells. Cells transfected with both constructs exhibited green fluorescence, which indicated the promoter activity of the genomic sequence upstream of the hpa-coding region. This reporter vector, enables the monitoring of hpa promoter activity, at various conditions and in different cell types and to characterize the factors involved regulation of hpa expression.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES

1. Wight, T. N., Kinsella, M. G., and Qwarnstromn, E. E. (1992). The role of proteoglycans in cell adhesion, migration and proliferation. *Curr. Opin. Cell Biol.,* 4, 793-801.

2. Jackson, R. L., Busch, S. J., and Cardin, A. L. (1991). Glycosaminoglycans: Molecular properties, protein interactions and role in physiological processes. *Physiol. Rev.,* 71, 481-539.

3. Wight, T. N. (1989). Cell biology of arterial proteoglycans. *Arteriosclerosis,* 9, 1-20.

4. Kjellen, L., and Lindahl, U. (1991). Proteoglycans: structures and interactions. *Annu. Rev. Biochem.,* 60, 443-475.

5. Ruoslahti, E., and Yamaguchi, Y. (1991). Proteoglycans as modulators of growth factor activities. *Cell,* 64, 867-869.

6. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. *Invasion & Metastasis,* 12, 112-127.

7. Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. *Invasion & Metastasis,* 14, 290-302.

8. Nakajima, M., Irimura, T., and Nicolson, G. L. (1988). Heparanase and tumor metastasis. *J. Cell Biochem.*, 36, 157-167.

9. Nicolson, G. L. (1988). Organ specificity of tumor metastasis: Role of preferential adhesion, invasion and growth of malignant cells at specific secondary sites. *Cancer Met. Rev.*, 7, 143-188.

10. Liotta, L. A., Rao, C. N., and Barsky, S. H. (1983). Tumor invasion and the extracellular matrix. *Lab. Invest.*, 49, 639-649.

11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. *Cancer Res.*, 43, 2704-2711.

12. Vlodavsky, I., Ishai-Michaeli, R., Bar-Ner, M., Fridman, R., Horowitz, A. T., Fuks,Z. and Biran, S. (1988). Involvement of heparanase in tumor metastasis and angiogenesis. Is. *J. Med.*, 24, 464-470.

13. Vlodavsky, I., Liu, G. M., and Gospodarowicz, D. (1980). Morphological appearance, growth behavior and migratory activity of human tumor cells maintained on extracellular matrix vs. plastic. *Cell*, 19, 607-616.

14. Gospodarowicz, D., Delgado, D., and Vlodavsky, I. (1980). Permissive effect of the extracellular matrix on cell proliferation in-vitro. *Proc. Natl. Acad. Sci. USA.*, 77, 4094-4098.

15. Bashkin, P., Doctrow, S., Klagsbrun, M., Svahn, C. M., Folkman, J., and Vlodavsky, I. (1989). Basic fibroblast growth factor binds to subendothelial extracellular matrix and is released by heparitinase and heparin-like molecules. *Biochemistry*, 28, 1737-1743.

16. Parish, C. R., Coombe, D. R., Jakobsen, K. B., and Underwood, P.A. (1987). Evidence that sulphated polysaccharides inhibit tumor metastasis by blocking tumor cell-derived heparanase. *Int. J. Cancer*, 40, 511-517.

16a. Vlodavsky, I., Hua-Quan Miao., Benezra, M., Lider, O., Bar-Shavit, R., Schmidt, A., and Peretz, T. (1997). Involvement of the extracellular matrix, heparan sulfate proteoglycans and heparan sulfate degrading enzymes in angiogenesis and metastasis. In: Tumor Angiogenesis. Eds. C. E. Lewis, R. Bicknell & N. Ferrara. Oxford University Press, Oxford UK, pp. 125-140.

17. Burgess, W. H., and Maciag, T. (1989). The heparin-binding (fibroblast) growth factor family of proteins. *Annu. Rev. Biochem.*, 58, 575-606.

18. Folkman, J., and Klagsbrun, M. (1987). Angiogenic factors. *Science*, 235, 442-447.

19. Vlodavsky, I., Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. *Proc. Natl. Acad. Sci. USA*, 84, 2292-2296.

20. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. *Am. J. Pathol.*, 130, 393-400.

21. Cardon-Cardo, C., Vlodavsky, I., Haimovitz-Friedman, A., Hicklin, D., and Fuks, Z. (1990). Expression of basic fibroblast growth factor in normal human tissues. *Lab. Invest.*, 63, 832-840.

22. Ishai-Michaeli, R., Svahn, C. -M., Chajek-Shaul, T., Korner, G., Ekre, H. -P., and Vlodavsky, I. (1992). Importance of size and sulfation of heparin in release of basic fibroblast factor from the vascular endothelium and extracellular matrix. *Biochemistry*, 31, 2080-2088.

23. Ishai-Michaeli, R., Eldor, A., and Vlodavsky, I. (1990). Heparanase activity expressed by platelets, neutrophils and lymphoma cells releases active fibroblast growth factor from extracellular matrix. *Cell Reg.*, 1, 833-842.

24. Vlodavsky, I., Bar-Shavit, R., Ishai-Michaeli, R., Bashkin, P., and Fuks, Z. (1991). Extracellular sequestration and release of fibroblast growth factor: a regulatory mechanism? *Trends Biochem. Sci.*, 16, 268-271.

25. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp327-343. Academic press Inc., Orlando, Fla.

26. Yayon, A., Klagsbrun, M., Esko, J. D., Leder, P., and Ornitz, D. M. (1991). Cell surface, heparin-like molecules are required for binding of basic fibroblast growth factor to its high affinity receptor. *Cell*, 64, 841-848.

27. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerization, activation, and cell proliferation. *Cell*, 79, 1015-1024.

28. Ornitz, D. M., Herr, A. B., Nilsson, M., West, a., J., Svahn, C. -M., and Waksman, G. (1995). FGF binding and FGF receptor activation by synthetic heparan-derived di- and trisaccharides. *Science*, 268, 432-436.

29. Gitay-Goren, H., Soker, S., Vlodavsky, I., and Neufeld, G. (1992). Cell surface associated heparin-like molecules are required for the binding of vascular endothelial growth factor (VEGF) to its cell surface receptors. *J. Biol. Chem.*, 267, 6093-6098.

30. Lider, O., Baharav, E., Mekori, Y., Miller, T., Naparstek, Y., Vlodavsky, I., and Cohen, I. R. (1989). Suppression of experimental autoimmune diseases and prolongation of allograft survival by treatment of animals with heparinoid inhibitors of T lymphocyte heparanase. *J. Clin. Invest.*, 83, 752-756.

31. Lider, O., Cahalon, L., Gilat, D., Hershkovitz, R., Siegel, D., Margalit, R., Shoseyov, O., and Cohn, I. R. (1995). A disaccharide that inhibits tumor necrosis factor a is formed from the extracellular matrix by the enzyme heparanase. *Proc. Natl. Acad. Sci USA.*, 92, 5037-5041.

31a. Rapraeger, A., Krufka, A., and Olwin, B. R. (1991). Requirement of heparan sulfate for bFGF-mediated fibroblast growth and myoblast differentiation. *Science*, 252, 1705-1708.

32. Eisenberg, S., Sehayek, E., Olivecrona, T., and Vlodavsky, I. (1992). Lipoprotein lipase enhances binding of lipoproteins to heparan sulfate on cell surfaces and extracellular matrix. *J. Clin. Invest.*, 90, 2013-2021.

33. Shieh, M-T., Wundunn, D., Montgomery, R. I., Esko, J. D., and Spear, P. G. J. (1992). Cell surface receptors for herpes simplex virus are heparan sulfate proteoglycans. *J. Cell Biol.*, 116, 1273-1281.

33a. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. *Nature Medicine* 3, 866-871.

33b. Putnak, J. R., Kanesa-Thasan, N., and Innis, B. L. (1997). A putative cellular receptor for dengue viruses. *Nature Medicine* 3, 828-829.

34. Narindrasorasak, S., Lowery, D., Gonzalez-DeWhitt, P., Poorman, R. A., Greenberg, B., Kisilevsky, R. (1991). High affinity interactions between the Alzheimer's beta-amyloid precursor protein and the basement membrane form of theparan sulfate proteoglycan. *J. Biol. Chem.*, 266, 12878-83.

35. Ross, R. (1993). The pathogenesis of atherosclerosis: a perspective for the 1990s. *Nature (Lond.)*., 362:801-809.

36. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. *J. Biol. Chem.*, 268, 10160-10167.

37. Ernst, S., Langer, R., Cooney, Ch.L., and Sasisekharan, R. (1995). Enzymatic degradation of glycosaminoglycans. Critical Reviews in Biochemistry and Molecular Biology, 30(5), 387-444.

38. Gospodarowicz, D., Mescher, A L., Birdwell, C R. (1977). Stimulation of corneal endothelial cell proliferation in vitro by fibroblast and epidermal growth factors. *Exp Eye Res* 25, 75-89.

39. Haimovitz-Friedman, A., Falcone, D. J., Eldor, A., Schirrmacher, V., Vlodavsky, I., and Fuks, Z. (1991) Activation of platelet heparitinase by tumor cell-derived factors. *Blood*, 78, 789-796

39a. Savitsky, K., Platzer, M., Uziel, T., Gilad, S., Sartiel, A., Rosental, A., Elroy-Stein, O., Siloh, Y. and Rotman, G. (1997). Ataxia-telangiectasia: structural diversity of untranslated sequences suggests complex post-translational regulation of ATM gene expression. Nucleic Acids Res. 25(9), 1678-1684.

40. Bar-Ner, M., Eldor, A., Wasserman, L., Matzner, Y., and Vlodavsky, 1. (1987). Inhibition of heparanase mediated degradation of extracellular matrix heparan sulfate by modified and non-anticoagulant heparin species. *Blood*, 70, 551-557.

41. Goshen, R., Hochberg, A., Korner, G., Levi, E., Ishai-Michaeli, R., Elkin, M., de Grot, N., and Vlodavsky, I. (1996). Purification and characterization of placental heparanase and its expression by cultured cytotrophoblasts. *Mol. Human Reprod.*, 2, 679-684.

42. Korb M., Ke Y. and Johnson L. F. (1993) Stimulation of gene expression by introns: conversion of an inhibitory intron to a stimulatory intron by alteration of the splice donor sequence. *Nucleic Acids Res.*, 25;21(25):5901-8.

43. Zheng B., Qiu X. Y., Tan M., Xing Y. N., Lo D., Xue J. L. and Qiu X. F. (1997) Increment of hFIX expression with endogenous intron 1 in vitro. *Cell Res.*, 7(l):21-29.

44. Kurachi S., Hitomi Y., Furukawa M. and Kurachi K. (1995) Role of intron I in expression of the human factor IX gene. *J. Biol. Chem.* 10, 270(10):5276-5281.

45. Shekhar P. V. and Miller F. R. (1994-5) Correlation of differences in modulation of ras expression with metastatic competence of mouse mammary tumor subpopulations. *Invasion Metastasis*, 14(1-6):27-37.

46. Zhou G., Garofalo S., Mukhopadhyay K., Lefebvre V., Smith C. N., Eberspaecher H. and de Crombrugghe B. (1995) A 182 bp fragment of the mouse pro alpha 1(II) collagen gene is sufficient to direct chondrocyte expression in transgenic mice. *J. Cell Sci.*, 108 (Pt 12):3677-3684.

47. Hormuzdi S. G., Penttinen R., Jaenisch R. and Bornstein P. (1998) A gene-targeting approach identifies a function for the first intron in expression of the alpha 1(I) collagen gene. *Mol. Cell,* 18(6):3368-3375.

48. Kang Y. K., Lee C. S., Chung A. S. and Lee K. K. (1998) Prolactin-inducible enhancer activity of the first intron of the bovine beta-casein gene. *Mol. Cells,* 30;8(3):259-265.

49. Chow Y. H., O'Brodovich H., Plumb J., Wen Y., Sohn K. J., Lu Z., Zhang F., Lukacs G. L., Tanswell A. K., Hui C. C., Buchwald M. and Hu J. (1997) Development of an epithelium-specific expression cassette with human DNA regulatory elements for transgene expression in lung airways. *Proc. Natl. Acad. Sci. USA,* 23;94(26):14695-14700.

50. Gottschalk U. and Chan S. (1998) Somatic gene therapy. Present situation and future perspective. *Arzneimittelforschung,* 48(11):1111-1120.

51. Ye S., Cole-Strauss A. C., Frank B. and Kmiec E. B. (1998) Targeted gene correction: a new strategy for molecular medicine. *Mol. Med. Today,* 4(10):431-437.

52. Lai L., and Lien Y. (1999) Homologous recombination based gene therapy. *Exp. Nephrol.,* 7(1):11-14.

53. Yazaki N., Fujita H., Ohta M., Kawasaki T. and Itoh N. (1993) The structure and expression of the FGF receptor-1 mRNA isoforms in rat tissues. *Biochim. Biophys. Acta.,* 20;1172(1-2):37-42.

54. Le Fur N., Kelsall S. R., Silvers W. K. and Mintz B. (1997) Selective increase in specific alternative splice variants of tyrosinase in murine melanomas: a projected basis for immunotherapy. *Proc. Natl. Acad. Sci. USA,* 13;94(10):5332-5337.

55. Miyake H., Okamoto I., Hara I., Gohji K., Yamanaka K., Arakawa S., Kamidono S. and Saya H. (1998) Highly specific and sensitive detection of malignancy in urine samples from patients with urothelial cancer by CD44v8-10/CD44v10 competitive RT-PCR. *Int. J. Cancer,* 18;79(6):560-564.

56. Guriec N., Marcellin L., Gairard B., Calderoli H., Wilk A., Renaud R., Bergerat J. P. and Oberling F. (1996) CD44 exon 6 expression as a possible early prognostic factor in primary node negative breast carcinoma. *Clin. Exp. Metastasis,* 14(5):434-439.

57. Gewirtz A. M., Sokol D. L. and Ratajczak M. Z. (1998) Nucleic acid therapeutics: state of the art and future prospects. Blood, 1;92(3):712-736.

58. Hida K., Shindoh M., Yasuda M., Hanzawa M., Funaoka K., Kohgo T., Amemiya A., Totsuka Y., Yoshida K. and Fujinaga K (1997) Antisense E1AF transfection restrains oral cancer invasion by reducing matrix metalloproteinase activities. *Am. J. Pathol.* 150(6):2125-2132.

59. Shastry B. S. (1998) Gene disruption in mice: models of development and disease. *Mol. Cell. Biochem.* 1998 Apr; 181(1-2):163-179.

60. Carpentier A. F., Rosenfeld M. R., Delattre J. Y., Whalen R. G., Posner J. B. and Dalmau J. (1998) DNA vaccination with HuD inhibits growth of a neuroblastoma in mice. *Clin. Cancer Res.,* 4(11):2 819-2824.

61. Lai W. C. and Bennett M. (1998) DNA vaccines. *Crit. Rev. Immunol.,* 18(5):449-484.

62. Welch P. J., Barber J. R., and Wong-Staal F. (1998) Expression of ribozymes in gene transfer systems to modulate target RNA levels. *Curr. Opin. Biotechnol.,* 9(5):486-496.

63. Durand P., Lehn P., Callebaunt I., Fabrega S., Henrissat B. and Mornon J. P. (1997) Active-site motifs of lysosomal acid hydrolyses: invariant features of clan GH-A glycosyl hydrolases deduced from hydrophobic cluster analysis. *Glycobiology,* 7(2):277-284.

64. Thuong and Helene (1993) Sequence specific recognition and modification of double helical DNA by oligonucleotides Angev. Chem. Int. Ed. Engl. 32:666

65. Dash P., Lotan I., Knapp M., Kandel E. R. and Goelet P. (1987) Selective elimination of mRNAs in vivo: complementary oligodeoxynucleotides promote RNA degradation by an RNase H-like activity. Proc. Natl. Acad. Sci. USA, 84:7896.

66. Chiang M. Y., Chan H., Zounes M. A., Freier S. M., Lima W. F. and Bennett C. F. (1991) Antisense oligonucleotides inhibit intercellular adhesion molecule 1 expression by two distinct mechanisms. J. Biol. Chem. 266:18162-71.

67. Paterson Paterson B. M, Roberts B. E and Kuff E L. (1977) Structural gene identification and mapping by DNA-mRNA hybrid-arrested cell-free translation. Proc. Natl. Acad. Sci. USA, 74:4370.

68. Cohen (1992) Oligonucleotide therapeutics. Trends in Biotechnology, 10:87.

69. Szczylik et al (1991) Selective inhibition of leukemia cell proliferation by BCR-ABL antisense oligodeoxynucleotides. Science 253:562.

70. Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351.

71. Heikhila et al. (1987) A c-myc antisense oligodeoxynucleotide inhibits entry into S phase but not progress from G(0) to G(1). Nature, 328:445.

72. Reed et al. (1990) Antisense mediated inhibition of BCL2 prooncogene expression and leukemic cell growth and survival: comparison of phosphodiester and phosphorothioate oligodeoxynucleotides. Cancer Res. 50:6565.

73. Burch and Mahan (1991) Oligodeoxynucleotides antisense to the interleukin I receptor m RNA block the effects of interleukin I in cultured murine and human fibroblasts and in mice. J. Clin. Invest. 88:1190.

74. Agrawal (1992) Antisense oligonucleotides as antiviral agents. TIBTECH 10:152.

75. Uhlmann et al. (1990) Chem. Rev. 90:544.

76. Cook (1991) Medicinal chemistry of antisense oligonucleotides—future opportunities. Anti-Cancer Drug Design 6:585.

77. Biotechnology research news (1993) Can DNA mimics improve on the real thing? Science 262:1647.

What is claimed is:

1. A preparation comprising protein molecules, said preparation including heparanase (endo-β-D-glucuronidase) protein, said heparanase protein having heparanase catalytic activity or being cleavable so as to acquire said heparanase catalytic activity, wherein said heparanase protein comprises SEQ ID NO: 10, provided that said amino acid sequence has a phenylalanine residue instead of a tyrosine residue at position 246, and wherein said preparation is pure enough to elicit anti-heparanase antibodies.

2. A purified heparanase protein comprising SEQ ID NO: 10, provided that said amino acid sequence has a phenylalanine residue instead of a tyrosine residue at position 246.

* * * * *

SEQUENCE LISTING

```
<160> NUMBER OF SEQ ID NOS: 47

<210> SEQ ID NO 1
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 1
ccatcctaat acgactcact atagggc                                      27

<210> SEQ ID NO 2
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 2
gtagtgatgc catgtaactg aatc                                         24

<210> SEQ ID NO 3
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 3
actcactata gggctcgagc ggc                                          23

<210> SEQ ID NO 4
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 4
gcatcttagc cgtctttctt cg                                           22

<210> SEQ ID NO 5
<211> LENGTH: 15
<212> TYPE: DNA
<213> ORGANISM: Artificial sequence
```

```
<220> FEATURE:
<223> OTHER INFORMATION: synthetic oligonucleotide

<400> SEQUENCE: 5
tttttttttt ttttt                                                    15

<210> SEQ ID NO 6
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 6
ttcgatccca agaaggaatc aac                                           23

<210> SEQ ID NO 7
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 7
gtagtgatgc catgtaactg aatc                                          24

<210> SEQ ID NO 8
<211> LENGTH: 9
<212> TYPE: PRT
<213> ORGANISM: Homo sapiens

<400> SEQUENCE: 8

Tyr Gly Pro Asp Val Gly Gln Pro Arg
1               5

<210> SEQ ID NO 9
<211> LENGTH: 1721
<212> TYPE: DNA
<213> ORGANISM: Homo sapiens

<400> SEQUENCE: 9
ctagagcttt cgactctccg ctgcgcggca gctggcgggg ggagcagcca ggtgagccca    60
agatgctgct gcgctcgaag cctgcgctgc cgccgccgct gatgctgctg ctcctggggc   120
cgctgggtcc cctctcccct ggcgccctgc cccgacctgc gcaagcacag gacgtcgtgg   180
acctggactt cttcacccag gagccgctgc acctggtgag ccctcgttc ctgtccgtca    240 ccattgacgc caacctggcc acggacccgc ggttcctcat cctcctgggt tctccaaagc   300
ttcgtacctt ggccagaggc ttgtctcctg cgtacctgag gtttggtggc accaagacag   360
acttcctaat tttcgatccc aagaaggaat caacctttga agagagaagt tactggcaat   420
ctcaagtcaa ccaggatatt tgcaaatatg gatccatccc tcctgatgtg gaggagaagt   480
tacggttgga atggcctac caggagcaat gctactccg agaacactac cagaaaaagt      540
tcaagaacag cacctactca agaagctctg tagatgtgct atacacttt gcaaactgct     600 caggactgga cttgatctt ggcctaaatg cgttattaag aacagcagat tgcagtggaa     660
acagttctaa tgctcagttg ctcctggact actgctcttc caaggggtat aacatttctt    720
gggaactagg caatgaacct aacagtttcc ttaagaaggc tgatatttc atcaatgggt     780 cgcagtagg agaagattat attcaattgc ataaacttct aagaaagtcc accttcaaaa      840
atgcaaaact ctatggtcct gatgttggtc agcctcgaag aaagacggct aagatgctga    900
```

```
agagcttcct gaaggctggt ggagaagtga ttgattcagt tacatggcat cactactatt      960
tgaatggacg gactgctacc agggaagatt ttctaaaccc tgatgtattg dcatttttta     1020
tttcatctgt gcaaaaagtt ttccaggtgg ttgagagcac caggcctggc aagaaggtct     1080
ggttaggaga acaagctct gcatatggag gcggagcgcc cttgctatcc gacacctttg      1140
cagctggctt tatgtggctg gataaattgg gcctgtcagc ccgaatggga atagaagtgg     1200
tgatgaggca agtattcttt ggagcaggaa actaccattt agtggatgaa acttcgatc      1260
ctttacctga ttattggcta tctcttctgt tcaagaaatt ggtgggcacc aaggtgttaa     1320
tggcaagcgt gcaaggttca agagaagga agcttcgagt ataccttcat tgcacaaaca     1380
ctgacaatcc aagtataaa gaaggagatt taactctgta tgccataaac ctccataacg      1440
tcaccaagta cttgcggtta ccctatcctt tttctaacaa gcaagtggat aaataccttc    1500
taagaccttt gggacctcat ggattacttt ccaaatctgt ccaactcaat ggtctaactc    1560
taaagatggt ggatgatcaa accttgccac ctttaatgga aaaacctctc cggccaggaa    1620
gttcactggg cttgccagct ttctcatata gtttttttgt gataagaaat gccaaagttg    1680
ctgcttgcat ctgaaaataa aatatactag tcctgacact g                        1721

<210> SEQ ID NO 10
<211> LENGTH: 543
<212> TYPE: PRT
<213> ORGANISM: Homo sapiens

<400> SEQUENCE: 10

Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
                20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Gly Ser Pro Lys Leu
65              70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220
```

| | | | | | | | | | | | |
|---|---|---|---|---|---|---|---|---|---|---|---|
| Glu | Pro | Asn | Ser | Phe | Leu | Lys | Lys | Ala | Asp | Ile | Phe | Ile | Asn | Gly | Ser |
| 225 | | | | 230 | | | | 235 | | | | 240 | | | |

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
            245                 250                 255

Thr Phe Lys Asn Ala Lys Leu Tyr Gly Pro Asp Val Gly Gln Pro Arg
                260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
            355                 360                 365

Leu Gly Leu Ser Ala Arg Met Gly Ile Glu Val Val Met Arg Gln Val
370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
                420                 425                 430

Val Tyr Leu His Cys Thr Asn Thr Asp Asn Pro Arg Tyr Lys Glu Gly
            435                 440                 445

Asp Leu Thr Leu Tyr Ala Ile Asn Leu His Asn Val Thr Lys Tyr Leu
450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
            515                 520                 525

Tyr Ser Phe Phe Val Ile Arg Asn Ala Lys Val Ala Ala Cys Ile
    530                 535                 540

```
<210> SEQ ID NO 11
<211> LENGTH: 1721
<212> TYPE: DNA
<213> ORGANISM: Homo sapiens
<220> FEATURE:
<221> NAME/KEY: CDS
<222> LOCATION: (63)..(1691)
<223> OTHER INFORMATION:

<400> SEQUENCE: 11
ctagagcttt cgactctccg ctgcgcggca gctggcgggg ggagcagcca ggtgagccca    60 ag atg ctg ctg cgc tcg aag cct gcg ctg ccg ccg ccg ctg atg ctg      107
   Met Leu Leu Arg Ser Lys Pro Ala Leu Pro Pro Pro Leu Met Leu
   1               5                   10                  15 ctg ctc ctg ggg ccg ctg ggt ccc ctc tcc cct ggc gcc ctg ccc cga    155
```

```
Leu Leu Leu Gly Pro Leu Gly Pro Leu Ser Pro Gly Ala Leu Pro Arg
            20                  25                  30 cct gcg caa gca cag gac gtc gtg gac ctg gac ttc ttc acc cag gag       203
Pro Ala Gln Ala Gln Asp Val Val Asp Leu Asp Phe Phe Thr Gln Glu
            35                  40                  45 ccg ctg cac ctg gtg agc ccc tcg ttc ctg tcc gtc acc att gac gcc       251
Pro Leu His Leu Val Ser Pro Ser Phe Leu Ser Val Thr Ile Asp Ala
            50                  55                  60 aac ctg gcc acg gac ccg cgg ttc ctc atc ctc ctg ggt tct cca aag       299
Asn Leu Ala Thr Asp Pro Arg Phe Leu Ile Leu Leu Gly Ser Pro Lys
 65              70                  75 ctt cgt acc ttg gcc aga ggc ttg tct cct gcg tac ctg agg ttt ggt       347
Leu Arg Thr Leu Ala Arg Gly Leu Ser Pro Ala Tyr Leu Arg Phe Gly
 80              85                  90                  95 ggc acc aag aca gac ttc cta att ttc gat ccc aag aag gaa tca acc       395
Gly Thr Lys Thr Asp Phe Leu Ile Phe Asp Pro Lys Lys Glu Ser Thr
                100                 105                 110 ttt gaa gag aga agt tac tgg caa tct caa gtc aac cag gat att tgc       443
Phe Glu Glu Arg Ser Tyr Trp Gln Ser Gln Val Asn Gln Asp Ile Cys
                115                 120                 125 aaa tat gga tcc atc cct cct gat gtg gag gag aag tta cgg ttg gaa       491
Lys Tyr Gly Ser Ile Pro Pro Asp Val Glu Glu Lys Leu Arg Leu Glu
            130                 135                 140 tgg ccc tac cag gag caa ttg cta ctc cga gaa cac tac cag aaa aag       539
Trp Pro Tyr Gln Glu Gln Leu Leu Leu Arg Glu His Tyr Gln Lys Lys
145                 150                 155 ttc aag aac agc acc tac tca aga agc tct gta gat gtg cta tac act       587
Phe Lys Asn Ser Thr Tyr Ser Arg Ser Ser Val Asp Val Leu Tyr Thr
160                 165                 170                 175 ttt gca aac tgc tca gga ctg gac ttg atc ttt ggc cta aat gcg tta       635
Phe Ala Asn Cys Ser Gly Leu Asp Leu Ile Phe Gly Leu Asn Ala Leu
                180                 185                 190 tta aga aca gca gat ttg cag tgg aac agt tct aat gct cag ttg ctc       683
Leu Arg Thr Ala Asp Leu Gln Trp Asn Ser Ser Asn Ala Gln Leu Leu
            195                 200                 205 ctg gac tac tgc tct tcc aag ggg tat aac att tct tgg gaa cta ggc       731
Leu Asp Tyr Cys Ser Ser Lys Gly Tyr Asn Ile Ser Trp Glu Leu Gly
        210                 215                 220 aat gaa cct aac agt ttc ctt aag aag gct gat att ttc atc aat ggg       779
Asn Glu Pro Asn Ser Phe Leu Lys Lys Ala Asp Ile Phe Ile Asn Gly
225                 230                 235 tcg cag tta gga gaa gat tat att caa ttg cat aaa ctt cta aga aag       827
Ser Gln Leu Gly Glu Asp Tyr Ile Gln Leu His Lys Leu Leu Arg Lys
240                 245                 250                 255 tcc acc ttc aaa aat gca aaa ctc tat ggt cct gat gtt ggt cag cct       875
Ser Thr Phe Lys Asn Ala Lys Leu Tyr Gly Pro Asp Val Gly Gln Pro
                260                 265                 270 cga aga aag acg gct aag atg ctg aag agc ttc ctg aag gct ggt gga       923
Arg Arg Lys Thr Ala Lys Met Leu Lys Ser Phe Leu Lys Ala Gly Gly
            275                 280                 285 gaa gtg att gat tca gtt aca tgg cac cac tac tat ttg aat gga cgg       971
Glu Val Ile Asp Ser Val Thr Trp His His Tyr Tyr Leu Asn Gly Arg
        290                 295                 300 act gct acc agg gaa gat ttt cta aac cct gat gta ttg gac att ttt      1019
Thr Ala Thr Arg Glu Asp Phe Leu Asn Pro Asp Val Leu Asp Ile Phe
305                 310                 315 att tca tct gtg caa aaa gtt ttc cag gtg gtt gag agc acc agg cct      1067
Ile Ser Ser Val Gln Lys Val Phe Gln Val Val Glu Ser Thr Arg Pro
320                 325                 330                 335
```

| | | | | | | | | | | | | | | |
|---|---|---|---|---|---|---|---|---|---|---|---|---|---|---|
| ggc | aag | aag | gtc | tgg | tta | gga | gaa | aca | agc | tct | gca | tat | gga ggc gga | 1115 |
| Gly | Lys | Lys | Val | Trp | Leu | Gly | Glu | Thr | Ser | Ser | Ala | Tyr | Gly Gly Gly | |
| | | | 340 | | | | | 345 | | | | | 350 | |

| | | | | | | | | | | | | | | |
|---|---|---|---|---|---|---|---|---|---|---|---|---|---|---|
| gcg | ccc | ttg | cta | tcc | gac | acc | ttt | gca | gct | ggc | ttt | atg | tgg ctg gat | 1163 |
| Ala | Pro | Leu | Leu | Ser | Asp | Thr | Phe | Ala | Ala | Gly | Phe | Met | Trp Leu Asp | |
| | | 355 | | | | | 360 | | | | | 365 | | |

| | | | | | | | | | | | | | | |
|---|---|---|---|---|---|---|---|---|---|---|---|---|---|---|
| aaa | ttg | ggc | ctg | tca | gcc | cga | atg | gga | ata | gaa | gtg | gtg | atg agg caa | 1211 |
| Lys | Leu | Gly | Leu | Ser | Ala | Arg | Met | Gly | Ile | Glu | Val | Val | Met Arg Gln | |
| | 370 | | | | | 375 | | | | | 380 | | | |

| | | | | | | | | | | | | | | |
|---|---|---|---|---|---|---|---|---|---|---|---|---|---|---|
| gta | ttc | ttt | gga | gca | gga | aac | tac | cat | tta | gtg | gat | gaa | aac ttc gat | 1259 |
| Val | Phe | Phe | Gly | Ala | Gly | Asn | Tyr | His | Leu | Val | Asp | Glu | Asn Phe Asp | |
| 385 | | | | | 390 | | | | | 395 | | | | |

| | | | | | | | | | | | | | | |
|---|---|---|---|---|---|---|---|---|---|---|---|---|---|---|
| cct | tta | cct | gat | tat | tgg | cta | tct | ctt | ctg | ttc | aag | aaa | ttg gtg ggc | 1307 |
| Pro | Leu | Pro | Asp | Tyr | Trp | Leu | Ser | Leu | Leu | Phe | Lys | Lys | Leu Val Gly | |
| 400 | | | | 405 | | | | | 410 | | | | | 415 |

| | | | | | | | | | | | | | | |
|---|---|---|---|---|---|---|---|---|---|---|---|---|---|---|
| acc | aag | gtg | tta | atg | gca | agc | gtg | caa | ggt | tca | aag | aga | agg aag ctt | 1355 |
| Thr | Lys | Val | Leu | Met | Ala | Ser | Val | Gln | Gly | Ser | Lys | Arg | Arg Lys Leu | |
| | | | 420 | | | | | 425 | | | | | 430 | |

| | | | | | | | | | | | | | | |
|---|---|---|---|---|---|---|---|---|---|---|---|---|---|---|
| cga | gta | tac | ctt | cat | tgc | aca | aac | act | gac | aat | cca | agg | tat aaa gaa | 1403 |
| Arg | Val | Tyr | Leu | His | Cys | Thr | Asn | Thr | Asp | Asn | Pro | Arg | Tyr Lys Glu | |
| | | | 435 | | | | | 440 | | | | | 445 | |

| | | | | | | | | | | | | | | |
|---|---|---|---|---|---|---|---|---|---|---|---|---|---|---|
| gga | gat | tta | act | ctg | tat | gcc | ata | aac | ctc | cat | aac | gtc | acc aag tac | 1451 |
| Gly | Asp | Leu | Thr | Leu | Tyr | Ala | Ile | Asn | Leu | His | Asn | Val | Thr Lys Tyr | |
| | | 450 | | | | | 455 | | | | | 460 | | |

| | | | | | | | | | | | | | | |
|---|---|---|---|---|---|---|---|---|---|---|---|---|---|---|
| ttg | cgg | tta | ccc | tat | cct | ttt | tct | aac | aag | caa | gtg | gat | aaa tac ctt | 1499 |
| Leu | Arg | Leu | Pro | Tyr | Pro | Phe | Ser | Asn | Lys | Gln | Val | Asp | Lys Tyr Leu | |
| | 465 | | | | | 470 | | | | | 475 | | | |

| | | | | | | | | | | | | | | |
|---|---|---|---|---|---|---|---|---|---|---|---|---|---|---|
| cta | aga | cct | ttg | gga | cct | cat | gga | tta | ctt | tcc | aaa | tct | gtc caa ctc | 1547 |
| Leu | Arg | Pro | Leu | Gly | Pro | His | Gly | Leu | Leu | Ser | Lys | Ser | Val Gln Leu | |
| 480 | | | | | 485 | | | | | 490 | | | | 495 |

| | | | | | | | | | | | | | | |
|---|---|---|---|---|---|---|---|---|---|---|---|---|---|---|
| aat | ggt | cta | act | cta | aag | atg | gtg | gat | gat | caa | acc | ttg | cca cct tta | 1595 |
| Asn | Gly | Leu | Thr | Leu | Lys | Met | Val | Asp | Asp | Gln | Thr | Leu | Pro Pro Leu | |
| | | | | 500 | | | | | 505 | | | | | 510 |

| | | | | | | | | | | | | | | |
|---|---|---|---|---|---|---|---|---|---|---|---|---|---|---|
| atg | gaa | aaa | cct | ctc | cgg | cca | gga | agt | tca | ctg | ggc | ttg | cca gct ttc | 1643 |
| Met | Glu | Lys | Pro | Leu | Arg | Pro | Gly | Ser | Ser | Leu | Gly | Leu | Pro Ala Phe | |
| | | | 515 | | | | | 520 | | | | | 525 | |

| | | | | | | | | | | | | | | |
|---|---|---|---|---|---|---|---|---|---|---|---|---|---|---|
| tca | tat | agt | ttt | ttt | gtg | ata | aga | aat | gcc | aaa | gtt | gct | gct tgc atc | 1691 |
| Ser | Tyr | Ser | Phe | Phe | Val | Ile | Arg | Asn | Ala | Lys | Val | Ala | Ala Cys Ile | |
| | | 530 | | | | | 535 | | | | | 540 | | | tgaaaataaa atatactagt cctgacactg                                           1721

<210> SEQ ID NO 12
<211> LENGTH: 824
<212> TYPE: DNA
<213> ORGANISM: Mus musculus

<400> SEQUENCE: 12
ctggcaagaa ggtctggttg ggagagacga gctcagctta cggtggcggt gcacccttgc     60
tgtccaacac ctttgcagct ggctttatgt ggctggataa atttgggcctg tcagcccaga    120 tgggcataga agtcgtgatg aggcaggtgt tcttcggagc aggcaactac cacttagtgg    180
atgaaaactt tgagccttta cctgattact ggctctctct tctgttcaag aaactggtag    240
gtcccagggt gttactgtca agagtgaaag gcccagacag gagcaaactc gagtgtatc     300 tccactgcac taacgtctat cacccacgat atcaggaagg agatctaact ctgtatgtcc    360
tgaacctcca taatgtcacc aagcacttga aggtaccgcc tcgttgttc aggaaaccag    420 tggatacgta ccttctgaag ccttcggggc cggatggatt acttttccaaa tctgtccaac    480 tgaacggtca aattctgaag atggtggatg agcagaccct gccagctttg acagaaaaac    540

```
ctctccccgc aggaagtgca ctaagcctgc ctgccttttc ctatggtttt tttgtcataa    600
gaaatgccaa aatcgctgct tgtatatgaa aataaaaggc atacggtacc cctgagacaa    660
aagccgaggg gggtgttatt cataaaacaa aaccctagtt taggaggcca cctccttgcc    720
gagttccaga gcttcgggag ggtggggtac acttcagtat tacattcagt gtggtgttct    780
ctctaagaag aatactgcag gtggtgacag ttaatagcac tgtg                     824
```

<210> SEQ ID NO 13
<211> LENGTH: 1899
<212> TYPE: DNA
<213> ORGANISM: Homo sapiens

<400> SEQUENCE: 13

```
gggaaagcga gcaaggaagt aggagagagc cgggcaggcg gggcggggtt ggattgggag     60
cagtgggagg gatgcagaag aggagtggga gggatggagg gcgcagtggg aggggtgagg    120
aggcgtaacg gggcggagga aaggagaaaa gggcgctggg gctcggcggg aggaagtgct    180
agagctctcg actctccgct gcgcggcagc tggcggggg agcagccagg tgagcccaag    240
atgctgctgc gctcgaagcc tgcgctgccg ccgccgctga tgctgctgct cctggggccg    300
ctgggtcccc tctcccctgg cgccctgccc cgacctgcgc aagcacagga cgtcgtggac    360
ctggacttct tcacccagga gccgctgcac ctggtgagcc cctcgttcct gtccgtcacc    420
attgacgcca acctggccac ggacccgcgg ttcctcatcc tcctgggttc tccaaagctt    480
cgtaccttgg ccagaggctt gtctcctgcg tacctgaggt ttggtggcac caagacagac    540
ttcctaattt tcgatcccaa gaaggaatca acctttgaag agagaagtta ctggcaatct    600
caagtcaacc aggatatttg caaatatgga tccatccctc ctgatgtgga ggagaagtta    660
cggttggaat ggccctacca ggagcaattg ctactccgag aacactacca gaaaaagttc    720
aagaacagca cctactcaag aagctctgta gatgtgctat acacttttgc aaactgctca    780
ggactggact tgatctttgg cctaaatgcg ttattaagaa cagcagattt gcagtggaac    840
agttctaatg ctcagttgct cctggactac tgctcttcca aggggtataa catttccttgg    900 gaactaggca atgaacctaa cagtttcctt aagaaggctg atattttcat caatgggtcg    960
cagttaggag aagattatat tcaattgcat aaacttctaa gaaagtccac cttcaaaaat   1020
gcaaaactct atggtcctga tgttggtcag cctcgaagaa agacggctaa gatgctgaag   1080
agcttcctga aggctggtgg agaagtgatt gattcagtta catggcatca ctactatttg   1140
aatggacgga ctgctaccag ggaagatttt ctaaaccctg atgtattgga cattttatt   1200 tcatctgtgc aaaaagtttt ccaggtggtt gagagcacca ggcctggcaa gaaggtctgg   1260
ttaggagaaa caagctctgc atatggaggc ggagcgccct tgctatccga cacctttgca   1320
gctggcttta tgtggctgga taaattgggc ctgtcagccc gaatgggaat agaagtggtg   1380
atgaggcaag tattctttgg agcaggaaac taccatttag tggatgaaaa cttcgatcct   1440
ttacctgatt attggctatc tcttctgttc aagaaattgg tggcaccaa ggtgttaatg   1500 gcaagcgtgc aaggttcaaa gagaaggaag cttcgagtat accttcattg cacaaacact   1560
gacaatccaa ggtataaaga aggagattta actctgtatg ccataaacct ccataacgtc   1620
accaagtact tgcggttacc ctatcctttt tctaacaagc aagtggataa ataccttcta   1680
agacctttgg gacctcatgg attactttcc aaatctgtcc aactcaatgg tctaactcta   1740
aagatggtgg atgatcaaac cttgccacct ttaatggaaa aacctctccg gccaggaagt   1800
```

```
tcactgggct tgccagcttt ctcatatagt ttttttgtga taagaaatgc caaagttgct  1860
gcttgcatct gaaaataaaa tatactagtc ctgacactg                         1899
```

<210> SEQ ID NO 14
<211> LENGTH: 592
<212> TYPE: PRT
<213> ORGANISM: Homo sapiens

<400> SEQUENCE: 14

| | | | | | | | | | | | | | | |
|---|---|---|---|---|---|---|---|---|---|---|---|---|---|---|
| Met | Glu | Gly | Ala | Val | Gly | Gly | Val | Arg | Arg | Arg | Asn | Gly | Ala | Glu |
| 1 | | | | 5 | | | | | 10 | | | | | 15 |
| Arg | Arg | Lys | Gly | Arg | Trp | Gly | Ser | Ala | Gly | Ser | Ala | Arg | Ala | Leu |
| | | | 20 | | | | | 25 | | | | | 30 | |
| Asp | Ser | Pro | Leu | Arg | Gly | Ser | Trp | Arg | Gly | Glu | Gln | Pro | Gly | Pro |
| | | | | 35 | | | | | 40 | | | | | 45 |
| Lys | Met | Leu | Leu | Arg | Ser | Lys | Pro | Ala | Leu | Pro | Pro | Leu | Met | Leu |
| | | | 50 | | | | | 55 | | | | | 60 | |
| Leu | Leu | Leu | Gly | Pro | Leu | Gly | Pro | Leu | Ser | Pro | Gly | Ala | Leu | Pro | Arg |
| 65 | | | | | 70 | | | | | 75 | | | | | 80 |
| Pro | Ala | Gln | Ala | Gln | Asp | Val | Val | Asp | Leu | Asp | Phe | Phe | Thr | Gln | Glu |
| | | | | 85 | | | | | 90 | | | | | 95 | |
| Pro | Leu | His | Leu | Val | Ser | Pro | Ser | Phe | Leu | Ser | Val | Thr | Ile | Asp | Ala |
| | | | | 100 | | | | | 105 | | | | | 110 | |
| Asn | Leu | Ala | Thr | Asp | Pro | Arg | Phe | Leu | Ile | Leu | Leu | Gly | Ser | Pro | Lys |
| | | | 115 | | | | | 120 | | | | | 125 | | |
| Leu | Arg | Thr | Leu | Ala | Arg | Gly | Leu | Ser | Pro | Ala | Tyr | Leu | Arg | Phe | Gly |
| | 130 | | | | | 135 | | | | | 140 | | | | |
| Gly | Thr | Lys | Thr | Asp | Phe | Leu | Ile | Phe | Asp | Pro | Lys | Lys | Glu | Ser | Thr |
| 145 | | | | | 150 | | | | | 155 | | | | | 160 |
| Phe | Glu | Glu | Arg | Ser | Tyr | Trp | Gln | Ser | Gln | Val | Asn | Gln | Asp | Ile | Cys |
| | | | | 165 | | | | | 170 | | | | | 175 | |
| Lys | Tyr | Gly | Ser | Ile | Pro | Pro | Asp | Val | Glu | Glu | Lys | Leu | Arg | Leu | Glu |
| | | | 180 | | | | | 185 | | | | | 190 | | |
| Trp | Pro | Tyr | Gln | Glu | Gln | Leu | Leu | Leu | Arg | Glu | His | Tyr | Gln | Lys | Lys |
| | | | 195 | | | | | 200 | | | | | 205 | | |
| Phe | Lys | Asn | Ser | Thr | Tyr | Ser | Arg | Ser | Ser | Val | Asp | Val | Leu | Tyr | Thr |
| | 210 | | | | | 215 | | | | | 220 | | | | |
| Phe | Ala | Asn | Cys | Ser | Gly | Leu | Asp | Leu | Ile | Phe | Gly | Leu | Asn | Ala | Leu |
| 225 | | | | | 230 | | | | | 235 | | | | | 240 |
| Leu | Arg | Thr | Ala | Asp | Leu | Gln | Trp | Asn | Ser | Ser | Asn | Ala | Gln | Leu | Leu |
| | | | | 245 | | | | | 250 | | | | | 255 | |
| Leu | Asp | Tyr | Cys | Ser | Ser | Lys | Gly | Tyr | Asn | Ile | Ser | Trp | Glu | Leu | Gly |
| | | | 260 | | | | | 265 | | | | | 270 | | |
| Asn | Glu | Pro | Asn | Ser | Phe | Leu | Lys | Lys | Ala | Asp | Ile | Phe | Ile | Asn | Gly |
| | | | 275 | | | | | 280 | | | | | 285 | | |
| Ser | Gln | Leu | Gly | Glu | Asp | Tyr | Ile | Gln | Leu | His | Lys | Leu | Leu | Arg | Lys |
| | 290 | | | | | 295 | | | | | 300 | | | | |
| Ser | Thr | Phe | Lys | Asn | Ala | Lys | Leu | Tyr | Gly | Pro | Asp | Val | Gly | Gln | Pro |
| 305 | | | | | 310 | | | | | 315 | | | | | 320 |
| Arg | Arg | Lys | Thr | Ala | Lys | Met | Leu | Lys | Ser | Phe | Leu | Lys | Ala | Gly | Gly |
| | | | | 325 | | | | | 330 | | | | | 335 | |
| Glu | Val | Ile | Asp | Ser | Val | Thr | Trp | His | His | Tyr | Tyr | Leu | Asn | Gly | Arg |
| | | | 340 | | | | | 345 | | | | | 350 | | |
| Thr | Ala | Thr | Arg | Glu | Asp | Phe | Leu | Asn | Pro | Asp | Val | Leu | Asp | Ile | Phe |

```
                   355                 360                 365
Ile Ser Ser Val Gln Lys Val Phe Gln Val Val Glu Ser Thr Arg Pro
    370                 375                 380

Gly Lys Lys Val Trp Leu Gly Glu Thr Ser Ser Ala Tyr Gly Gly Gly
385                 390                 395                 400

Ala Pro Leu Leu Ser Asp Thr Phe Ala Ala Gly Phe Met Trp Leu Asp
                405                 410                 415

Lys Leu Gly Leu Ser Ala Arg Met Gly Ile Glu Val Val Met Arg Gln
                420                 425                 430

Val Phe Phe Gly Ala Gly Asn Tyr His Leu Val Asp Glu Asn Phe Asp
                435                 440                 445

Pro Leu Pro Asp Tyr Trp Leu Ser Leu Leu Phe Lys Lys Leu Val Gly
            450                 455                 460

Thr Lys Val Leu Met Ala Ser Val Gln Gly Ser Lys Arg Arg Lys Leu
465                 470                 475                 480

Arg Val Tyr Leu His Cys Thr Asn Thr Asp Asn Pro Arg Tyr Lys Glu
                485                 490                 495

Gly Asp Leu Thr Leu Tyr Ala Ile Asn Leu His Asn Val Thr Lys Tyr
            500                 505                 510

Leu Arg Leu Pro Tyr Pro Phe Ser Asn Lys Gln Val Asp Lys Tyr Leu
        515                 520                 525

Leu Arg Pro Leu Gly Pro His Gly Leu Leu Ser Lys Ser Val Gln Leu
    530                 535                 540

Asn Gly Leu Thr Leu Lys Met Val Asp Asp Gln Thr Leu Pro Pro Leu
545                 550                 555                 560

Met Glu Lys Pro Leu Arg Pro Gly Ser Ser Leu Gly Leu Pro Ala Phe
                565                 570                 575

Ser Tyr Ser Phe Phe Val Ile Arg Asn Ala Lys Val Ala Ala Cys Ile
            580                 585                 590

<210> SEQ ID NO 15
<211> LENGTH: 1899
<212> TYPE: DNA
<213> ORGANISM: Homo sapiens
<220> FEATURE:
<221> NAME/KEY: CDS
<222> LOCATION: (94)..(1869)
<223> OTHER INFORMATION:

<400> SEQUENCE: 15
gggaaagcga gcaaggaagt aggagagagc cgggcaggcg gggcggggtt ggattgggag      60
cagtgggagg gatgcagaag aggagtggga ggg atg gag ggc gca gtg gga ggg     114
                                    Met Glu Gly Ala Val Gly Gly
                                     1               5 gtg agg agg cgt aac ggg gcg gag gaa agg aga aaa ggg cgc tgg ggc      162
Val Arg Arg Arg Asn Gly Ala Glu Glu Arg Arg Lys Gly Arg Trp Gly
    10                  15                  20 tcg gcg gga gga agt gct aga gct ctc gac tct ccg ctg cgc ggc agc      210
Ser Ala Gly Gly Ser Ala Arg Ala Leu Asp Ser Pro Leu Arg Gly Ser
25                  30                  35 tgg cgg ggg gag cag cca ggt gag ccc aag atg ctg ctg cgc tcg aag      258
Trp Arg Gly Glu Gln Pro Gly Glu Pro Lys Met Leu Leu Arg Ser Lys
40                  45                  50                  55 cct gcg ctg ccg ccg ccg ctg atg ctg ctg ctc ctg ggg ccg ctg ggt      306
Pro Ala Leu Pro Pro Pro Leu Met Leu Leu Leu Leu Gly Pro Leu Gly
                60                  65                  70 ccc ctc tcc cct ggc gcc ctg ccc cga cct gcg caa gca cag gac gtc      354
```

```
Pro Leu Ser Pro Gly Ala Leu Pro Arg Pro Ala Gln Ala Gln Asp Val
         75                  80                  85 gtg gac ctg gac ttc ttc acc cag gag ccg ctg cac ctg gtg agc ccc       402
Val Asp Leu Asp Phe Phe Thr Gln Glu Pro Leu His Leu Val Ser Pro
         90                  95                 100 tcg ttc ctg tcc gtc acc att gac gcc aac ctg gcc acg gac ccg cgg       450
Ser Phe Leu Ser Val Thr Ile Asp Ala Asn Leu Ala Thr Asp Pro Arg
    105                 110                 115 ttc ctc atc ctc ctg ggt tct cca aag ctt cgt acc ttg gcc aga ggc       498
Phe Leu Ile Leu Leu Gly Ser Pro Lys Leu Arg Thr Leu Ala Arg Gly
120             125                 130                 135 ttg tct cct gcg tac ctg agg ttt ggt ggc acc aag aca gac ttc cta       546
Leu Ser Pro Ala Tyr Leu Arg Phe Gly Gly Thr Lys Thr Asp Phe Leu
                140                 145                 150 att ttc gat ccc aag aag gaa tca acc ttt gaa gag aga agt tac tgg       594
Ile Phe Asp Pro Lys Lys Glu Ser Thr Phe Glu Glu Arg Ser Tyr Trp
                155                 160                 165 caa tct caa gtc aac cag gat att tgc aaa tat gga tcc atc cct cct       642
Gln Ser Gln Val Asn Gln Asp Ile Cys Lys Tyr Gly Ser Ile Pro Pro
        170                 175                 180 gat gtg gag gag aag tta cgg ttg gaa tgg ccc tac cag gag caa ttg       690
Asp Val Glu Glu Lys Leu Arg Leu Glu Trp Pro Tyr Gln Glu Gln Leu
185                 190                 195 cta ctc cga gaa cac tac cag aaa aag ttc aag aac agc acc tac tca       738
Leu Leu Arg Glu His Tyr Gln Lys Lys Phe Lys Asn Ser Thr Tyr Ser
200                 205                 210                 215 aga agc tct gta gat gtg cta tac act ttt gca aac tgc tca gga ctg       786
Arg Ser Ser Val Asp Val Leu Tyr Thr Phe Ala Asn Cys Ser Gly Leu
                220                 225                 230 gac ttg atc ttt ggc cta aat gcg tta tta aga aca gca gat ttg cag       834
Asp Leu Ile Phe Gly Leu Asn Ala Leu Leu Arg Thr Ala Asp Leu Gln
            235                 240                 245 tgg aac agt tct aat gct cag ttg ctc ctg gac tac tgc tct tcc aag       882
Trp Asn Ser Ser Asn Ala Gln Leu Leu Leu Asp Tyr Cys Ser Ser Lys
        250                 255                 260 ggg tat aac att tct tgg gaa cta ggc aat gaa cct aac agt ttc ctt       930
Gly Tyr Asn Ile Ser Trp Glu Leu Gly Asn Glu Pro Asn Ser Phe Leu
265                 270                 275 aag aag gct gat att ttc atc aat ggg tcg cag tta gga gaa gat tat       978
Lys Lys Ala Asp Ile Phe Ile Asn Gly Ser Gln Leu Gly Glu Asp Tyr
280                 285                 290                 295 att caa ttg cat aaa ctt cta aga aag tcc acc ttc aaa aat gca aaa      1026
Ile Gln Leu His Lys Leu Leu Arg Lys Ser Thr Phe Lys Asn Ala Lys
                300                 305                 310 ctc tat ggt cct gat gtt ggt cag cct cga aga aag acg gct aag atg      1074
Leu Tyr Gly Pro Asp Val Gly Gln Pro Arg Arg Lys Thr Ala Lys Met
            315                 320                 325 ctg aag agc ttc ctg aag gct ggt gga gaa gtg att gat tca gtt aca      1122
Leu Lys Ser Phe Leu Lys Ala Gly Gly Glu Val Ile Asp Ser Val Thr
        330                 335                 340 tgg cat cac tac tat ttg aat gga cgg act gct acc agg gaa gat ttt      1170
Trp His His Tyr Tyr Leu Asn Gly Arg Thr Ala Thr Arg Glu Asp Phe
345                 350                 355 cta aac cct gat gta ttg gac att ttt att tca tct gtg caa aaa gtt      1218
Leu Asn Pro Asp Val Leu Asp Ile Phe Ile Ser Ser Val Gln Lys Val
360                 365                 370                 375 ttc cag gtg gtt gag agc acc agg cct ggc aag aag gtc tgg tta gga      1266
Phe Gln Val Val Glu Ser Thr Arg Pro Gly Lys Lys Val Trp Leu Gly
                380                 385                 390
```

| | | | | | | | | | | | | | | | |
|---|---|---|---|---|---|---|---|---|---|---|---|---|---|---|---|
| gaa | aca | agc | tct | gca | tat | gga | ggc | gga | gcg | ccc | ttg | cta | tcc | gac | acc | 1314 |
| Glu | Thr | Ser | Ser | Ala | Tyr | Gly | Gly | Gly | Ala | Pro | Leu | Leu | Ser | Asp | Thr | |
| | | 395 | | | | | 400 | | | | | 405 | | | | |

```
gaa aca agc tct gca tat gga ggc gga gcg ccc ttg cta tcc gac acc      1314
Glu Thr Ser Ser Ala Tyr Gly Gly Gly Ala Pro Leu Leu Ser Asp Thr
            395                 400                 405 ttt gca gct ggc ttt atg tgg ctg gat aaa ttg ggc ctg tca gcc cga      1362
Phe Ala Ala Gly Phe Met Trp Leu Asp Lys Leu Gly Leu Ser Ala Arg
            410                 415                 420 atg gga ata gaa gtg gtg atg agg caa gta ttc ttt gga gca gga aac      1410
Met Gly Ile Glu Val Val Met Arg Gln Val Phe Phe Gly Ala Gly Asn
        425                 430                 435 tac cat tta gtg gat gaa aac ttc gat cct tta cct gat tat tgg cta      1458
Tyr His Leu Val Asp Glu Asn Phe Asp Pro Leu Pro Asp Tyr Trp Leu
440                 445                 450                 455 tct ctt ctg ttc aag aaa ttg gtg ggc acc aag gtg tta atg gca agc      1506
Ser Leu Leu Phe Lys Lys Leu Val Gly Thr Lys Val Leu Met Ala Ser
                460                 465                 470 gtg caa ggt tca aag aga agg aag ctt cga gta tac ctt cat tgc aca      1554
Val Gln Gly Ser Lys Arg Arg Lys Leu Arg Val Tyr Leu His Cys Thr
            475                 480                 485 aac act gac aat cca agg tat aaa gaa gga gat tta act ctg tat gcc      1602
Asn Thr Asp Asn Pro Arg Tyr Lys Glu Gly Asp Leu Thr Leu Tyr Ala
            490                 495                 500 ata aac ctc cat aac gtc acc aag tac ttg cgg tta ccc tat cct ttt      1650
Ile Asn Leu His Asn Val Thr Lys Tyr Leu Arg Leu Pro Tyr Pro Phe
        505                 510                 515 tct aac aag caa gtg gat aaa tac ctt cta aga cct ttg gga cct cat      1698
Ser Asn Lys Gln Val Asp Lys Tyr Leu Leu Arg Pro Leu Gly Pro His
520                 525                 530                 535 gga tta ctt tcc aaa tct gtc caa ctc aat ggt cta act cta aag atg      1746
Gly Leu Leu Ser Lys Ser Val Gln Leu Asn Gly Leu Thr Leu Lys Met
                540                 545                 550 gtg gat gat caa acc ttg cca cct tta atg gaa aaa cct ctc cgg cca      1794
Val Asp Asp Gln Thr Leu Pro Pro Leu Met Glu Lys Pro Leu Arg Pro
            555                 560                 565 gga agt tca ctg ggc ttg cca gct ttc tca tat agt ttt ttt gtg ata      1842
Gly Ser Ser Leu Gly Leu Pro Ala Phe Ser Tyr Ser Phe Phe Val Ile
            570                 575                 580 aga aat gcc aaa gtt gct gct tgc atc tgaaaataaa atatactagt            1889
Arg Asn Ala Lys Val Ala Ala Cys Ile
        585                 590 cctgacactg                                                            1899

<210> SEQ ID NO 16
<211> LENGTH: 594
<212> TYPE: DNA
<213> ORGANISM: Homo sapiens

<400> SEQUENCE: 16
attactatag ggcacgcgtg gtcgacggcc cgggctggta ttgtcttaat gagaagttga      60
taaagaattt tgggtggttg atctctttcc agctgcagtt tagcgtatgc tgaggccaga     120 tttttttcagg caaaagtaaa atacctgaga aactgcctgg ccagaggaca atcagatttt    180
ggctggctca agtgacaagc aagtgtttat aagctagatg ggagaggaag ggatgaatac     240
tccattggag gctttactcg agggtcagag ggatacccgg cgccatcaga atgggatctg     300
ggagtcggaa acgctgggtt ccacgagag cgcgcagaac acgtgcgtca ggaagcctgg     360
tccgggatgc ccagcgctgc tccccgggcg ctcctcccg ggcgctcctc cccaggcctc     420
ccgggcgctt ggatcccggc catctccgca cccttcaagt gggtgtgggt gatttcgtaa    480
gtgaacgtga ccgccaccgg ggggaaagcg agcaaggaag taggagagag ccgggcaggc    540
```
ggggcggggt tggattggga gcagtgggag ggatgcagaa gaggagtggg aggg        594

<210> SEQ ID NO 17
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 17
ccccaggagc agcagcatca g        21

<210> SEQ ID NO 18
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 18
aggcttcgag cgcagcagca t        21

<210> SEQ ID NO 19
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 19
gtaatacgac tcactatagg gc        22

<210> SEQ ID NO 20
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 20
actatagggc acgcgtggt        19

<210> SEQ ID NO 21
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 21
cttgggctca cctggctgct c        21

<210> SEQ ID NO 22
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 22
agctctgtag atgtgctata cac        23

<210> SEQ ID NO 23
<211> LENGTH: 22
<212> TYPE: DNA

```
<213> ORGANISM: Artificial sequence
<220> FEATURE:
<223> OTHER INFORMATION: synthetic oligonucleotide

<400> SEQUENCE: 23
gcatcttagc cgtctttctt cg                                          22

<210> SEQ ID NO 24
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 24
gagcagccag gtgagcccaa gat                                         23

<210> SEQ ID NO 25
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 25
ttcgatccca agaaggaatc aac                                         23

<210> SEQ ID NO 26
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 26
agctctgtag atgtgctata cac                                         23

<210> SEQ ID NO 27
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 27
tcagatgcaa gcagcaactt tggc                                        24

<210> SEQ ID NO 28
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 28
gcatcttagc cgtctttctt cg                                          22

<210> SEQ ID NO 29
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 29
gtagtgatgc catgtaactg aatc                                        24
```

```
<210> SEQ ID NO 30
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 30
aggcaccctc gagatgttcc ag                                                 22

<210> SEQ ID NO 31
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 31
gaagatttct gtttccatga cgtg                                               24

<210> SEQ ID NO 32
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 32
ccacactgaa tgtaatactg aagtg                                              25

<210> SEQ ID NO 33
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 33
cgaagctctg gaactcggca ag                                                 22

<210> SEQ ID NO 34
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 34
gccagctgca aggtgttgg ac                                                  22

<210> SEQ ID NO 35
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 35
aacacctgcc tcatcacgac ttc                                                23

<210> SEQ ID NO 36
<211> LENGTH: 22
<212> TYPE: DNA
<213> ORGANISM: Artificial sequence
<220> FEATURE:
```

<223> OTHER INFORMATION: synthetic oligonucleotide

<400> SEQUENCE: 36
gccaggctgg cgtcgatggt ga                                              22

<210> SEQ ID NO 37
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 37
gtcgatggtg atggacagga ac                                              22

<210> SEQ ID NO 38
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 38
gtaatacgac tcactatagg gc                                              22

<210> SEQ ID NO 39
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 39
actatagggc acgcgtggt                                                  19

<210> SEQ ID NO 40
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 40
ccatcctaat acgactcact atagggc                                         27

<210> SEQ ID NO 41
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 41
actcactata gggctcgagc ggc                                             23

<210> SEQ ID NO 42
<211> LENGTH: 44848
<212> TYPE: DNA
<213> ORGANISM: Homo sapiens

<400> SEQUENCE: 42
ggatcttggc tcactgcaat ctctgcctcc catgcaattc ttatgcatca gcctcctgag       60
tagcttggat tataggtctg cgccaccact cctggctaca ccatgttgcc caggctggtc      120
ttgaactctt gggctctagt gatccacccg ccttggcctc ccaaagtgct gggattacag      180

```
gtgtgagcca tcacacccgg cccccgttt ccatattagt aactcacatg tagaccacaa    240
ggatgcacta tttagaaaac ttgcaatggt ccacttttca aatcacccaa acatgttaaa    300
gaaattggta tgactgggca tggcacagtg gctcatgcct gcaatcctag cattttgtga    360
ggctgagacg ggcagatcac gaggtcagga gattgagacc atcctgacag acatggtgaa    420
atcccatctc tactaaaaat acaaaacaat tagccggggg tgatggcagg cccctgtagt    480
cccagctact cgggaggctg aggcaggaga atggcgtgaa tccaggaggc agagcttgca    540
gtgagccgag atggtgccac tgcactccag cctgggcgac agagcgagac tccgtctcaa    600
aaaaaaaaaa aagaaagaa attggtatga ctgttgactc acaacaggag tcaggggcat    660
ggggtggggt gtaagattaa tgtcatgaca aatgtggaaa agaaacttct gttttccaa    720
ctccacgtct gctaccatat tattacactc ttctggtagt gtggtgttta tgtgtgaatt    780
ttttttcata tgtatacagt aattgtagga tatgaacctg attctagttg caaaactcac    840
tatgagctta gcttttaagt tgcttaagaa taggtagatc tatgcaaata atgataatta    900
ttattattat tttaagagag ggtctcactt tgtcacccag gctggagtgc agtggtgtga    960
ttaagggtca ctgcaacctc cacctcccag gctcaaataa acctcccacc tcagcctccc   1020
cagtagctgg aaccacaggc acgggccacc acgcctggct aatttttttgt attttttgta   1080
gagatggggt ttcatcatgt tgcccaggct gttcttgaat cctcggctc aagcaatcct    1140
cccaccttgg cctcccaaaa tgctggcatc acaggcatga tggcatcact ggcatcacat    1200
accatgcctg gcctgattta tgcaaattag atatgcattt caaataatc tattttatt    1260
tgttgcctta ttggtggtac aatctcaagt ggaaaaatct aagggttttg gtgttatttg    1320
cttactcaac caatatttat tagactctta ctaagcacca acatgatcac atgcctgagc    1380
tatggctagc atagcgtgtg agacaaactt aatctctgtt ttggtggagc atataatcta    1440
gtagatgaag ccaatgttga gcaacatcac aatactaaca aattgaggat gctacgagag    1500
tgtctaacaa attgaggatg ctacgagagt gtctaacaaa ttgaggatgc tatgagagtg    1560
tgtcatggag agctgcctgg agattgagag aaagcttcct tgagggaagt tacatttcag    1620
ctgaaacaca ctgccatctg ctcgaggttt tgtaactgca ttcacatccc gattctgaca    1680
cttcacatcc cgattctgac acttcaccca gttactgtct cagagcttgg gtccgcatgt    1740
gtaaaacaag gacagtatgc acttggcagg gttgtgagaa gggaagagaa cacaagtaaa    1800
gcacctgtat caggcataca gtaggcacta agcgtgcgat gcttgctatg attatacatc    1860
agtgtaagca tcaaggaaaa gctgaagaaa agtctgacca acagcgaaag ataaatgcgc    1920
agaggagaaa tttggcaaag gctccaaatt caggggcagt ccgtactcta cactttgtat    1980
ggggcttca ggtcctgagt tccagacatt ggagcaacta acccctttaag attgctaaat    2040
attgtcttaa tgagaagttg ataagaatt ttgggtggtt gatctctttc cagctgcagt    2100
ttagcgtatg ctgaggccag atttttttcaa gcaaaagtaa aatacctgag aaactgcctg    2160
gccagaggac aatcagattt tggctggctc aagtgacaag caagtgttta taagctagat    2220
gggagaggaa gggatgaata ctccattgga ggttttactc gagggtcaga gggatacccg    2280
gcgccatcag aatgggatct gggagtcgga acgctgggt tcccacgaga gcgcgcagaa    2340
cacgtgcgtc aggaagcctg gtccgggatg cccagcgctg ctccccgggc gctcctcccc   2400
gggcgctcct cccaggcct cccgggcgct tggatcccgg ccatctccgc acccttcaag    2460
tgggtgtggg tgatttcgta agtgaacgtg accgccaccg aggggaaagc gagcaaggaa    2520
```

```
gtaggagaga gccgggcagg cggggcgggg ttggattggg agcagtggga gggatgcaga    2580
agaggagtgg gagggatgga gggcgcagtg ggaggggtga ggaggcgtaa cggggcggag    2640
gaaaggagaa aagggcgctg gggctcggcg ggaggaagtg ctagagctct cgactctccg    2700
ctgcgcggca gctggcgggg ggagcagcca ggtgagccca agatgctgct gcgctcgaag    2760
cctgcgctgc cgccgccgct gatgctgctg ctcctgggggc cgctgggtcc cctctcccct    2820
ggcgccctgc cccgacctgc gcaagcacag gacgtcgtgg acctggactt cttcacccag    2880
gagccgctgc acctggtgag cccctcgttc ctgtccgtca ccattgacgc caacctggcc    2940
acggacccgc ggttcctcat cctcctgggg taagcgccag cctcctggtc ctgtcccctt    3000
tcctgtcctc ctgacaccta tgtctgcccc gccagcggct ctccttcttt tgcgcggaaa    3060
caacttcaca ccggaacctc cccgcctgtc tctccccacc ccacttcccg cctctcattc    3120
tccctctccc tcccttactc tcagacccca aaccgctttt tggggggtat catttaaaaa    3180
atagatttag gggttacaag tgcagttctg ttccatgggt atattgcatt gtggtggcat    3240
ctgggctctt agtgtaactg tcacccgaat gttgtacatt gtatctaata ggtaatttct    3300
catccctcat ccctctccca ccctcccacc ttttggagtc tccagtgtct actattccac    3360
taagtccatg tgtacacatt gtttagcgcc cactctaaat gagccttttt gtttcattca    3420
ttctgtaagt gttgaatagg caccacctaa ggtcaggtat aagtggaaat ttgaaaaaga    3480
aactgcccac ttgccccagt acttccctag ccaagaggag ggaaaccagg caggtgcacc    3540
tgaaggcctg tgagtgcttg atttgctgtg cagtgtagga caagtaagat tgtgcatagc    3600
cttctgtatt taagactgtg ttaggaagat ttctcttttct tttctttttct ttttctttt    3660 tcttttcttt tttttttta ggcagatgaa aagggcgtca cagaacagga ataaaaatct    3720
aaatattcaa taaatgagac ctaggagact actgcagtga cttacaaagt cctaataaaa    3780
agatgtctct ccaaaatggg gctgcaaaat gtggtgctgc cttatcagct ctaagttttt    3840
tccttacctg agaaagaagg aacctgatgc aggttcaggg ctcctgcccc atgaatgcag    3900
gctgactcca agatggggag ctacagggac aatcccaggt cttctaggcc tcttatttag    3960
gccctgggag cctccagaga tggccacatc ttgaccagcc cagatagagg gaaagatcac    4020
cattatctca cctctgtgtc aaatacctag atgctgtcct ccctgagccc acactatagt    4080
tgccagcgct aatttaatgg gtagtgtact ggttaagaga tggacagacc atcctggctt    4140
gactctcagc tctggcaaag atgagtgact tggtttttcc atatctcttg gccacaccaa    4200
ccttgatttc ttcagctgta gaatggaatt tctcaagctt gcctcaagga ttattgcccg    4260
aggatttgat gatatggtaa gagcttctca gtgtttgacc catagtaagt gtttgacgtt    4320
tcaaacgaat tgtttctttc taggacatgg tgagcatttg gtagccattc accggttttc    4380
tgtttctttg gatcatagtt aacctctcct tttccttctg gcactacaat tttctggtgg    4440
ggaagaatcc ttactttctg cccttcccct taaggatagg aagctgatac taggcagcaa    4500
ctagttgggg gataggaaga ttgttccaga gaaatgctga accataggggc tccagatcac    4560 aggaccccag tcttagcttg ctgggtgtg ggtgggggg gggcggttac tgaacatggg    4620
tatgaagtag atgtccattt actgaaatgt gaggacctga ggcctcttct attgctgtag    4680
ccagcatatt ccccaacctc tccccaagaa aggacagatg ggggttcccc cctggagtaa    4740
caggtccaaa agaaaaaaca tacagtggga cttccaggat ctgggcctga tcacccagca    4800
gtcaagctcc ccgcaattga ctaacacccc cctaacacgt agaaattcca atctgcaatt    4860
tagtgaggat gataccttta ttcttcttaa atacatctct tcatttccca gagcacccctt    4920
```

-continued

```
ttttcccctc ctctgcacct ttttgttaaa gactggagta taatgaaata ccaagagagc    4980
ataacatgtg atacataaaa ctttttttct ggtttacaaa acagttcatt cttgtccata    5040
cgtgcttctc tccaaggctg gctgctgtct gttccagccc gcttcgcttg gagaggccat    5100
ctgccatacc tgctccccag acgcatcgac aagcacaccc agagtgttat ctgctaagac    5160
ctaaaagagg gaggaacccc ctctcctcat ctaagaccta gcttctaaat tagagtgtga    5220
gggtccatct ccccaggagg ggcacagggc ccaaacagcc cagccatctc agaagacaac    5280
actaagcttt gtaggggtcc acagtagagg agagtaagac gcctgttgtt taatttatta    5340
cagttcctca aaagtgaaga tgtgtgggcg ggatggcaag agctgagcag acgaaagctg    5400
aaggaataag gaaagagagg aggacacaaa cagctgacac ttcctcagtt cttgtcattt    5460
gcctggccct gttctaagca ccttctaggt attaatccat ttagtcttgg ctacaacact    5520
gtgagtaact agttttgtca cccccatttt aaaaatgaag aaagtgaggc tcagggaggt    5580
taagtaactt ggccacagtt tgaaactaga ctctgatcac atgagataat agtgcccata    5640
aaaagggaaa gcagattata ttttttaaag gaaagagagt aggatatggt agaaaaagat    5700
tgtttggaaa ggaattgaga gattgatata atgaaaagaa gcattcacat gagagtaaca    5760
gtatcagggc ccaaaccttc atctaaggta cttcaaagag gcctaagcaa acttagtcac    5820
tggcgtggtt ctagtctcca tgatggcaaa tacattgtgt acagcccaac tccacacaaa    5880
acttaaatac caatgataga gcaatctaaa atttgaaaga aaaatctttt caatttgtcg    5940
tcttcccaga gggacttaat caagaaacca atcaaaatac ttcctaagcc taactgtgtg    6000
cagaactcca aagagagccc agccctaaat caacactgtc caatggaaat ataatataat    6060
gtgggcctca tatgcaaggt catatgtaat tttaaatttt ctagtagcca tattaaaaag    6120
gtaaaaagaa acaagtgaaa ttaattttaa taatttatt tagttcaata gatccaaaat    6180
gttttctcag catgtaatca atataaaaat attaatgagg tatttattat tccttttctc    6240
aaaccaagtc tattctataa tctggcgtgt attatttaca gcacttctca gactatattt    6300 cttctttct tttttttttc cgagacaatt ttgctcttgt cacccaagct agagtacaat    6360
ggcgttacct cggctcactg caacctccgc ctcccgggtt caagttattc tcctgcctca    6420
gtctcccaag tagctgggac tagaggcatg caccaccacg cctggctaat tgtgtatttt    6480
tagtagagac agggtttcac catgttggcc aggctaatct caaactcctg agctcaggtg    6540
atatgcccac ctcggcctcc caaagtgttg ggattacagg cgtgagccac tgcacccggc    6600
ctcagattaa ctatatttca agcgttcagt agccacatgt agctagtgct atggtagtgg    6660
acagtacaga tctgcatttc aattaagaca cgtatacaag catagttcac taatgcacgg    6720
taaaaaaaag tatagtgctg agtcggtggt agaaatccta aatactgcag agcaaaagtg    6780
gtacgaacag caatctcagt gataatgcaa ccatgcttgc ttttcattgc aatttgctta    6840
ttttccttca gcaaagttca tccattttg ccaattcaat aaatatttac tgataaaaac    6900
tttcaatatt agattcttgc atcttcatag acagagttgc ttttcacatt tagaaaatta    6960
cttatcaatg ttaaacacac gttttgataa ccagtgttgg aaagaggtgc agactcccca    7020
tgtgcctatt gatggcagaa atattcacag ccaaagggaa acaaagggct ggggacaatc    7080
acacacctca tgtctcctaa ctcctgggaa gtgctgtccc tctgattgag ctcttattat    7140
tgccttcccc actaaccctg tccactgtgc cctggagccc tttgcagggt tacctgctct    7200
gtcctcctca cagaatatct cctctacctc cttgtccaag ctacaacttg gctattctct    7260
```

```
gatgacactg tcttccctgt agcccttttg agtaatggct gcatattctc ccatagtcca   7320
gttcttttcc tgttctccag tctggcttct ggatgacagc ccactagttt gaactccata   7380
ctgctatagt tcaagtccct tttgacttgt taccttgggc aaattacctc cttttgttca   7440
ggttccttgt ttgtaaaatg acgataataa tgccatttgc ttcagtgggt tattttgaaa   7500
ttgagtgaaa gaaggcgggt agcttcccta cacgctcagt gtagactagc ctgatgtgca   7560
ttacgggtga tgccatgact cagtgtgttt tcctcatctc cacatctggc tctcatccag   7620
tgctcctgct tacggcactc tgtcccccctc ttacttactc ccccttatta actgaagact   7680
ggcactgatc tcacagtttc ctctccactt cctagtctca ccatcatcct agatgacttc   7740
aagtcaccta gataaactgt ctcagtttct tcactcacat ttttttataa cagataatgt   7800
tacactcaag ttgtaacaga accagcttat ccagctcatg aaatgtatgc atttcatctc   7860
aactctgtat tcagtgacat cctgtgggta tctggaaatc agccatggtg agaatattta   7920
ccatggaaat tggcaaatac taaaaagcag agcacctttt tttctgagag ccagaccata   7980
gctcttctac tccatagcac ccatcataac aattttttaaa tacctccact gaacagcttc   8040
ttcctctctc tacttcttcc atatctgatt tgagcttctt aatttatcat gtgaaccact   8100
cttgtaataa taaccccaaa tccctgttcc attgttcttc ctgctaaaat actaaacctg   8160
gtttagtcca accatatttt ctctctttgg aatctacagg gtggcccaaa aacctggaaa   8220
tggaaaaata ttacttatta attttaatgt atattaataa gccatttaa tgcttcattt   8280 ccagtctcag tggccaccct gtatagctgg gctattgagc tcttgcggga ggagggagtg   8340
gacagtctcc cagccacaca gactgatgtt gcaccaaaca ttttttagct tccagacttc   8400
cctgcccctt agtgttaccc ttaactctcc atttctctgc ctttcacatt tctactttt    8460 taaaaatctc tgactccacc ttcaccttat cattcttagc acatgaccat acttctgctt   8520
cccaaagaaa atgagcaatt acttccttttt ccttttcctc ctgtcatcaa atctgcagac   8580
atgtcatgcc taagtccagc tttcctcctt tctctgatct cagtctgctt cttccatttc   8640
tgccctgaat cccgtcccct ccccaacccc caaggacttc gctctatcag tcacctcttc   8700
cctctcctgt atcttcaact cctcccattt tactggcttc ttcctcaagc ctttccccaa   8760
gcctttccca tctcaattac ctcctcgcac atgcctctgc agaaaccacc ccgtttcttc   8820
cctcccctcg gcagcctgtt cttcctgttc tgccctcatg atggcaccat cattgtgtca   8880
ctaaaatcaa tctctccgac atcatcaatg gccttccttt gttgggaaac ctaataaaca   8940
ctttatctta tttggtcttt gttatgggtt gaatgaggtt accccgaaat ccatattaga   9000
agtcctaacc cccagtacct cagaatgtga ctttatttgg gaatagggtc attgcagacg   9060
ttattagtta ggatgaggtc atactggaat gtgatgggc gcttatctaa tatgactgat    9120
gtccttataa caaggagaaa tttggagaca gacacgcaca tagggagaat accatgtgat   9180
gacaggagtt atggagttgg agtcaaaaag ctatgggaac ttaggagaaa gacctggaac   9240
aaatcctttc ctgcgcctag agagggagta tggccctgcc actaccttga attcaacgtt   9300
tcggcttttc aaaactgtaa gacaatacat ttctgttgtt caaaccaatt agtttgcagt   9360
actctgcgac tgcagcccta acaaactaat acagtctctt ggaggcattt ggcaaggttg   9420
acaatggaag cactttctta ccccctttagg tctgtcgcct ttcttgttgg ggggtgtttt   9480
ctaacaattc ctctccatct ctctctctct agtttgtctt aaacattggt gttcttcaga   9540
cttctgacct aggccttctt ttcacttcac atattcccct gggtggtctc acccacttcc   9600
agaaattact taaattactg ctcatgcagt actgtgctgg aaactgttta acaactggct   9660
```

-continued

```
ctctgggaag aggggagact ggttgatggt ttttgctgat ttctgtggtg taaatactcc    9720
ctccatggcc aattccaaac tgccaacagt ttaacaactg gctcacaaat tttctccaaa    9780
tttaacattt ggcttccaca ggccaacaac gtggtacagc caactccagc acacctctgc    9840
ttttgtgtca gagagaagta acttatttt gtacaaaagg taaaataaaa acacctgcag     9900
gcccccttt ttccttaac aaactgctct agaaatagaa tagctgaagc ttcttttatg      9960
cattcatctg ttatttccat gtcactgtgg tggtgggatt attttcctt tattttcctt    10020
gtatatggtt gaaatactgt acctttgatc agttttagtt ttatggcatg ttttgcaccc   10080
atattaaatc tagttttgt cagagggcgt caatattatt ttctcaaaac aagaaaatat    10140
ttcattgcaa aggagacaaa caaaaaggtc cttaatacca aaactttgaa atgtgatttc    10200
ttgtacttgg cagtgtccaa gtggtaaacc caaacagtat tgggttttca ttttgttcag   10260
gaaagtcttt gtctggcagc gacttaccct tacatcaggc gggccttgct cattcattca   10320
cttaagtatt tattaaacac cagcggtgtg ccaagtactt atctaggtat cgggtagatt   10380
ctgataagtc agtcaggtcc ctgctctcag ggagcttgca gcagagatgg gggctgcaat   10440
agagagtaag ccaaggaaat gaaaaaggaa gttgatttca gagagtgatg aatgctatga   10500
agaaaatgaa ggcagcgcag tgtgatggag agtgacccaa ggtggtacag tttgtacctc   10560
taaggaccag actgtgaccc aggtcactca cagatgcccg tcatgtgatg ccacagcaac   10620
ttttccaggt gctcgtttcc tcccacttcc cagtctcttg cccagccgcg actgcttaca   10680
aatacagcta gaggaatcta aatgaggttc ctctatcatc aaacccaatc aaaatgccaa   10740
ggaacagaat cagtgcctgg ctgaaggcag tggaacaggg ccagcctgga gtggttctct   10800
ctgaggaagt tcctcatctt ggttttaggg ccataccttg tgacctgtga gctaggggtt   10860
gccagtccct gacatttcta ctgaggactc gcctgtctat attcccggcc tgtatgtgtc   10920
tcctgagttc cagacacaca gggcgaagcg cctgatggat ggaagtatgt ttttggtgt    10980
tccattggta tctcaaattc tacaaaactt agtgccccctt ctcctccctg ttcctcccca   11040
tcttcagtct atcacctgtt cctcatccag caaatgatat taccatcttc caaggagctt   11100
cccaggagta atccttgact cctcctcaac atccaattaa taatcaaatc taggccaggt   11160
acaatagctc acgcctataa tcccagcact ttgggaggct gaggcaggtg gatcatttga   11220
ggccaggagt tcaagaccag cctggccaac aaggtgaaac ctgtctcatt taaaaaaagt   11280
tattttaaaa actcaaatct attatttcta cctctaagtg tgtcttgaat ttatccatct   11340
ctctccatct ctgagctgtt accttacctc agtccatcac gttttgtcta cgttaacatg   11400
accagagtct tgttcttagt ctggtgaggt cactccagct gcttcagatc cttccatggc   11460
tcaccgttgc cctcatataa agttggcact cctggacatg tggcttacgg ggccctccgt   11520
gatgtggccc tatttgcttc tccattctgt tctctcccag cctctctgcc cccatctcta   11580
ggcaccaacc acacccttct gctcgtcaat ggtgccagct tctcttctat ctctggtctt   11640
tggacagact tttcccttca cctggaatgc tttcttcaat cctacccac tctctttaat    11700
ctagataagg tttattcttt ttgaatgtct agcagtgaaa ccatttcccc tgaaaaacct   11760
tctctaacca accccctacc ctcagcccaa ggtctagatt aggagtccct ctgaatgttt   11820
ccatagcatt tttaaagaat tgcctattta cttgttcgta tctatcacta aactacaaat   11880
tgtatgagaa cagccactat ctctgcctgg ttcaccattc atctccagca actagcataa   11940
tgcctggcag agtcagcctg caacaaatat ttgttgaata aattaacaga tggctttatc   12000
```

```
tccttaagta aatcttgctt ttttcaccta ttaaaacaga cgcacaggcc aggtgtggtg    12060
gcccatgcct gtaatcccag cactttggca ggctgaggtg ggcggatcac ctgaggtcag    12120
gagttcaaga ccagcctggc caacatggtg aaaccccatc tctaataaaa atacaaaaat    12180
tagctgggca tggtggtggg tgcgtatagt cccagctact agggaggctg aggcaagaga    12240
atcgcttgaa cccaggaggc agaggtggca gtgagccgag atcatgccac tgtactccag    12300
cctggatgac agagaccctg tctcaaaaca cacacacaca cacacacaca cacacacaca    12360
cacacacaca cacacacacc aagttgtata atttaaaata taacgtgctt gttatggaac    12420
acttgtaaaa tacaggaaag taatgaaaaa gtctaccatc tagctcacca cataatgacc    12480
attgctatca tcctggcata attctctcct gtatataaat atatattctt ttattgttaa    12540
aattacacta tgagtactat ttatttattt tactgtggca aaatgcgcaa aacataaaat    12600
cttgccattt taaggtatgc agtttggtgc attcaccaca ctcacattgt tgtgcaaata    12660
tcaccactat ctatctcaga acttcttcgt cttcccaaac tgaaactctg tacccattaa    12720
acaatagtgc atcctctgtt ttcccctccc tacaatttat ttttatttgg gtttgtacca    12780
aactgaaaat agctgcttct tccttactta gttcagatta gcatttccat ttatttagcc    12840
gtggttttga ggatgccatg acagatgcca tccttcctag agctctttgg ggctgtcagg    12900
tatttcagtc agggtgaatt cgggttgata acattttaaa atctcacttt attctgaggt    12960
tcctagtgtc agagcccacc gtatttttag ggactcccaa gttacaaaca aaaatatggt    13020
gaggaggaat cactgaagtt ttaacacaag agacttacat tttgttcaat ttctatcttt    13080
tagtttattt cctaagcata aagaaatact ttgaaaattt tacatagcat tatacatatt    13140
taattaagca tgagcacatc ttaaaacttt aaattttaga tcagatcttt aattcctagg    13200
atattaagag gtactggcaa tttggccagg tgtggtggtt cacgcctata atcccaacac    13260
tttgggaggg tgaagtgggc gaattgctag agcccaggag gtggaggctg caatggcctg    13320
agatcacgcc atcgtactcc agcctggatg atgagaatga aatcctgtct caaaaaaaaa    13380
aaaaaaaaaa aaaagaagaa gaagaagtat tggcaatcag tgctccagga ataatttcct    13440
gacttgaaat aaacctacat gtagacaaac taattaggcc attccaagag ttgctagcat    13500
tggtttaata tgttttcaga gcattccagg aagcagtgtg gccagcattg catgtttgat    13560
acttcagaaa tgtatgacag gtgttttctct tacccaggtc ttctgttttc ttagttttgc    13620
tcatgtaaat atttatgaac atcctcatct ttttgaggga agggattata gatcattcta    13680
attccatttt ctagcatttg gtaccattct aagcacatga taggcaccca tttggagcat    13740
ttttggcttg acagaatatg catttagaat tgttcaaatt agaggtgtca gtgatgggaa    13800
ttagaatact atataattct aagtcatttg acttaaatac aaaagaatga ttttccttgg    13860
tggggaatgg tgaagggagg caggagttaa gaagaggaga agagatccta agtcatttat    13920
aaacttctct ggaaagacag gtgtgtgaag acttttttaaa aagtcattca ccaaattgtg    13980
tgtgtgtgtg tgtgtgtgtt ttaaatagac ttttatttttt agagcagttt taggttcaca    14040
gcaaaattga atgcaaggac agagatttcc cataaaccc ctgcccacac acatgcatag    14100
cctccctcat tatcaacatc cccaccagag aggtgtttgt tctagttgat gaacctacac    14160
tgacacatca ttatcaccca aagtccatag ttcacggcag ggttcactgt cggtgtacat    14220
tctatgggtt tgagcaaatg tataatgaca tgtatccacc attatagtaa catacagagt    14280
attttcagtg ccctgcaaat cccctgttct ccacctattc atccctccct ctctgctttt    14340
ccacccccag cccctggtaa ccgctgatct ttttactgtc ccatagtttc ggacgatcta    14400
```

```
tttttcagac agacacagag ctgtctttcc cttagtttct attctatcat ttctttctcc   14460
ccatccatca taaaaggcta tgagtttttt ttaagtgttg aacaccatcc tacttgtcaa   14520
gttaaaacat aagctcctgg ctgggtacag tggctcatgc ctgtaatctc agcattttgg   14580
gaggctgtgg cagaagcatc acttgaagcc agaagtttga gaccagcctg ggcaacatag   14640
caagacccca tccctccaca cacaaacaca cacacacaca cacacacaca cacacacaca   14700
cacacacaca cacaaaaaca agctcttgcc agaattagag ctacaaattg ccctcaggtt   14760
cctagaagat cagtccttca attagattca gattgagatg cttcctcttt taaacaatga   14820 ttcccttct atcatgccca ataagaaaac aaataaaaat taaacaatac tgcctgtaat   14880
ctcagctacc caggaggcag aagcagaact gcttcaaccc ggcaagcaga agttgcagtg   14940
aagtgagatc gcgccactgc actccagcct gggaaacaga gcaagattct gtctcaaaaa   15000
caaaacaatg tgatttcctc ctctaagtcc tgcacaggaa aatgttaaga aataggtcca   15060
ccaggaaaga aggaagtaag aatgtttgac tagattgtct tggaaaaaat agttatactt   15120
tcttgcttgt cttcctaaca gttctccaaa gcttcgtacc ttggccagag gcttgtctcc   15180
tgcgtacctg aggtttggtg gcaccaagac agacttccta attttcgatc ccaagaagga   15240
atcaaccttt gaagagagaa gttactggca atctcaagtc aaccagggtg aaaattttta   15300
aagattcact ctatatttta attaacgtca gtccgtcatg agaatgcttt gagaaaactg   15360
ttatttctca cacctaacaa ttaatgagat taacttcctc tcccctcatc tgacctgtgg   15420
aggaatctga acaagaggag gaggcagtgg gcaggtttcc ttatcatgat gtttgtcatg   15480
ttcagtgtga ggcctcacaa aaaaaaaaaa aaaaaaaaaa ggcgtcctgg atataactga   15540
gagctcattg tacagtaaat attaataaaa cagtgattgt agctgaagga tagaactgct   15600
tggagggagc aagtgggtag aatcgcgtca aactaaagag catttctagc caaagacaca   15660
atgatagatt gaaggatatt tattctaaat atagaatatg ggtgaacgag atctgtggac   15720
ttctgggctc caacgttaga ttctgatttt agcaagcttg tcagggatt ctgatattga   15780 aaggctgtgg ccttcacctg agaaacctgc cctaggggc catgaaaatt tgtcctgtct   15840
ttcagaagtg ctatcagaca tcaaatggaa gttaaatcgt atcttaacaa ttactaggat   15900
gggcgcagtg actcacacct gtaatcccaa cactttggga ggctgaggca ggaggatcac   15960
ttgagcccag gagttcggga ccagcctggg caacatagag agacgttgtc tctatttttt   16020
aataatttaa agagaaaaaa atactgaaaa tattgtatac accactgaat tataataatg   16080
tgtatataat gtatatattc attatgagga atatttgatt atttcatata ttatatcttt   16140
tccttctgtt tattttatcc agttatgaag tatttagaac aattcatcag taattggggc   16200
taaattgaca gaatagtaat cagagaaaat agaaaaagac agatgggtta tctttgaata   16260
ccaggttgga gttgtttatg ggtttgtttt ttgttttggg ggcgttttt tagacagagt   16320 cccactctgt tgcccaggct ggagtgcagt ggcacaagca tgggccactg catccttgac   16380
ctcttgggct caagcaatct tcccaccttta gcctcctgag tagctgggac acaggtgca   16440 tgtcaccaca cccagctaat ttttttattt tttgtagaga cagtctttct atgttatcca   16500
ggctgatctc aaactcctgc actcaagtga tccccctgcc ttggcgtccc aaagtattgg   16560
gattataggc atagccacca cacccaacct agtttctatt tagacttggc cctttcccac   16620
cagtcatttg tgtccaaaag atctcataaa tgtagacagg aaactgtcct ttgctcatca   16680
gttttcttca tcctgtgtct aggggatgg tcggtggggg aaactggggt tatgcaagtt   16740
```

```
cctctgaaac atcctctgtg agcccaggga tggatgaggc accagccgcc agcgagtcag   16800
tgtgcagctt tccagaaagg aagtcatcag ccagtcagcc ggccctggca gccagcaccc   16860
ggcaaccctg ctgtcttgtg ataaagaaat ggtctgcctg acaggatggt gtggattttt   16920
ctttttcctt ttttttttt ttgagacagg gtctggctct gtcgcccagg ctggagtgca   16980
atggcgggat cttggctcac tgcagcctct gcctcccagg ctcaaggcat cctcccacct   17040
cggtctcccg agtagctggg accacaggca cacaccacca cgcccaacta agttttcgta   17100
tttttagtag aggcagggtt ttactatgtt gtccaggcta gtctcaaact cctgagctca   17160
agctatccat ctgccttggc ctcccaaaga gctggaatta caagcgtgag ccactgtgcc   17220
tgaccagggt ggattttttc aagtgcacat gttgtggtcc cagaagctct gatggtacca   17280
aattccaagc gaaaaaagt caatggttcc cacccatcct acctcccatg atggcaagag   17340
gaaatcacca cactgcagat acagtccatg taaaacaaat tgctatggat tttgaaagtg   17400
aaccttaaga gaactgcact atgttttctt cattagagtt ctctggtaat ttccagcttt   17460
ttttttttt tttttagac agtgtctcgc tttgtcgccc agtgtcaccc aggctggagt   17520
gcagtgacgt gatctcggct cactgcaacc tccgcctcgt gggttgaagt gattctcctg   17580
cctcagcctc ctgagtagct gtattttagt agagacgagg tttcaccatt tggccaggct   17640
ggtctcgaac tcctgacctc aagtgattcg cccatctcag cctcccaaag tgctgggatt   17700
acaggtgtga gccactgcac ccggccagta atttcaagct tctgaggagc cctttgaatt   17760
gttaaataac ttgtagctat gtccaacata tccatgttca gtgtatgttc gatatttctt   17820
aggaaacctg cccttggttg ttttctttgt ggtaattcat gagccggcaa atttgacatg   17880
tgttacagaa tatacctttt ctctgctctc ctacctcata accagaactt aattatcctg   17940
ctttagtcac ataaatagct aactaaataa atatatgaga tttcagtctg ctcactgtga   18000
aaatagacct tctaaatgat ctcttccact tgcagatatt tgcaaatatg gatccatccc   18060
tcctgatgtg gaggagaagt tacggttgga atggccctac caggagcaat tgctactccg   18120
agaacactac cagaaaaagt tcaagaacag cacctactca agtaagaaat gaaaggcacc   18180
ctagagatgt tccagcccca aagatatttg aataggttgg actcgggcac caatctagca   18240
agtcctacgg aagttgtata aagctgaaaa tactgaagca tttcccaaat gggaaatcct   18300
aaactcaaaa cttgcttttt ggtttttttg tttgtttgtt ttttcttcat ctgacattgc   18360
ttagtagtca cagaatgaaa gataaatcaa tcattcatga tctaacaatg accttcagtg   18420
ctctaaaaaa ctacggagtc aaggaaaaca tgaatatatt cctcatgtaa aattaaaata   18480
cagacatata aagggcaaaa catgaacatc attcatacct tgaggtccgt cccctccca   18540
gaaataaccc ccagtatgcc ttggtttaga gcattaagca ggagggccct gagtcactcc   18600
agacagtctt gaccaccaag cagcattctc tttttgtttc ctctgtggct tttgcaaaca   18660
cagggctagc tcagctaccc attagtatgt tttcagtcac taaaacagtc ttccagtctt   18720
caaattagga tgacattgtc acatgggggct ttaaagcaag tgaaacaagg aacccccttt   18780
tttttttttt ttgagatgga atctcactct tgtcgcccag cctggagtgc aatgcgcaa   18840
tcttggctca ctgcaaccctc cacctcccag gttcaagaga ttctcctgcc ttagcctcct   18900
attcattatg aggaatattt gattattcag ttcctgtagg gtaaagatat taccccccgat   18960
catattattg attattgagt agctgagatt acaggtgcct gccaccacga ccggctaatt   19020
ttttgtattt tttagtagag acagggtttc accatgttgg ccaggctcca ggctcgtctc   19080
gaactcctga cctcaggtga tccacccacc tcagcctccc aaagttctgg gattacaggc   19140
```

-continued

```
gtgagccacc actcctggcc acaatccttt tttaactatg aaatatattt ttatctgaag    19200
tttgatgttt atacccaact gagggatgat gttcccatat ctcagttaaa gaaataaacct   19260
gctcagatac ttcaagctct tcttttgact tttgaaaata aatgatcttg aagttactat    19320
actttgtttg ggttagttaa cattatttaa agtatattat tttaattaat tatctttgta    19380
agattttact gtatactacc tggagttcaa tgtatcagat ggatttcaaa tttatgtaca    19440
ttttttatgt atatggtaca gaaaaaaatg tgatccataa gaaatcagaa aatagcgcat    19500
atgctaatag ctaatgttgt cctctaaaaa acttattttt gcattttaa gaggggata     19560
tactctgaca ctttaataag tgtaattaat tattgactgg aatttggcat gaggcagggc    19620
catttcagat cccattaaag gaatgacaca taccagagaa ccacagaagt aaggccacat    19680
ttgtaataaa tcattatagc tctgctagga gaagacccag ttgtattagg taattaatgg    19740
atttgctctt aaaacacatg tcccggaaga tataggtgag tcttggggg ccgcattaaa     19800
cattatacca atgtatctta catttctaag aaagttttac tactttacag gatctttctg    19860
ttaccaaaat ggaaggtttc caactccagg acttggcttt catagttcct acaccagggg    19920
aaatgccttc ctttgctaac tatgcaacca ggttagttag tgtaagtcca gccaccctgt    19980
tggcaatgct aaaaggtaca acaaacacag aattttattt gcatttgtaa acatttgatt    20040
tctggctcga aattttcagt tttcatgggc acgtcatgga aacagaaatc ttctgtgttt    20100
agtttgggca cctactcatt gtagtgacaa atatttcaga agccaatagg ggattccaca    20160
aattgttctg aacctgtggc tgagactggt aatggctgag tgacatgggg acataccaca    20220
aaagaagagg tagcaaaagg ctgctgagat aaggacatgt tcattgctta gctagtggcc    20280
tgcacccta aaacacatgt cccaggctgg gtgctgtggc tcacgcctgt aatcccagca     20340
ctttgggagg ctgaggcggg tggattacct gaggtcagga gttcgagacc aacctggcca    20400
acatagtgaa acctcatttc tactaaaaat acaaaaatta gccaggcatg gtggcgggcg    20460
cctgtagtcc cagctactca ggaggcaggc aggagaatta cttgaatctg ggaggcagag    20520
gttgtggtga ccgagattg cgccaccgca cgctagcctg ggcgacaaag tgagactctg     20580
tctcaaaaaa acaaaaacaa aaacaaaca aacaaaaaac aacaacaaca aaaaacggg      20640
tatcccagaa gatacaggta agttttctaa cacaggtcct cttgtatggt gcgttccact    20700
taagtagaag atgacaaaaa catttgtcat gagaatatag actcacattt taaacctgtt    20760
tgagcaggaa aaggaagcaa tgttacagat gtaattctgg gtgtgactgc agaaaggatg    20820
actcccttat taaagtagtc atcctgagtg agctaactct ttgtacttcc tcttctcctc    20880
ctgttcccct catcacccca ttcttccgtt gcctacaccc aggcccacat tggatgctga    20940
catagactta catggtacag tccaagggaa agatctgcca ttttttttcaa tgtgtcatct   21000
tggttatctt cattccaagg atctctccac tctttataca gtaagagatg agagtctgga    21060
aaggattggg aataagataa tgaattgtaa gttttaaatt gttcttcgta ttttggggaa    21120
ggagtaggct aggtggtcct tctgtttttt ttttgttttt tttttttaaag tagatgtggc   21180
cagacgtggt ggctcacgcc tgtaatccca gcactttgag aggctgaggc aggtggatca    21240
cttgatgtca ggagttcaag accagcctgg ccaacacagt gaaacccgt ctttactaaa     21300
aatacaaaaa ctagccgggc ttggtggcgt ccacctgtag tcccagctac tgcagaggtg    21360
gaggcaggag aatcacttga acccgggagg tggaggttgc agtgagccaa gatcatgcca    21420
ttgtactcca gcctgggcga cagaacaata ctctgtctca aaaaaaaaga gaaagaaaa     21480
```

```
gaaaaaaaga atggatttga actcagtcgt caatagcctc tattccagga gatgttacag   21540
ttgattatgt tataggggt  gtataataga atttcgagct atgtaaattc caagtgcatt   21600
tggaagaatg aagaaatgga ggaagggtaa agtatgagtg caagcattcc aggttttttg   21660
aaaatgctat aatctttgtt cagggctagt acaaagtgct atttagctgt aagggttttt   21720
tgtgatttac agacagtttt cacatgtgtc atttcaacct tggttttatg gcgaaggcat   21780
gtgatggtgc ttgtcccagg actttagatc catatctgag gttcctgtcg ggcaaagata   21840
ttacccctga tcatattata gtctataagt gggagagttg tgcctggagc tcaagtctta   21900
tgatttctga tccagggcac ttcctacaac atgattttgc aatataaaag cctataatgt   21960
gtgactaaag caggtcactc accccttgta acagactcta gtaatggtac tgccaccaaa   22020
cggctgcgtg atattgggca aagacttacc ttatttgaat ctcagtttcc tcctagaaaa   22080
atgagggtgg aggttaagca taggctgatg atcctaaagc ctccatactg ccctaaactg   22140
tggctctaag atccagtaga atgctgggtc acaggactct agggagcttt tcaaacccaa   22200
atgtctgtca ttccttgatg gtaggcagca gtttatggaa gtgggcgaca cagcaaatat   22260
caaaatacct aaagcagctt gcaagagttg tttctgccta gtggtcttta tagttaatat   22320
taaatagtta atttttttt  ttttgagac  agagtcttgc tctgttaccc aggctgcagt   22380
gcagtggcac aatctcggct cactgcaacc tccacctccc gggttgagc  aattctgtct   22440 cagcctccca gtagctggg  actacaggtg catgccactg cacccagcta ttttttgtat   22500
ttttagtaga cacggggttt caccatattg gcaggctgg  tctcgaactc ttgacctcag   22560
gtgatccacc tgcctcagcc tcccaaagtg ctgggattac aggcatgagc cactgcaccc   22620
agcttaaata gctaatattt aatattattc tatagttatt caagtaattc aggccaaaga   22680
cttagaaaca aaacaaaaag ccacttttaa ggagaaaggg tgtaagtttg ccagatagat   22740
agagatcttt cttttttaac tacaagagtt caggaatgaa ttactcttta acaaacgact   22800
atagatatac atgaaaattg gaaggactta ttatgcatat gataatcaat ttaaagacaa   22860
cacttaaaat tatattgttg ccactctcaa aaagtggtaa tagaacagct aatggtttaa   22920
aaagcagagt acagaagttc ccaaacttat ggcaccttaa tatcgcagaa aactttttaa   22980
agcatgccta ggccacaaaa aatacctgta ttttgattat taaattgtaa ggtctacaca   23040
acctaatagt aataggtcca atagtaatgc tgtccaatag atgttgatgt ttttttcctt   23100
gcaaacttaa aagatcctac agtgcctctg taaatagcac tgcctggtta gagttgaatt   23160
tcagataaat aattttttc  atgttaatta ttttctttt  ctttactttt ttttttgttt   23220
ttttgttttt ttgttttttt ttttgagaca gggtctcatt ctgttgccca ggctgctgtg   23280
caatggcatg atcatggctc actgcagcct tgacctccct gggctcaggt gatcctccca   23340
cctcagcctc ccaagtagct agctgggact acaggtgctt accatcatgc ccggctaatt   23400
tttgtgtttt ttgtagagat gtggttttgc catgttgccc aggctggtct tgaactcctg   23460
ggctcaagtg atccgcccgc ctcggcctcc caaagtgcta ggatgacagg catgagccac   23520
tgcacctggc ccctgggcga agtatttctt aatggttaca taggacatac actaaacatt   23580
atttattgtc tatatgaagt tcaagtttaa ctaggtgccc tgcactttta gttgctaaat   23640
cctgtagctc tacccatgca ttcactggtg ctccccagct tgccttgcac agagtttgga   23700
aaccatagtc ctataactct aggccaattt tttaatgtaa aatttgattc attttaaatt   23760
aataaataat aacaggaatt ttttaaaaa  ttgttttaaa tataattaaa attatcaaaa   23820 tatttttaa  ctgaacttgt gactagagat atttagatta tgaagagtgg ggtttatgct   23880
```

```
aactaatgac agtctggcta tgcatgtgga gcactgagct ataaattgtg gcttccccaa    23940
ttctcctgat gtcacttgaa caaaacctaa gtgtcagacc agagcttctg gtatcttcca    24000
tgggatttca ttcaacagct ggagcaaatg aagtcagatt gatttttttt aatttgtcca    24060
attttgttgt ctcaaaaaca taattataat catttattag aactagaatt tcttcagttt    24120
aacaacagaa atagttattc attatgaaaa gcgaatctgg aggccttcat tgtggtgcca    24180
atctaaccat taaattgtga cgttttcctt ttaggaagct ctgtagatgt gctatacact    24240
tttgcaaact gctcaggact ggacttgatc tttggcctaa atgcgttatt aagaacagca    24300
gatttgcagt ggaacagttc taatgctcag ttgctcctgg actactgctc ttccaagggg    24360
tataacattt cttgggaact aggcaatggt gagtacccca gggaacaatt cattaataag    24420
gagattcccc actagcatta tttctttcct tttctttttc ttttctttt tttttttttt    24480 gagacagagt ctcgcactgc tgcccaggct ggagtgcagt ggcgccacct cggctcactt    24540
gaagctctgc ctcccaaaac gccattctcc tgcctcagcc tcccgagtag ctgggactac    24600
aggcacccgc caccgcgccc ggctaatttt tttttttttt tttttttttt tttttttgca    24660
tttttagtag agacggggtt tcaccgtgtt agccaggatg gtcttgatct cctgacctcg    24720
tgatctgccc tcctcggcct cccaaagtgc tgggattaca ggcgtgagcc accaggcccg    24780
gctagcatta tttcttatga cactttttt tttttttga gacggagtct cgctctgtcg    24840
cccaggctgg agtgcagtgg cgccatctcg gctcactgca agctccacct cccaggttca    24900
cgccattctc ctgcctcagc ctcccgagta gctgggacta cacgcacccg ccaccacgcc    24960
cggctaattt ttttgtattt ttagtagaga cggggtttca ccgtgttagc caggatggtc    25020
tctatatcct gaccccatga tctgcccgcc tcggcctccc aaagtggtgg gattacaggc    25080
gtgagccact gcgcccggcc aacactcttt ttattattag caaatatact tctgcctggg    25140
cacattcttg caagtgctca acaatgcaac ttttggaagt gcatgtggca gaaactcctg    25200
ctgtatttat tccagaacct attattgcta atcccagttt atgttacatt tgaagtgaga    25260
accagttgga gccagcaacg ttcccagctc caaagttccc ttgagatttt cagaatcact    25320 taacccatt atgcttggca acctggactc agcaaaactg ggaagtcagc agtttgtttt    25380
attcatccct tcctttctca gtttctcaaa tgtgtcagtt aatctcagta accccattgc    25440
aaccttcatt acctgcccaa gcggtctaga acttgccagt atagaatcct acgtgggtca    25500
agctcctgac tgtctccttc ttcactcttt ttttgcaaag aacttgtaaa ttttaactat    25560
aagtattcat gattcgccac atttattcaa aacatagagt gcttttttcca catatcagcc    25620 aatggaaata aggattaaat gggaaatgaa atgtagtaat aggataagca caagtcttct    25680
tcctgctcaa acttttttt tttttttt cagacaagat cttgctctgt tacccaggct    25740
ggagtgcagt ggcgtgttca tagctcaatg taacctccaa ctcctgggct catgcaatct    25800
ctcacacctc agcccctga ttagctagga ctacactatg cctagccaat ttttttcctt    25860
ttgtctggtt gtgttgccca ggctgtctcg atctcctggc ctcaagtaat cctcctgcct    25920
cggccttcta aagtgctggg attataggca tgagccactg tgcccggtct caaaccttt    25980 tttcaaagt aaatgaagtt attagatatg gaatatagtc tagttcccag atatccatat    26040
ccattggttt attaccctca ttattaactt caaattgttt aatagaccct catatctcag    26100
ttatacagtt aaaattttg ttttgttttt ctggagtatc ttatttataa ctatgagttt    26160
tactttactt atttatttta tttttgaga cagacgcttg ctctgtcact caggctggag    26220
```

```
tgcggttgcg tgatcatggc tcactatggc ctcgaccttc tgggctcaag tgatcctctc    26280
cctcagcctc ccaagctgag actacaggca tgcaccacca catctagcta atttttttt    26340 ttccccatgg aacaaggctt tactatgtta cccagagtgg tctcaaactc ctggcctcag    26400
gggatcctcc tgtctcagcc taccaaaatg ctgggattac aggcatgagc catagcgcca    26460
gacctggttt tacttttctt gactttgaat tacaagtttt tgtaatttgg aaaatgtttt    26520
gttgctttta aatactgctg tatgtttgct tttaaataca acatttctcg atatatattt    26580
tgagaattgc tgtctttcag aacctaacag tttccttaag aaggctgata ttttcatcaa    26640
tgggtcgcag ttaggagaag attttattca attgcataaa cttctaagaa agtccacctt    26700
caaaaatgca aaactctatg gtcctgatgt tggtcagcct cgaagaaaga cggctaagat    26760
gctgaagagg taggaactag aggatgcaga atcactttac ttttcttctt tttcctttg    26820 agacagagtc tcactctgtc agccagactg gagtgcagtg gtacaatcat ggctcactgc    26880
aacttcgacc tcccaggctc aagcaatcct cccatctcag tcccacaaat agctgggact    26940
acaggtgcac atcaccacac ctggctactt taaaaaaatt ttttttgtaga gatggggtct    27000 ccctgtgttg cccaggctgg tctcttgaat tcctgtgctc aagccatcct tccacctcag    27060
cctcccagag tgccaggatt acaggcatga gccaccacac ccagccacca cttttcttaa    27120
aaaaaaaaaa agattctctc tggtagacaa tcctcaatag tccacatgtt attaaacaat    27180
ctgctgcctg aatacatgat ttaccaaaaa aaggaaattt tgacgggttc agaatatcaa    27240
gggatctgag gcaaatgtca cctatgataa aatttgctat caaaattagg aagtttgtgt    27300
ttacctgatc ctaaagcagt aaccagccca tttctaggga ataaaactct catgcgtata    27360
ttgtgcatat atatgtatta tatgactgag tgataataaa attttttttc tagcttcctg    27420
aaggctggtg gagaagtgat tgattcagtt acatggcatc agtaagtatg tctcctattc    27480
ttaatactag gaaagtaagg ctagctttat ttattaccta gtattcaaaa agttagttca    27540
tttaactgcc aattgactgc agttcaaata agaaacaaat agtgtctcaa gtagcactgt    27600
actccaattt taatattaat aaaaaaaatt ttaagttatt ttaataatg tagtggtttc    27660 tataaagatc actttataca gaagaacagt gccaattaac ccatggaaca tataagtagc    27720
taaaaccaat tgcttgccaa agaaccagta acccaggagt acatgtcctt gccactgtgt    27780 ttttttcaaga cagagtaact gatttctagt tacttgcata gaatggactc ctcctcataa    27840
ctcccttcca tcttggtctt tccctagtag aacttctacc tttttttagt aacaggtgag    27900
tgggagaggt aagaaggaga ataaggtcag caattaacct aaaagcagaa agtaaaattt    27960
gttatttttt ttctgaatat tttctgtgta atttagctac tatttgaatg gacggactgc    28020
taccagggaa gattttctaa accctgatgt attggacatt tttatttcat ctgtgcaaaa    28080
agttttccag gtaatagtct ttttaaactt tttaatgtaa aaccagaatc cttatttat    28140 agtctagcta gttctaaatt ctataggtat gtatatttac atgttttct aattttagag    28200 aacaagcact atgacttatc cactgttagt tttcccctta gcattgggtc ttaccccatg    28260
tacgtgatta gaaatttgaa atatttccaa tagcctttag tagaattaac tcacatagat    28320
gataagaatg ggttggttca cttcatgttc cttccacagc ctactatttc aataaaagaa    28380
agtttcccaa gacctaaatg actatgaaca tatttataa ctatataggga ggggtgggtc    28440 taggaataca aagttttgaa tgctgttaat cttcaacacc acagttgaaa ccacaggtca    28500
gcttttttgc aattaccatg gatacttttc tgttctatag gtggttgaga gcaccaggcc    28560
tggcaagaag gtctggttag gagaaacaag ctctgcatat ggaggcggag cgcccttgct    28620
```

```
atccgacacc tttgcagctg gctttatgtg agtgaagcag cgctggcctt aggggtcaga   28680
gtgcagctct tctccatcct tctattctgc tgaaatagct ccccagccaa aaagcagatc   28740
aaagaccgtt tcagtggctg agccccaaaa ttcatgccag attttgcaag aaaatgattt   28800
actaaagctt gagggacatc tttaacaagt gttccaaatt aatcactata aggatgaatt   28860
gtttcagaaa ttttggcctt taattatggc ccataaatat gtcaagtagt ccttactcta   28920
aagaagtaca ctgtaaaaga atgcatatag ccggatatgg tagttccctg taatcccaat   28980
actttgggag gccaaggtgg gaggattgct tgagcccagg agtttgaggc tgcagtgagt   29040
tatgatggtg ccactgcact ctagactggg caacagagtg agactgtctt ttttttctcc   29100
ctctgtcacc cagactggag ggcagtggca cgatctcacc tcactgcaac ctctgcctcc   29160
cggattgaag cgattctcct gcctcagcgt cctgagtagc tgggactaca ggagtatcac   29220
cgcactgggc taattttgt attttagta gagacgggt tttgacatgt tgcccaggct   29280
ggtctgaaac ccatgagctc aagtgatctg cctacctcag ccttccaaaa tgctgggatt   29340
acggacatga gctaccacgc ccggccacac cctgtctctt aaaaaaaaaa aaaatgcaag   29400
ttagagcata ttacagcttt gtctctcagg aggatactta gtgtatgtag ctataattca   29460
tagattccca agaagtttag agcctaaagt atgaggtccc accagagggg ctatcattaa   29520
atttaaagat ttgttaaatc atctcattgt ccaacaccac aaacttgatt gctttaaaat   29580
actggtttag ttacatttag taactctatt agtgctttta atctatactg ctatatcctc   29640
acattgagat ttttttttctt ttctcttcca tcttcattct tttttctctc atcctcattc   29700
ttataagcct agaatacatc acaaatcctt tatgcccatg gaagcaagag gaataaagaa   29760
tggagatgtt tgttttgcca ttaactaaag atctggggtg tcggggagaa ggggataga   29820 gaaggagaag tgggaagagg tgtccataat agcttaggtg caattctgct tattttacat   29880
tttacccccg ctgactgcca cttttcttc agccctcaca cattgtttgt gcagggacct   29940
cataggacca ggaattgtct atagaggtgg gaatttgtct caccctgaaa gggatacctc   30000
tagcatggta atagtcttct aggatttgtt atcatatgga aagatgtaaa gggagggatt   30060
ctgctgctgc tgctgctgct gcatgcagtt gccatttcat ttaaatgact tatttataat   30120
tgatgacact tttctggctt cctgttaatt cctccctcaa agatcaataa accagaacca   30180
ggcatggtgg catgcacttg tggtcctgta accacccaac aggttcacct tgcctgctgt   30240
ctagatagag ccaattatca agacagggga attgcaaagg agaaagagta atttatgcag   30300
agccagctgt gcaggagacc agagttttat tattactcaa atcagtctcc ccgaacattc   30360
gaggatcaga gcttttaagg ataatttggc cggtagggc ttaggaagtg gagagtgctg   30420
gttggtcagg ttggagatgg aatcacaggg agtggaagtg aggttttctt gctgtcttct   30480
gttcctggat gggatggcag aactggttgg gccagattac cggtctgggt ggtctcaaat   30540
gatccaccca gttcagggtc tgcaagatat ctcaagcact gatcttaggt tttacaacag   30600
tgatgttatc cccaggaaca atttggggag gttcagactc ttggagccag aggctgcatt   30660
atccctaaac cgtaatctct aatgttgtag ctaatttgtt agtcctgcaa aggtagactt   30720
gtccccaggc aagaaggggg tcttttcaga aagggctat tatcattttt gtttcagagt   30780
caaaccatga actgaatttc ttcccaaagt tagttcagcc tacacccagg aatgaagaag   30840
gacagcttaa aggttagaag caagatggag tcaatgaggt ctgatctctt tcactgtcat   30900
aatttcctca gttataattt ttgcaaaggc ggtttcagtc ccagctactt gggaggctga   30960
```

```
gacaggagga ttaatggagc ccaggagttt gaggttgcag agagctatga tcacgccact    31020
gcactccagc ctgggtgaca gagtgagacc ctgtctctaa ataaataaat aagtaaataa    31080
ataaatacat aaataaaatc aagatggtgt gcaattagaa ttgagcgatt ttgtttccaa    31140
acctcaagaa agcttggtct tgctctgtcc caggtggctg gataaattgg gcctgtcagc    31200
ccgaatggga atagaagtgg tgatgaggca agtattcttt ggagcaggaa actaccattt    31260
agtggatgaa aacttcgatc ctttacctgt aagtgaccat tattttccta attctagtgg    31320
agtagattaa agtcaactca ggacctctgg tgttaacctc ctatgaacag tcagtcctct    31380
cagtaactag ccaaatcatg agatgatgaa ttagaaggag ccttagatag catccaatct    31440 aacattttt tgtgtgtttg aagagaagaa atcaagagct aggaataact ttttaaaggt    31500
aagccatttg cagtatagtg tggatttttgt ttaaaagggg ataatttgaa attttatgac    31560
tcattataca agacaaaata agttggattt tcaaatgttt tacaaagtaa atcaaagtta    31620
taattgccta cagtacgcaa agcttcaaaa cattttttat gttatgaaat tgtaattttat    31680 ttaaccttaa aatgagccag taccatgtgt ttgcttaaaa atctcatgct aagaatttac    31740
tatgttgtta ataatcttca agatatttat gaataaagtc ttatttctaa tccttcctcc    31800
aactgtatct ggtgctaaat caggaaatgt ttcttcccaa aaagcctcgt ggaagatctg    31860
tatgtctaaa tatatgtcag ggataataca gatgtagccc tgcgaagcat gaccttgatt    31920
tttatagtct aaaatgtcat ttgcagatat ctattttcta agaataattc ctaaaagaat    31980
tatttgaatg ttgtaggaaa gctaagaaat tttgcaaaga gcgtacgtga aaatataagc    32040
taggcttttg tggtttgtgg atagacttcc caacaaaatt gcttttatc tatagtgatc    32100 caagcttgtg gaacatatta gtcatctttt tttagaaaat tcttagaaaa gtgatcttgc    32160
aaaaatggaa tttatctttc cccaagtata ttctgtcatg tatagagtta aactaagcat    32220
agtaatttca ccagacaaac attcaaaatc tactcctgac cttttatct catccaaatt    32280 ttcccagggc ccagacataa acctttgcct tacgaactct ttgtatatgc actaaatatg    32340
cttctccttc aaggttctca gtcagctaga aaaatgtgca agagtaaatg gtacccttct    32400
cacttgtaga tccaagagaa ttagacttaa actcactcta catgtctgtg actttatttt    32460
atttgcatga cagtcctgtg aggtggcaag gcaggtatct tggatccatt ttttagataa    32520
ggaagttcaa attgagaaga ggttgcatga tttacaggaa gccatactgt agtcctatgt    32580
tactcttaaa aatcccattc aaatcctgct tctgaggcct gcatactttc taccctacca    32640
gtcattgacc catgcttatg tctcctttga aaacattgat tccactcttg tctccagtga    32700
aaaagtggaa tttaagcaga gaaacaaaag ccatttgtct tgttaagtct actttccctc    32760
tactttcaag aaggaaagtt gggggtatgtg ttgaatggtg atttatttat ttatttatta    32820
ttttaaaaat tgatacaagg tcttactgta ttgtgcaggc tggtctcaaa ctcctgggct    32880
caagtgatca tcccacctca gcctcccagt gttgggatta cagcatgaac cattgtgccc    32940
accaccgatc cgcagttttt taagaaaaac ttttactata gaaaatttta atcatataca    33000
aaatacagag gaaagtatat gaacccactt taggagacta gaatatgcca ccccaaaata    33060
tgccactttg gcataaggat tatttcgagc taaaggcaac tgggaagaaa cacatagaag    33120
aaaagttctc tgtccttctc catttgccta aaagcaggac atgaatctta aaagtccccc    33180
tccttccctt tctaccagga aaaacaagag ttaatcactg aagataactt cagacccta    33240 tcagtgtaga gatggcacta gaagaatcta tattacatac tcatttattt tccttcccac    33300
aacttgccac cccagagact aaaaatcctt ttcctttgtc atgtctcttg tccaaaaatt    33360
```

```
tgctctataa gctggagttc taagccacct ctttgagaat tacttgttcc ctggtatttt   33420
ctgttaacat acatgtatta atatacatgt taacaagctt ctgtttgttt ttctcctgtt   33480
ttctgtcttg ttacagaggt ccatcccaac taagaactaa agagtaggag gaaaatataa   33540
tttcctcctg catactttga tcttgtttaa tccgtaaccc ttcccacttt tcacctccta   33600
cctattagat tactttgaag caaatttcag atatattact ttatctataa atatttcagt   33660
atgtgctagg tgtggtggct cacacctgta atcccaacac tttgggaagc tgaggcagga   33720
ggatcacttg agcccaggag ttcaagacca gctacggcaa caaaaaatca aaaacttatc   33780
tgggcatggt ggcacatgcc tgtggtccca gctacatgag aggctgaggc aggaggatcg   33840
ctttagccca ggaggttgag gctgcagtaa gctgcattca caccactgca ctccagcctg   33900
ggtgacagag taagaccatg tctcaaaaaa atacatattt tagtatgtat ccttttttgta  33960 aaaacacaat acttttatca tactttaaat aataacaata attccttagt atcaccaaat   34020
attttgtcag tgtctcacat tttccttatt gtctaaaata ttgttgatag ttattcaaat   34080
cagaatccaa acaaggtcca tatattacat ttggttgaca agtctcttaa gtttgttcat   34140
ctttaagttc ttcctccctc tctttcatct cttgtaattt attaatgtga aaaaacaggt   34200
aatttgttct atagtatttc ctacattata gagtttgcta catttattcc ctatgatatc   34260
atttagcatg ttcctctgtc ccctgtgttt cctgtaaact ggtagttata cctagaagct   34320
tgagtttatt caggttttta attgtatttt ttttgcaaga attctttatt atctgcttct   34380
ggaagcacag aatgtctggt tgtgtctggt tttgatcttg acagctactg atgaccattg   34440
cctaatccat tactttattg gggtgggggg aataaggttt taaataaaat ttttttttaaa 34500 gatttttta actgttattt tgagacagtg tctcatttcg tttcccaggc tggagtgcag   34560
tggcacaatc acggctcact gcagccttga cctcctggga tcaggtgatc ttctcacctc   34620
agcctcctgg gtacctggaa ctacaggtgc acaccaccac acctggctaa ttttttgtat   34680
tttgtgtaca gaagggggttt catcatgttt cccagactgg tcttgaactc ctgggttcaa   34740
gtgatctacc cacttcagct tcccaaaatc ctgggattac actttggcca ccgtgcctgg   34800
cctaaatgaa attatttgtc tctaaacaga cagaagtttt actttaaaaa tttgtctttg   34860
tgtgtacatg tgtttgtgta tgtgtgtgtg tctaaaagtt tggctttgag cttttgctttg  34920 aattcttgga tgaacaataa ccaagaatac ttaaactctg atcattcttg acagatatcc   34980
cctacaggct atggccttttt gaattgtgtc ctccagtgat aaaaagcagc aagcacgata   35040
ctgctctcag attcatggtg gtcacatgtg aggtgaaaaa aaaaaaaaag atgaatccta   35100
tttaaatgcc cccaggataa cagtgatact ctttgtagga taactatttg cttgccactg   35160
gtttcattaa ataaggacat aagtaaagat ctattttgt ctctttctcc ccaaccacca    35220
caactaggat tattggctat ctcttctgtt caagaaattg gtgggcacca aggtgttaat   35280
ggcaagcgtg caaggttcaa agagaaggaa gcttcgagta taccttcatt gcacaaacac   35340
tgacaagtaa gtatgaaaca cacccttttac caatcatcaa gttttagtgg gtaagcctgt   35400
aactttactc aaacaccctg ttgcatgtgt ctatacattg cataagtata ggcagttgca   35460
atttagtaaa gttttataca acgatttttat tttattttat tttttagaaga aaaatgctac  35520 ttttgttgtt gttgtttttt gagacggggc ctcgctcgtc acccaggctg gagtgcagtg   35580
gtgcaatctc agctcactgc aacctccgcc tcccgggttc aagtgattct tgaagaggag   35640
aacaataata acaacaatat tattttcaaa agttgtgacc gcagtttctg gagttgagaa   35700
```

```
gacatcgaga ttttttgtagc ctcatactct tgctttaggt agcaaaaaat gttcctaaat   35760
ctcaggaata ttctctagat aggtttcaat ctatcattcc tgataagatg atgctgaaat   35820
actaattcta gccaaaaaag accagctacc atttccgatt gttggggact gggaactctg   35880
gatagtgagg accccagtag gaagtagcga ggggaatggt ttgaatggat aaattcataa   35940
aaaatgtcag tagatttaat tttcttatac atttcagtct ttttataagg ctaggaaaag   36000
cccctgtttt tatggtttat aatttgaatt cacatgaacc cacaaaattt gccttttacc   36060
ttcctatgtc tgaaaatgga tagtctggct ggcctcttaa caacccagct ggcagagctg   36120
tgaggatctc agtgtgctct agcccagaca ttggtagcat gaacggcaac attttttaatt   36180
gtgttttcaa aataggagca cactagcggt ctaaaacgat cataaaagaa ggatactaag   36240
agggcccact gtcattatgg atcctaatac ttaggatgca ttatgattg tcattatgga   36300
tactaatact taggatcaca tttgtaattg agttttttaat tgcttaaatt agatacatat   36360
ttctattaag ttaacctctt tgcttttagt ccaaggtata agaaggaga tttaactctg   36420
tatgccataa acctccataa tgtcaccaag tacttgcggt taccctatcc ttttttctaac   36480
aagcaagtgg ataaatacct tctaagacct ttgggacctc atggattact ttccaagtaa   36540
gtaatttttcc ttgttcattc caaactttca ataaatttat tggtgtttat cagaatagag   36600
agtttggaca gggagcaaaa gacaaagtca actatatcaa gttctaataa ttcttaatat   36660
tcaggaaatt tatgtatgaa tacttactaa tatgagtata actcatccta agagtctaaa   36720
gcaaaaggat gtgaacacaa actagcagtt atcttagaga ataagtttgc atttcaaaat   36780
aacttgacat atcaagatcc actcaacgca tttaaattat ttactctaaa aagacataat   36840
tcttggtaac acattcacta aagcaaaata tacctttata taattgctat caaaggtatg   36900
tgggttggta taaatatca taccatgtga gatcagtgtg attcctttac agcattaatt   36960
tttattggtt agagtaagaa aaagaatagc tagagtatat ttcttaagta gattctcata   37020
cactttggtt tcaaaaacca attattgact acatcttata aaagcctgta ttcaatggag   37080
tgccaaaaaa tgactatgag tcttaaagag ttaggcatat aaatatttta aggtttctgt   37140
tcaatgtatg ttggaaggag ttcctttctc atgactattc tcatattgga gcataaaaag   37200
agtttacagg cttggcgcag tggctcatgc ctgtaatccc aatactttgg gaagctgaag   37260
caggcagatc acttcagccc aggagtttga gaccagcctg gcaatatgg caaaactctc   37320
tctacaaaat ataccaaaat tagccaggcg tggtggtgca tgcctgtagt cccagctact   37380
tgggaagctg aggtgggagg attgcttgag cccagggggg tcatggctgc agtgagctgt   37440
gatggtgcct ctgtcaccca gcctgggtga cagagtgaga ccctgtctca aaaaataaa   37500
taaataaaaa ttaagagttt acaaaattct caccatctcc tcccatcttt gcaaatgcca   37560
cataagtgat gtgttccagg actattagcc tcggaacctg aggcagtaca gtaagcacgc   37620
tttctccaaa gtcctgtccc ccacagacaa acattattta cactgggtac tgctctttta   37680
tttttttcccc tctatgcttt attttactat aactataatc atataacatg taataggaaa   37740
aaggcagggt cggggagag atccagaagt cttcccaaga gcctttccaa catagcctct   37800
gtagacattt tttctttctt cttttttttt ttttttttt ttctgagaca gagtctcact   37860
ctgttgtcca ggctagagtg cagtggcgtg atctaggctc actgcaacct ccgcctcctg   37920
ggttcaagca attctcccac ctcagcctcc ctagtagctg ggattagagg catgcatcac   37980
cacgcctggc taattttttgt attttttagta gagatgaggt ttcaccatgt gggccaggct   38040
ggtcttgaac tcctgacctc aagtgatcca cctgccttag cctcccaaag tgctaggatt   38100
```

```
acacgagtga gccaccgtgc cctgcccta ttacattctg atcacacatt tcatgttta    38160 taattggaaa actggtgaaa ttatagacaa tgttttgttc ccctaaattc tctttgatga    38220
gtatatatta cttacactct tctgtcttta aaattttgca aaatagtatc ctagataagt    38280
ttatgagtgc acagtctgta cgcttactca tattaatgac ctcggagagt taaacaacag    38340
tcacctttaa aaattattac tatcattatc attattttg aggcgggggt ctcattctgt    38400
ctcccaggct ggagagtagt ggtgcggtca cagctcactg cagccaccgc tacctgggct    38460
caagtgatcc ttcctcctca gccttctgag tagctgagac cacaggctta tgctaccaca    38520
cctggctaat tttttaactt tttgtagaga cgatgtctca ttatgttgcc caggctggtc    38580
tcaaactcct aagctcaagt gatcttcctc agcctcccaa agtgctggga ttacaggcat    38640
gaaaaactgc acccagccct aaaaattatt agggtcctgc atagtaagac tttaataaat    38700
atttaaatga acatctggtt ttttaaaaa aaaaatagag acaaggtctc actatattgc    38760
ccaagctggt ctcgaactcc tggactcacg caatcctgct gccttagccg cccaaagtgc    38820
tgggattaca ggcatgaccc acctcatctg ggctgagtga acatattttt aacataaagg    38880
ccgtatttta tatttatctc atacattttg cccagcatcc ccatttccgc cgaatctgtt    38940
gcttgctaat tccttccagc ttcatttcat ctgaaatttg acaaacatct tctatttctt    39000
tgtcgtcatg ttattgactt cagaatataa aataaaacac tatacccaaa ttaaacccca    39060
ccctcattgc ccagcctgat gtgaaaataa tcagcataca ttaagcttac ccttgatata    39120
tgtgtagcat cttttagata aatatacagc tgattaagca atatagcctg atggtataat    39180
atcttgccca tgtacctcat cttatctcca gcaggattaa ttcacagtga tcagatttac    39240
cttaaaactt tgtagcaaaa tatcctctcc aaaagcatat ctaaaacttt tgtgtgtact    39300
cttgcaagtt tcttaatttc atgcagaaca ggctcttacc actgttagct ggagatattt    39360
tcaagaccta ttttttgtttg tggtttcctg atgatggtca tggcatttcc cccttcactc    39420
catctaaaaa ttgaggtgat acaggctttt aaacaaaacc aactcatata gactgagtac    39480
aactgcaatg caggcatgct aacctctgct acaatcatgg gcgtgctatt gatatgtctt    39540
aagttacaga acacagggct gagcgtctca ttaggtcaaa atgtaaacca gttttttctgc    39600 tcactgatgc ttaatgagga cagggtgtga gagatttctt taaggaaaac aaatatataa    39660
taatgctaca tggaaaaata tctaacatta gagaattaag taaataaact aatatactca    39720
caccatggaa tcttgtgcag acattaaaat tatgtagtgg atggatgttt aatggtgtga    39780 gaaaagtta ggatgtgctg gggtggggggg aagaatcaag ttttaagaaa atacagtata    39840
cccatactta agtaaaaaaa aaaaaaaagg tatgtacagt catgtgttgc ttaatgatgg    39900
ggatacattc cgagaaatgt gtcgataggt gatttcatcc ttgtgtgaac atcatagagt    39960
gaacttacac aaacctagat ggtctagcct actatgtatc taggctatat gactagcctg    40020
ttgctcctag gctacaaacc tgtaaagcat gttactgtag cgaatataca aatacttaac    40080
acaatggcaa gctatcattg tgttaagtag ttgtgtatct aaacatatct aaaacataga    40140
aaactaatgt gttgtgctac aatgttacaa tgactatgac attgctaggc aataggaatt    40200 ataatttat ccttttatgg aaccacactt atatatgcgg tccatggtgg accaaaacat    40260
ccttatgtgg catatgactg tatacatgta cacaaaaaat agatgaaaga atgaatatac    40320
atcaaaatat ttaaatggt tataatgact taggttactt ttatttatct tagtaataat    40380
aatgatgata gataatactt ttatagtgtt tactatataa aagacactgt tataagtgtt    40440
```

```
ctacatactt tacatgtatt acctaaatga tataaatata actctgacag taactaatct    40500
tatacgttct cttttctttt tttttttttt ctttttttag acagaatctt gctctaccag    40560
gctggagtgc agggtgcaat ctcggctcac tgcaacctcc gcctcccagg ttcaaacgat    40620
tctcatgtct cagcctcctg agtagctggg actacaggca cacaccacca tgcccggcta    40680 attttttgtat ttttgggtag agatggagtt ttgccatgtt ggccaggctg atcttgaact    40740
cctggcctca agtgatctgc ctgcctcagc ctcccaaagt gctgggatta caggtgtgaa    40800
ccactgtgct cggcctaatc ttacaagttt tcaatattta agagtgcta actttgttga    40860 caatataaaa catatttgag aaaagagat ataagcatct tatttagaat tatgaaaata    40920
tcaatagacc tacagccgac taaagctttt cttcataagc tcttgcctat attgattcgc    40980
tcctgtgaat atgcattaat ttgatttaaa taataagtat gtataagaaa taacactttt    41040
ccttaatttt taagaacgtt caacagtttt taatttgaat tccaatagtg aaatacatag    41100
aaaatataaa attttctgta gtttagccaa attgttttttg tttcaccaca gcattctacc    41160
aaaatttctt aataacagta agaaaatgaa tgcatacctc ctgcagggag aggggagtta    41220
ggcagtttat gggcatagtt acaagtgaga aatttcattg gctaccattt acgctaaatt    41280
cataaaaact gcattcaatt ctatatatct attttctttta cataaaaag gtttcaatta    41340 ttggccatta aataaaatag ccaccattcc agaagttgtg tcatgtttat ccttttatata    41400 ccaccatcat attgcctatt atatagattg tgtgtgttcc attttctgta atgggccaga    41460
cagtaagtat ttctggcttt ggagtccata tggtctctat cataactact catctctgcc    41520
attgtagctt aaagattatc taggtcaaat gcctaagtga tatagtgttg aaatacaagt    41580
tatataatat aggctgccac aaaaaaaaat ttatttggtc taaaaaagat ttcatgactt    41640
ttgtagcagc atgggtgggg catgcaccac ttggttaact cggtgtatct ttctcctttg    41700
cagatctgtc caactcaatg gtctaactct aaagatggtg gatgatcaaa ccttgccacc    41760
tttaatggaa aaacctctcc ggccaggaag ttcactgggc ttgccagctt tctcatatag    41820
tttttttgtg ataagaaatg ccaaagttgc tgcttgcatc tgaaaataaa atatactagt    41880
cctgacactg aattttttcaa gtatactaag agtaaagcaa ctcaagttat aggaaaggaa    41940 gcagataacct tgcaaagcaa ctagtgggtg cttgagagac actgggacac tgtcagtgct    42000
agatttagca cagtattttg atctcgctag gtagaacact gctaataata atagctaata    42060
ataccttgtt ccaaatactg cttagcattt tgcatgtttt acttttatct aaagttttgt    42120
tttgttttat tatttatttta tttatttatt ttgagacaga atctctctct gtcacccagg    42180
ctggagtgcc atggtgcgat cttggctcac tgcaacttta agcaattctc ctgcctcagc    42240
ttcctgagta gctgggatta taggcgtgtg ccaccacgcc cagctacttt ctatatttttt    42300 tgtagagatg gagtttcgcc atattggcca agctggtctc gaactcctgt cctcgaactc    42360
ctgtcctcaa gtgatccacc cgcctcagcc tctcaaagtg ctgggattac aggtgtgagc    42420
caccacaccc agcagtgttt tatttttgag acagggtatc attctgttgc ccaggcttga    42480
gtgcagtggt gcaatcatag atcactgcag ccttttaact cctgggctca agtcatcctc    42540
ctgcttagcc tcccaagtag ctaggaccac agacacatgc catcacactt ggctattttt    42600
aaaaaatttt ttgtagagat ggggtctcgc tatgttaccc aaactggtcc tgaactcctg    42660
gactcaattg atcctcccac cttggccttc caggtgctgg gatttctttg ggagtacagc    42720
atggtacagc aggagatcat ttgatgttac ctctgtgcag tgttgctagt cagcgaaaga    42780
ctataatacc tgtggggaca gcgattagcc accacaacca gtctttatttt aaagttatta    42840
```

```
aaaatggctg ggcgcagtgg ctcacacctg taatcctagc actttgggag gccgaggcag    42900
atggatcacc tgacgtgagg aatttgagac cagcctggcc aacatggtga acccccatct    42960
ctactaaaaa atacaaaaat tagctgggtg tggtcctgta gtcccagcta cttgggaggc    43020
tggggcagga gaattacttg aacccaggag gcagaggttg cagtgagccg agattgtgcc    43080
actgcactcc agcctgggtg acagagagag attccatctc aaaaaaacaa gttattaaaa    43140
atgtatatga atgctcctaa tatggtcagg aagcaaggaa gcgaaggata tattatgagt    43200
tttaagaagg tgcttagctg tatatttatc tttcaaaatg tattagaaga ttttagaatt    43260 cttccttca tgtgccatct ctacaggcac ccatcagaaa aagcatactg ccgttaccgt    43320
gaaactggtt gtaaaagaga aactatctat ttgcacctta aaagacagct agattttgct    43380
gattttcttc tttcggtttt ctttgtcagc aataatatgt gagaggacag attgttagat    43440
atgatagtat aaaaaatggt taatgacaat tcagaggcga ggagattctg taaacttaaa    43500
attactataa atgaaattga tttgtcaaga ggataaattt tagaaaacac ccaatacctt    43560
ataactgtct gttaatgctt gctttttctc tacctttctt ccttgtttca gttgggaagc    43620
ttttggctgc aagtaacaga aactcctaat tcaaatggct taagcaataa ggaaatgtat    43680
attcccacat aactagacgt tcaaacaggc caggctccag cacttcagta cgtcaccagg    43740
gatctgggtt cttcccagct ctctgctctg ccatctttag cgctggcttc attctcagac    43800
tctggtagca tgatggctgt agctgtttca tgggcccctt caaacctcat agcaaccaga    43860
ggaagaaaat gagccatttt ttgagtctcc ttcatagact tgaataactc ttttcagag    43920 cttctcacag caaacctctc ctcatgtctc ctcatgtctt attgttcaga aatgggtaat    43980
gtggccattt caccagtcac tgccaacaac aacgaggttc ctataattgt ctctgagtaa    44040
ccctttggaa tggagagggt gttggtcagt ctacaaactg aacactgcag ttctgcgctt    44100
tttaccagtg aaaaaatgta attattttcc cctcttaagg attaatattc ttcaaatgta    44160
tgcctgttat ggatatagta tctttaaaat tttttatttt aatagcttta ggggtacaca    44220 cttttttgctt acaggggtga attgtgtagt ggtgaagact cggcttttaa tgtacttgtc    44280
acctgagtga tgtacattgt acccaatagg taattttttca tccattaccc tccttccgcc    44340 ctcttcccctt ctgagtctcc aacatcccctt ataccactgt gtatgttctt gtgtacctac    44400
agctaagctt ccacttataa gtgagaacat gcagtatttg gttttccatt cctgagttac    44460 ttccctagg ataacagccc ccagttccgt ccaagttgct gcaaaataca ttattcttct    44520
ttatggctga gtaatagtcc atggtacata tataccacat tttctttatc cacttatcag    44580
ttgatggaca cttaggttaa ttccattcaa tttcattcaa tttaagtata tttgtaagga    44640
gctaaagctg aaaattaaat tttagatctt tcaatactct taaattttat atgtaagtgg    44700 ttttatatt ttcacatttg aaataaagta attttttataa ccttgatatt gtatgactat    44760
tcttttagta atgtaaagcc tacagactcc tacatttgga accactagtg tgttgtttca    44820
ccccttgtta tactatcagg atcctcga                                      44848
```

<210> SEQ ID NO 43
<211> LENGTH: 2396
<212> TYPE: DNA
<213> ORGANISM: Homo sapiens

<400> SEQUENCE: 43

```
tttctagttg cttttagcca atgtcggatc aggttttca agcgacaaag agatactgag        60
```

```
atcctgggca gaggacatcc tagctcggtc agatttgggc aggctcaagt gaccagtgtc    120
ttaaggcaga agggagtcgg ggtagggtct ggctgaaccc tcaaccgggg cttttaactc    180
agggtctagt cctggcgcca aatggatggg acctagaaaa ggtgacagag tgcgcaggac    240
accaggaagc tggtcccacc cctgcgcggc tcccgggcgc tccctcccca ggcctccgag    300
gatcttggat tctggccacc tccgcaccct ttggatgggt gtggatgatt caaaagtgg     360 acgtgaccgc ggcggagggg aaagccagca cggaaatgaa agagagcgag gaggggaggg    420
cggggagggg agggcgctag ggagggactc ccgggagggg tgggagggat ggagcgctgt    480
gggagggtac tgagtcctgg cgccagaggc gaagcaggac cggttgcagg gggcttgagc    540
cagcgcgccg gctgccccag ctctcccggc agcgggcggt ccagccaggt gggatgctga    600
ggctgctgct gctgtggctc tggggccgc tcggtgccct ggcccagggc gccccgcgg      660 ggaccgcgcc gaccgacgac gtggtagact ggagttttta caccaagcgg ccgctccgaa    720
gcgtgagtcc ctcgttcctg tccatcacca tcgacgccag cctggccacc gacccgcgct    780
tcctcacctt cctgggctct ccaaggctcc gtgctctggc tagaggctta tctcctgcat    840
acttgagatt tggcggcaca aagactgact tccttatttt tgatccggac aaggaaccga    900
cttccgaaga aagaagttac tggaaatctc aagtcaacca tgatatttgc aggtctgagc    960
cggtctctgc tgcggtgttg aggaaactcc aggtggaatg gcccttccag gagctgttgc   1020
tgctccgaga gcagtaccaa aaggagttca agaacagcac ctactcaaga agctcagtgg   1080
acatgctcta cagttttgcc aagtgctcgg ggttagacct gatctttggt ctaaatgcgt   1140
tactacgaac cccagactta cggtggaaca gctccaacgc ccagcttctc cttgactact   1200
gctcttccaa gggttataac atctcctggg aactgggcaa tgagcccaac agtttctgga   1260
agaaagctca cattctcatc gatgggttgc agttaggaga agactttgtg gagttgcata   1320
aacttctaca aaggtcagct ttccaaaatg caaaactcta tggtcctgac atcggtcagc   1380
ctcgagggaa gacagttaaa ctgctgagga gtttcctgaa ggctggcgga gaagtgatcg   1440
actctcttac atggcatcac tattacttga atggacgcat cgctaccaaa gaagattttc   1500
tgagctctga tgcgctggac actttttattc tctctgtgca aaaaattctg aaggtcacta   1560
aagagatcac acctggcaag aaggtctggt tgggagagac gagctcagct tacggtggcg   1620
gtgcaccctt gctgtccaac acctttgcag ctggctttat gtggctggat aaattgggcc   1680
tgtcagccca gatgggcata gaagtcgtga tgaggcaggt gttcttcgga gcaggcaact   1740
accacttagt ggatgaaaac tttgagcctt tacctgatta ctggctctct cttctgttca   1800
agaaactggt aggtcccagg gtgttactgt caagagtgaa aggcccagac aggagcaaac   1860
tccgagtgta tctccactgc actaacgtct atcacccacg atatcaggaa ggagatctaa   1920
ctctgtatgt cctgaacctc cataatgtca ccaagcactt gaaggtaccg cctccgttgt   1980
tcaggaaacc agtggatacg taccttctga agccttcggg gccggatgga ttactttcca   2040
aatctgtcca actgaacggt caaattctga agatggtgga tgagcagacc ctgccagctt   2100
tgacagaaaa acctctcccc gcaggaagtg cactaagcct gcctgccttt tcctatggtt   2160
tttttgtcat aagaaatgcc aaaatcgctg cttgtatatg aaaataaaag gcatacggta   2220
cccctgagac aaaagccgag gggggtgtta ttcataaaac aaaaccctag tttaggaggc   2280
cacctccttg ccgagttcca gagcttcggg agggtggggt acacttcagt attacattca   2340
gtgtggtgtt ctctctaaga agaatactgc aggtggtgac agttaatagc actgtg        2396
```

<210> SEQ ID NO 44
<211> LENGTH: 535
<212> TYPE: PRT
<213> ORGANISM: Homo sapiens

<400> SEQUENCE: 44

Met Leu Arg Leu Leu Leu Leu Trp Leu Trp Gly Pro Leu Gly Ala Leu
1               5                   10                  15

Ala Gln Gly Ala Pro Ala Gly Thr Ala Pro Thr Asp Asp Val Val Asp
            20                  25                  30

Leu Glu Phe Tyr Thr Lys Arg Pro Leu Arg Ser Val Ser Pro Ser Phe
        35                  40                  45

Leu Ser Ile Thr Ile Asp Ala Ser Leu Ala Thr Asp Pro Arg Phe Leu
    50                  55                  60

Thr Phe Leu Gly Ser Pro Arg Leu Arg Ala Leu Ala Arg Gly Leu Ser
65                  70                  75                  80

Pro Ala Tyr Leu Arg Phe Gly Gly Thr Lys Thr Asp Phe Leu Ile Phe
                85                  90                  95

Asp Pro Asp Lys Glu Pro Thr Ser Glu Glu Arg Ser Tyr Trp Lys Ser
            100                 105                 110

Gln Val Asn His Asp Ile Cys Arg Ser Glu Pro Val Ser Ala Ala Val
        115                 120                 125

Leu Arg Lys Leu Gln Val Glu Trp Pro Phe Gln Glu Leu Leu Leu Leu
    130                 135                 140

Arg Glu Gln Tyr Gln Lys Glu Phe Lys Asn Ser Thr Tyr Ser Arg Ser
145                 150                 155                 160

Ser Val Asp Met Leu Tyr Ser Phe Ala Lys Cys Ser Gly Leu Asp Leu
                165                 170                 175

Ile Phe Gly Leu Asn Ala Leu Leu Arg Thr Pro Asp Leu Arg Trp Asn
            180                 185                 190

Ser Ser Asn Ala Gln Leu Leu Leu Asp Tyr Cys Ser Ser Lys Gly Tyr
        195                 200                 205

Asn Ile Ser Trp Glu Leu Gly Asn Glu Pro Asn Ser Phe Trp Lys Lys
    210                 215                 220

Ala His Ile Leu Ile Asp Gly Leu Gln Leu Gly Glu Asp Phe Val Glu
225                 230                 235                 240

Leu His Lys Leu Leu Gln Arg Ser Ala Phe Gln Asn Ala Lys Leu Tyr
                245                 250                 255

Gly Pro Asp Ile Gly Gln Pro Arg Gly Lys Thr Val Lys Leu Leu Arg
            260                 265                 270

Ser Phe Leu Lys Ala Gly Gly Glu Val Ile Asp Ser Leu Thr Trp His
        275                 280                 285

His Tyr Tyr Leu Asn Gly Arg Ile Ala Thr Lys Glu Asp Phe Leu Ser
    290                 295                 300

Ser Asp Ala Leu Asp Thr Phe Ile Leu Ser Val Gln Lys Ile Leu Lys
305                 310                 315                 320

Val Thr Lys Glu Ile Thr Pro Gly Lys Lys Val Trp Leu Gly Glu Thr
                325                 330                 335

Ser Ser Ala Tyr Gly Gly Gly Ala Pro Leu Leu Ser Asn Thr Phe Ala
            340                 345                 350

Ala Gly Phe Met Trp Leu Asp Lys Leu Gly Leu Ser Ala Gln Met Gly
        355                 360                 365

Ile Glu Val Val Met Arg Gln Val Phe Phe Gly Ala Gly Asn Tyr His
    370                 375                 380

```
Leu Val Asp Glu Asn Phe Glu Pro Leu Pro Asp Tyr Trp Leu Ser Leu
385                 390                 395                 400

Leu Phe Lys Lys Leu Val Gly Pro Arg Val Leu Ser Arg Val Lys
            405                 410                 415

Gly Pro Asp Arg Ser Lys Leu Arg Val Tyr Leu His Cys Thr Asn Val
            420                 425                 430

Tyr His Pro Arg Tyr Gln Glu Gly Asp Leu Thr Leu Tyr Val Leu Asn
            435                 440                 445

Leu His Asn Val Thr Lys His Leu Lys Val Pro Pro Leu Phe Arg
    450                 455                 460

Lys Pro Val Asp Thr Tyr Leu Leu Lys Pro Ser Gly Pro Asp Gly Leu
465                 470                 475                 480

Leu Ser Lys Ser Val Gln Leu Asn Gly Gln Ile Leu Lys Met Val Asp
                485                 490                 495

Glu Gln Thr Leu Pro Ala Leu Thr Glu Lys Pro Leu Pro Ala Gly Ser
            500                 505                 510

Ala Leu Ser Leu Pro Ala Phe Ser Tyr Gly Phe Phe Val Ile Arg Asn
            515                 520                 525

Ala Lys Ile Ala Ala Cys Ile
    530                 535

<210> SEQ ID NO 45
<211> LENGTH: 2396
<212> TYPE: DNA
<213> ORGANISM: Homo sapiens
<220> FEATURE:
<221> NAME/KEY: CDS
<222> LOCATION: (594)..(2198)
<223> OTHER INFORMATION:

<400> SEQUENCE: 45
tttctagttg cttttagcca atgtcggatc aggttttttca agcgacaaag agatactgag      60
atcctgggca gaggacatcc tagctcggtc agatttgggc aggctcaagt gaccagtgtc     120
ttaaggcaga agggagtcgg ggtagggtct ggctgaaccc tcaaccgggg ctttttaactc    180 agggtctagt cctggcgcca atggatggg acctagaaaa ggtgacagag tgcgcaggac     240
accaggaagc tggtcccacc cctgcgcggc tcccgggcgc tccctcccca ggcctccgag    300
gatcttggat tctggccacc tccgcaccct ttggatgggt gtggatgatt tcaaaagtgg    360
acgtgaccgc ggcggagggg aaagccagca cggaaatgaa agagagcgag gaggggaggg    420
cggggagggg agggcgctag ggagggactc ccggagggg tggagggat ggagcgctgt    480 gggagggtac tgagtcctgg cgccagaggc gaagcaggac cggttgcagg gggcttgagc    540
cagcgcgccg gctgccccag ctctcccggc agcgggcggt ccagccaggt ggg atg      596
                                                             Met
                                                              1 ctg agg ctg ctg ctg ctg tgg ctc tgg ggg ccg ctc ggt gcc ctg gcc   644
Leu Arg Leu Leu Leu Leu Trp Leu Trp Gly Pro Leu Gly Ala Leu Ala
                5                   10                  15 cag ggc gcc ccc gcg ggg acc gcg ccg acc gac gac gtg gta gac ttg   692
Gln Gly Ala Pro Ala Gly Thr Ala Pro Thr Asp Asp Val Val Asp Leu
            20                  25                  30 gag ttt tac acc aag cgg ccg ctc cga agc gtg agt ccc tcg ttc ctg   740
Glu Phe Tyr Thr Lys Arg Pro Leu Arg Ser Val Ser Pro Ser Phe Leu
        35                  40                  45 tcc atc acc atc gac gcc agc ctg gcc acc gac ccg cgc ttc ctc acc   788
Ser Ile Thr Ile Asp Ala Ser Leu Ala Thr Asp Pro Arg Phe Leu Thr
50                  55                  60                  65
```

-continued

| | |
|---|---|
| ttc ctg ggc tct cca agg ctc cgt gct ctg gct aga ggc tta tct cct<br>Phe Leu Gly Ser Pro Arg Leu Arg Ala Leu Ala Arg Gly Leu Ser Pro<br>          70                     75                     80 | 836 |
| gca tac ttg aga ttt ggc ggc aca aag act gac ttc ctt att ttt gat<br>Ala Tyr Leu Arg Phe Gly Gly Thr Lys Thr Asp Phe Leu Ile Phe Asp<br>         85                     90                     95 | 884 |
| ccg gac aag gaa ccg act tcc gaa gaa aga agt tac tgg aaa tct caa<br>Pro Asp Lys Glu Pro Thr Ser Glu Glu Arg Ser Tyr Trp Lys Ser Gln<br>       100                     105                 110 | 932 |
| gtc aac cat gat att tgc agg tct gag ccg gtc tct gct gcg gtg ttg<br>Val Asn His Asp Ile Cys Arg Ser Glu Pro Val Ser Ala Ala Val Leu<br>115                     120                 125 | 980 |
| agg aaa ctc cag gtg gaa tgg ccc ttc cag gag ctg ttg ctc ctc cga<br>Arg Lys Leu Gln Val Glu Trp Pro Phe Gln Glu Leu Leu Leu Leu Arg<br>130                     135                 140                 145 | 1028 |
| gag cag tac caa aag gag ttc aag aac agc acc tac tca aga agc tca<br>Glu Gln Tyr Gln Lys Glu Phe Lys Asn Ser Thr Tyr Ser Arg Ser Ser<br>           150                     155                 160 | 1076 |
| gtg gac atg ctc tac agt ttt gcc aag tgc tcg ggg tta gac ctg atc<br>Val Asp Met Leu Tyr Ser Phe Ala Lys Cys Ser Gly Leu Asp Leu Ile<br>         165                     170                 175 | 1124 |
| ttt ggt cta aat gcg tta cta cga acc cca gac tta cgg tgg aac agc<br>Phe Gly Leu Asn Ala Leu Leu Arg Thr Pro Asp Leu Arg Trp Asn Ser<br>180                     185                 190 | 1172 |
| tcc aac gcc cag ctt ctc ctt gac tac tgc tct tcc aag ggt tat aac<br>Ser Asn Ala Gln Leu Leu Leu Asp Tyr Cys Ser Ser Lys Gly Tyr Asn<br>       195                     200                 205 | 1220 |
| atc tcc tgg gaa ctg ggc aat gag ccc aac agt ttc tgg aag aaa gct<br>Ile Ser Trp Glu Leu Gly Asn Glu Pro Asn Ser Phe Trp Lys Lys Ala<br>210                     215                 220                 225 | 1268 |
| cac att ctc atc gat ggg ttg cag tta gga gaa gac ttt gtg gag ttg<br>His Ile Leu Ile Asp Gly Leu Gln Leu Gly Glu Asp Phe Val Glu Leu<br>           230                     235                 240 | 1316 |
| cat aaa ctt cta caa agg tca gct ttc caa aat gca aaa ctc tat ggt<br>His Lys Leu Leu Gln Arg Ser Ala Phe Gln Asn Ala Lys Leu Tyr Gly<br>               245                 250                 255 | 1364 |
| cct gac atc ggt cag cct cga ggg aag aca gtt aaa ctg ctg agg agt<br>Pro Asp Ile Gly Gln Pro Arg Gly Lys Thr Val Lys Leu Leu Arg Ser<br>260                     265                 270 | 1412 |
| ttc ctg aag gct ggc gga gaa gtg atc gac tct ctt aca tgg cat cac<br>Phe Leu Lys Ala Gly Gly Glu Val Ile Asp Ser Leu Thr Trp His His<br>       275                     280                 285 | 1460 |
| tat tac ttg aat gga cgc atc gct acc aaa gaa gat ttt ctg agc tct<br>Tyr Tyr Leu Asn Gly Arg Ile Ala Thr Lys Glu Asp Phe Leu Ser Ser<br>290                     295                 300                 305 | 1508 |
| gat gcg ctg gac act ttt att ctc tct gtg caa aaa att ctg aag gtc<br>Asp Ala Leu Asp Thr Phe Ile Leu Ser Val Gln Lys Ile Leu Lys Val<br>               310                 315                 320 | 1556 |
| act aaa gag atc aca cct ggc aag aag gtc tgg ttg gga gag acg agc<br>Thr Lys Glu Ile Thr Pro Gly Lys Lys Val Trp Leu Gly Glu Thr Ser<br>               325                 330                 335 | 1604 |
| tca gct tac ggt ggc ggt gca ccc ttg ctg tcc aac acc ttt gca gct<br>Ser Ala Tyr Gly Gly Gly Ala Pro Leu Leu Ser Asn Thr Phe Ala Ala<br>         340                     345                 350 | 1652 |
| ggc ttt atg tgg ctg gat aaa ttg ggc ctg tca gcc cag atg ggc ata<br>Gly Phe Met Trp Leu Asp Lys Leu Gly Leu Ser Ala Gln Met Gly Ile<br>355                     360                 365 | 1700 |
| gaa gtc gtg atg agg cag gtg ttc ttc gga gca ggc aac tac cac tta<br>Glu Val Val Met Arg Gln Val Phe Phe Gly Ala Gly Asn Tyr His Leu | 1748 |

```
                370             375             380             385
gtg gat gaa aac ttt gag cct tta cct gat tac tgg ctc tct ctt ctg    1796
Val Asp Glu Asn Phe Glu Pro Leu Pro Asp Tyr Trp Leu Ser Leu Leu
                    390             395             400 ttc aag aaa ctg gta ggt ccc agg gtg tta ctg tca aga gtg aaa ggc    1844
Phe Lys Lys Leu Val Gly Pro Arg Val Leu Leu Ser Arg Val Lys Gly
            405             410             415 cca gac agg agc aaa ctc cga gtg tat ctc cac tgc act aac gtc tat    1892
Pro Asp Arg Ser Lys Leu Arg Val Tyr Leu His Cys Thr Asn Val Tyr
        420             425             430 cac cca cga tat cag gaa gga gat cta act ctg tat gtc ctg aac ctc    1940
His Pro Arg Tyr Gln Glu Gly Asp Leu Thr Leu Tyr Val Leu Asn Leu
    435             440             445 cat aat gtc acc aag cac ttg aag gta ccg cct ccg ttg ttc agg aaa    1988
His Asn Val Thr Lys His Leu Lys Val Pro Pro Pro Leu Phe Arg Lys
450             455             460             465 cca gtg gat acg tac ctt ctg aag cct tcg ggg ccg gat gga tta ctt    2036
Pro Val Asp Thr Tyr Leu Leu Lys Pro Ser Gly Pro Asp Gly Leu Leu
                470             475             480 tcc aaa tct gtc caa ctg aac ggt caa att ctg aag atg gtg gat gag    2084
Ser Lys Ser Val Gln Leu Asn Gly Gln Ile Leu Lys Met Val Asp Glu
            485             490             495 cag acc ctg cca gct ttg aca gaa aaa cct ctc ccc gca gga agt gca    2132
Gln Thr Leu Pro Ala Leu Thr Glu Lys Pro Leu Pro Ala Gly Ser Ala
        500             505             510 cta agc ctg cct gcc ttt tcc tat ggt ttt ttt gtc ata aga aat gcc    2180
Leu Ser Leu Pro Ala Phe Ser Tyr Gly Phe Phe Val Ile Arg Asn Ala
    515             520             525 aaa atc gct gct tgt ata tgaaaataaa aggcatacgg taccccctgag          2228
Lys Ile Ala Ala Cys Ile
530             535 acaaaagccg agggggtgt tattcataaa acaaaaccct agtttaggag gccacctcct   2288
tgccgagttc cagagcttcg ggagggtggg gtacacttca gtattacatt cagtgtggtg  2348
ttctctctaa gaagaatact gcaggtggtg acagttaata gcactgtg              2396

<210> SEQ ID NO 46
<211> LENGTH: 385
<212> TYPE: DNA
<213> ORGANISM: Rattus norvegicus

<400> SEQUENCE: 46
cggccgctgc tgctgctgtg gctctggggg cggctccgtg ccctgaccca aggcactccg     60
gcggggaccg cgccgaccaa agacgtggtg gacttggagt tttacaccaa gaggctattc    120
caaagcgtga gtccctcgtt cctgtccatc accatcgacg ccagtctggc caccgaccct    180
cggttcctca ccttcctgag ctctccacgg cttcgagccc tgtctagagg cttatctcct    240
gcgtacttga gatttggcgg caccaagact gacttcctta tttttgatcc caacaacgaa    300
cccacctctg aagaaagaag ttactggcaa tctcaagaca caatgatat  ttgcgggtct    360 gaccgggtct ccgctgacgt gttga                                          385

<210> SEQ ID NO 47
<211> LENGTH: 541
<212> TYPE: DNA
<213> ORGANISM: Rattus norvegicus
<220> FEATURE:
<221> NAME/KEY: misc_feature
<222> LOCATION: (507)..(507)
<223> OTHER INFORMATION: Any nucleotide
```

-continued

```
<400> SEQUENCE: 47
aaatcaggac atatccttca cttatttgcc tcttggtcat attggaggca tttgtattca      60
tttttaataa ccctcaaaat agtgcatgca aagtgctaag cgtcatttgc cacatggtgc     120
cattaactgt caccacctgc agtggtctac ttagagaaca ccgcactgga tgttaacact     180
gaagcgcgtg ccccgccctc ccgaggctct ggatccagcg ttgaagcttg ccccgccctc     240
ccgaggctct ggatccagca ctggagcatg ccccgccctc ccgaggctct ggagcttgct     300
aaggagtccg ctccctaccg ctggggtttt gctttattct tatgaatgac acccctgacc     360
gctttcgtct cagggtact gtaatgcctt ttattttcat atacaagctg cgattttggc      420
atttcttatg acaaaaaacc cataggaaaa ggcgggcacg cttagtgagc ttcctgcggg     480
gagaggtttt tctgttagag ctggcanggt ctgctcatcg accatcttca ggcctcgtgc     540
c                                                                     541
```